(12) United States Patent
Amans et al.

(10) Patent No.: US 9,670,221 B2
(45) Date of Patent: Jun. 6, 2017

(54) FUROPYRIDINES AS BROMODOMAIN INHIBITORS

(71) Applicant: GlaxoSmithKline Intellectual Property (No.2) Limited, Brentford Middlesex (GB)

(72) Inventors: Dominique Amans, Brentford (GB); Paul Bamborough, Stevenage (GB); Michael David Barker, Stevenage (GB); Rino Antonio Bit, Stevenage (GB); John Alexander Brown, Stevenage (GB); Matthew Campbell, Stevenage (GB); Neil Stuart Garton, Stevenage (GB); Matthew J. Lindon, Stevenage (GB); Tracy Jane Shipley, Stevenage (GB); Natalie Hope Theodoulou, Stevenage (GB); Christopher Roland Wellaway, Stevenage (GB); Susan Marie Westaway, Stevenage (GB)

(73) Assignee: GlaxoSmithKline Intellectual Property (No. 2) Limited, Brentford, Middlesex (GB)

( * ) Notice: Subject to any disclaimer, the term of this patent is extended or adjusted under 35 U.S.C. 154(b) by 0 days.

(21) Appl. No.: 14/770,922

(22) PCT Filed: Mar. 12, 2014

(86) PCT No.: PCT/EP2014/054796
§ 371 (c)(1),
(2) Date: Aug. 27, 2015

(87) PCT Pub. No.: WO2014/140077
PCT Pub. Date: Sep. 18, 2014

(65) Prior Publication Data
US 2016/0016966 A1    Jan. 21, 2016

Related U.S. Application Data

(60) Provisional application No. 61/781,602, filed on Mar. 14, 2013, provisional application No. 61/882,804, filed on Sep. 26, 2013.

(51) Int. Cl.
| | | |
|---|---|---|
| C07D 491/048 | (2006.01) | |
| A61K 31/496 | (2006.01) | |
| A61K 31/4355 | (2006.01) | |
| A61K 31/4545 | (2006.01) | |
| A61K 31/5377 | (2006.01) | |
| A61K 31/5025 | (2006.01) | |
| A61K 31/541 | (2006.01) | |
| A61K 31/551 | (2006.01) | |
| A61K 31/553 | (2006.01) | |
| A61K 31/554 | (2006.01) | |
| C07D 519/00 | (2006.01) | |

(52) U.S. Cl.
CPC ...... *C07D 491/048* (2013.01); *A61K 31/4355* (2013.01); *A61K 31/4545* (2013.01); *A61K 31/496* (2013.01); *A61K 31/5025* (2013.01); *A61K 31/5377* (2013.01); *A61K 31/541* (2013.01); *A61K 31/551* (2013.01); *A61K 31/553* (2013.01); *A61K 31/554* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 9,034,900 B2 * | 5/2015 | Bennett | C07D 498/04 514/309 |
| 2007/0191373 A1 | 8/2007 | McGuigan et al. | |
| 2012/0208794 A1 | 8/2012 | Sasaki et al. | |

FOREIGN PATENT DOCUMENTS

| | | |
|---|---|---|
| CN | 102276616 A | 12/2011 |
| CN | 102574851 A | 7/2012 |
| EP | 1 217 000 A1 | 6/2002 |
| WO | WO 2010/111483 A1 | 9/2010 |
| WO | WO 2011/054553 A1 | 5/2011 |
| WO | WO 2013/027168 A1 | 2/2013 |
| WO | WO 2013/097052 A1 | 7/2013 |

OTHER PUBLICATIONS

Muller et al. Expert Reviews in Molecular Medicine, vol. 13; e29 pp. 1-21 Sep. 2011.*
Zhang et al. Chem. Rev. 2015, 115, 11625-11668.*
Chung et al., "Discovery and Characterization of Small Molecule Inhibitors of the BET Family Bromodomains," *Journal of Medicinal Chemistry*, vol. 54, Issue 11, pp. 3827-3838 (2011).
Clive et al., "Model Studies and First Synthesis of the Antifungal and Antibacterial Agent Cladobotryal," *Journal of Organic Chemistry*, vol. 69, pp. 1872-1879 (2004).

* cited by examiner

*Primary Examiner* — Emily Bernhardt
(74) *Attorney, Agent, or Firm* — Jane F. Djung; Kathryn A. Lutomski

(57) ABSTRACT

The present invention relates to novel compounds, pharmaceutical compositions containing such compounds and to their use in therapy.

13 Claims, No Drawings

FUROPYRIDINES AS BROMODOMAIN INHIBITORS

CROSS-REFERENCE TO RELATED APPLICATIONS

This application is filed pursuant to 35 USC 371 as a United States National Phase Application of International Patent Application Serial No. PCT/EP2014/054796 filed on Mar. 12, 2014, which claims priority from 61/781,602 filed on Mar. 14, 2013 and 61/882,804 filed on Sep. 26, 2013 in the United States.

FIELD OF THE INVENTION

The present invention relates to novel compounds, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B, H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins recognise and bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRDT) which contain tandem bromodomains capable of binding to two acetylated lysine residues in close proximity, increasing the specificity of the interaction. Numbering from the N-terminal end of each BET protein the tandem bromodomains are typically labelled Binding Domain 1 (BD1) and Binding Domain 2 (BD2) (Chung et al, *J Med. Chem.* 2011, 54, 3827-3838).

A novel class of compounds have been found which inhibit the binding of bromodomains with its cognate acetylated proteins, more particularly a class of compounds that inhibit the binding of BET family bromodomains to aceylated lysine residues, even more particularly a class of compounds that selectively inhibit the binding and function of BET family bromodomains via Binding Domain 1 (BD1). Such compounds will hereafter be referred to as "bromodomain inhibitors".

BRIEF SUMMARY OF THE INVENTION

In a first aspect of the present invention, there is provided a compound of formula (I) or a salt thereof, more particularly a compound of formula (I)

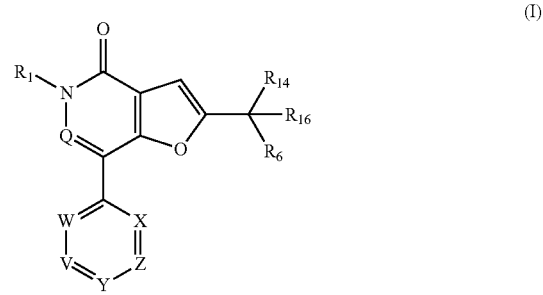

(I)

or a pharmaceutically acceptable salt thereof.

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to a compound of formula (I):

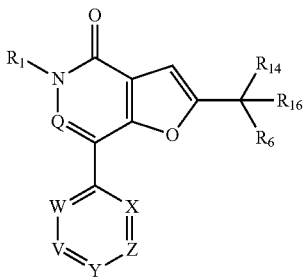

(I)

wherein:
V is N or C—R$_2$
W is N or C—R$_8$;
X is N, CH or C(CH$_3$);
Y is N or C—R$_5$;
Z is N or C—R$_{15}$;
Q is N or CH;
R$_1$ is C$_{1-4}$ alkyl or deuterated C$_{1-4}$ alkyl;
R$_2$, when present, is H, OH, C$_{1-4}$alkyl, halo, —CF$_3$, —NH$_2$, —OC$_{1-4}$alkyl, —NHC(O)H, —NHC(O)C$_{1-4}$alkyl, —N(CH$_3$)C(O)C$_{1-4}$alkyl, —NHC(O)NH$_2$, —NHC(O)C$_{1-4}$alkyleneNH$_2$, —N(CH$_3$)C(O)NH$_2$, —N(CH$_3$)C(O)C$_{1-4}$alkyleneNH$_2$, —NHC$_{2-4}$alkyleneOCH$_3$, —N(CH$_3$)C$_{2-4}$alkyleneOCH$_3$, —OC$_{2-4}$alkyleneOCH$_3$, —OC$_{2-4}$alkyleneOH or
R$_2$ is a group selected from -G-CH$_2$CH(R$_3$)(R$_4$), -G-CH(R$_3$)(R$_4$) and -G-R$_3$ in which
  G is NH, N(CH$_3$), O, C(O)NH or NHC(O);
  R$_3$ is phenyl, pyridinyl, C$_{3-7}$cycloalkyl or a heterocycle optionally substituted by =O; and
  R$_4$ is H or C$_{1-4}$ alkyl;
R$_5$, when present, is H, C$_{1-4}$alkyl, halo, —CF$_3$, CN, OH, —OC$_{1-4}$ alkyl, —CH$_2$NH$_2$, —OCF$_3$, —SO$_2$CH$_3$, —C(O)NHC$_{1-4}$alkyl or —CO$_2$H;
R$_6$ is —NR$_{11}$R$_{12}$ or a group

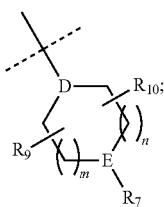

D is CH or N;
E is N, O, CH or SO$_2$;
R$_7$, when present, is H, OH, C$_{1-4}$alkyl, —NH$_2$, —SO$_2$C$_{1-4}$alkyl, —SO$_2$phenyl, —SO$_2$benzyl, —SO$_2$N(CH$_3$)$_2$, —NHSO$_2$CH$_3$, —C(O)C$_{1-4}$alkyl, —C(O)phenyl;
R$_8$, when present, is H, C$_{1-4}$alkyl, halo, —CF$_3$, CN, OH, —OC$_{1-4}$alkyl, —OC$_{2-4}$alkyleneOC$_{1-4}$alkyl, —OCF$_3$, —OC$_{1-4}$alkyleneF, —OC$_{1-4}$alkyleneCHF$_2$, —OC$_{2-4}$alkyleneOH, —Ophenyl, —OC$_{1-4}$alkylenephenyl, —NHC$_{3-7}$cycloalkyl, —NHC$_{1-4}$alkyleneC$_{3-7}$cycloalkyl, —OC$_{3-7}$cycloalkyl, —OC$_{1-4}$alkyleneC$_{3-7}$cycloalkyl, —NHC$_{4-6}$heterocycle-NHC$_{1-4}$alkyleneC$_{4-6}$heterocycle, —OC$_{4-6}$heterocycle or —OC$_{1-4}$alkyleneC$_{4-6}$heterocycle wherein the C$_{3-7}$cycloalkyl or the C$_{4-6}$heterocycle are each optionally substituted by one or two substituents independently selected from halo, OH, oxo, C$_{1-4}$alkyl and —NH$_2$; or R$_8$ and R$_2$ together with the carbon atoms to which they are attached, form a heterocycle optionally substituted by oxo;
R$_9$ is H, C$_{1-4}$alkyl, —C(O)NH$_2$, —CO$_2$CH$_3$, —CF$_3$, halo, OH, —OC$_{1-4}$alkyl, —CH$_2$OH, —C(O)NHCH$_3$, —C(O)NH(CH$_3$)$_2$, —CH$_2$OC$_{1-4}$alkyl or —CH$_2$OCH$_2$C$_{3-7}$cycloalkyl;
R$_{10}$ is H, —C(O)NH$_2$, —CO$_2$CH$_3$, —CF$_3$, halo, OH, —OC$_{1-4}$alkyl or oxo;
R$_{11}$ is H, C$_{1-4}$alkyl or SO$_2$CH$_3$;
R$_{12}$ is H, C$_{1-4}$alkyl, C$_{2-4}$alkyleneNHR$_{13}$, SO$_2$CH$_3$, a heterocycle or a heterocycle comprising SO$_2$;
R$_{13}$ is H or SO$_2$CH$_3$;
R$_{14}$ is H or C$_{1-4}$alkyl;
R$_{15}$ is H, C$_{1-4}$alkyl or NHC(O)C$_{1-4}$alkyl;
R$_{16}$ is H or C$_{1-4}$alkyl: and
n and m are each an integer independently selected from 0, 1 and 2; subject to proviso that no more than 2 of V, W, X, Y and Z are N; or a salt thereof.

In one embodiment V is C—R$_2$. In another embodiment V is N.

In one embodiment, W is C—R$_8$. In another embodiment W is N.

In one embodiment R$_8$ is H, OH, —OC$_{1-4}$alkyl, —OC$_{2-4}$alkyleneOCH$_3$, —OC$_{1-4}$alkyleneF, —OC$_{1-4}$alkyleneCHF$_2$, —OC$_{2-4}$alkyleneOH, —NHC$_3$-7cycloalkyl, —OC$_{3-7}$cycloalkyl, —OCH$_2$C$_{3-7}$cycloalkyl, —O—C$_{4-6}$heterocycle, —OCH$_2$C$_{4-6}$heterocycle or —OCH$_2$C$_{4-6}$heterocycle, wherein the C$_{3-7}$cycloalkyl or the C$_{4-6}$heterocycle are each optionally substituted by one or two substituents independently selected from fluoro and oxo. In another embodiment R$_8$ is H, OH, —OCH$_2$CH$_3$, —OCH(CH$_3$)$_2$, —OCH$_2$CH$_2$OCH$_3$, —OCH$_2$CH(CH$_3$)OCH$_3$, —OCH(CH$_3$)CH$_2$OCH$_3$, —OCH$_2$CH$_2$F, —OCH$_2$CHF$_2$, —OCH$_2$CH$_2$OH, —NHCH$_2$cyclopropyl, —Ocyclopropyl, —OCH$_2$cyclopropyl, —Otetrahydrofuranyl, —Ooxetanyl, —OCH$_2$tetrahydrofuranyl, —OCH$_2$oxetanyl or —OCH$_2$CH$_2$pyrrolidinyl, wherein the C$_{3-7}$cycloalkyl or the C$_{4-6}$heterocycle are each optionally substituted by one or two substituents independently selected from fluoro and oxo. In one embodiment R$_8$ is H, C$_{1-4}$alkyl or —OCH$_2$C$_{3-7}$cycloalkyl. In another embodiment R$_8$ is H, methyl, ethyl or —OCH$_2$cyclopropyl. In another embodiment R$_8$ is H. In another embodiment R$_8$ is —OCH$_2$cyclopropyl. In another embodiment R$_8$ is —OCH$_2$oxetane. In a further embodiment R$_8$ is (R)—OCH$_2$-2-oxetane.

In one embodiment R$_8$ and R$_2$ together with the carbon atoms to which they are attached, form a heterocycle optionally substituted by oxo. In another embodiment R$_8$ and R$_2$ together with the carbon atoms to which they are attached, form 2,3-dihydro-1H-pyrrolo[2,3-b]pyridine optionally substituted by oxo.

In one embodiment X is CH. In another embodiment X is C(CH$_3$). In further embodiment X is N.

In one embodiment Y is C—R$_5$. In another embodiment Y is N.

In one embodiment R$_5$ is H, —CH$_3$, —CH$_2$CH$_3$, halo, —CF$_3$, CN, OH, —OCH$_3$, —CH$_2$NH$_2$, —OCF$_3$, —SO$_2$CH$_3$, —C(O)NHCH$_2$CH$_3$ or —CO$_2$H. In another embodiment R$_5$ is H, —CF$_3$, CN, —OCH$_3$, —CH$_2$NH$_2$ or —SO$_2$CH$_3$. In another embodiment R$_5$ is H, —OCH$_3$ or —CH$_2$NH$_2$. In a further embodiment R$_5$ is H or —OCH$_3$.

In one embodiment Z is N. In another embodiment Z is C—R$_{15}$.

In one embodiment R$_{15}$ is H.

In one embodiment Q is CH. In another embodiment Q is N.

In one embodiment R$_1$ is methyl or ethyl. In another embodiment R$_1$ is methyl.

In one embodiment $R_2$ is H, —$NH_2$, —$OC_{1-4}$alkyl, —$NHC(O)C_{1-4}$alkyl, —$N(CH_3)C(O)C_{1-4}$alkyl, —$NHC(O)C_{1-4}$alkyleneNH$_2$ or —$OC_{2-4}$alkyleneOCH$_3$. In another embodiment $R_2$ is H, OH, methyl, fluoro, chloro, —$CF_3$, —$NH_2$, —$OCH_3$, —$OCH(CH_3)_2$, —$NHC(O)H$, —$NHC(O)Me$, —$NCH(CH_3)CH_2OCH_3$, —$N(CH_3)CH_2CH_2OCH_3$, —$OCH_2CH_2OCH_3$, —$OCH_2CH_2CH_2OH$ or —$OCH(CH_3)CH_2OCH_3$. In another embodiment $R_2$ is H, —$OCH_3$, —$OCH(CH_3)_2$, —$NHC(O)Me$, —$NCH(CH_3)CH_2OCH_3$ or —$N(CH_3)CH_2CH_2OCH_3$. In another embodiment $R_2$ is H, —$OC_{1-4}$alkyl, —$NHC(O)C_{1-4}$alkyl or —$N(CH_3)C(O)C_{1-4}$alkyl. In another embodiment $R_2$ is H, —$OCH_3$, —$NHC(O)CH_3$, —$NHC(O)CH_2CH_3$ or —$N(CH_3)C(O)CH_3$. In another embodiment $R_2$ is H, —$NH_2$, —$OCH_3$, —$NHC(O)CH_3$, —$NHC(O)CH_2CH_3$, —$N(CH_3)C(O)CH_3$, —$NHC(O)CH_2CH_2CH_2NH_2$ or —$OCH_2CH_2OCH_3$. In another embodiment $R_2$ is H. In another embodiment $R_2$ is —$NHC(O)CH_3$. In another embodiment $R_2$ is a group -G-CH($R_3$)($R_4$). In another embodiment $R_2$ is a group -G-CH$_2$CH($R_3$)($R_4$). In a further embodiment $R_2$ is a group -G-$R_3$. In one embodiment G is NH, N(CH$_3$), O or NHC(O). In another embodiment G is NH, O or NHC(O). In another embodiment G is N(CH$_3$). In another embodiment G is NHC(O). In another embodiment G is NH. In a further embodiment G is O.

In one embodiment $R_3$ is phenyl, pyridinyl, cyclopropyl, tetrahydropyranyl, pyrrolidinyl or pyrrolidinyl substituted by =O. In another embodiment $R_3$ is selected from

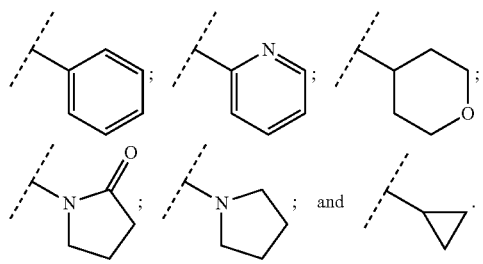

In a further embodiment $R_3$ is selected from

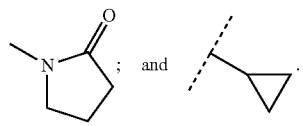

In one embodiment $R_4$ is H or methyl. In another embodiment $R_4$ is H. In a further embodiment $R_4$ is methyl.

In one embodiment $R_6$ is —$NR_{11}R_{12}$.

In one embodiment $R_{11}$ is H or methyl. In another embodiment $R_{11}$ is H.

In one embodiment $R_{12}$ is —$CH_2CH_2CH_2NH_2$, —$CH_2CH_2NH_2$, —$CH_2CH_2NHSO_2CH_3$, —$SO_2CH_3$, —$CH_3$ or

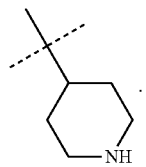

In another embodiment $R_{12}$ is —$CH_2CH_2NHR_{13}$ and $R_{13}$ is H.

In one embodiment $R_6$ is a group

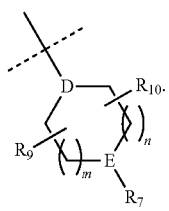

In one embodiment D is CH. In another embodiment D is N.

In one embodiment E is N, O or CH. In another embodiment E is N. In another embodiment E is O.

In another embodiment E is CH. In a further embodiment E is SO$_2$.

In one embodiment $R_7$ is H, methyl, ethyl, iso-propyl, —$SO_2CH_3$, —$SO_2CH_2CH_3$ or —C(O)phenyl. In another embodiment $R_7$ is H or —$SO_2CH_3$. In a further embodiment $R_7$ is —$SO_2CH_3$.

In one embodiment $R_9$ is H, methyl, ethyl, butyl, —$CONH_2$, —$CO_2CH_3$, —$CF_3$, fluoro, OH or —$OCH_3$. In another embodiment $R_9$ is H, methyl or fluoro. In another embodiment $R_9$ is H or methyl.

In one embodiment $R_{10}$ is H, methyl or fluoro. In another embodiment $R_{10}$ is H or fluoro.

In one embodiment $R_9$ and $R_{10}$ are attached to the same atom. In another embodiment $R_9$ and $R_{10}$ are attached to different atoms.

In one embodiment $R_{14}$ is H. In another embodiment $R_{14}$ is $C_{1-4}$alkyl. In a further embodiment $R_{14}$ is —$CH_3$.

In one embodiment $R_{16}$ is H. In another embodiment $R_{16}$ is $C_{1-4}$alkyl. In a further embodiment $R_{16}$ is —$CH_3$.

In one embodiment n is 1 or 2. In another embodiment n is 0. In another embodiment n is 1. In a further embodiment n is 2.

In one embodiment m is 1 or 2. In another embodiment m is 0. In another embodiment m is 1. In a further embodiment m is 2.

In one embodiment both n and m are 1. In another embodiment n is 1 and m is 2.

In one embodiment $R_6$ is a group selected from:

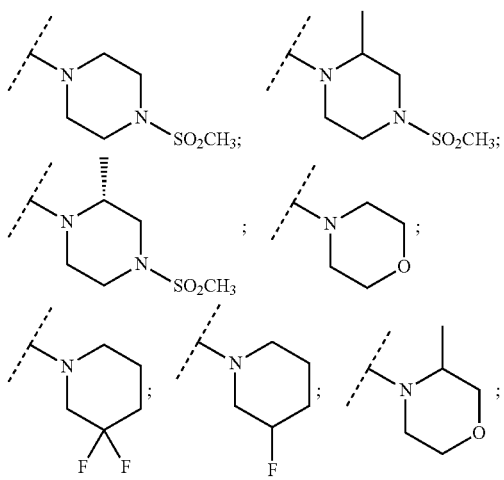

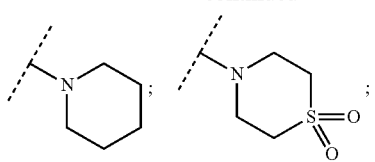

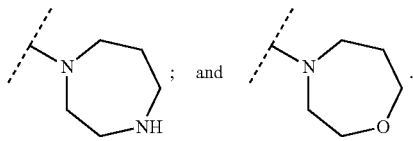

In another embodiment R$_6$ is a group selected from:

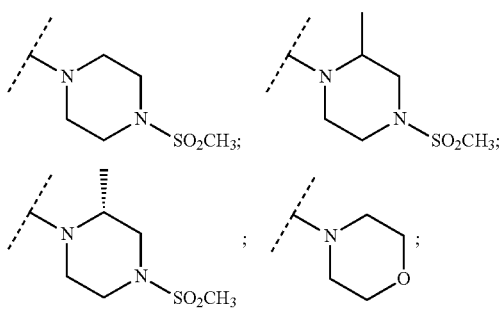

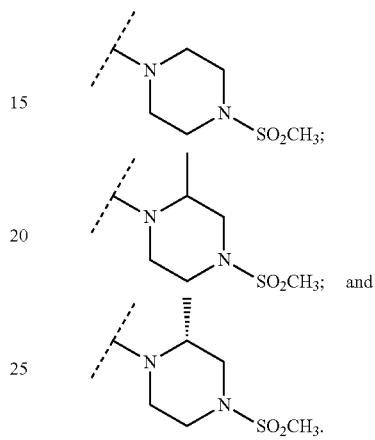

In further embodiment R$_6$ is a group selected from:

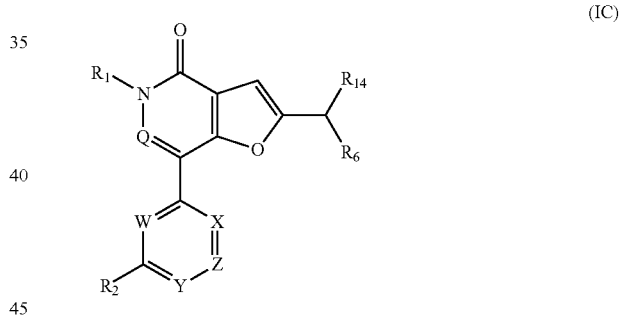

In one embodiment, the present invention relates to a compound of formula (IC):

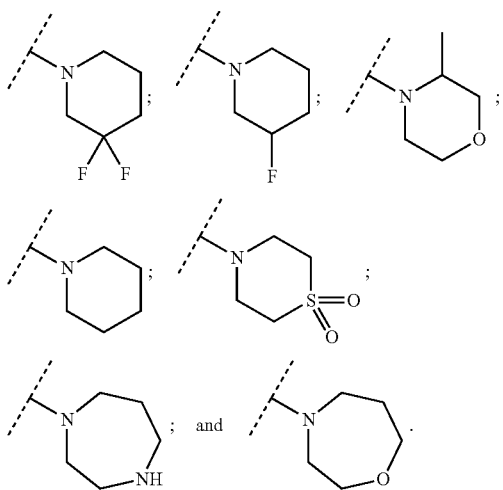

(IC)

wherein:
W is N or C—R$_8$;
X is N, CH or C(CH$_3$);
Y is N or C—R$_5$;
Z is N or C—R$_{15}$;
Q is N or CH;
R$_1$ is C$_{1-4}$ alkyl;
R$_2$ is H, OH, C$_{1-4}$alkyl, halo, —CF$_3$, —NH$_2$, —OC$_{1-4}$alkyl, —NHC(O)H, —NHC(O)C$_{1-4}$alkyl, —N(CH$_3$)C(O)C$_{1-4}$alkyl, —NHCH(CH$_3$)CH$_2$OCH$_3$, —N(CH$_3$)CH$_2$CH$_2$OCH$_3$, —OCH$_2$CH$_2$OCH$_3$, —OCH$_2$CH$_2$CH$_2$OH, —OCH(CH$_3$)CH$_2$OCH$_3$, or R$_2$ is a group selected from -G-CH$_2$CH(R$_3$)(R$_4$), -G-CH(R$_3$)(R$_4$) and -G-R$_3$ in which
   G is NH, N(CH$_3$), O, C(O)NH or NHC(O);
   R$_3$ is phenyl, pyridinyl, C$_{3-7}$cycloalkyl or a heterocycle optionally substituted by =O; and
   R$_4$ is H or C$_{1-4}$ alkyl;
R$_5$ is H, C$_{1-4}$alkyl, halo, —CF$_3$, CN, OH, —OC$_{1-4}$alkyl, —CH$_2$NH$_2$, —OCF$_3$ or —SO$_2$CH$_3$;

In another embodiment R$_6$ is a group selected from:

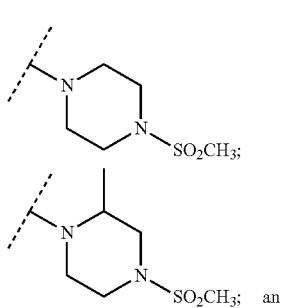

$R_6$ is —$NR_{11}R_{12}$ or a group

[structure with D, E, $R_7$, $R_9$, $R_{10}$, n, m]

D is CH or N;
E is N, O, CH or $SO_2$;
$R_7$, when present, is H, OH, $C_{1-4}$alkyl, —$NH_2$, —$SO_2C_{1-4}$ alkyl, —$SO_2$phenyl, —$SO_2$benzyl, —$SO_2N(CH_3)_2$, —$NHSO_2CH_3$, —$C(O)C_{1-4}$alkyl, —$C(O)$phenyl;
$R_8$ is H, $C_{1-4}$alkyl, halo, —$CF_3$, CN, OH, —$OC_{1-4}$ alkyl, —$OCF_3$, —$OCH_2$phenyl, —$NHCH_2C_{3-7}$cycloalkyl or —$OCH_2C_{3-7}$cycloalkyl;
$R_9$ is H, $C_{1-4}$ alkyl, —$C(O)NH_2$, —$CO_2CH_3$, —$CF_3$, halo, OH, —$OC_{1-4}$alkyl, —$CH_2OH$, —$C(O)NHCH_3$ or —$C(O)NH(CH_3)_2$, —$CH_2OC_{1-4}$alkyl or —$CH_2OCH_2C_{3-7}$cycloalkyl;
$R_{10}$ is H, —$C(O)NH_2$, —$CO_2CH_3$, —$CF_3$, halo, OH or —$OC_{1-4}$alkyl;
$R_{11}$ is H, $C_{1-4}$alkyl or $SO_2CH_3$;
$R_{12}$ is H, $C_{1-4}$alkyl, $C_{1-4}$alkyleneNHR$_{13}$, $SO_2CH_3$, a heterocycle or a heterocycle comprising $SO_2$;
$R_{13}$ is H or $SO_2CH_3$;
$R_{14}$ is H or $C_{1-4}$alkyl;
$R_{15}$ is H, $C_{1-4}$alkyl or NHC(O)$C_{1-4}$alkyl; and
n and m are each an integer independently selected from 0, 1 and 2; subject to proviso that no more than 2 of W, X, Y and Z are N; or a salt thereof.

In one embodiment the compound of formula (I) is a compound of formula (IA)

(IA)

wherein:
W is C—$R_8$;
Y is N or C—$R_5$;
Z is N or CH;
$R_2$ is H, —$OCH_3$, —$NHC(O)CH_3$, —$NHC(O)CH_2CH_3$, —$N(CH_3)C(O)CH_3$, or
$R_2$ is a group selected from -G-$CH_2CH(R_3)(R_4)$ and -G-CH($R_3$)($R_4$) in which
  G is NH, O or NHC(O);
  $R_3$ is phenyl, pyridinyl, cyclopropyl or a heterocycle optionally substituted by =O; and
  $R_4$ is H or methyl;
$R_5$ is H, —$OCH_3$ or —$CH_2NH_2$;
E is N, O, CH or $SO_2$;
$R_7$, when present, is H or —$SO_2CH_3$;

$R_8$ is H, —$NHCH_2$cyclopropyl or —$OCH_2$cyclopropyl;
$R_9$ is H, methyl or fluoro;
$R_{10}$ is H or fluoro;
$R_{14}$ is H or methyl; and
n and m are each an integer independently selected from 1 and 2; or a salt thereof.

In another embodiment the compound of formula (I) is a compound of formula (IB):

(IB)

wherein:
W is N or C—$R_8$;
X and Z are each independently N or CH;
Y is N or C—$R_5$;
$R_1$ is $C_{1-4}$ alkyl;
$R_2$ is H, OH, $C_{1-4}$alkyl, halo, —$CF_3$, —$NH_2$, —$OC_{1-4}$alkyl, —NHC(O)H, —NHC(O)Me, —$NHC(CH_3)CH_2OCH_3$, —$N(CH_3)CH_2OCH_3$, —$N(CH_3)CH_2CH_2OCH_3$, —$OCH_2CH_2OCH_3$, —$OCH_2CH_2CH_2OH$, —$OCH(CH_3)CH_2OCH_3$, or
$R_2$ is a group -G-CH($R_3$)($R_4$) in which
  G is NH, $NCH_3$, O or C(O)NH;
  $R_3$ is phenyl, pyridinyl, $C_{3-7}$cycloalkyl or a heterocycle; and
  $R_4$ is H or $C_{1-4}$ alkyl;
$R_5$ is H, $C_{1-4}$alkyl, halo, —$CF_3$, CN, OH, —$OC_{1-4}$alkyl, —$CH_2NH_2$, —$OCF_3$ or —$SO_2CH_3$;
$R_6$ is —$NR_{11}R_{12}$ or a group

[structure with D, E, $R_7$, $R_9$, $R_{10}$, n]

D is CH or N;
E is N, O, CH or $SO_2$;
$R_7$, when present, is H, OH, $C_{1-4}$alkyl, —$NH_2$, —$SO_2C_{1-4}$ alkyl, —$SO_2$phenyl, —$SO_2$benzyl, —$SO_2N(CH_3)_2$, —$NHSO_2CH_3$, —$C(O)C_{1-4}$alkyl or —$C(O)$phenyl;
$R_8$ is H, $C_{1-4}$alkyl, halo, —$CF_3$, CN, OH, —$OC_{1-4}$alkyl, —$OCF_3$ or —$OCH_2$phenyl;
$R_9$ is H, $C_{1-4}$ alkyl, —$CONH_2$ or —$CO_2CH_3$;
$R_{10}$ is H, —$CONH_2$ or —$CO_2CH_3$;
$R_{11}$ is H or $C_{1-4}$alkyl;
$R_{12}$ is H, $C_{1-4}$ alkyl, $C_{1-4}$alkyleneNHR$_{13}$, $SO_2CH_3$ or a heterocycle;
$R_{13}$ is H or $SO_2CH_3$; and
n is 0, 1 or 2; or a salt thereof.

It is to be understood that the present invention covers all combinations of substituent groups described hereinabove.

Compounds of the invention include the compounds of Examples 1 to 114 and salts thereof. In another embodiment, compounds of the invention include the compounds of Examples 1 to 81b and salts thereof. In another embodiment, compounds of the invention include the compounds of Examples 1 to 36 and 37 to 40 and salts thereof.

In one embodiment, the compound of formula (I) is selected from

7-[3,4-bis(methyloxy)phenyl]-5-methyl-2-{[4-(methylsulfonyl)-1-piperazinyl]methyl}furo[3,2-c]pyridin-4(5H)-one;

(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide;

7-(3-(benzyloxy)phenyl)-5-methyl-2-((4-(methylsulfonyl)piperazin-1-yl)methyl)furo[3,2-c]pyridin-4(5H)-one;

7-(3-(benzylamino)phenyl)-5-methyl-2-((4-(methylsulfonyl)piperazin-1-yl)methyl)furo[3,2-c]pyridin-4(5H)-one;

2-(((2-aminoethyl)amino)methyl)-7-(3,4-dimethoxyphenyl)-5-methylfuro[3,2-c]pyridin-4(5H)-one;

7-(4-(aminomethyl)phenyl)-5-methyl-2-((4-(methylsulfonyl)piperazin-1-yl)methyl)furo[3,2-c]pyridin-4(5H)-one;

5-methyl-2-((4-(methylsulfonyl)piperazin-1-yl)methyl)-7-(2-((tetrahydro-2H-pyran-4-yl)methoxy)pyridin-4-yl)furo[3,2-c]pyridin-4(5H)-one;

7-(3,4-dimethoxyphenyl)-5-methyl-2-(piperidin-1-ylmethyl)furo[3,2-c]pyridin-4(5H)-one;

7-(3,4-dimethoxyphenyl)-5-methyl-2-(morpholinomethyl)furo[3,2-c]pyridin-4(5H)-one;

(R)-7-(3,4-dimethoxyphenyl)-5-methyl-2-((2-methyl-4-(methylsulfonyl)piperazin-1-yl)methyl)furo[3,2-c]pyridin-4(5H)-one;

2-((1,4-diazepan-1-yl)methyl)-7-(3,4-dimethoxyphenyl)-5-methylfuro[3,2-c]pyridin-4(5H)-one;

5-methyl-2-((4-(methylsulfonyl)piperazin-1-yl)methyl)-7-(5-(1-phenylethoxy)pyridin-3-yl)furo[3,2-c]pyridin-4(5H)-one;

2-((3,3-difluoropiperidin-1-yl)methyl)-5-methyl-7-(2-((tetrahydro-2H-pyran-4-yl)methoxy)pyridin-4-yl)furo[3,2-c]pyridin-4(5H)-one;

5-methyl-2-((4-(methylsulfonyl)piperazin-1-yl)methyl)-7-(2-((1-phenylethyl)amino)pyridin-4-yl)furo[3,2-c]pyridin-4(5H)-one;

5-methyl-2-((4-(methylsulfonyl)piperazin-1-yl)methyl)-7-(3-((1-phenylethyl)amino)phenyl)furo[3,2-c]pyridin-4(5H)-one;

7-(3,4-dimethoxyphenyl)-5-methyl-2-((3-methylmorpholino)methyl)furo[3,2-c]pyridin-4(5H)-one;

N-(4-(2-((3-fluoropiperidin-1-yl)methyl)-5-methyl-4-oxo-4,5-dihydrofuro[3,2-c]pyridin-7-yl)pyridin-2-yl)acetamide;

N-(4-(2-((3,3-difluoropiperidin-1-yl)methyl)-5-methyl-4-oxo-4,5-dihydrofuro[3,2-c]pyridin-7-yl)pyridin-2-yl)acetamide;

2-((3-fluoropiperidin-1-yl)methyl)-7-(4-methoxyphenyl)-5-methylfuro[3,2-c]pyridin-4(5H)-one;

5-methyl-2-(morpholinomethyl)-7-(2-((tetrahydro-2H-pyran-4-yl)methoxy)pyridin-4-yl)furo[3,2-c]pyridin-4(5H)-one;

5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one;

(S)-5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one;

(R)-5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one;

2-((1,4-oxazepan-4-yl)methyl)-5-methyl-7-(2-((tetrahydro-2H-pyran-4-yl)methoxy)pyridin-4-yl)furo[3,2-c]pyridin-4(5H)-one;

(R)-7-(2-(cyclopropylmethoxy)pyridin-4-yl)-5-methyl-2-((2-methyl-4-(methylsulfonyl)piperazin-1-yl)methyl)furo[3,2-c]pyridin-4(5H)-one;

(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)cyclopropanecarboxamide;

(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)propionamide;

(R)-7-(2-(2-methoxyethoxy)pyridin-4-yl)-5-methyl-2-((2-methyl-4-(methylsulfonyl)piperazin-1-yl)methyl)furo[3,2-c]pyridin-4(5H)-one;

(R)-5-methyl-2-((2-methyl-4-(methylsulfonyl)piperazin-1-yl)methyl)-7-(2-(2-(pyrrolidin-1-yl)ethoxy)pyridin-4-yl)furo[3,2-c]pyridin-4(5H)-one;

2-((1,1-dioxidothiomorpholino)methyl)-5-methyl-7-(2-((tetrahydro-2H-pyran-4-yl)methoxy)pyridin-4-yl)furo[3,2-c]pyridin-4(5H)-one;

5-methyl-2-((4-(methylsulfonyl)piperazin-1-yl)methyl)-7-(2-((tetrahydro-2H-pyran-4-yl)methoxy)pyridin-4-yl)furo[2,3-d]pyridazin-4(5H)-one;

(R)—N-methyl-N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide;

7-(3-(cyclopropylmethoxy)pyridin-4-yl)-5-methyl-2-((4-(methylsulfonyl)piperazin-1-yl)methyl)furo[3,2-c]pyridin-4(5H)-one;

(R)-7-(3-(cyclopropylmethoxy)pyridin-4-yl)-5-methyl-2-((2-methyl-4-(methylsulfonyl)piperazin-1-yl)methyl)furo[3,2-c]pyridin-4(5H)-one;

7-(3,4-dimethoxyphenyl)-5-methyl-2-((4-(methylsulfonyl)piperazin-1-yl)methyl)furo[2,3-d]pyridazin-4(5H)-one;

2-((1,4-diazepan-1-yl)methyl)-5-methyl-7-(2-((pyridin-2-ylmethyl)amino)pyridine-4-yl)furo[3,2-c]pyridin-4(5H)-one;

(R)-5-methyl-2-((2-methyl-4-(methylsulfonyl)piperazin-1-yl)methyl)-7-(2-(2-(2-oxopyrrolidin-1-yl)ethoxy)pyridin-4-yl)furo[3,2-c]pyridin-4(5H)-one;

N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide;

(R)—N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide;

(S)—N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide;

N-(4-(5-methyl-2-((4-(methylsulfonyl)piperazin-1-yl)methyl)-4-oxo-4,5-dihydrofuro[3,2-c]pyridin-7-yl)pyridin-2-yl)acetamide;

(R)—N-(5-(5-methyl-2-((2-methyl-4-(methylsulfonyl)piperazin-1-yl)methyl)-4-oxo-4,5-dihydrofuro[3,2-c]pyridin-7-yl)pyridin-3-yl)acetamide;

7-(3-((cyclopropylmethyl)amino)pyridin-4-yl)-5-methyl-2-((4-(methylsulfonyl)piperazin-1-yl)methyl)furo[3,2-c]pyridin-4(5H)-one;

(R)-7-(3-((cyclopropylmethyl)amino)pyridin-4-yl)-5-methyl-2-((2-methyl-4-(methylsulfonyl)piperazin-1-yl)methyl)furo[3,2-c]pyridin-4(5H)-one;

5-methyl-2-(((R)-2-methyl-4-(methylsulfonyl)piperazin-1-yl)methyl)-7-(3-(oxetan-2-ylmethoxy)pyridin-4-yl)furo[3,2-c]pyridin-4(5H)-one;

5-methyl-2-(((R)-2-methyl-4-(methylsulfonyl)piperazin-1-yl)methyl)-7-(3-((R)-oxetan-2-ylmethoxy)pyridin-4-yl)furo[3,2-c]pyridin-4(5H)-one;

5-methyl-2-(((R)-2-methyl-4-(methylsulfonyl)piperazin-1-yl)methyl)-7-(3-((S)-oxetan-2-ylmethoxy)pyridin-4-yl)furo[3,2-c]pyridin-4(5H)-one;

(R)-7-(3-(cyclopropylmethoxy)pyridin-2-yl)-5-methyl-2-((2-methyl-4-(methylsulfonyl)piperazin-1-yl)methyl)furo[3,2-c]pyridin-4(5H)-one;

5-methyl-2-((2-methylpiperazin-1-yl)methyl)-7-(2-((tetrahydro-2H-pyran-4-yl)methoxy)pyridin-4-yl)furo[3,2-c]pyridin-4(5H)-one;

(R)-5-methyl-2-((2-methyl-4-(methylsulfonyl)piperazin-1-yl)methyl)-7-(3-(oxetan-3-ylmethoxy)pyridin-4-yl)furo[3,2-c]pyridin-4(5H)-one;

2-((4-acetyl-2-methylpiperazin-1-yl)methyl)-5-methyl-7-(2-((tetrahydro-2H-pyran-4-yl)methoxy)pyridin-4-yl)furo[3,2-c]pyridin-4(5H)-one;

N-(3-(5-methyl-2-((4-(methylsulfonyl)piperazin-1-yl)methyl)-4-oxo-4,5-dihydrofuro[3,2-c]pyridin-7-yl)phenyl)acetamide;

(R)-7-(2-((cyclopropylmethyl)amino)pyridin-3-yl)-5-methyl-2-((2-methyl-4-(methylsulfonyl)piperazin-1-yl)methyl)furo[3,2-c]pyridin-4(5H)-one;

(R)-7-(3-aminophenyl)-5-methyl-2-((2-methyl-4-(methylsulfonyl)piperazin-1-yl)methyl)furo[3,2-c]pyridin-4(5H)-one;

2-((1,4-diazepan-1-yl)methyl)-5-methyl-7-(3-((pyridin-2-ylmethyl)amino)phenyl)furo[3,2-c]pyridin-4(5H)-one;

(R)-7-(3-ethoxypyridin-4-yl)-5-methyl-2-((2-methyl-4-(methylsulfonyl)piperazin-1-yl)methyl)furo[3,2-c]pyridin-4(5H)-one;

N-(3-(2-((1,4-diazepan-1-yl)methyl)-5-methyl-4-oxo-4,5-dihydrofuro[3,2-c]pyridin-7-yl)phenyl)picolinamide;

(R)—N-(6-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide;

2-((1,4-diazepan-1-yl)methyl)-7-(3-(cyclopropylmethoxy)pyridin-4-yl)-5-methylfuro[3,2-c]pyridin-4(5H)-one;

7-(3-(cyclopropylmethoxy)pyridin-4-yl)-5-methyl-2-((4-methyl-1,4-diazepan-1-yl)methyl)furo[3,2-c]pyridin-4(5H)-one;

5-methyl-2-((4-methyl-1,4-diazepan-1-yl)methyl)-7-(3-((pyridin-2-ylmethyl)amino)phenyl)furo[3,2-c]pyridin-4(5H)-one;

(R)-7-(3-isopropoxypyridin-4-yl)-5-methyl-2-((2-methyl-4-(methylsulfonyl)piperazin-1-yl)methyl)furo[3,2-c]pyridin-4(5H)-one;

(R)-7-(2-aminopyridin-4-yl)-5-methyl-2-((2-methyl-4-(methylsulfonyl)piperazin-1-yl)methyl)furo[3,2-c]pyridin-4(5H)-one;

(R)-7-(3-hydroxypyridin-4-yl)-5-methyl-2-((2-methyl-4-(methylsulfonyl)piperazin-1-yl)methyl)furo[3,2-c]pyridin-4(5H)-one;

7-(3-((2,2-difluorocyclopropyl)methoxy)pyridin-4-yl)-5-methyl-2-(((R)-2-methyl-4-(methylsulfonyl)piperazin-1-yl)methyl)furo[3,2-c]pyridin-4(5H)-one;

(R)—N-(4-(5-($^{2}H_3$)methyl-2-((2-methyl-4-(methylsulfonyl)piperazin-1-yl)methyl)-4-oxo-4,5-dihydrofuro[3,2-c]pyridin-7-yl)pyridin-2-yl)acetamide;

(R)-5-methyl-2-((2-methyl-4-(methylsulfonyl)piperazin-1-yl)methyl)-7-(3-(2-(2-oxopyrrolidin-1-yl)ethoxy)pyridin-4-yl)furo[3,2-c]pyridin-4(5H)-one;

(R)-5-amino-N-(3-(5-methyl-2-((2-methyl-4-(methylsulfonyl)piperazin-1-yl)methyl)-4-oxo-4,5-dihydrofuro[3,2-c]pyridin-7-yl)phenyl)pentanamide;

N-(4-(5-methyl-2-(2-(4-(methylsulfonyl)piperazin-1-yl)propan-2-yl)-4-oxo-4,5-dihydrofuro[3,2-c]pyridin-7-yl)pyridin-2-yl)acetamide;

(R)-7-(3-(2-methoxyethoxy)pyridin-4-yl)-5-methyl-2-((2-methyl-4-(methylsulfonyl)piperazin-1-yl)methyl)furo[3,2-c]pyridin-4(5H)-one;

3-(cyclopropylmethoxy)-4-(5-methyl-2-((4-(methylsulfonyl)piperazin-1-yl)methyl)-4-oxo-4,5-dihydrofuro[3,2-c]pyridin-7-yl)benzoic acid;

3-(cyclopropylmethoxy)-N-ethyl-4-(5-methyl-2-((4-(methylsulfonyl)piperazin-1-yl)methyl)-4-oxo-4,5-dihydrofuro[3,2-c]pyridin-7-yl)benzamide;

5-methyl-2-(((R)-2-methyl-4-(methylsulfonyl)piperazin-1-yl)methyl)-7-(3-((tetrahydrofuran-3-yl)methoxy)pyridin-4-yl)furo[3,2-c]pyridin-4(5H)-one;

5-methyl-2-(((R)-2-methyl-4-(methylsulfonyl)piperazin-1-yl)methyl)-7-(3-((tetrahydrofuran-2-yl)methoxy)pyridin-4-yl)furo[3,2-c]pyridin-4(5H)-one;

7-(3-(cyclopropylmethoxy)pyridin-4-yl)-5-methyl-2-((3-oxopiperazin-1-yl)methyl)furo[3,2-c]pyridin-4(5H)-one;

(R)-7-(3-(2-fluoroethoxy)pyridin-4-yl)-5-methyl-2-((2-methyl-4-(methylsulfonyl)piperazin-1-yl)methyl)furo[3,2-c]pyridin-4(5H)-one;

(R)-7-(3-cyclopropoxypyridin-4-yl)-5-methyl-2-((2-methyl-4-(methylsulfonyl)piperazin-1-yl)methyl)furo[3,2-c]pyridin-4(5H)-one;

(R)-7-(3-(2,2-difluoroethoxy)pyridin-4-yl)-5-methyl-2-((2-methyl-4-(methylsulfonyl)piperazin-1-yl)methyl)furo[3,2-c]pyridin-4(5H)-one;

(R)-7-(3-(2-hydroxyethoxy)pyridin-4-yl)-5-methyl-2-((2-methyl-4-(methylsulfonyl)piperazin-1-yl)methyl)furo[3,2-c]pyridin-4(5H)-one;

7-(3-(cyclopropylmethoxy)pyridin-4-yl)-5-methyl-2-((4-methyl-3-oxopiperazin-1-yl)methyl)furo[3,2-c]pyridin-4(5H)-one;

(R)-5-methyl-2-((2-methyl-4-(methylsulfonyl)piperazin-1-yl)methyl)-7-(2-oxo-2,3-dihydro-1H-pyrrolo[2,3-b]pyridin-4-yl)furo[3,2-c]pyridin-4(5H)-one;

7-(3-(2-methoxypropoxy)pyridin-4-yl)-5-methyl-2-(((R)-2-methyl-4-(methylsulfonyl)piperazin-1-yl)methyl)furo[3,2-c]pyridin-4(5H)-one;

7-(3-((1-methoxypropan-2-yl)oxy)pyridin-4-yl)-5-methyl-2-(((R)-2-methyl-4-(methylsulfonyl)piperazin-1-yl)methyl)furo[3,2-c]pyridin-4(5H)-one;

(R)-5-methyl-2-((2-methyl-4-(methylsulfonyl)piperazin-1-yl)methyl)-7-(3-(oxetan-3-yloxy)pyridin-4-yl)furo[3,2-c]pyridin-4(5H)-one;

5-methyl-2-(((R)-2-methyl-4-(methylsulfonyl)piperazin-1-yl)methyl)-7-(3-((tetrahydrofuran-3-yl)oxy)pyridin-4-yl)furo[3,2-c]pyridin-4(5H)-one;

5-methyl-2-(((R)-2-methyl-4-(methylsulfonyl)piperazin-1-yl)methyl)-7-(3-(((S)-tetrahydrofuran-3-yl)oxy)pyridin-4-yl)furo[3,2-c]pyridin-4(5H)-one; and 5-methyl-2-(((R)-2-methyl-4-(methylsulfonyl)piperazin-1-yl)methyl)-7-(3-(((R)-tetrahydrofuran-3-yl)oxy)pyridin-4-yl)furo[3,2-c]pyridin-4(5H)-one;

N-(4-(5-methyl-4-oxo-2-((5-oxo-1,4-diazepan-1-yl)methyl)-4,5-dihydrofuro[3,2-c]pyridin-7-yl)pyridin-2-yl)acetamide;

N-(4-(2-((1,4-oxazepan-4-yl)methyl)-5-methyl-4-oxo-4,5-dihydrofuro[3,2-c]pyridin-7-yl)pyridin-2-yl)acetamide;

N-(4-(5-methyl-2-((4-methylpiperazin-1-yl)methyl)-4-oxo-4,5-dihydrofuro[3,2-c]pyridin-7-yl)pyridin-2-yl)acetamide;

N-(4-(5-methyl-2-((4-methyl-1,4-diazepan-1-yl)methyl)-4-oxo-4,5-dihydrofuro[3,2-c]pyridin-7-yl)pyridin-2-yl)acetamide;

N-(4-(2-((1,4-diazepan-1-yl)methyl)-5-methyl-4-oxo-4,5-dihydrofuro[3,2-c]pyridin-7-yl)pyridin-2-yl)acetamide;

N-(4-(2-((1,1-dioxidothiomorpholino)methyl)-5-methyl-4-oxo-4,5-dihydrofuro[3,2-c]pyridin-7-yl)pyridin-2-yl)acetamide;

N-(4-(5-methyl-4-oxo-2-((3-oxopiperazin-1-yl)methyl)-4,5-dihydrofuro[3,2-c]pyridin-7-yl)pyridin-2-yl)acetamide;

N-(4-(5-methyl-2-((4-(methylsulfonamido)piperidin-1-yl)methyl)-4-oxo-4,5-dihydrofuro[3,2-c]pyridin-7-yl)pyridin-2-yl)acetamide;

(S)—N-(4-(2-((3-hydroxypiperidin-1-yl)methyl)-5-methyl-4-oxo-4,5-dihydrofuro[3,2-c]pyridin-7-yl)pyridin-2-yl)acetamide;

N-(4-(5-methyl-4-oxo-2-(piperazin-1-ylmethyl)-4,5-dihydrofuro[3,2-c]pyridin-7-yl)pyridin-2-yl)acetamide;

N-(4-(2-((4-ethyl-3-oxopiperazin-1-yl)methyl)-5-methyl-4-oxo-4,5-dihydrofuro[3,2-c]pyridin-7-yl)pyridin-2-yl)acetamide;

N-(4-(5-methyl-2-((4-(methylsulfonyl)piperidin-1-yl)methyl)-4-oxo-4,5-dihydrofuro[3,2-c]pyridin-7-yl)pyridin-2-yl)acetamide;

N-(4-(2-(((1,1-dioxidotetrahydro-2H-thiopyran-3-yl)amino)methyl)-5-methyl-4-oxo-4,5-dihydrofuro[3,2-c]pyridin-7-yl)pyridin-2-yl)acetamide;

N-(4-(2-(((1,1-dioxidotetrahydrothiophen-3-yl)amino)methyl)-5-methyl-4-oxo-4,5-dihydrofuro[3,2-c]pyridin-7-yl)pyridin-2-yl)acetamide;

N-(4-(2-((2,5-dimethyl-4-(methylsulfonyl)piperazin-1-yl)methyl)-5-methyl-4-oxo-4,5-dihydrofuro[3,2-c]pyridin-7-yl)pyridin-2-yl)acetamide;

N-(4-(2-((4-ethyl-2-methylpiperazin-1-yl)methyl)-5-methyl-4-oxo-4,5-dihydrofuro[3,2-c]pyridin-7-yl)pyridin-2-yl)acetamide;

N-(4-(5-methyl-2-((4-methyl-5-oxo-1,4-diazepan-1-yl)methyl)-4-oxo-4,5-dihydrofuro[3,2-c]pyridin-7-yl)pyridin-2-yl)acetamide;

N-(4-(5-methyl-2-((7-methyl-5-oxo-1,4-diazepan-1-yl)methyl)-4-oxo-4,5-dihydrofuro[3,2-c]pyridin-7-yl)pyridin-2-yl)acetamide;

N-(4-(5-methyl-2-((2-methyl-5-oxo-1,4-diazepan-1-yl)methyl)-4-oxo-4,5-dihydrofuro[3,2-c]pyridin-7-yl)pyridin-2-yl)acetamide;

N-(4-(2-((1,1-dioxido-1,4-thiazepan-4-yl)methyl)-5-methyl-4-oxo-4,5-dihydrofuro[3,2-c]pyridin-7-yl)pyridin-2-yl)acetamide;

N-(4-(5-methyl-2-((3-methyl-1,1-dioxidothiomorpholino)methyl)-4-oxo-4,5-dihydrofuro[3,2-c]pyridin-7-yl)pyridin-2-yl)acetamide;

N-(4-(5-methyl-2-((2-methyl-1,1-dioxidothiomorpholino)methyl)-4-oxo-4,5-dihydrofuro[3,2-c]pyridin-7-yl)pyridin-2-yl)acetamide;

N-(4-(2-((4-acetyl-1,4-diazepan-1-yl)methyl)-5-methyl-4-oxo-4,5-dihydrofuro[3,2-c]pyridin-7-yl)pyridin-2-yl)acetamide;

N-(4-(5-methyl-2-(morpholinomethyl)-4-oxo-4,5-dihydrofurox[3,2-c]pyridin-7-yl)pyridin-2-yl)acetamide N-(4-(2-((4-acetyl-2-methylpiperazin-1-yl)methyl)-5-methyl-4-oxo-4,5-dihydrofuro[3,2-c]pyridin-7-yl)pyridin-2-yl)acetamide;

N-(4-(5-methyl-2-((4-methyl-3-oxopiperazin-1-yl)methyl)-4-oxo-4,5-dihydrofuro[3,2-c]pyridin-7-yl)pyridin-2-yl)acetamide;

(S)—N-(4-(5-methyl-2-((3-methyl-4-(methylsulfonyl)piperazin-1-yl)methyl)-4-oxo-4,5-dihydrofuro[3,2-c]pyridin-7-yl)pyridin-2-yl)acetamide;

N-(4-(5-methyl-2-((4-(methylsulfonyl)-2-oxopiperazin-1-yl)methyl)-4-oxo-4,5-dihydrofuro[3,2-c]pyridin-7-yl)pyridin-2-yl)acetamide;

N-(4-(2-((4-ethylpiperazin-1-yl)methyl)-5-methyl-4-oxo-4,5-dihydrofuro[3,2-c]pyridin-7-yl)pyridin-2-yl)acetamide;

N-(4-(5-methyl-4-oxo-2-(pyrrolidin-1-ylmethyl)-4,5-dihydrofuro[3,2-c]pyridin-7-yl)pyridin-2-yl)acetamide N-(4-(5-methyl-4-oxo-2-(piperidin-1-ylmethyl)-4,5-dihydrofuro[3,2-c]pyridin-7-yl)pyridin-2-yl)acetamide;

N-(4-(5-methyl-4-oxo-2-((3-oxo-1,4-diazepan-1-yl)methyl)-4,5-dihydrofuro[3,2-c]pyridin-7-yl)pyridin-2-yl)acetamide;

(R)—N-(4-(5-methyl-2-((2-methyl-3-oxopiperazin-1-yl)methyl)-4-oxo-4,5-dihydrofuro[3,2-c]pyridin-7-yl)pyridin-2-yl)acetamide;

or a salt thereof.

In another embodiment, the compound of formula (I) is selected from:

5-methyl-2-(((R)-2-methyl-4-(methylsulfonyl)piperazin-1-yl)methyl)-7-(3-(oxetan-2-ylmethoxy)pyridin-4-yl)furo[3,2-c]pyridin-4(5H)-one;

5-methyl-2-(((R)-2-methyl-4-(methylsulfonyl)piperazin-1-yl)methyl)-7-(3-((R)-oxetan-2-ylmethoxy)pyridin-4-yl)furo[3,2-c]pyridin-4(5H)-one; and 5-methyl-2-(((R)-2-methyl-4-(methylsulfonyl)piperazin-1-yl)methyl)-7-(3-((S)-oxetan-2-ylmethoxy)pyridin-4-yl)furo[3,2-c]pyridin-4(5H)-one; or a salt thereof.

In further embodiment, the compound of formula (I) is:

5-methyl-2-(((R)-2-methyl-4-(methylsulfonyl)piperazin-1-yl)methyl)-7-(3-((R)-oxetan-2-ylmethoxy)pyridin-4-yl)furo[3,2-c]pyridin-4(5H)-one; or a salt thereof.

The term "$C_{1-4}$alkyl" means a straight or branched alkyl containing at least one, and at most four, carbon atoms. Examples of "$C_1$-$C_4$alkyl" as used herein include, but are not limited to, methyl, ethyl, n-propyl, n-butyl, isobutyl, isopropyl and t-butyl.

The term "deuterated $C_{1-4}$alkyl" means a $C_{1-4}$alkyl wherein one or more of the hydrogen atoms are replaced with deuterium.

The term "$C_{1-4}$alkylene" means a straight or branched alkyl chain containing at least one, and at most four, carbon atoms. Examples of "$C_{1-4}$alkylene" as used herein include, but are not limited to, methylene, ethylene, propylene and butylene.

The term "$C_{2-4}$alkylene" means a straight or branched alkyl chain containing at least two, and at most four, carbon atoms. Examples of "$C_{2-4}$alkylene" as used herein include, but are not limited to, ethylene, propylene and butylene.

The term "$C_{3-7}$cycloalkyl" is used to describe a non-aromatic carbocyclic ring containing at least three and at most seven carbon atoms. Examples of $C_{3-7}$cycloalkyl groups include cyclopropyl, cyclobutyl, cyclopentyl, cyclohexyl and cycloheptyl.

The term "heterocycle" refers to a 5 or 6 membered saturated ring that includes one or more (e.g. 2) ring heteroatoms selected from nitrogen, oxygen and sulfur. Examples of saturated heterocycle groups include, but are not limited to, tetrahydropyran, tetrahydrofuran, tetrahydrothiophene, piperidine, piperazine, morpholine, 1,4-dioxane, thiomorpholine, 1,4-oxathiane and 1,4-dithane. The point of attachment to the rest of the molecule may be by any suitable carbon or nitrogen atom.

The term "$C_{4-6}$heterocycle" refers to a 4, 5 or 6 membered saturated ring that includes one or more (e.g. 2) ring heteroatoms selected from nitrogen, oxygen and sulfur. Examples of saturated $C_{4-6}$heterocycle groups include, but are not limited to, oxetane, azetidine, thietiane, tetrahydropyran, tetrahydrofuran, tetrahydrothiophene, piperidine, piperazine, morpholine, 1,4-dioxane, thiomorpholine, 1,4-oxathiane and 1,4-dithane. The point of attachment to the rest of the molecule may be by any suitable carbon or nitrogen atom.

The term "heterocycle comprising $SO_2$" refers to a 5 or 6 membered saturated ring that includes one or more (e.g. 2) ring heteroatoms selected from nitrogen, oxygen, sulfur and sulfur dioxide wherein at least one of the heteroatoms is sulfur dioxide. Examples of heterocycle groups comprising $SO_2$ include, but are not limited to, tetrahydrothiophenyl 1,2-dioxide and tetrahydro-2H-thiopyranyl 1,1-dioxide.

The term "halo" as used herein refers to fluoro, chloro, bromo or iodo.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Unless otherwise noted, all starting materials were obtained from commercial suppliers and used without further purification.

The compounds of formula (I) may contain a chiral atom such that optical isomers, e.g. enantiomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

It will be appreciated that the present invention covers compounds of formula (I) as the free base and as salts thereof, for example as a pharmaceutically acceptable salt thereof. In one embodiment the invention relates to compounds of formula (I) in the form of a free base. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid addition salts. For a review of suitable pharmaceutically acceptable salts see Berge et al., *J. Pharm. Sci.*, 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable acid addition salt can be formed by reaction of a compound of formula (I) with a suitable inorganic or organic acid (such as hydrobromic, hydrochloric, sulphuric, nitric, phosphoric, succinic, maleic, acetic, propionic, fumaric, citric, tartaric, lactic, benzoic, salicylic, glutamaic, aspartic, p-toluenesulphonic, benzenesulphonic, methanesulphonic, ethanesulphonic, naphthalenesulphonic such as 2-naphthalenesulphonic, or hexanoic acid), optionally in a suitable solvent such as an organic solvent, to give the salt which is usually isolated for example by crystallisation and filtration or by evaporation followed by trituration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulphonate, benzenesulphonate, methanesulphonate, ethanesulphonate, naphthalenesulphonate (e.g. 2-naphthalenesulphonate) or hexanoate salt. In one embodiment the pharmaceutically acceptable salt of a compound of formula (I) is the hydrochloride.

Other non-pharmaceutically acceptable salts, e.g. formates, oxalates or trifluoroacetates, may be used, for example in the isolation of the compounds of formula (I), and are included within the scope of this invention The invention includes within its scope all possible stoichiometric and non-stoichiometric forms of the salts of the compounds of formula (I).

It will be appreciated that many organic compounds can form complexes with solvents in which they are reacted or from which they are precipitated or crystallised. These complexes are known as "solvates". For example, a complex with water is known as a "hydrate". Solvents with high boiling points and/or capable of forming hydrogen bonds such as water, xylene, N-methyl pyrrolidinone, MeOH and EtOH may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of formula (I) or a pharmaceutically acceptable salt thereof, which upon administration to the recipient is capable of providing (directly or indirectly) the compound of formula (I) or a pharmaceutically acceptable salt thereof, or an active metabolite or residue thereof. Such derivatives are recognisable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

It will be appreciated from the foregoing that included within the scope of the invention are solvates, isomers and polymorphic forms of the compounds of formula (I) and salts thereof.

The compounds of formula (I) or salts thereof may be made by a variety of methods, including standard chemistry. Illustrative general synthetic methods are set out below and then specific compounds of formula (I) and pharmaceutically acceptable salts thereof, are prepared in the Examples.

Compounds of formula (I) may be prepared as described in any one of Schemes 1 to 6 below:

Scheme 1

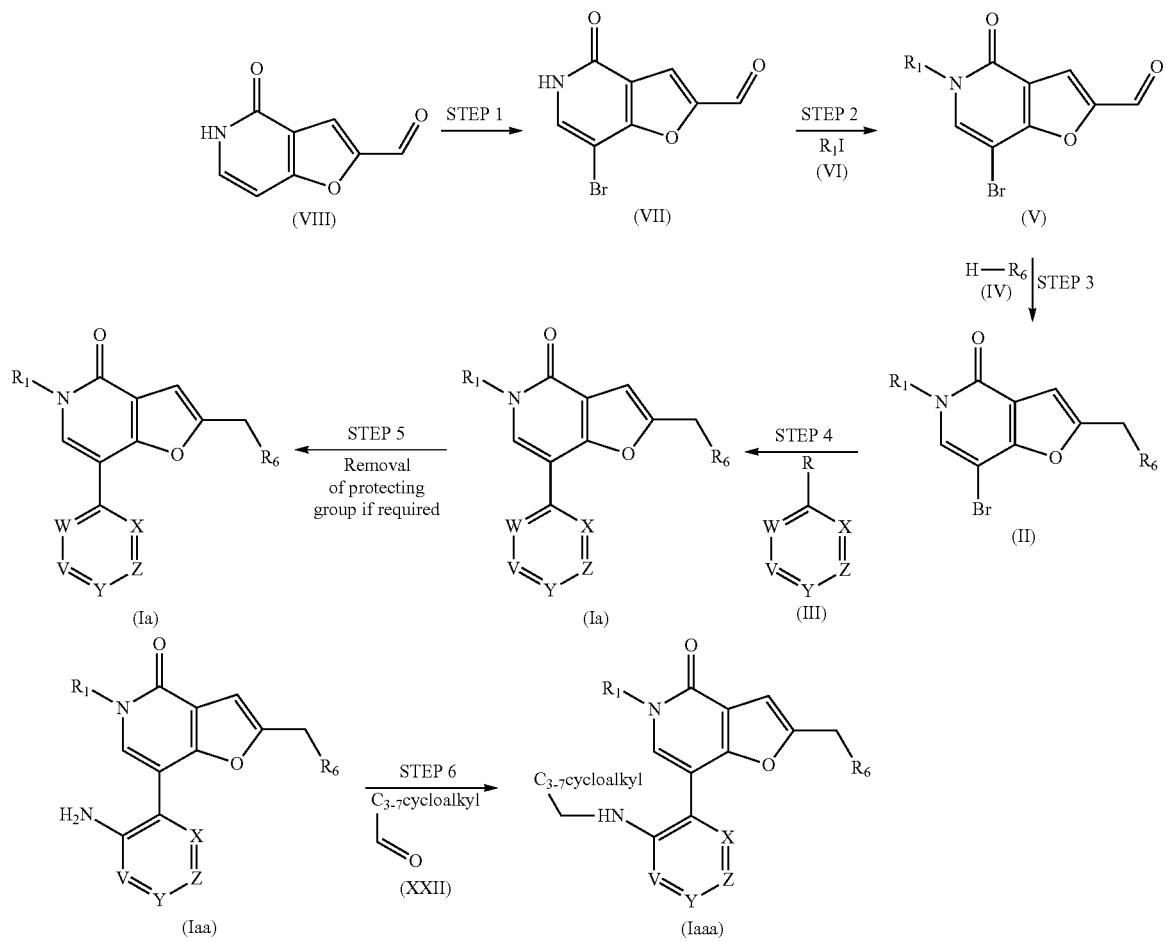

wherein $R_1$, $R_6$, V, W, X, Y and Z are as defined for a compound of formula (I); and R is selected from —B(OH)$_2$, —BF$_3$K and

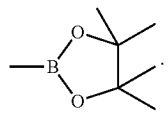

If $R_6$ is —NR$_{11}$R$_{12}$ and R$_{12}$ is C$_{1-4}$alkyleneNHR$_{13}$, R$_{12}$ is protected by a suitable protecting group such as BOC, FMOC or benzyl, which is removed in Step 5 of the synthesis. H—R$_6$ is a compound of formula (IVa) or a compound of formula (IVb)

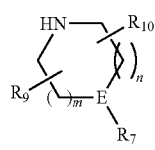

wherein m, n, R$_7$, R$_9$, R$_{10}$, R$_{11}$, R$_{12}$ and E are as defined for a compound of formula (I).

In one embodiment V is C—R$_2$, wherein R$_2$ is as defined for a compound of formula (I).

In respect of steps shown in Scheme 1 the following reaction conditions may be utilised.

Step 1 may be carried out by treating with a suitable brominating agent such as n-bromosuccinimide or Br$_2$, in a suitable solvent, such as THF, AcOH or CH$_3$CN, at a suitable temperature and time period, such as room temperature when using NBS for, for example, 6 hours or under reflux if using Br$_2$, for, for example, 30 minutes.

Step 2 may be carried out in the presence of a suitable base, for example Cs$_2$CO$_3$, K$_2$CO$_3$ or NaH, in a suitable solvent, such as THF or DMF, at a suitable temperature, such as room temperature for a period of, for example overnight.

Step 3 may be carried out with a suitable reducing agent, such as sodium triacetoxyborohydride, 2-picoline borane complex or sodium cyanoborohydride, in the presence of a suitable acid, such as acetic acid, in the presence of a suitable solvent, such as methanol, DCM, 1,2-DCE, chloroform, THF or diethyl ether, at a suitable temperature, such as room temperature, 40° C. or 50° C. for a total reaction period of 1-72 hr which includes a period of 0-4 hr before addition of the reducing agent.

Step 4 may be carried out with a suitable palladium catalyst, such as PdCl$_2$(PPh$_3$)$_2$, Pd$_2$(dba)$_3$, PdCl$_2$(dppf), Pd(OAc)$_2$ or Pd(PPh$_3$)$_4$, a suitable phosphine ligand if required, such as BrettPhos, DavePhos, Xantphos or BINAP, a suitable base, such as NaOtBu, KOtBu, Na$_2$CO$_3$, Cs$_2$CO$_3$ or K$_2$CO$_3$, in a suitable solvent, such as aqueous 1,2-DME, EtOH in toluene, toluene, THF or 1,4-dioxane, at a suitable temperature, such as 80° C., in a microwave, for a suitable period, such as 20 minutes.

Step 5a (wherein the protecting group is BOC) may be carried out with a suitable acid, such as HCl in 1, 4-dioxane or TFA in DCM, at a suitable temperature, such as room temperature, for a suitable period, for example 1 hour.

Step 5b (wherein the protecting group is FMOC) may be carried out with a piperidine solution, at a suitable temperature, such as room temperature, for a suitable period, for example 1 hour.

Step 5c (wherein the protecting group is Cbz or benzyl) may be carried out by hydrogenation in the presence of Pd/C and H$_2$ in a suitable solvent, such as methanol, ethanol or water, at a suitable temperature such as 21° C., for a period of, for example, 16 hours.

Step 6 may be carried out with a suitable reducing agent, such as sodium triacetoxyborohydride, 2-picoline borane complex or sodium cyanoborohydride, in the presence of a suitable acid, such as acetic acid, in the presence of a suitable solvent, such as methanol, DCM, 1,2-DCE, chloroform, THF or diethyl ether, at a suitable temperature, such as room temperature, 40° C. or 50° C. for a total reaction period of 1-72 hr which includes a period of 0-4 hr before addition of the reducing agent.

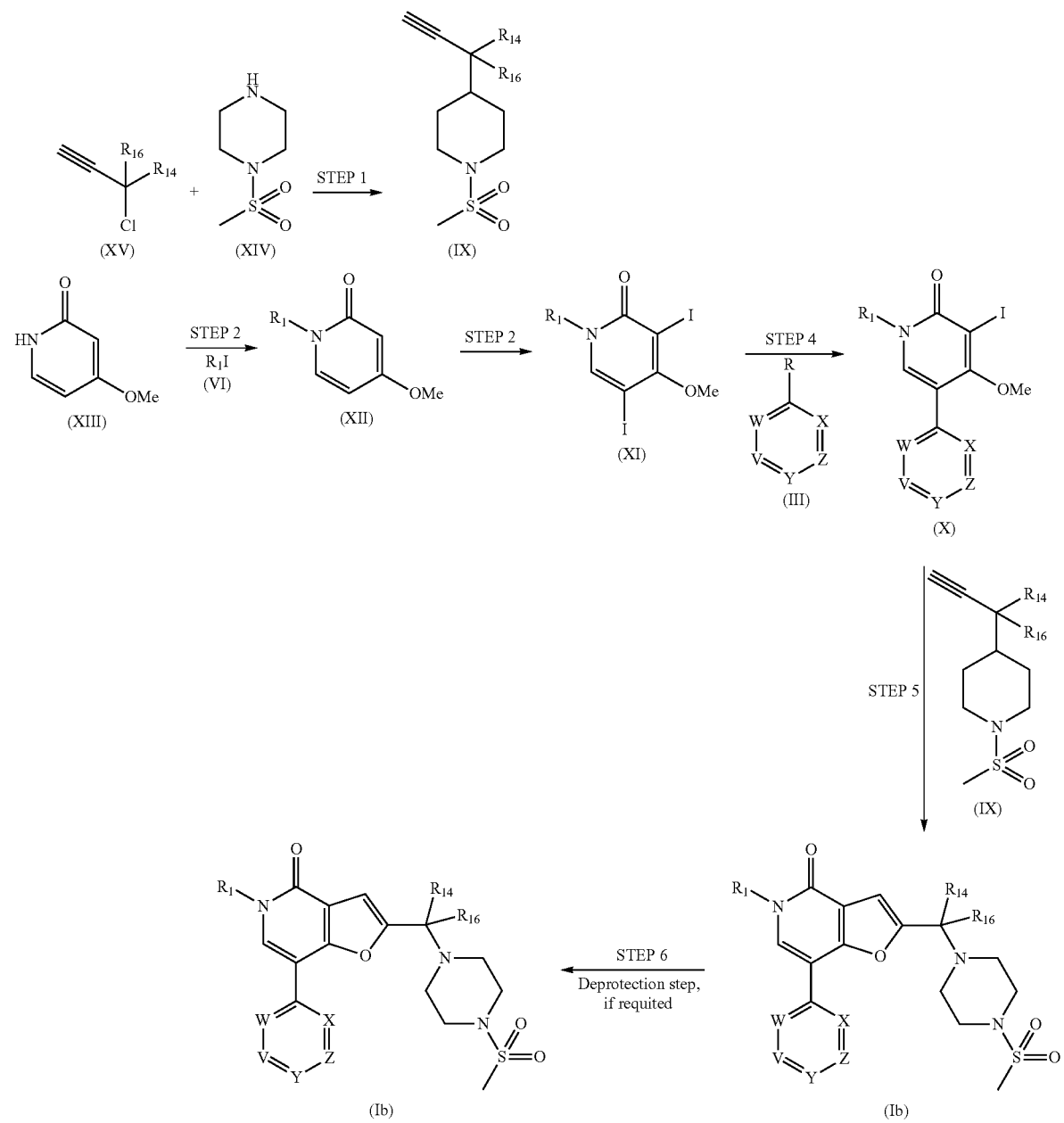

Scheme 2 wherein $R_1$, $R_{14}$, $R_{16}$, V, W, X, Y and Z are as defined for a compound of formula (I); R is selected from —B(OH)$_2$, —BF$_3$K and

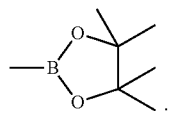

In one embodiment V is C—$R_2$, wherein $R_2$ is as defined for a compound of formula (I).

In respect of steps shown in Scheme 2 the following reaction conditions may be utilised.

Step 1 may be carried out in the presence of copper and copper chloride; in a suitable solvent, such as aqueous Et$_2$O, at a suitable temperature, such as room temperature, for a period of, for example 16 hours.

Step 2 may be carried out in the presence of a suitable base, for example Cs$_2$CO$_3$, K$_2$CO$_3$ or NaH, in a suitable solvent, such as DMF or THF, at a suitable temperature, such as room temperature or 60° C., for a period of, for example overnight.

Step 3 may be carried out by treating with 1-iodopyrrolidine-2,5-dione, iodosuccinimide or I$_2$, in the presence of MeCN or CHCl$_3$, in the presence of an acid such as TFA, AcOH or HNO$_3$, at a suitable temperature, such as room temperature, for a period of, for example 2 hours.

Step 4 may be carried out with a suitable palladium catalyst, such as Pd(OAc)$_2$, PdCl$_2$(PPh$_3$)$_2$, Pd$_2$(dba)$_3$, PdCl$_2$(dppf), or Pd(PPh$_3$)$_4$, a suitable phosphine ligand if required, such as TPPTS, BrettPhos, DavePhos, Xantphos or BINAP, a suitable base, such as DIPEA, NaOtBu, Cs$_2$CO$_3$ or K$_2$CO$_3$, in a suitable solvent, such as aqueous CH$_3$CN, aqueous 1,2-DME, EtOH in toluene, toluene, THF or 1,4-dioxane, at a suitable temperature, such as 60° C., for a suitable period, such as overnight.

Step 5 may be carried out with a suitable palladium catalyst, such as PdCl$_2$(PPh$_3$)$_2$, Pd$_2$(dba)$_3$, PdCl$_2$(dppf), Pd(OAc)$_2$ or Pd(PPh$_3$)$_4$, a suitable phosphine ligand if required, such as PPh$_3$ or P(2-furyl)$_3$, copper iodide, a suitable base, such as triethylamine, Cs$_2$CO$_3$ or K$_2$CO$_3$, in a suitable solvent, such as ACN, toluene, THF, DMF, NMP or 1,4-dioxane, at a suitable temperature, such as 80° C., for a suitable period, such as 4 days, or at a suitable temperature, such as 120° C., for a suitable period, such as 6 hours in a microwave.

Step 6a may be carried out with a suitable acid, such as HCl in 1, 4-dioxane or TFA in DCM, at a suitable temperature, such as room temperature, for a suitable period, for example 1 hour.

Step 6b (wherein the protecting group is FMOC) may be carried out with a piperidine solution, at a suitable temperature, such as room temperature, for a suitable period, for example 1 hour.

Step 6c (wherein the protecting group is benzyl) may be carried out by hydrogenation in the presence of Pd/C and H$_2$ in a suitable solvent, such as methanol, ethanol or water, at a suitable temperature such as 21° C., for a period of, for example, 16 hours.

Scheme 3

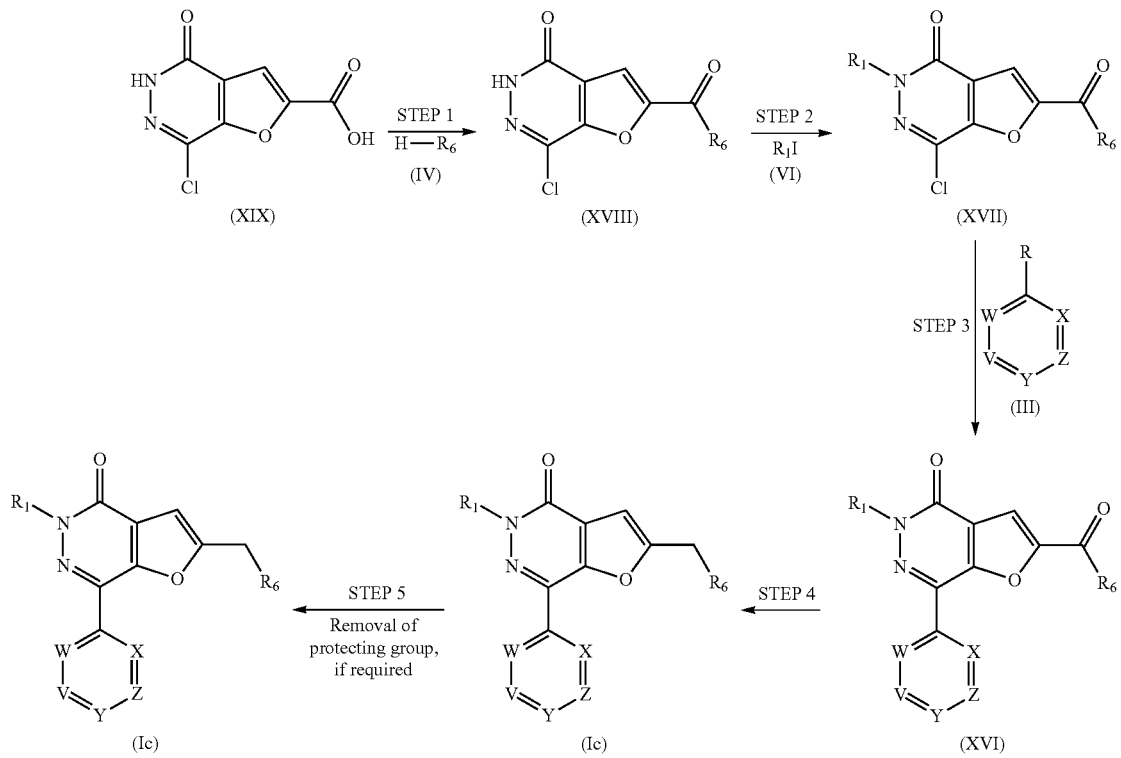

wherein $R_1$, $R_6$, V, W, X, Y and Z are as defined for a compound of formula (I); and R is selected from —B(OH)$_2$, —BF$_3$K and

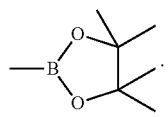

If $R_6$ is —NR$_{11}$R$_{12}$ and $R_{12}$ is C$_{1-4}$alkyleneNHR$_{13}$, $R_{12}$ is protected by a suitable protecting group such as BOC, FMOC or benzyl, which is removed in Step 5 of the synthesis. H—R$_6$ is a compound of formula (IVa) or a compound of formula (IVb)

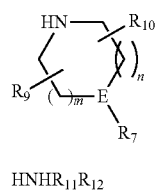

(IVa)

HNHR$_{11}$R$_{12}$ (IVb)

wherein m, n, R$_7$, R$_9$, R$_{10}$, R$_{11}$, R$_{12}$ and E are as defined for a compound of formula (I).

In one embodiment V is C—R$_2$, wherein R$_2$ is as defined for a compound of formula (I).

In respect of steps shown in Scheme 3 the following reaction conditions may be utilised.

Step 1 may be carried out by treating with a suitable coupling agent such as HOBt, HOAt or HATU in the presence of a suitable base, for example Et$_3$N or DIPEA, in a suitable solvent, such as THF or DMF, at a suitable temperature, such as room temperature, for a period of, for example 16 hours.

Step 2 may be carried out in the presence of a suitable base, for example Cs$_2$CO$_3$, K$_2$CO$_3$ or NaH in a suitable solvent, such as THF or DMF, at a suitable temperature, such as room temperature, for a period of, for example 16 hours.

Step 3 may be carried out with a suitable palladium catalyst, such as Pd(OAc)$_2$, PdCl$_2$(PPh$_3$)$_2$, Pd$_2$(dba)$_3$, PdCl$_2$(dppf), or Pd(PPh$_3$)$_4$, a suitable phosphine ligand if required, such as TPPTS, BrettPhos, DavePhos, Xantphos or BINAP, a suitable base, such as DIPEA, NaOtBu, Cs$_2$CO$_3$ or K$_2$CO$_3$, in a suitable solvent, such as aqueous CH$_3$CN, aqueous 1,2-DME, EtOH in toluene, toluene, THF or 1,4-dioxane, at a suitable temperature, such as 60° C., for a suitable period, such as overnight.

Step 4 may be carried out with a suitable reducing agent, such as borane-THF complex or LiAlH$_4$ in a suitable solvent, such as THF or Et$_2$O, at a suitable temperature, such as room temperature, for a suitable period, such as 16 hours.

Step 5a may be carried out with a suitable acid, such as HCl in 1, 4-dioxane or TFA in DCM, at a suitable temperature, such as room temperature, for a suitable period, for example 1 hour.

Step 5b (wherein the protecting group is FMOC) may be carried out with a piperidine solution, at a suitable temperature, such as room temperature, for a suitable period, for example 1 hour.

Step 5c (wherein the protecting group is benzyl) may be carried out by hydrogenation in the presence of Pd/C and H$_2$ in a suitable solvent, such as methanol, ethanol or water, at a suitable temperature such as 21° C., for a period of, for example, 16 hours.

Scheme 4

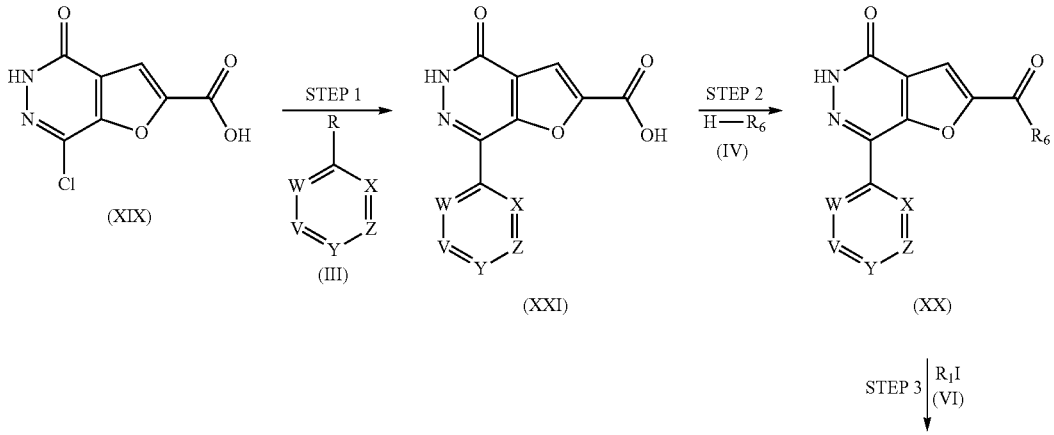

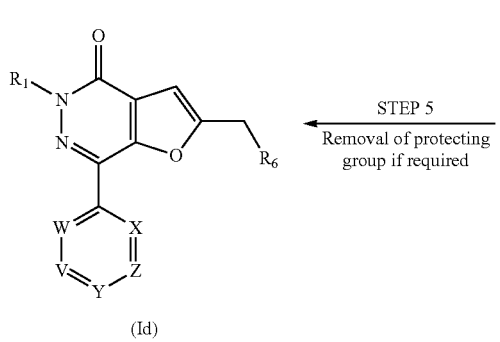

(Id)

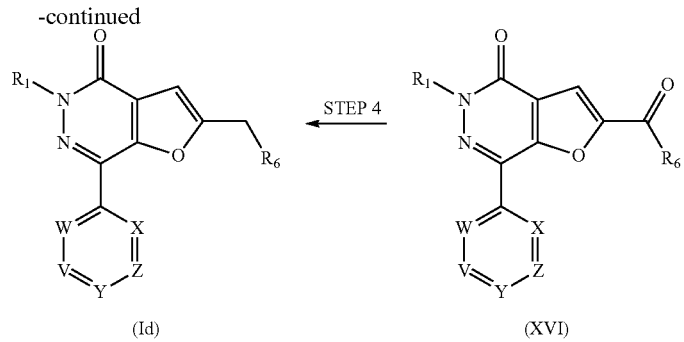

(Id)                                    (XVI)

wherein $R_1$, $R_6$, V, W, X, Y and Z are as defined for a compound of formula (I); and R is selected from —B(OH)$_2$, —BF$_3$K and

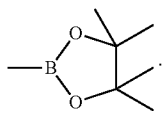

If $R_6$ is —NR$_{11}$R$_{12}$ and $R_{12}$ is C$_{1-4}$alkyleneNHR$_{13}$, $R_{12}$ is protected by a suitable protecting group such as BOC, FMOC or benzyl, which is removed in Step 5 of the synthesis. H—R$_6$ is a compound of formula (IVa) or a compound of formula (IVb)

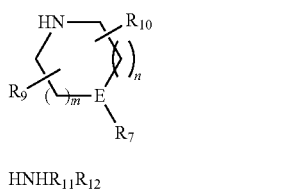

(IVa)

HNHR$_{11}$R$_{12}$   (IVb)

wherein m, n, $R_7$, $R_9$, $R_{10}$, $R_{11}$, $R_{12}$ and E are as defined for a compound of formula (I).

In one embodiment V is C—R$_2$ wherein R$_2$ is as defined for a compound of formula (I).

In respect of steps shown in Scheme 4 the following reaction conditions may be utilised.

Step 1 may be carried out with a suitable palladium catalyst, such as Pd(OAc)$_2$, PdCl$_2$(PPh$_3$)$_2$, Pd$_2$(dba)$_3$, PdCl$_2$(dppf), or Pd(PPh$_3$)$_4$, a suitable phosphine ligand if required, such as TPPTS, BrettPhos, DavePhos, Xantphos or BINAP, a suitable base, such as DIPEA, NaOtBu, Cs$_2$CO$_3$ or K$_2$CO$_3$, in a suitable solvent, such as aqueous CH$_3$CN, aqueous 1,2-DME, ethanol in toluene, toluene, THF or 1,4-dioxane, at a suitable temperature, such as 60° C., for a suitable period, such as overnight.

Step 2 may be carried out by treating with a suitable coupling agent such as HOBt, HOAt or HATU in the presence of a suitable base, for example Et$_3$N or DIPEA, in a suitable solvent, such as THF or DMF, at a suitable temperature, such as room temperature, for a period of for example 16 hours.

Step 3 may be carried out in the presence of a suitable base, for example Cs$_2$CO$_3$, K$_2$CO$_3$ or NaH in a suitable solvent, such as THF or DMF, at a suitable temperature, such as room temperature, for a period of for example 16 hours.

Step 4 may be carried out with a suitable reducing agent, such as borane-THF complex or LiAlH$_4$ in a suitable solvent, such as THF or Et$_2$O, at a suitable temperature, such as room temperature, for a suitable period, such as 16 hours.

Step 5a may be carried out with a suitable acid, such as HCl in 1, 4-dioxane or TFA in DCM, at a suitable temperature, such as room temperature, for a suitable period, for example 1 hour.

Step 5b (wherein the protecting group is FMOC) may be carried out with a piperidine solution, at a suitable temperature, such as room temperature, for a suitable period, for example 1 hour.

Step 5c (wherein the protecting group is Cbz or benzyl) may be carried out by hydrogenation in the presence of Pd/C and H$_2$ in a suitable solvent, such as methanol, ethanol or water, at a suitable temperature such as 21° C., for a period of, for example, 16 hours.

Scheme 5

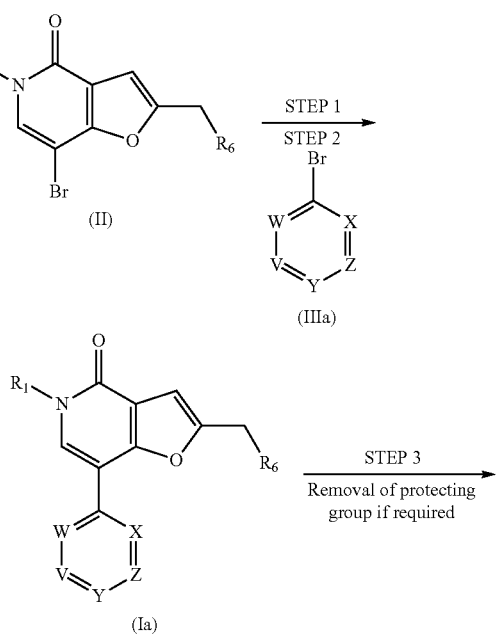

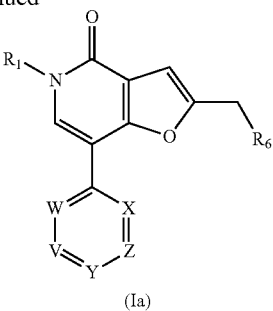

(Ia)

wherein $R_1$, $R_6$, V, W, X, Y and Z are as defined for a compound of formula (I).

In one embodiment V is C—$R_2$, wherein $R_2$ is as defined for a compound of formula (I).

In respect of steps shown in Scheme 5 the following reaction conditions may be utilised.

Step 1 may be carried out by treatment with 4,4,5,5-tetramethyl-1,3,2-dioxaborolane in the presence of a suitable catalyst, for example PEPPSI-SIPr, PEPPSI-IPr or Pd(PPh$_3$)$_4$, in the presence of a suitable base, for example triethylamine, in suitable solvent, such as 1,4-dioxane, at a suitable temperature, such as 100° C., for a suitable period, such as 3 h.

Step 2 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ PEPPSI-IPr or PEPPSI-SIPr, a suitable base, such as NaOtBu, KOtBu, Na$_2$CO$_3$, Cs$_2$CO$_3$ or K$_2$CO$_3$, in a suitable solvent, such as 1,2-DME, aqueous 1,2-DME, methanol in toluene, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 h.

When the protecting group is BOC, Step 3 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 h.

Scheme 6

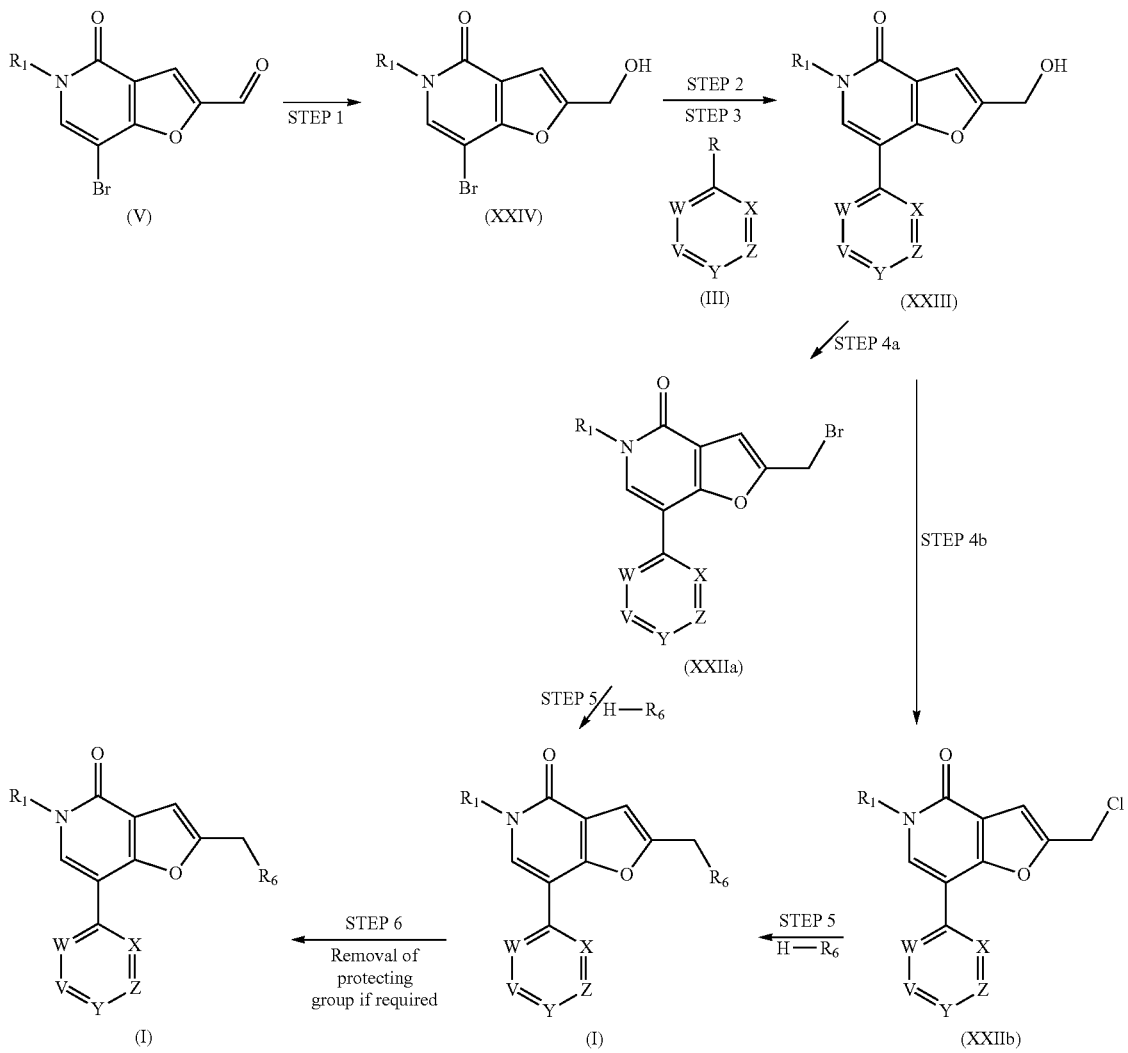

wherein $R_1$, $R_6$, V, W, X, Y and Z are as defined for a compound of formula (I); and R is selected from —B(OH)$_2$, —BF$_3$K and

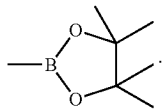

If $R_6$ is —NR$_{11}$R$_{12}$ and $R_{12}$ is C$_{1-4}$alkyleneNHR$_{13}$, $R_{12}$ is protected by a suitable protecting group such as BOC, FMOC or benzyl, which is removed in Step 6 of the synthesis. H—R$_6$ is a compound of formula (IVa) or a compound of formula (IVb)

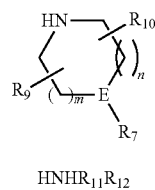
(IVa)

HNHR$_{11}$R$_{12}$ (IVb)

wherein m, n, $R_7$, $R_9$, $R_{10}$, $R_{11}$, $R_{12}$ and E are as defined for a compound of formula (I).

In one embodiment V is C—R$_2$, wherein R$_2$ is as defined for a compound of formula (I).

In respect of steps shown in Scheme 6 the following reaction conditions may be utilised.

Step 1 may be carried out by treatment with a suitable reducing agent, such as sodium borohydride, in a suitable solvent, such as ethanol, at a suitable temperature, such as room temperature and for a suitable time period, for example 2 hr.

Step 2 may be carried out by treatment with 4,4,5,5-tetramethyl-1,3,2-dioxaborolane in the presence of a suitable catalyst, for example PEPPSI-SIPr, PEPPSI-IPr or Pd(PPh$_3$)$_4$, in the presence of a suitable base, for example triethylamine, in suitable solvent, such as 1,4-dioxane, at a suitable temperature, such as 100° C., for a suitable period, such as 3-18 h.

Step 3 may be carried out with a suitable palladium catalyst, such as PdCl$_2$(PPh$_3$)$_2$, Pd$_2$(dba)$_3$, PdCl$_2$(dppf).DCM, Pd(OAc)$_2$, Pd(PPh$_3$)$_4$ PEPPSI-IPr or PEPPSI-SIPr, a suitable base, such as NaOtBu, KOtBu, Na$_2$CO$_3$, Cs$_2$CO$_3$ or K$_2$CO$_3$, in a suitable solvent, such as 1,2-DME, aqueous 1,2-DME, methanol in toluene, ethanol in toluene, toluene, THF, aqueous THF, aqueous isopropanol, DMF or aqueous 1,4-dioxane, at a suitable temperature, such as 80-150° C., optionally in a microwave reactor, for a suitable period, such as 20 min to 20 h.

Step 4a may be carried out by treatment with a suitable brominating agent, such as PBr$_3$, in a suitable solvent, such as 1,4-dioxane, at a suitable temperature, such as 40-60° C. and for a suitable time period, for example 2 hr to overnight.

Step 4b may be carried out by treatment with methanesulfonyl chloride, in a suitable solvent, such as DCM, with a suitable base, such as pyridine, at a suitable temperature, such as room temperature and for a suitable time period, for overnight.

Step 5 may be carried out in the presence of a suitable base, such as DIPEA, K$_2$CO$_3$ or NaH in a suitable solvent, such as DMSO or DMF, at a suitable temperature, such as 110° C. in a microwave reactor, or room temperature and for a suitable time period, for example 30 min to 3 h. When the protecting group is BOC, Step 6 may be carried out in the presence of a suitable acid, such as trifluoroacetic acid or hydrochloric acid, in a suitable solvent, such as DCM or 1,4-dioxane, at a suitable temperature, such as room temperature and for a suitable time period, such as 1 to 24 hr.

Thus, in one embodiment the invention provides a process for preparing a compound of formula (I) comprising reacting a compound of formula (II)

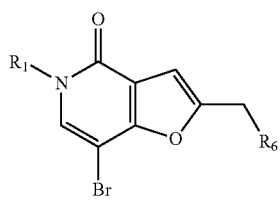
(II)

wherein $R_1$ and $R_6$ are as defined above, with a compound of formula (III)

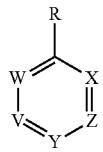
(III)

wherein V, W, X, Y and Z are as defined above and R is selected from B(OH)$_2$, BF$_3$K and

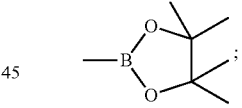
;

optionally followed by a deprotection step if required. In one embodiment V is C—R$_2$, wherein R$_2$ is as defined above.

In another embodiment the invention provides a process for preparing a compound of formula (II) comprising reacting a compound of formula (V)

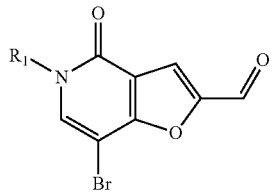
(V)

wherein $R_1$ is as defined above, with an amine of formula (IVa) or formula (IVb)

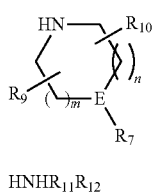

(IVa)

HNHR₁₁R₁₂ (IVb)

wherein $R_7$, $R_9$, $R_{10}$, $R_{11}$, $R_{12}$, m, n and E are as defined above, and if $R_{12}$ is $C_{1-4}$alkyleneNHR$_{13}$ then $R_{12}$ is protected by a suitable protecting group, such as BOC, FMOC Cbz or benzyl.

In another embodiment the invention provides a process for preparing a compound of formula (V) comprising reacting a compound of formula (VII)

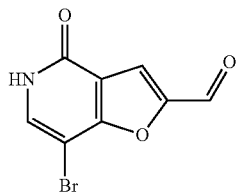

(VII)

with a compound of formula (VI)

R₁I (VI)

wherein $R_1$ is as defined above.

In another embodiment the invention provides a process for preparing a compound of formula (VII) comprising reacting a compound of formula (VIII)

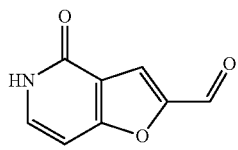

(VIII)

with a brominating agent, for example n-bromosuccinimide.

In another embodiment the invention provides a process for preparing a compound of formula (I) comprising reacting a compound of formula (X)

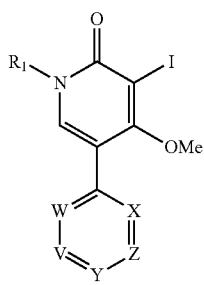

(X)

wherein $R_1$, V, W, X, Y and Z are as defined above, with a compound of formula (IX)

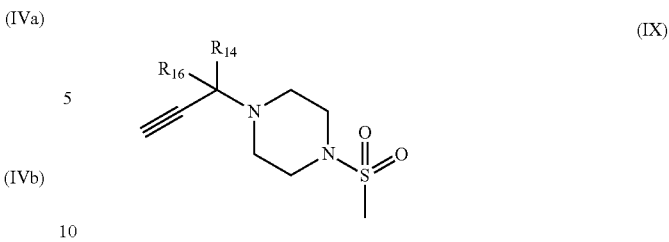

(IX)

wherein $R_{14}$ and $R_{16}$ are as defined above; optionally followed by a deprotection step if required. In one embodiment V is C—R$_2$, wherein $R_2$ is as defined above.

In another embodiment the invention provides a process for preparing a compound of formula (X) comprising reacting a compound of formula (XI)

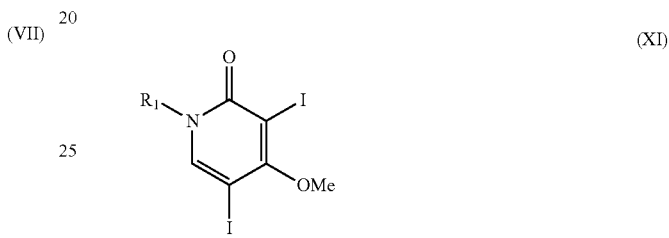

(XI)

wherein $R_1$ is as defined above, with a compound of formula (III)

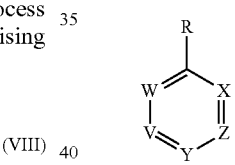

(III)

wherein V, W, X, Y and Z are as defined above; and R is selected from B(OH)$_2$, BF$_3$K and

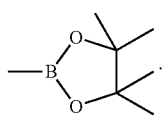

In one embodiment V is C—R$_2$, wherein $R_2$ is as defined above.

In a further embodiment the invention provides a process for preparing a compound of formula (IX) comprising reacting a compound of formula (XIV)

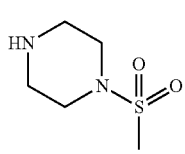

(XIV)

with a compound of formula (XV)

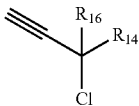
(XV)

wherein $R_{14}$ and $R_{16}$ are as defined above.

In another embodiment the invention provides a process for preparing a compound of formula (I) comprising reacting a compound of formula (XVI)

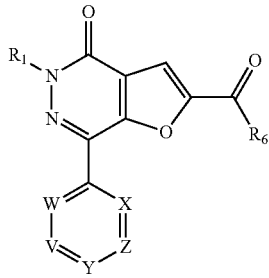
(XVI)

wherein $R_1$, $R_6$, V, W, X, Y and Z are as defined above, with a reducing agent; optionally followed by a deprotection step if required. In one embodiment the reducing agent is Borane-THF complex or $LiAlH_4$. In one embodiment V is C—$R_2$, wherein $R_2$ is as defined above.

In another embodiment the invention provides a process for preparing a compound of formula (XVI) comprising reacting m compound of formula (XVII)

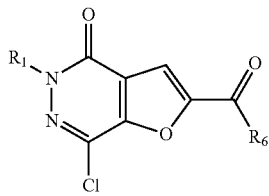
(XVII)

wherein $R_1$ and $R_6$ are as defined above, with a compound of formula (III)

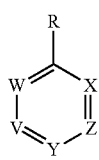
(III)

wherein V, W, X, Y and Z are as defined above; and R is selected from $B(OH)_2$, $BF_3K$ and

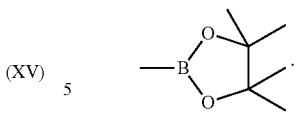

In one embodiment V is C—$R_2$, wherein $R_2$ is as defined above.

In another embodiment the invention provides a process for preparing a compound of formula (XVII) comprising reacting a compound of formula (XVIII)

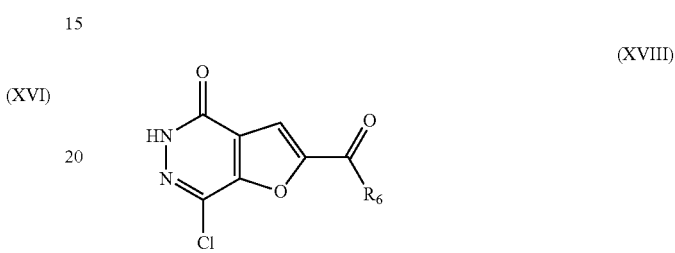
(XVIII)

wherein $R_6$ is as defined above, with a compound of formula (VI)

$R_1I$ (VI)

wherein $R_1$ is as defined above.

In another embodiment the invention provides a process for preparing a compound of formula (XVIII) comprising reacting a compound of formula (XIX)

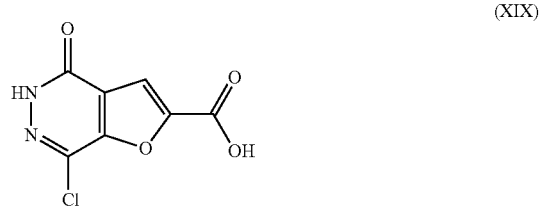 [SMILES: O=C(O)c1cc2c(=O)[nH]nc(Cl)c2o1]
(XIX)

with an amine of formula (IVa) or formula (IVb)

(IVa)

$HNHR_{11}R_{12}$ (IVb)

wherein $R_7$, $R_9$, $R_{10}$, $R_{11}$, $R_{12}$, m, n and E are as defined above, and if $R_{12}$ is $C_{1-4}$alkyleneNHR$_{13}$ then $R_{12}$ is protected by a suitable protecting group, such as BOC, FMOC, Cbz or benzyl.

In another embodiment the invention provides a process for preparing a compound of formula (XVI) comprising reacting a compound of formula (XX)

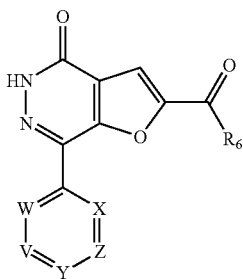

(XX)

wherein R$_6$, V, W, X, Y and Z are as defined above; with a compound of formula (VI)

R$_1$I (VI)

wherein R$_1$ is as defined above. In one embodiment V is C—R$_2$, wherein R$_2$ is as defined above.

In another embodiment the invention provides a process for preparing a compound of formula (XX) comprising reacting a compound of formula (XXI)

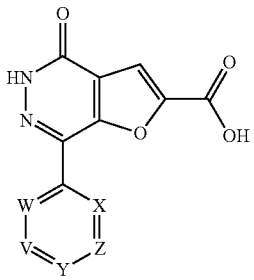

(XXI)

wherein V, W, X, Y and Z are as defined above; with an amine of formula (IVa) or formula (IVb)

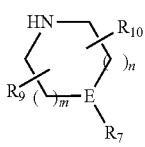

(IVa)

HNHR$_{11}$R$_{12}$ (IVb)

wherein R$_7$, R$_9$, R$_{10}$, R$_{11}$, R$_{12}$, m, n and E are as defined above, and if R$_{12}$ is C$_{1-4}$alkyleneNHR$_{13}$ then R$_{12}$ is protected by a suitable protecting group, such as BOC, FMOC, Cbz or benzyl. In one embodiment V is C—R$_2$, wherein R$_2$ is as defined above In a further embodiment the invention provides a process for preparing a compound of formula (XXI) comprising reacting a compound of formula (XIX)

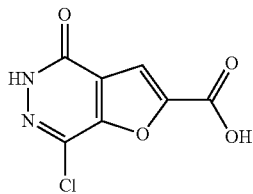

(XIX)

with a compound of formula (III)

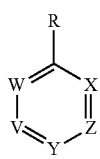

(III)

wherein V, W, X, Y and Z are as defined above; and R is selected from B(OH)$_2$, BF$_3$K and

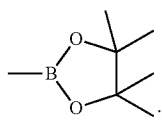

.

In one embodiment V is C—R$_2$, wherein R$_2$ is as defined above.

In another embodiment the invention provides a process for preparing a compound of formula (I) comprising reacting a compound of formula (II)

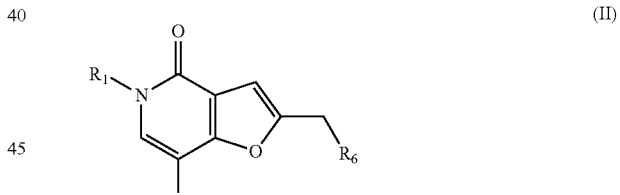

(II)

wherein R$_1$ and R$_6$ are as defined above, via a boronate ester intermediate, with a compound of formula (IIIa)

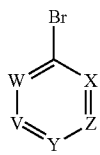

(IIIa)

wherein V, W, X, Y and Z are as defined above; optionally followed by a deprotection step if required. In one embodiment V is C—R$_2$ wherein R$_2$ is as defined above.

In another embodiment the invention provides a process for preparing a compound of formula (I) comprising reacting a compound of formula (XXIIa) or (XXIIb)

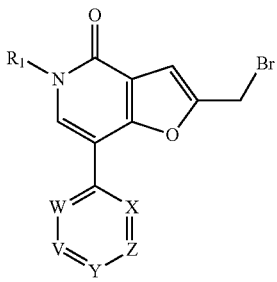
(XXIIa)

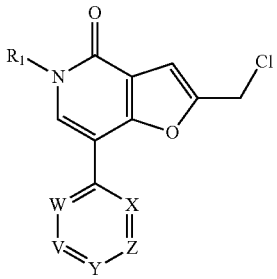
(XXIIb)

wherein $R_1$, V, W, X, Y and Z are as defined above, with an amine of formula (IVa) or formula (IVb)

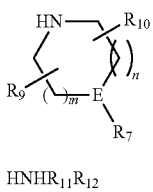
(IVa)

$HNHR_{11}R_{12}$ (IVb)

wherein $R_7$, $R_9$, $R_{10}$, $R_{11}$, $R_{12}$, m, n and E are as defined above, and if $R_{12}$ is $C_{1-4}$alkyleneNHR$_{13}$ then $R_{12}$ is protected by a suitable protecting group, such as BOC, FMOC Cbz or benzyl. In one embodiment V is C—$R_2$ wherein $R_2$ is as defined above.

In another embodiment the invention provides a process for preparing a compound of formula (XXIIa) or (XXIIb) comprising reacting a compound of formula XXIII)

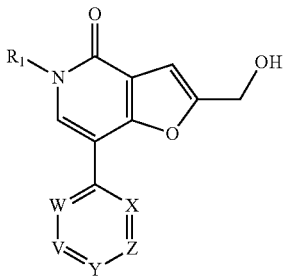
(XXIII)

wherein $R_1$, V, W, X, Y and Z are as defined above, under conditions suitable for halogenation. In one embodiment V is C—$R_2$ wherein $R_2$ is as defined above.

In another embodiment the invention provides a process for preparing a compound of formula (XXIII) comprising reacting a compound of formula (XXIV)

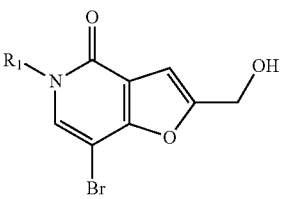
(XXIV)

wherein $R_1$ is as defined above, with a compound of formula (III)

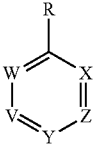
(III)

wherein V, W, X, Y and Z are as defined above and R is selected from B(OH)$_2$, BF$_3$K and

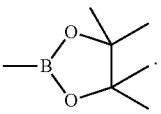

In one embodiment V is C—$R_2$ wherein $R_2$ is as defined above.

In another embodiment the invention provides a process for preparing a compound of formula (XXIV) comprising reacting a compound of formula (V)

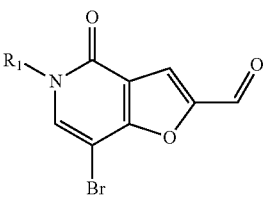
(V)

wherein $R_1$ is as defined above, with a suitable reducing agent.

Compounds of formulae (III), (IIIa), (IV), (VI), (VIII), (XIII), (XIV), (XV) and (XIX) are commercially available or can be readily synthesised by known methods, for example as reported by Suzuki in Chem. Rev., 1995, vol. 95, p 2457-2483.

It will be appreciated by those skilled in the art that it may be advantageous to protect one or more functional groups of the compounds described above. Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in 1,4-dioxane or trifluoroacetic acid in DCM) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above form a yet further aspect of the invention.

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. The compound of formula (I) or a pharmaceutically acceptable salt thereof can be used in the treatment of diseases or conditions for which a bromodomain inhibitor is indicated.

The present invention thus provides a compound of formula (I) or a pharmaceutically acceptable salt thereof for use in the treatment of any diseases or conditions for which a bromodomain inhibitor is indicated. In one embodiment there is provided a compound of formula (I) or a pharmaceutically acceptable salt thereof for use in the treatment of acute or chronic auto-immune and/or inflammatory conditions. In another embodiment there is provided a compound of formula (I) or a pharmaceutically acceptable salt thereof for use in the treatment of diseases or conditions which involve inflammatory responses to infections with bacteria, viruses, fungi, parasites or their toxins. In another embodiment there is provided a compound of formula (I) or a pharmaceutically acceptable salt thereof for use in the treatment of viral infections. In a further embodiment there is provided a compound of formula (I) or a pharmaceutically acceptable salt thereof for use in the treatment of cancer.

Also provided is the use of a compound of formula (I) or a pharmaceutically acceptable salt thereof in the manufacture of a medicament for the treatment of diseases or conditions for which a bromodomain inhibitor is indicated. In one embodiment there is provided the use of a compound of formula (I) or a pharmaceutically acceptable salt thereof in the manufacture of a medicament for the treatment of acute or chronic auto-immune and/or inflammatory conditions. In another embodiment there is provided the use of a compound of formula (I) or a pharmaceutically acceptable salt thereof in the manufacture of a medicament for the treatment of diseases or conditions which involve inflammatory responses to infections with bacteria, viruses, fungi, parasites or their toxins. In another embodiment there is provided the use of a compound of formula (I) or a pharmaceutically acceptable salt thereof in the manufacture of a medicament for the treatment of viral infections. In another embodiment there is provided the use of a compound of formula (I) or a pharmaceutically acceptable salt thereof in the manufacture of a medicament for the treatment of cancer.

Also provided is a method of treating diseases or conditions for which a bromodomain inhibitor is indicated in a subject in need thereof which comprises administering a therapeutically effective amount of compound of formula (I) or a pharmaceutically acceptable salt thereof. In one embodiment there is provided a method of treating acute or chronic auto-immune and/or inflammatory conditions in a subject in need thereof which comprises administering a therapeutically effective amount of a compound of formula (I) or a pharmaceutically acceptable salt thereof. In another embodiment there is provided a method of treating diseases or conditions which involve inflammatory responses to infections with bacteria, viruses, fungi, parasites or their toxins in a subject in need thereof which comprises administering a therapeutically effective amount of a compound of formula (I) or a pharmaceutically acceptable salt thereof. In another embodiment there is provided a method of treating viral infections in a subject in need thereof which comprises administering a therapeutically effective amount of a compound of formula (I) or a pharmaceutically acceptable salt thereof. In further embodiment there is provided a method of treating cancer in a subject in need thereof which comprises administering a therapeutically effective amount of a compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, or subject (e.g. a human) that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of acute or chronic autoimmune and/or inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis (including atopic dermatitis), alopecia, vitiligo, bullous skin diseases, nephritis, vasculitis, hypercholesterolemia, atherosclerosis, Alzheimer's disease, depression, Sjögren's syndrome, sialoadenitis, central retinal vein occlusion, branched retinal vein occlusion, Irvine-Gass syndrome (post cataract and post-surgical), retinitis pigmentosa, pars planitis, birdshot retinochoroidopathy, epiretinal membrane, cystic macular edema, parafoveal telengiectasis, tractional maculopathies, vitreomacular traction syndromes, retinal detachment, neuroretinitis, idiopathic macular edema, retinitis, dry eye (keratoconjunctivitis Sicca), vernal keratoconjunctivitis, atopic keratoconjunctivitis, uveitis (such as anterior uveitis, pan uveitis, posterior uveitis, uveitis-associated macular edema), scleritis, diabetic retinopathy, diabetic macula edema, age-related macular dystrophy, hepatitis, pancreatitis, primary biliary cirrhosis, sclerosing cholangitis, Addison's disease, hypophysitis, thyroiditis, type I diabetes, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, pyoderma gangrenosum, vasculitis with organ involvement and acute rejection of transplanted organs.

In one embodiment the acute or chronic autoimmune and/or inflammatory condition is a disorder of lipid metabolism via the regulation of APO-A1 such as hypercholesterolemia, atherosclerosis and Alzheimer's disease.

In another embodiment the acute or chronic autoimmune and/or inflammatory condition is a respiratory disorder such as asthma or chronic obstructive airways disease.

In another embodiment the acute or chronic autoimmune and/or inflammatory condition is a systemic inflammatory disorder such as rheumatoid arthritis, osteoarthritis, acute gout, psoriasis, systemic lupus erythematosus, multiple sclerosis or inflammatory bowel disease (Crohn's disease and Ulcerative colitis).

In another embodiment the acute or chronic autoimmune and/or inflammatory condition is multiple sclerosis.

In a further embodiment the acute or chronic autoimmune and/or inflammatory condition is Type I diabetes.

Bromodomain inhibitors may be useful in the treatment of diseases or conditions which involve inflammatory responses to infections with bacteria, viruses, fungi, parasites or their toxins, such as sepsis, acute sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus. In one embodiment the disease or condition which involves an inflammatory response to an infection with bacteria, a virus, fungi, a parasite or their toxins is acute sepsis.

Bromodomain inhibitors may be useful in the treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of fibrotic conditions such as idiopathic pulmonary fibrosis, renal fibrosis, post-operative stricture, keloid scar formation, scleroderma (including morphea) and cardiac fibrosis.

Bromodomain inhibitors may be useful in the treatment of viral infections such as herpes simplex infections and reactivations, cold sores, herpes zoster infections and reactivations, chickenpox, shingles, human papilloma virus (HPV), human immunodeficiency virus (HIV), cervical neoplasia, adenovirus infections, including acute respiratory disease, poxvirus infections such as cowpox and smallpox and African swine fever virus. In one embodiment the viral infection is a HPV infection of skin or cervical epithelia. In another embodiment the viral infection is a latent HIV infection.

Bromodomain inhibitors may be useful in the treatment of cancer, including hematological (such as leukaemia, lymphoma and multiple myeloma), epithelial including lung, breast and colon carcinomas, midline carcinomas, mesenchymal, hepatic, renal and neurological tumours.

Bromodomain inhibitors may be useful in the treatment of one or more cancers selected from brain cancer (gliomas), glioblastomas, Bannayan-Zonana syndrome, Cowden disease, Lhermitte-Duclos disease, breast cancer, inflammatory breast cancer, colorectal cancer, Wilm's tumor, Ewing's sarcoma, rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma, megakaryoblastic leukemia, acute megakaryocytic leukemia, promyelocytic leukemia, mixed lineage leukaemia, erythroleukemia, malignant lymphoma, Hodgkins lymphoma, non-Hodgkins lymphoma, lymphoblastic T-cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), NUT-midline carcinoma and testicular cancer.

In one embodiment the cancer is a leukaemia, for example a leukaemia selected from acute monocytic leukemia, acute myelogenous leukemia, chronic myelogenous leukemia, chronic lymphocytic leukemia and mixed lineage leukaemia (MLL). In another embodiment the cancer is NUT-midline carcinoma. In another embodiment the cancer is multiple myeloma. In another embodiment the cancer is a lung cancer such as small cell lung cancer (SCLC). In another embodiment the cancer is a neuroblastoma. In another embodiment the cancer is Burkitt's lymphoma. In another embodiment the cancer is cervical cancer. In another embodiment the cancer is esophageal cancer. In another embodiment the cancer is ovarian cancer. In another embodiment the cancer is breast cancer. In another embodiment the cancer is colarectal cancer.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac or gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock and endotoxaemia. In another embodiment, the bromodomain inhibitor is indicated for the treatment of acute or chronic pancreatitis. In another embodiment the bromodomain is indicated for the treatment of burns.

As used herein the reference to the "treatment" of a particular disease or condition includes the prevention or prophylaxis of such a disease or condition.

The term "diseases or conditions for which a bromodomain inhibitor is indicated", is intended to include each of or all of the above diseases or conditions.

The invention further provides for a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents or excipients. The compounds of formula (I) and pharmaceutically acceptable salts are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be used in the treatment of any of the conditions described herein.

Since the compounds of formula (I) are intended for use in pharmaceutical compositions it will be readily understood that they are each preferably provided in substantially pure form, for example, at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), ocular (including topical, intraocular, subconjunctival, episcleral, sub-Tenon), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

In one embodiment the pharmaceutical composition is adapted for topical administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as EtOH, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Compositions for oral administration may be designed to provide a modified release profile so as to sustain or otherwise control the release of the therapeutically active agent.

Where appropriate, dosage unit compositions for oral administration can be microencapsulated. The composition may be prepared to prolong or sustain the release as for example by coating or embedding particulate material in polymers, wax or the like.

The compounds of formula (I) and pharmaceutically acceptable salts thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, emulsions, lotions, powders, solutions, pastes, gels, foams, sprays, aerosols or oils. Such pharmaceutical compositions may include conventional additives which include, but are not limited to, preservatives, solvents to assist drug penetration, co-solvents, emollients, propellants, viscosity modifying agents (gelling agents), surfactants and carriers. In one embodiment there is provided a pharmaceutical composition adapted for topical administration which comprises between 0.01-10%, or between 0.01-1% of the compound of formula (I), or a pharmaceutically acceptable salt thereof, by weight of the composition.

For treatments of the eye or other external tissues, for example mouth and skin, the compositions are preferably applied as a topical ointment, cream, gel, spray or foam. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent. Compositions to be administered to the eye will have ophthalmically compatible pH and osmolality. One or more ophthalmically acceptable pH adjusting agents and/or buffering agents can be included in a composition of the invention, including acids such as acetic, boric, citric, lactic, phosphoric and hydrochloric acids; bases such as sodium hydroxide, sodium phosphate, sodium borate, sodium citrate, sodium acetate, and sodium lactate; and buffers such as citrate/dextrose, sodium bicarbonate and ammonium chloride. Such acids, bases, and buffers can be included in an amount required to maintain pH of the composition in an ophthalmically acceptable range. One or more ophthalmically acceptable salts can be included in the composition in an amount sufficient to bring osmolality of the composition into an ophthalmically acceptable range. Such salts include those having sodium, potassium or ammonium cations and chloride, citrate, ascorbate, borate, phosphate, bicarbonate, sulfate, thiosulfate or bisulfite anions.

The ocular delivery device may be designed for the controlled release of one or more therapeutic agents with multiple defined release rates and sustained dose kinetics and permeability. Controlled release may be obtained through the design of polymeric matrices incorporating different choices and properties of biodegradable/bioerodable polymers (e.g. poly(ethylene vinyl) acetate (EVA), superhydrolyzed PVA), hydroxyalkyl cellulose (HPC), methylcellulose (MC), hydroxypropyl methyl cellulose (HPMC), polycaprolactone, poly(glycolic) acid, poly(lactic) acid, polyanhydride, of polymer molecular weights, polymer crystallinity, copolymer ratios, processing conditions, surface finish, geometry, excipient addition and polymeric coatings that will enhance drug diffusion, erosion, dissolution and osmosis.

Pharmaceutical compositions for ocular delivery also include in situ gellable aqueous composition. Such a composition comprises a gelling agent in a concentration effective to promote gelling upon contact with the eye or with lacrimal fluid. Suitable gelling agents include but are not limited to thermosetting polymers. The term "in situ gellable" as used herein is includes not only liquids of low viscosity that form gels upon contact with the eye or with lacrimal fluid, but also includes more viscous liquids such as semi-fluid and thixotropic gels that exhibit substantially increased viscosity or gel stiffness upon administration to the eye. See, for example, Ludwig (2005) *Adv. Drug Deliv. Rev.* 3; 57:1595-639, herein incorporated by reference for purposes of its teachings of examples of polymers for use in ocular drug delivery.

Dosage forms for nasal or inhaled administration may conveniently be formulated as aerosols, solutions, suspensions, gels or dry powders.

For compositions suitable and/or adapted for inhaled administration, it is preferred that the compound of formula (I) or a pharmaceutically acceptable salt thereof, is in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as EtOH.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metal salt of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof, will depend upon a number of factors including, for example, the age and weight of the subject, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of formula (I) or a pharmaceutically acceptable salt thereof, calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) and pharmaceutically acceptable salts thereof, can be administered in a daily dose (for an adult patient) of, for example, an oral or parenteral dose of 0.01 mg to 3000 mg per day, 0.5 to 1000 mg per day or 100 mg to 2500 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other therapeutically active agent. Preferably, combination therapies according to the present invention comprise the administration of at least one compound of formula (I) or a pharmaceutically acceptable salt thereof, and at least one other therapeutically active agent. The compound(s) of formula (I) and pharmaceutically acceptable salts thereof, and the other therapeutically active agent(s) may be administered together in a single pharmaceutical composition or separately and, when administered separately this may occur simultaneously or sequentially in any order. The amounts of the compound(s) of formula (I) and pharmaceutically acceptable salts thereof, and the other therapeutically active agent(s) and the relative timings of administration will be selected in order to achieve the desired combined therapeutic effect. Thus in a further aspect, there is provided a combination comprising a compound of formula (I) or a pharmaceutically acceptable salt thereof, together with one or more other therapeutically active agents.

Thus in one aspect, the compound of formula (I) or a pharmaceutically acceptable salt thereof, and pharmaceutical compositions comprising a compound of formula (I) or a pharmaceutically acceptable salt thereof, according to the invention may be used in combination with or include one or more other therapeutic agents, for example selected from antibiotics, anti-virals, glucocorticosteroids, muscarinic antagonists beta-2 agonists and Vitamin D3 analogues. In a further embodiment a compound of formula (I) or a pharmaceutically acceptable salt thereof may be used in combination with a further therapeutic agent which is suitable for the treatment of cancer. Examples of such further therapeutic agents are desfibed in Cancer Principles and Practice of Oncology by V. T. Devita and S. Hellman (editors), 6$^{th}$ edition (2001), Lippincott Williams & Wilkins Publishers. A person of ordinary skill in the art would be able to discern which combinations of agents would be useful based on the particular characteristics of the drugs and the cancer involved. Further therapeutic agents to be used in combination with the compound of formula (I) or a pharmaceutically acceptable salt thereof include, but are not limited to, anti-microtubule agents (such as diterpenoids and vinca alkaloids); platinum coordination complexes; alkylating agents (such as nitrogen mustards, oxazaphosphorines, alkylsulphonates, nitrosoureas, and triazenes); antibiotic agents (such as anthracyclins, actinomycins and bleomycins); topoisomerase II inhibitors (such as epipodophyllotoxins); antimetabolites (such as purine and pyrimidine analogues and anti-folate compounds); topoisomerase I inhibitors (such as camptothecins; hormones and hormonal analogues); signal transduction pathway inhibitors (such as tyropsine receptor inhibitors); non-receptor tyrosine kinase angiogenesis inhibitors; immunotherapeutic agents; proapoptotic agents; epigenetic or transcriptional modulators (such as histone deacetylase inhibitors) and cell cycle signaling inhibitors.

It will be appreciated that when the compound of formula (I) or a pharmaceutically acceptable salt thereof, is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof, may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

General Experimental Details

All temperatures referred to are in ° C.

The names of the following compounds have been obtained using the compound naming programme "ACD Name Pro 6.02" or ChemDraw Ultra 12.0.

Abbreviations
AcOH acetic acid
ACN acetonitrile
BINAP 2,2'-bis(diphenylphosphino)-1,1'-binaphthyl
$BBr_3$ boron tribromide
BOC tert-butyloxycarbonyl
BrettPhos 2-(dicyclohexylphosphino)-3,6-dimethoxy-2'-4'-6'-tri-i-propyl-1,1'-biphenyl
BuLi butyllithium
tBuOH tert-butanol
$CaCO_3$ calcium carbonate
Cbz carbobenzyloxy
$CDCl_3$ deuterochloroform
Comin's reagent N-(5-chloropyridin-2-yl)-1,1,1-trifluoro-N-((trifluoromethyl)sulfonyl) methanesulfonamide
$Cs_2CO_3$ cesium carbonate
$CHCl_3$ chloroform
$CH_3CN$ acetonitrile
CV column volume
DavePhos 2-dicyclohexylphosphino-2'-(dimethylamino)biphenyl
DCE 1,2-dichloroethane
DCM dichloromethane
DIAD diisopropyl azodicarboxylate
DIPEA diisopropylethylamine
DMAP 4-dimethylaminopyridine
1,2-DME 1, 2-dimethoxyethane
DMF N,N-dimethylformamide
DMSO dimethylsulfoxide
DMSO-d6 deuterated dimethylsulfoxide
DPPA diphenylphosphoryl azide
$Et_3N$ triethylamine
$Et_2O$ diethylether
EtOH ethanol
EtOAc ethyl acetate
FMOC fluorenylmethyloxycarbonyl
h hour(s)
HATU O-(7-azabenzotriazol-1-yl)-N,N,N',N'-tetramethyluronium hexafluorophosphate
HCl hydrochloric acid
$HCO_2H$ formic acid
HOAt 1-hydroxy-7-azabenzotriazole
HOBt 1-hydroxybenzotriazole
HPLC high performance liquid chromatography
i-PrOAc isopropylacetate
i-$Pr_2O$ diisopropyl ether
i-PrOH isopropyl alcohol
$K_2CO_3$ potassium carbonate
KOH potassium hydroxide
LCMS liquid chromatography-mass spectrometry
LDA lithium diisopropylamide
LiCl lithium chloride
LiOH lithium hydroxide
M molar (concentration)
mCPBA meta-chloroperoxybenzoic acid
MeCN acetonitrile
MeI methyl iodide
MeOH-$d_4$ deuterated methanol
MeOH methanol
2-MeTHF 2-methyltetrahydrofuran
MDAP mass directed autopreparative chromatography
$MgSO_4$ magnesium sulfate
min minute(s)
MS mass spectrometry
N normal (concentration)
$N_2$ nitrogen
$Na_2CO_3$ sodium carbonate
NaI sodium iodide
NaH sodium hydride
$NaHCO_3$ sodium hydrogen carbonate
$NaNO_2$ sodium nitrite
Na(OAc)$_3$BH sodium triacetoxy borohydride
NaO$^t$Bu sodium tert-butoxide
NaOH sodium hydroxide
$Na_2SO_4$ sodium sulphate
NBS N-bromosuccinimide
$NEt_3$ triethylamine
$NH_3$ ammonia
NMP N-methyl-2-pyrrolidone
NMR nuclear magnetic resonance
OTf trifluoromethanesulfonate
PEPPSI pyridine-enhanced precatalyst preparation stabilization and initiation
Pd/C palladium on carbon
$PdCl_2(PPh_3)_2$ bis(triphenylphosphine)palladium(II) dichloride
$PdCl_2$(dppf) [1,1'-bis(diphenylphosphino)ferrocene]palladium(II) dichloride
$Pd_2(dba)_3$ tris(dibenzylideneacetone)dipalladium(0)
$Pd(PPh_3)_4$ tetrakis(triphenylphosphine)palladium(0)
P(OPh)$_2$(O)OH diphenyl phosphoric acid
$PPh_3$ triphenylphosphine
ppm parts per million
Rh cat. rhodium catalyst
Rt retention time
rt room temperature
SCX strong cation exchange
SPE solid phase extraction
TBAF tetra-n-butylammonium fluoride
TBME tert-butyl methyl ether
$Tf_2O$ trifluoromethanesulfonic anhydride TFA trifluoroacetic acid
THF tetrahydrofuran
TMSCl trimethylsilyl chloride
TPPTS 3,3',3''-phosphinidynetris(benzenesulfonic acid) trisodium salt
UPLC ultra performance liquid chromatograpy
Xantphos 1,1'-(9,9-dimethyl-9H-xanthene-4,5-diyl)bis[1,1-diphenylphosphine]
LCMS Methodology
Formic Method
LC Conditions The UPLC analysis was conducted on an Acquity UPLC BEH C18 column (50 mm×2.1 mm, i.d. 1.7 µm packing diameter) at 40° C.
The solvents employed were:
A=0.1% v/v solution of formic acid in water
B=0.1% v/v solution of formic acid in acetonitrile
The gradient employed was:

| Time (min) | Flow rate (mL/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
Formic Method (2.5 minute run)

The LCMS analysis was conducted on an Agilent 1200-6110 LCMS, Halo-C18 column (4.6 mm×50 mm, 2.7 µm packing diameter) at 40° C.
The solvents employed were:
A=0.05% v/v solution of formic acid in water
B=0.05% v/v solution of formic acid in acetonitrile
The gradient employed was: total time is 2.5 min

| Time (min) | Flow rate (mL/min) | % A | % B |
|---|---|---|---|
| 0 | 1.8 | 95 | 5 |
| 1.0 | 1.8 | 5 | 95 |
| 2.0 | 1.8 | 5 | 95 |
| 2.1 | 1.8 | 95 | 5 |

The UV detection was a summed signal from wavelength of 214 nm and 254 nm.
MS Conditions
MSAgilent: 1200-6120 LCMS
Ionisation mode: ESI positive and negative Scan Range 100 to 1000 AMU
Drying Gas Flow (L/Min): 12
Nebulizer Pressure (psig): 35
Drying Gas Temperature (° C.): 350
Capillary Voltage (v): 3000
High pH Method
LC Conditions The UPLC analysis was conducted on an Acquity UPLC BEH C18 column (50 mm×2.1 mm, i.d. 1.7 µm packing diameter) at 40° C.

The solvents employed were:
A=10 mM ammonium hydrogen carbonate in water adjusted to pH10 with ammonia solution
B=acetonitrile
The gradient employed was:

| Time (min) | Flow rate (mL/min) | % A | % B |
|---|---|---|---|
| 0 | 1 | 99 | 1 |
| 1.5 | 1 | 3 | 97 |
| 1.9 | 1 | 3 | 97 |
| 2.0 | 1 | 0 | 100 |

The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.27 sec
Inter scan delay: 0.10 sec
NMR
Spectra were run on a 400 or 600 MHz NMR machine at either 302 K or for VT spectra at 392-393 K.

Intermediate 1

7-bromo-4-oxo-4,5-dihydrofuro[3,2-c]pyridine-2-carbaldehyde

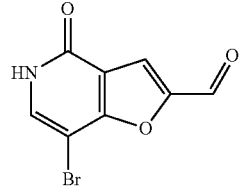 [SMILES: O=Cc1cc2c(=O)[nH]cc(Br)c2o1]

N-Bromosuccinimide (3.93 g, 22.07 mmol) was added portionwise to a stirred suspension of 4-oxo-4,5-dihydrofuro[3,2-c]pyridine-2-carbaldehyde (3.0 g, 18.4 mmol) in dry tetrahydrofuran (50 mL). The reaction mixture was stirred at room temperature for 6 hours. The solvent was evaporated and the residue was triturated with diethyl ether. The solid was filtered off, washed with diethyl ether and dried to give 7-bromo-4-oxo-4,5-dihydrofuro[3,2-c]pyridine-2-carbaldehyde (3.96 g, 16.36 mmol, 89% yield) as a brown solid. LCMS (2 min, Formic): Rt=0.57 min, MH+ 242/244

Intermediate 2

7-bromo-5-methyl-4-oxo-4,5-dihydrofuro[3,2-c]pyridine-2-carbaldehyde

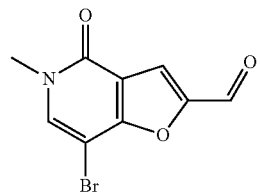

Iodomethane (4.63 g, 2.04 mL, 32.6 mmol) was added to a stirred suspension of 7-bromo-4-oxo-4,5-dihydrofuro[3,2-c]pyridine-2-carbaldehyde (for a preparation see Intermediate 1, 3.95 g, 16.32 mmol) and cesium carbonate (15.95 g, 49.0 mmol) in dry tetrahydrofuran (100 mL). The reaction mixture was stirred at room temperature overnight. A further portion of iodomethane (4.63 g, 2.04 mL, 32.6 mmol) was added. The reaction mixture was stirred at room temperature for a further 4 hours. The solvent was evaporated. The residue was suspended in water (100 mL) and stirred for 30 minutes. The solid was filtered off, washed thoroughly with water and dried to give 7-bromo-5-methyl-4-oxo-4,5-dihydrofuro[3,2-c]pyridine-2-carbaldehyde (4.00 g, 15.62 mmol, 96% yield) as a yellow solid. LCMS (2 min, Formic): Rt=0.63 min, MH+ 256/258

Intermediate 3

7-bromo-5-methyl-2-((4-(methylsulfonyl)piperazin-1-yl)methyl)furo[3,2-c]pyridin-4(5H)-one

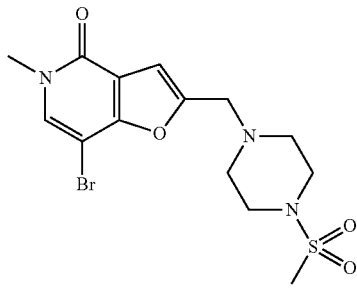 [SMILES: Cn1cc(Br)c2oc(CN3CCN(S(C)(=O)=O)CC3)cc2c1=O]

1-(Methylsulfonyl)piperazine (242.09 mg, 1.474 mmol) was added to a stirred solution of 7-bromo-5-methyl-4-oxo-4,5-dihydrofuro[3,2-c]pyridine-2-carbaldehyde (for a preparation see Intermediate 2, 251.54 mg, 0.982 mmol) in MeOH (9 mL) and acetic acid (1 mL). The mixture was stirred at room temperature for 1 h then 2-picoline borane complex (115.43 mg, 1.079 mmol) was added. The reaction mixture was stirred at room temperature for 2 hours. The solvent was evaporated. Saturated sodium bicarbonate solution (20 mL) was added slowly—gas evolved. The mixture was extracted with DCM (3×20 mL). The combined organics were dried using sodium sulphate and the solvent evaporated. The crude material was purified by silica gel chromatography using a 0-6% MeOH in DCM gradient. Appropriate fractions were combined and evaporated to give 7-bromo-5-methyl-2-((4-(methylsulfonyl)piperazin-1-yl)methyl)furo[3,2-c]pyridin-4(5H)-one (284 mg, 0.702 mmol, 71.5% yield) as a yellow oil. LCMS (2 min, Formic): Rt=0.50 min, MH+ 404/406

Intermediate 4

(R)-3-methyl-1-(methylsulfonyl)piperazine

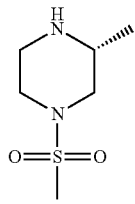

A solution of methanesulfonyl chloride (6 g, 52.4 mmol) in THF (50 mL) was added, over 2 min, to a solution of (R)-2-methylpiperazine (5 g, 49.9 mmol) in NaOH (2M) (50 mL) and THF (50 mL) at 0° C. The reaction mixture was stirred at 0° C. for 1 hour, then left to warm to room temperature overnight and poured onto 2M hydrochloric acid (100 mL). The mixture was washed with ethyl acetate (3×50 mL). The aqueous phase was separated and basified (pH=12) by the addition of solid sodium hydroxide. The mixture was extracted with DCM (2×100 mL). The combined extracts were dried and evaporated to give (R)-3-methyl-1-(methylsulfonyl)piperazine (1.781 g, 9.99 mmol, 20.02% yield) as a white solid.

$^1$H NMR (400 MHz, DMSO-d6) δ-ppm 3.32 (m, 2H), 2.9 (m, 1H), 2.83 (s, 3H), 2.7-2.54 (m, 3H), 2.3 (broad s, 1H), 2.2 (t, 1H), 0.97 (d, 3H)

Intermediate 4a (R)-tert-butyl 2-methyl-4-(methylsulfonyl)piperazine-1-carboxylate

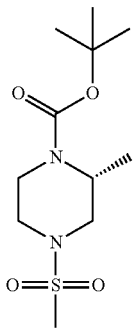 [SMILES: C[C@@H]1CN(S(C)(=O)=O)CCN1C(=O)OC(C)(C)C]

(R)-Tert-butyl 2-methylpiperazine-1-carboxylate (49 g, 245 mmol) was taken up in THF (150 mL) and 2M NaOH (220 mL, 440 mmol) and cooled in an ice bath. The reaction was stirred vigorously as methanesulfonyl chloride (20.97 mL, 269 mmol) in THF (150 mL) was slowly added. The reaction was left to stir overnight. Additional methanesulfonyl chloride (2 mL) was added and the reaction stirred for 4 h. The reaction mixture was poured into 2N HCl (400 mL) and ice (~200 mL) and extracted with EtOAc (2×500 mL). The combined organics were washed with 2N NaOH (400 mL) and brine (500 mL) then dried with Na$_2$SO$_4$, filtered and concentrated in vacuo to give (R)-tert-butyl 2-methyl-4-(methylsulfonyl)piperazine-1-carboxylate (62.673 g, 214 mmol, 87% yield) as a white solid. $^1$H NMR (400 MHz, DMSO-d6) δ-ppm 4.27 (m, 1H), 3.84 (m, 1H), 3.48 (m, 1H), 3.31 (m, 1H), 3.03 (m, 1H), 3.86 (s, 3H), 2.84 (m, 1H), 2.67 (m, 1H), 1.41 (s, 9H), 1.13 (d, 3H).

Intermediate 4b (R)-3-methyl-1-(methylsulfonyl)piperazine hydrochloride

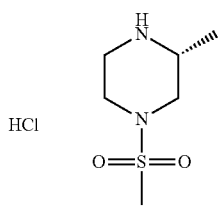

(R)-Tert-butyl 2-methyl-4-(methylsulfonyl)piperazine-1-carboxylate (for a preparation see Intermediate 4a, 58.506 g, 210 mmol) was taken up in DCM and cooled in an ice-bath. HCl (400 mL, 1600 mmol) was added and the reaction left to warm and stir at room temperature over the weekend. A thick precipitate formed. The reaction mixture was concentrated in vacuo and the residue azeotroped with $Et_2O$ to give (R)-3-methyl-1-(methylsulfonyl)piperazine, hydrochloride (49.835 g) as a white solid. $^1$H NMR (400 MHz, DMSO-d6) δ-ppm 9.18 (br. s, 2H), 3.63 (m, 2H), 3.38 (m, 2H), 3.08 (m, 2H), 3.00 (s, 3H), 2.87 (m, 1H), 1.26 (d, 3H).

Intermediate 5

(R)-7-bromo-5-methyl-2-((2-methyl-4-(methylsulfonyl)piperazin-1-yl)methyl)furo[3,2-c]pyridin-4(5H)-one

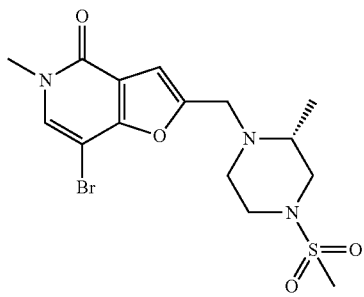 [SMILES: C[C@@H]1CN(S(C)(=O)=O)CCN1Cc1cc2c(=O)n(C)cc(Br)c2o1]

(R)-3-Methyl-1-(methylsulfonyl)piperazine (for a preparation see Intermediate 4, 522 mg, 2.93 mmol) was added to a suspension 7-bromo-5-methyl-4-oxo-4,5-dihydrofuro[3,2-c]pyridine-2-carbaldehyde (for a preparation see Intermediate 2, 500 mg, 1.953 mmol) in methanol (18 mL) and acetic acid (2 mL) and stirred for 15 min at room temperature. 2-Picoline borane complex (1.592 g, 14.88 mmol) was added and the mixture was left stirring at room temperature overnight. Further portions of 2-picoline borane complex (104 mg, 0.977 mmol) and (R)-3-methyl-1-(methylsulfonyl) piperazine (70 mg 0.393 mmol) were added and the reaction was stirred for 2 days. The solvent was evaporated and sodium bicarbonate was added (20 mL). The aqueous was extracted with DCM (3×15 mL), filtered through a hydrophobic frit and concentrated in vacuo. The residue was purified by chromatography on silica gel eluting with a 2-4% MeOH in DCM gradient. Appropriate fractions were concentrated in vacuo to give (R)-7-bromo-5-methyl-2-((2-methyl-4-(methylsulfonyl)piperazin-1-yl)methyl)furo[3,2-c]pyridin-4(5H)-one (416 mg, 0.994 mmol, 50.9% yield) as a white solid.

LCMS (2 min, Formic): Rt=0.53 min, MH$^+$ 418/420

Alternative Preparation

7-Bromo-5-methyl-4-oxo-4,5-dihydrofuro[3,2-c]pyridine-2-carbaldehyde (for a preparation see Intermediate 2, 45 g, 176 mmol) and (R)-3-methyl-1-(methylsulfonyl)piperazine, hydrochloride (for a preparation see Intermediate 4b, 71.7 g, 334 mmol) were suspended in 2-MeTHF (2192 mL) under nitrogen. $Et_3N$ (61.2 mL, 439 mmol) was added and the mixture stirred for 10 min. Sodium triacetoxyborohydride (74.5 g, 351 mmol) was added portion-wise over ~10 min and the mixture stirred at room temperature. After 2 h the reaction was concentrated in vacuo. The residue was carefully quenched with sat. $NaHCO_3$ (1000 mL) and then extracted with DCM (2×1000 mL). The combined organics were dried with $Na_2SO_4$, filtered and concentrated in vacuo to yield an orange solid. This was combined with a batch of crude product from a 5 g scale reaction for purification. An attempt to take the combined product up in the minimum of DCM failed as there was some insoluble material so the mixture was filtered. The filtrate was concentrated to ~200 mL DCM which was loaded onto a 1500 g SNAP cartridge and eluted with 0% 2M $NH_3$ in methanol in DCM for 1.6 CV then 0-5% 2M $NH_3$ in methanol over 10.6 CV then held at 5% for 3 CV; 15 mA threshold collection; 400 mL fractions. The appropriate fractions were concentrated in vacuo to give a cream solid. Mixed fractions were combined and concentrated in vacuo then re-columned using a 340 g SNAP cartridge and the same conditions; 51 mL fractions. The appropriate fractions were concentrated in vacuo to give a cream solid. The two batches were combined in the minimum of DCM and concentrated in vacuo to give (R)-7-bromo-5-methyl-2-((2-methyl-4-(methylsulfonyl)piperazin-1-yl)methyl)furo[3,2-c]pyridin-4(5H)-one (64.055 g)) as a cream solid. $^1$H NMR (400 MHz, $CDCl_3$) δ-ppm 7.37 (1H, s), 6.88 (1H, s), 3.92 (2H, AB d), 3.63 (3H, s), 3.53 (2H, m), 2.97 (2H, m), 2.78 (3H, s), 2.64 (3H, m), 1.26 (3H, d). LCMS (2 min, High pH): Rt=0.77 min, MH$^+$ 418/420.

Intermediate 5a (R)-5-methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one

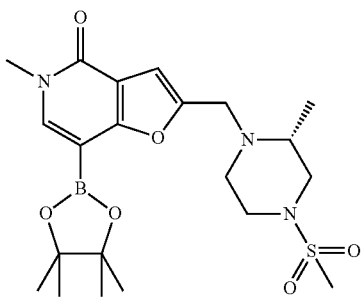 [SMILES: C[C@@H]1CN(S(C)(=O)=O)CCN1Cc1cc2c(=O)n(C)cc(B3OC(C)(C)C(C)(C)O3)c2o1]

A solution of (R)-7-bromo-5-methyl-2-((2-methyl-4-(methylsulfonyl)piperazin-1-yl)methyl)furo[3,2-c]pyridin-4(5H)-one (for a preparation see Intermediate 5, 30 g, 71.7 mmol) in 1,4-dioxane (100 mL) was treated with triethylamine (60.1 mL, 430 mmol), 4,4,5,5-tetramethyl-1,3,2-dioxaborolane (62.4 mL, 430 mmol) then Pd(PPh$_3$)$_4$(8.29 g, 7.17 mmol) and the mixture was flushed with nitrogen, then heated at 100° C. for 18 h The mixture was cooled in an ice bath and quenched with i-PrOH (30 mL), which was added very cautiously, dropwise, due to vigorous effervescence on addition. The resulting suspension was transferred to a round bottomed flask and evaporated. i-PrOH (100 mL) was added, giving a clear, brown solution, which on stirring for 30 min, gave a dense, beige precipitate. This was collected by filtration and washed with isopropanol (30 mL) then dried in the vacuum oven to give The product was suspended in i-PrOH (100 mL) and stirred for 30 min, then filtered and the solid was washed with i-PrOH to give (R)-5-methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one (32 g, 68.8 mmol, 96% yield) as a grey solid. $^1$H NMR (400 MHz, CDCl$_3$) δ-ppm 7.67 (1H, s), 6.77 (1H, s), 3.94 (2H, AB d), 3.65 (3H, s), 3.54 (2H, m), 2.95 (2H, m), 2.78 (3H, s), 2.66 (3H, m), 1.38 (12H, s), 1.29 (3H, d). Used in the next step without further purification.
Alternative Preparation Nitrogen was bubbled through a mixture of (R)-7-bromo-5-methyl-2-((2-methyl-4-(methylsulfonyl)piperazin-1-yl)methyl)furo[3,2-c]pyridin-4(5H)-one (for a preparation see Intermediate 5, 230 mg, 0.550 mmol), triethylamine (0.307 mL, 2.199 mmol) and PEPPSI-IPr (37.5 mg, 0.055 mmol) in 1,4-dioxane (3 mL) for 2 min. 4,4,5,5-tetramethyl-1,3,2-dioxaborolane (0.479 mL, 3.30 mmol) was added dropwise and nitrogen was bubbled through the solution which was then heated to 100° C. for 3 h in the microwave. The reaction mixture was diluted with ethyl acetate and filtered through Celite, then concentrated in vacuo to leave a yellow semi solid (522 mg, 234%).

LCMS showed presence of (R)-5-methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one (4%), Rt=0.70 min, MH$^+$ 466; (R)-(5-methyl-2-((2-methyl-4-(methylsulfonyl)piperazin-1-yl)methyl)-4-oxo-4,5-dihydrofuro[3,2-c]pyridin-7-yl)boronic acid (36%), Rt=0.38 min, MH$^+$ 384; and (R)-5-methyl-2-((2-methyl-4-(methylsulfonyl)piperazin-1-yl)methyl)furo[3,2-c]pyridin-4(5H)-one (50%), Rt=0.40 min, MH$^+$ 340. Conversion to desired intermediates assumed to be 40% (36% boronic acid+4% boronate ester). Theoretical maximum yield 223 mg therefore material used crude in next step assuming 17% purity w/w.

Intermediate 6 tert-butyl (2-(((7-bromo-5-methyl-4-oxo-4,5-dihydrofuro[3,2-c]pyridin-2-yl)methyl)amino)ethyl)carbamate

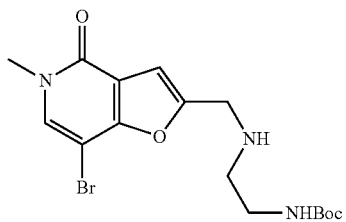 [SMILES: Cn1cc(Br)c2oc(CNCCNC(=O)OC(C)(C)C)cc2c1=O]

tert-Butyl (2-aminoethyl)carbamate hydrochloride (115 mg, 0.586 mmol) was added to a solution of 7-bromo-5-methyl-4-oxo-4,5-dihydrofuro[3,2-c]pyridine-2-carbaldehyde (for a preparation see Intermediate 2, 100 mg, 0.391 mmol) in MeOH (7 mL) and acetic acid (0.778 mL). The mixture was stirred at room temperature for 15 minutes then 2-picoline borane complex (46.4 mg, 0.434 mmol) was added and the mixture was stirred for 2 hours. The solvent was evaporated and saturated sodium bicarbonate solution (15 mL) was added. The mixture was extracted with DCM (3×15 mL) and the combined organics were dried and evaporated. The residue was purified by chromatography on silica gel eluting with a 0-5% MeOH/DCM gradient to give tert-butyl (2-(((7-bromo-5-methyl-4-oxo-4,5-dihydrofuro[3,2-c]pyridin-2-yl)methyl)amino)ethyl)carbamate (38 mg, 0.095 mmol, 24.31% yield). LCMS (2 min, Formic): Rt=0.59 min, MH$^+$ 400/402

Intermediate 7 tert-butyl (2-(((7-(3,4-dimethoxyphenyl)-5-methyl-4-oxo-4,5-dihydrofuro[3,2-c]pyridin-2-yl)methyl)amino)ethyl)carbamate

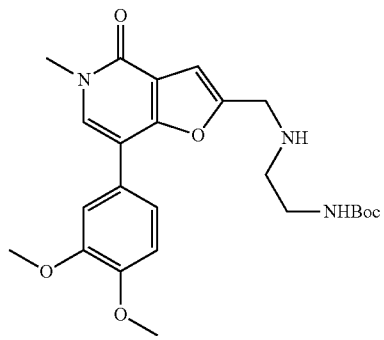 [SMILES: COc1ccc(-c2cn(C)c(=O)c3cc(CNCCNC(=O)OC(C)(C)C)oc23)cc1OC]

A mixture of tert-butyl (2-(((7-bromo-5-methyl-4-oxo-4,5-dihydrofuro[3,2-c]pyridin-2-yl)methyl)amino)ethyl)carbamate (for a preparation see Intermediate 6, 34 mg, 0.085 mmol), (3,4-dimethoxyphenyl)boronic acid (22.85 mg, 0.126 mmol), potassium carbonate (58.7 mg, 0.425 mmol) and bis(triphenylphosphine)palladium(II) chloride (5.96 mg, 8.49 μmol) in EtOH (2 mL) and toluene (2 mL) was heated in a microwave at 100° C. for 1 hour. The mixture was diluted with ethyl acetate, filtered and concentrated in vacuo. The residue was purified by MDAP. Fractions containing product were combined and concentrated in vacuo to give tert-butyl (2-(((7-(3,4-dimethoxyphenyl)-5-methyl-4-oxo-4,5-dihydrofuro[3,2-c]pyridin-2-yl)methyl)amino)ethyl)carbamate (25 mg, 0.055 mmol, 64.3% yield) as a colourless gum. LCMS (2 min, Formic): Rt=0.69 min, MH$^+$ 458

Intermediate 8 tert-butyl 4-(5-methyl-2-((4-(methylsulfonyl)piperazin-1-yl)methyl)-4-oxo-4,5-dihydrofuro[3,2-c]pyridin-7-yl)benzylcarbamate

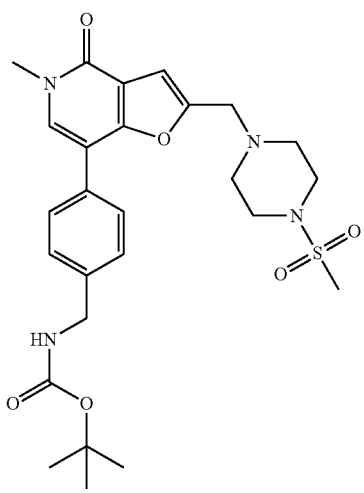 [SMILES: Cn1cc(-c2ccc(CNC(=O)OC(C)(C)C)cc2)c2oc(CN3CCN(S(C)(=O)=O)CC3)cc2c1=O]

A mixture of 7-bromo-5-methyl-2-((4-(methylsulfonyl)piperazin-1-yl)methyl)furo[3,2-c]pyridin-4(5H)-one (for a preparation see Intermediate 3, 280 mg, 0.693 mmol), (4-(((tert-butoxycarbonyl)amino)methyl)phenyl)boronic acid (257 mg, 1.024 mmol), potassium carbonate (479 mg, 3.46 mmol) and bis(triphenylphosphine)palladium(II) chloride (23.33 mg, 0.033 mmol) in toluene (2 mL) and EtOH (2 mL) was heated in a microwave at 80° C. for 20 minutes. The cooled reaction mixture was diluted with ethyl acetate (50 mL), dried with Na$_2$SO$_4$, filtered and evaporated in vacuo to give a brown oil. The residue was purified by chromatography on silica gel eluting with a 0-4% MeOH in DCM gradient. Appropriate fractions were combined and evaporated in vacuo to give tert-butyl 4-(5-methyl-2-((4-(methylsulfonyl)piperazin-1-yl)methyl)-4-oxo-4,5-dihydrofuro[3,2-c]pyridin-7-yl)benzylcarbamate (160.54 mg, 0.303 mmol, 43.7% yield) as a brown oil.

LCMS (2 min, Formic): Rt=0.76 min, MH$^+$ 531

Further fractions containing product were combined and evaporated. Trituration with diethyl ether and DCM gave tert-butyl 4-(5-methyl-2-((4-(methylsulfonyl)piperazin-1-yl)methyl)-4-oxo-4,5-dihydrofuro[3,2-c]pyridin-7-yl)benzylcarbamate (94 mg, 26%) as a yellow/brown foam.

LCMS (2 min, Formic): Rt=0.77 min, MH$^+$ 531

Intermediate 9

7-bromo-5-methyl-2-(piperidin-1-ylmethyl)furo[3,2-c]pyridin-4(5H)-one

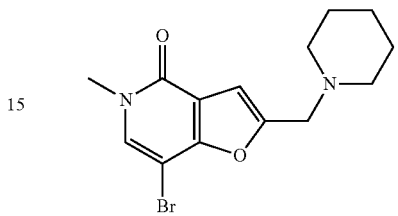

To a stirred solution of 7-bromo-5-methyl-4-oxo-4,5-dihydrofuro[3,2-c]pyridine-2-carbaldehyde (for a preparation see Intermediate 2, 200 mg, 0.781 mmol) in MeOH (18 mL) and acetic acid (2 mL), was added piperidine (200 mg, 2.343 mmol) and the reaction was left to stir for 1 hour at room temperature. 2-Picoline borane complex (251 mg, 2.343 mmol) was added and the reaction mixture was left to stir for 48 hours. The solvent was evaporated under reduced pressure. Saturated sodium bicarbonate (15 mL) was added and the mixture was extracted with DCM (3×15 mL). The combined organics were dried and evaporated under reduced pressure. The residue was purified by chromatography on silica gel (25 g) eluting with a 0-6% MeOH in DCM gradient. Appropriate fractions were concentrated in vacuo to give 7-bromo-5-methyl-2-(piperidin-1-ylmethyl)furo[3,2-c]pyridin-4(5H)-one (40 mg, 15.8%) as an off-white solid.

LCMS (2 min, Formic): Rt=0.47 min, MH$^+$ 325/327

Intermediate 10

7-bromo-5-methyl-2-(morpholinomethyl)furo[3,2-c]pyridin-4(5H)-one

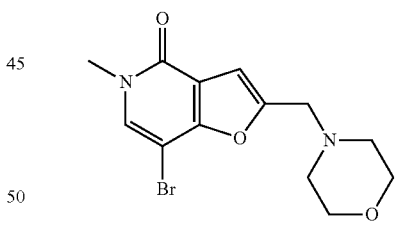

A mixture of 7-bromo-5-methyl-4-oxo-4,5-dihydrofuro[3,2-c]pyridine-2-carbaldehyde (for a preparation see Intermediate 2, 150 mg, 0.59 mmol), morpholine (77 mg, 76 µL, 0.88 mmol) and acetic acid (0.5 mL) in MeOH (9.5 mL) was stirred for 15 minutes. 2-Picoline borane complex (188 mg, 1.76 mmol) was added and the reaction mixture stirred at room temperature overnight. The solvent was evaporated. Saturated sodium bicarbonate solution (20 mL) was added to the residue. The mixture was extracted with DCM (2×20 mL). The combined organics were dried and evaporated. The residue was purified by chromatography on silica gel eluting with a 0-5% MeOH/DCM gradient. Trituration with diethyl ether gave 7-bromo-5-methyl-2-(morpholinomethyl)furo[3,2-c]pyridin-4(5H)-one (90 mg, 0.275 mmol, 47.0% yield) as a pale yellow solid. LCMS (2 min, Formic): Rt=0.4 min, MH$^+$ 327/329

Intermediate 11 tert-butyl 4-((7-bromo-5-methyl-4-oxo-4,5-dihydrofuro[3,2-c]pyridin-2-yl)methyl)-1,4-diazepane-1-carboxylate

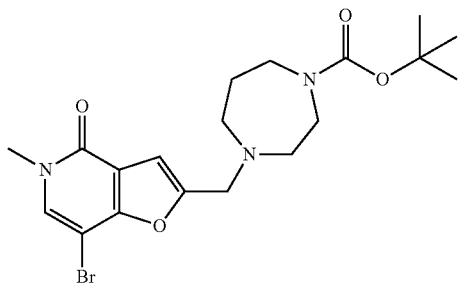 [SMILES: Cn1cc(Br)c2oc(CN3CCCN(C(=O)OC(C)(C)C)CC3)cc2c1=O]

7-Bromo-5-methyl-4-oxo-4,5-dihydrofuro[3,2-c]pyridine-2-carbaldehyde (for a preparation see Intermediate 2, 100 mg, 0.391 mmol) and tert-butyl 1,4-diazepane-1-carboxylate (0.114 mL, 0.586 mmol) were dissolved in acetic acid (1 mL) and MeOH (9 mL). 2-picoline borane complex (45.9 mg, 0.430 mmol) was added and the reaction mixture was stirred at room temperature for 48 h. The reaction mixture was evaporated in vacuo. Saturated sodium bicarbonate solution (15 mL) was added. The mixture was extracted with DCM (3×15 mL). The organic layers were combined, dried over magnesium sulfate and evaporated. The residue was purified by chromatography on silica gel using a 0-5% MeOH/DCM gradient. Appropriate fractions were combined and evaporated to give a yellow solid. The impure solid was dissolved in MeOH and applied to an SCX (5 g) column and eluted with MeOH and then NH$_3$/MeOH. The NH$_3$/MeOH fractions were evaporated to give tert-butyl 4-((7-bromo-5-methyl-4-oxo-4,5-dihydrofuro[3,2-c]pyridin-2-yl)methyl)-1,4-diazepane-1-carboxylate (52 mg, 0.118 mmol, 30.2% yield) as a yellow oil.

LCMS (2 min, High pH): Rt=1.05 min, MH$^+$ 440/442

Intermediate 12 tert-butyl 4-((7-(3,4-dimethoxyphenyl)-5-methyl-4-oxo-4,5-dihydrofuro[32-c]pyridin-2-yl)methyl)-1,4-diazepane-1-carboxylate

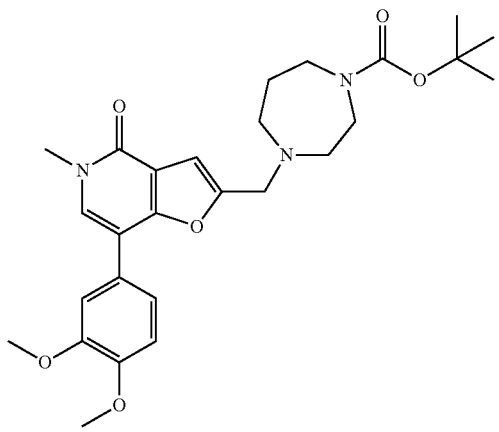 [SMILES: COc1ccc(-c2cn(C)c(=O)c3cc(CN4CCCN(C(=O)OC(C)(C)C)CC4)oc23)cc1OC]

tert-Butyl 4-((7-bromo-5-methyl-4-oxo-4,5-dihydrofuro[3,2-c]pyridin-2-yl)methyl)-1,4-diazepane-1-carboxylate (for a preparation see Intermediate 11, 52 mg, 0.118 mmol), (3,4-dimethoxyphenyl)boronic acid (32.2 mg, 0.177 mmol), potassium carbonate (82 mg, 0.590 mmol) and bis(triphenylphosphine)palladium(II) chloride (4.14 mg, 5.90 µmol) were dissolved in EtOH (2 mL) and toluene (2 mL) and heated in a microwave for 20 min at 120° C. Ethyl acetate (20 mL) was added and the mixture was dried over MgSO$_4$, filtered and the solvent removed in vacuo. The residue was purified by chromatography on silica gel using a 0-5% MeOH/DCM gradient. Appropriate fractions were combined and evaporated to give tert-butyl 4-((7-(3,4-dimethoxyphenyl)-5-methyl-4-oxo-4,5-dihydrofuro[3,2-c]pyridin-2-yl)methyl)-1,4-diazepane-1-carboxylate (50 mg, 0.100 mmol, 85% yield) as a yellow oil. LCMS (2 min, High pH): Rt=1.05 min, MH$^+$ 498

Intermediate 13

7-bromo-2-((3,3-difluoropiperidin-1-yl)methyl)-5-methylfuro[3,2-c]pyridin-4(5H)-one

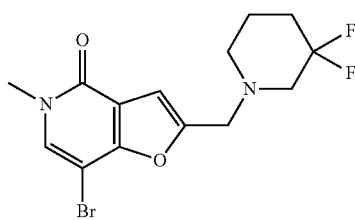 [SMILES: Cn1cc(Br)c2oc(CN3CCCC(F)(F)C3)cc2c1=O]

7-Bromo-5-methyl-4-oxo-4,5-dihydrofuro[3,2-c]pyridine-2-carbaldehyde (for a preparation see Intermediate 2, 200 mg, 0.781 mmol) and 3,3-difluoropiperidine (185 mg, 1.172 mmol) were dissolved in MeOH (20 mL) and acetic acid (2 mL). 2-Picoline borane complex (92 mg, 0.859 mmol) was added and the reaction mixture was stirred at room temperature for 48 h. The reaction mixture was evaporated in vacuo. Saturated sodium bicarbonate solution (35 mL) was added and the mixture was extracted with DCM (3×35 mL). The organic layers were combined, dried over magnesium sulfate and evaporated. The crude product was purified by chromatography on silica gel using a 0-5% MeOH/DCM gradient. The appropriate fractions were combined and evaporated to give 7-bromo-2-((3,3-difluoropiperidin-1-yl)methyl)-5-methylfuro[3,2-c]pyridin-4(5H)-one (150 mg, 53%) as a white powder. LCMS (2 min, High pH): Rt=0.94 min, MH$^+$ 361/363

Intermediate 14

7-bromo-5-methyl-2-((3-methylmorpholino)methyl)furo[3,2-c]pyridin-4(5H)-one

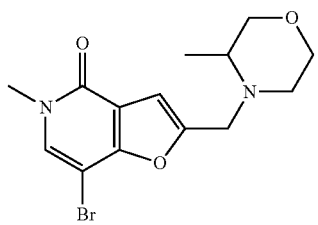 [SMILES: CC1COCCN1Cc1cc2c(=O)n(C)cc(Br)c2o1]

3-Methylmorpholine (79 mg, 89 μL, 0.78 mmol) was added to a stirred solution of 7-bromo-5-methyl-4-oxo-4,5-dihydrofuro[3,2-c]pyridine-2-carbaldehyde (for a preparation see Intermediate 2, 100 mg, 0.39 mmol) in MeOH (5 mL) and acetic acid (0.5 mL). The mixture was stirred at room temperature for 15 minutes. 2-Picoline borane complex (125 mg, 1.17 mmol) was added and the reaction mixture stirred at room temperature for 3 hours. The solvent was evaporated. Saturated sodium bicarbonate solution (10 mL) was added to the residue. The mixture was extracted with DCM (3×10 mL). The combined extracts were dried and evaporated. The residue was purified by chromatography on silica gel eluting with 0-2% MeOH/DCM. The product was dissolved in MeOH and loaded on to an SCX column. This was eluted with MeOH followed by 2M ammonia in MeOH. The ammonia in MeOH fraction was evaporated to give 7-bromo-5-methyl-2-((3-methylmorpholino)methyl)furo[3,2-c]pyridin-4(5H)-one (56 mg, 0.164 mmol, 42.0% yield) as a yellow oil.

LCMS (2 min, Formic): Rt=0.43 min, MH+ 341/343

Intermediate 15

7-bromo-2-((3-fluoropiperidin-1-yl)methyl)-5-methylfuro[3,2-c]pyridin-4(5H)-one

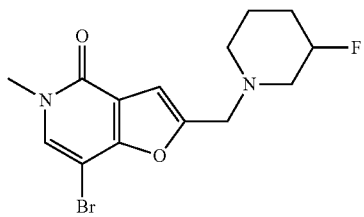 [SMILES: Cn1cc(Br)c2oc(CN3CCCC(F)C3)cc2c1=O]

7-Bromo-5-methyl-4-oxo-4,5-dihydrofuro[3,2-c]pyridine-2-carbaldehyde (for a preparation see Intermediate 2, 200 mg, 0.781 mmol) and 3-fluoropiperidine (169 mg, 1.172 mmol) were dissolved in MeOH (20 mL) and acetic acid (2 mL). 2-Picoline borane complex (92 mg, 0.859 mmol) was added and the reaction mixture was stirred at room temperature for 48 h. The reaction mixture was evaporated in vacuo. Saturated sodium bicarbonate solution (35 mL) was added and the mixture was extracted with DCM (3×35 mL). The organic layers were combined, dried over magnesium sulfate and evaporated. The crude product was purified by chromatography on silica gel using a 0-5% MeOH/DCM gradient. Appropriate fractions were combined and evaporated to give 7-bromo-2-((3-fluoropiperidin-1-yl)methyl)-5-methylfuro[3,2-c]pyridin-4(5H)-one (165 mg, 62%).

LCMS (2 min, High pH): Rt=0.89 min, MH+ 343/345

Intermediate 16

2-((1,4-oxazepan-4-yl)methyl)-7-bromo-5-methylfuro[3,2-c]pyridin-4(5H)-one

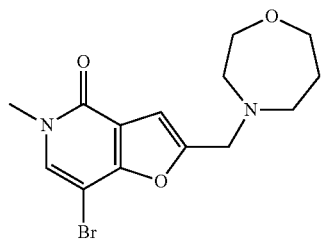 [SMILES: Cn1cc(Br)c2oc(CN3CCCOCC3)cc2c1=O]

A mixture of 7-bromo-5-methyl-4-oxo-4,5-dihydrofuro[3,2-c]pyridine-2-carbaldehyde (for a preparation see Intermediate 2, 150 mg, 0.59 mmol), homomorpholine hydrochloride (121 mg, 0.88 mmol) and acetic acid (0.5 mL) in MeOH (9.5 mL) was stirred for 15 minutes. 2-Picoline borane complex (188 mg, 1.76 mmol) was added and the reaction mixture stirred at room temperature overnight. The solvent was evaporated. Saturated sodium bicarbonate solution (20 mL) was added to the residue. The mixture was extracted with DCM (2×20 mL). The combined organics were dried and evaporated. The residue was purified by chromatography on silica gel eluting with a 0-5% MeOH/DCM gradient. The resulting residue was triturated with diethyl ether to give 2-((1,4-oxazepan-4-yl)methyl)-7-bromo-5-methylfuro[3,2-c]pyridin-4(5H)-one (40 mg, 20%) as a pale yellow solid. The material was used crude in the next step without further purification.

LCMS (2 min, Formic): Rt=0.43 min, MH+ 341/343. Product contains ~30% of 7-bromo-2-(hydroxymethyl)-5-methylfuro[3,2-c]pyridin-4(5H)-one (Rt=0.56 min).

Intermediate 17

4-methoxy-1-methylpyridin-2(1H)-one

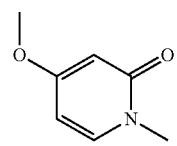

A solution of 4-methoxypyridin-2(1H)-one (2 g, 15.98 mmol) in DMF (40 mL) was treated with potassium carbonate (4.42 g, 32.0 mmol) followed by iodomethane (1.499 mL, 23.98 mmol) and the reaction mixture heated at 60° C. for 16 h. The reaction mixture was concentrated under reduced pressure to dryness. The resulting solid was purified by chromatography on silica gel (100 g) using a 0-33% (20% 2M ammonia in MeOH)/DCM gradient. Appropriate fractions were combined and concentrated under reduced pressure to give 4-methoxy-1-methylpyridin-2(1H)-one (1.8 g, 81%) as a yellow solid. LCMS (2 min, Formic): Rt=0.43 min, MH+ 140

Intermediate 18

3,5-diiodo-4-methoxy-1-methylpyridin-2(1H)-one

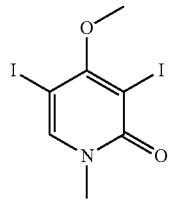

A solution of 4-methoxy-1-methylpyridin-2(1H)-one (for a preparation see Intermediate 17, 1.8 g, 12.94 mmol) in acetonitrile (50 mL) was treated with 1-iodopyrrolidine-2,5-dione (2.91 g, 12.94 mmol) and the reaction mixture stirred at room temperature for 2 h. Further 1-iodopyrrolidine-2,5-dione (4.37 g) was added to the reaction mixture, followed by TFA (0.997 mL, 12.94 mmol) and the reaction allowed to stir under nitrogen for 16 h. The gum was purified by chromatography on silica gel eluting with 0-80% cyclohexane/EtOAc. Appropriate fractions were combined and concentrated under reduced pressure to give 3,5-diiodo-4-methoxy-1-methylpyridin-2(1H)-one (5.1 g, >99% yield) as a yellow solid. LCMS (2 min, Formic): Rt=0.79 min, MH⁺ 392

Intermediate 19

5-iodo-4-methoxy-1-methyl-2'-((tetrahydro-2H-pyran-4-yl)methoxy)-[3,4'-bipyridin]-6(1H)-one

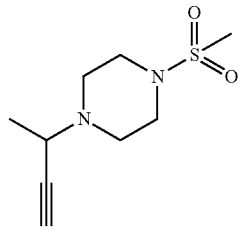

A solution of TPPTS (20 mg, 0.035 mmol), 3,5-diiodo-4-methoxy-1-methylpyridin-2(1H)-one (for a preparation see Intermediate 18, 180 mg, 0.460 mmol), 2-((tetrahydro-2H-pyran-4-yl)methoxy)-4-(4,4,5,5-tetramethyl-1,3,2-dioxaborolan-2-yl)pyridine (BoroPharm Inc) (191 mg, 0.599 mmol), and diacetoxypalladium (3 mg, 0.013 mmol) in acetonitrile (4 mL) and water (1.333 mL) was treated with DIPEA (0.105 mL, 0.599 mmol). The reaction mixture was heated at 60° C. under nitrogen for 16 h. Further diacetoxypalladium (3 mg, 0.013 mmol) was added, followed by further 2-((tetrahydro-2H-pyran-4-yl)methoxy)-4-(4,4,5,5-tetramethyl-1,3,2-dioxaborolan-2-yl)pyridine (55 mg) and the reaction stirred for 4 h at 60° C. under nitrogen.

The reaction mixture was concentrated under reduced pressure and the resulting crude material partitioned between DCM (20 mL) and water (20 mL). The aqueous layer was extracted with DCM (2×20 mL). The combined organic layers were passed through a hydrophobic frit and concentrated under reduced pressure. The crude material was purified by chromatography on silica gel eluting with a 0-100% gradient of EtOAc/cyclohexane. Appropriate fractions were combined and concentrated under reduced pressure to give 5-iodo-4-methoxy-1-methyl-2'-((tetrahydro-2H-pyran-4-yl)methoxy)-[3,4'-bipyridin]-6(1H)-one (90 mg, 43%) as a white solid.

LCMS (2 min, Formic): Rt=0.89 min, MH⁺ 457

Intermediate 20

1-(but-3-yn-2-yl)-4-(methylsulfonyl)piperazine

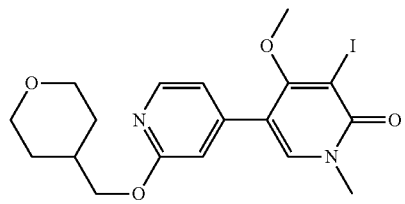 [SMILES: COc1c(-c2ccnc(OCC3CCOCC3)c2)cn(C)c(=O)c1I]

A mixture of 3-chlorobut-1-yne (1 g, 11.29 mmol), 1-(methylsulfonyl)piperazine (3.71 g, 22.59 mmol), copper (0.014 g, 0.226 mmol), and copper(I) chloride (0.022 g, 0.226 mmol), in diethyl ether (15 mL) and water (5 mL) was stirred at room temperature under nitrogen for 16 h. Water (40 mL) and diethyl ether (40 mL) were added. The organic layer was isolated and the aqueous layer was re-extracted with diethyl ether (2×40 mL). The combined organic layers were passed through a hydrophobic frit and concentrated under reduced pressure. The crude material was purified by chromatography on silica gel eluting with an 80-100% EtOAc/cyclohexane gradient. Fractions containing product (as detected by KMnO₄ dip) were combined and concentrated under reduced pressure to give 1-(but-3-yn-2-yl)-4-(methylsulfonyl)piperazine (1.6 g, 66%) as a clear yellow gum that solidified to a waxy solid on standing.

¹H NMR (400 MHz, DMSO-d₆) δ-ppm 3.58 (1H, m), 3.21 (1H, d), 3.15-3.09 (4H, m), 2.86 (3H, s), 2.64-2.60 (2H, m), 2.51-2.44 (2H, m), 1.25 (3H, d)

Intermediate 21

1-(benzyloxy)-3-bromobenzene

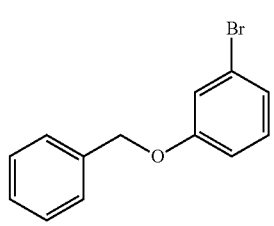 [SMILES: Brc1cccc(OCc2ccccc2)c1]

A mixture of 3-bromophenol (2.60 g, 1.59 mL, 15 mmol), benzyl bromide (2.82 g 1.96 mL, 16.5 mmol) and potassium carbonate (2.07 g, 15 mmol) in acetone (25 mL) was refluxed for 4 hours. The reaction mixture was cooled to room temperature. The mixture was filtered and the solvent was evaporated from the filtrate. The residue was purified by chromatography on silica gel eluting with 0-25% ethyl acetate/hexane. Appropriate fractions were combined and evaporated. The impure product was re-purified by chromatography on silica gel eluting with 0-10% ethyl acetate/ hexane to give 1-(benzyloxy)-3-bromobenzene (2.25 g, 8.55 mmol, 57.0% yield) as a white solid.

¹H NMR (400 MHz, DMSO-d₆) δ-ppm 7.46-7.32 (m, 5H), 7.27-7.22 (m, 2H), 7.13 (m, 1H), 7.03 (m, 1H), 5.13 (s, 2H)

Intermediate 22

2-(3-(benzyloxy)phenyl)-4,4,5,5-tetramethyl-1,3,2-dioxaborolane

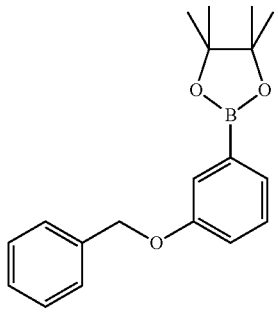 [SMILES: CC1(C)OB(c2cccc(OCc3ccccc3)c2)OC1(C)C]

A solution of 1-(benzyloxy)-3-bromobenzene (for a preparation see Intermediate 21, 263 mg, 1.0 mmol) in 1,4-dioxane (8 mL) was added to a mixture of bis(pinacolato)diboron (1.27 g, 5.0 mmol), potassium acetate (392 mg, 4.0 mmol) and [1,1'-bis(diphenylphosphino)ferrocene]dichloropalladium(II), (PdCl2(dppf)) (37 mg, 5 mol %). The reaction mixture was heated in a microwave at 110° C. for 60 minutes. The cooled reaction mixture was diluted with ethyl acetate (20 mL) and filtered through Celite. The filtrate was dried and evaporated to give 2-(3-(benzyloxy)phenyl)-4,4,5,5-tetramethyl-1,3,2-dioxaborolane (310 mg, 1.000 mmol, 100% yield). Quantitative yield assumed. The material was used crude in the next step without further purification. LCMS (2 min, Formic): Rt=1.42 min, MH⁺ 311

Intermediate 23

N-benzyl-3-bromoaniline

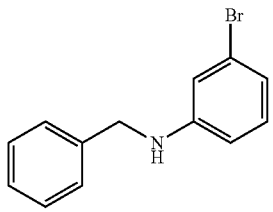 [SMILES: Brc1cccc(NCc2ccccc2)c1]

3-Bromoaniline (3.10 g, 18.0 mmol) was added to a stirred solution of benzaldehyde (1.59 g, 15.0 mmol) in MeOH (18 mL) and glacial acetic acid (2 mL). The mixture was stirred at room temperature for 15 minutes then 2-picoline borane complex (1.765 g, 16.5 mmol) was added portionwise over 5 minutes (exothermic). The reaction mixture was stirred at room temperature for 2 hours then allowed to stand at room temperature over the weekend. The solvent was evaporated. Saturated sodium bicarbonate solution (30 mL) was added. The mixture was extracted with DCM (3×50 mL). The combined extracts were dried and evaporated. The residue was purified by chromatography on silica gel eluting with 10-30% ethyl acetate/hexane to give N-benzyl-3-bromoaniline (3.52 g, 13.43 mmol, 90% yield) as a colourless oil. LCMS (2 min, Formic): Rt=1.27 min, MH⁺ 262/264

Intermediate 24

N-benzyl-3-(4,4,5,5-tetramethyl-1,3,2-dioxaborolan-2-yl)aniline

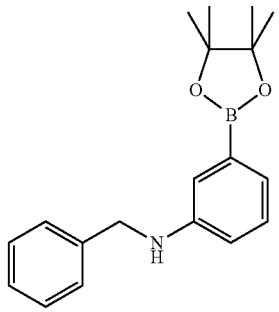 [SMILES: CC1(C)OB(c2cccc(NCc3ccccc3)c2)OC1(C)C]

A solution of N-benzyl-3-bromoaniline (for a preparation see Intermediate 23, 262 mg, 1.0 mmol) in 1,4-dioxane (8 mL) was added to a mixture of bis(pinacolato)diboron (1.27 g, 5.0 mmol), potassium acetate (392 mg, 4.0 mmol) and [1,1'-bis(diphenylphosphino)ferrocene]dichloropalladium (II) (37 mg, 5 mol %). The reaction mixture was heated in a microwave at 110° C. for 30 minutes. The cooled reaction mixture was diluted with ethyl acetate (20 mL) and filtered through Celite. The filtrate was dried and evaporated to give N-benzyl-3-(4,4,5,5-tetramethyl-1,3,2-dioxaborolan-2-yl)aniline (309 mg, 0.999 mmol, 100% yield). Quantitative yield assumed. The material was used crude in the next step without further purification. LCMS (2 min, Formic): Rt=1.31 min, MH⁺ 310

Intermediate 25

4-bromo-N-(1-phenylethyl)pyridin-2-amine

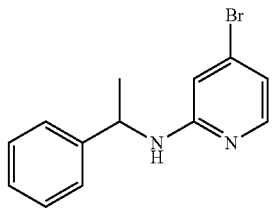 [SMILES: CC(Nc1cc(Br)ccn1)c1ccccc1]

1-Phenylethanamine (7.38 mL, 57.3 mmol) and 4-bromo-2-chloropyridine (3.177 mL, 28.6 mmol) were dissolved in EtOH (10 mL). N-ethyl-N-isopropylpropan-2-amine (7.25 mL, 42.9 mmol) was added and the reaction mixture was heated to reflux for 24 h. LCMS showed no reaction. The solvent was removed in vacuo and the mixture was transferred to a microwave vial with NMP (5 mL). The reaction mixture was heated in a microwave at 180° C. for 1 h. The reaction mixture was purified by chromatography on silica gel (120 g) eluting with 10-50% EtOAc in cyclohexane. Appropriate fractions were combined and evaporated to give 4-bromo-N-(1-phenylethyl)pyridin-2-amine (787 mg, 2.84 mmol, 9.92% yield) LCMS (2 min, High pH): Rt=1.21 min, MH+ 277/279

Intermediate 26

N-(1-phenylethyl)-4-(4,4,5,5-tetramethyl-1,3,2-dioxaborolan-2-yl)pyridin-2-amine

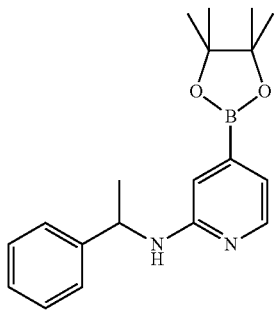 [SMILES: CC(Nc1cc(B2OC(C)(C)C(C)(C)O2)ccn1)c1ccccc1]

4-Bromo-N-(1-phenylethyl)pyridin-2-amine (for a preparation see Intermediate 25, 250 mg, 0.902 mmol), bis(pinacolato)diboron (1145 mg, 4.51 mmol), potassium acetate (354 mg, 3.61 mmol) and PdCl$_2$(dppf) (66.0 mg, 0.090 mmol) were dissolved into 1,4-dioxane (8 mL) and heated in a microwave at 110° C. for 1 h. Further portions of bis(pinacolato)diboron (1145 mg, 4.51 mmol) and PdCl$_2$(dppf) (66.0 mg, 0.090 mmol) were added the reaction was heated in a microwave at 110° C. for 2 h. The cooled reaction mixture was diluted with ethyl acetate (20 mL) and filtered through Celite. The filtrate was dried and evaporated to give N-(1-phenylethyl)-4-(4,4,5,5-tetramethyl-1,3,2-dioxaborolan-2-yl)pyridin-2-amine (292 mg, 0.902 mmol, 100% yield). Quantitative yield assumed. The material was used crude in the next step without further purification.

LCMS (2 min, High pH): Rt=0.59 min, MH+ 243 (observed mass ion corresponds to the boronic acid)

Intermediate 27

3-bromo-5-(1-phenylethoxy)pyridine

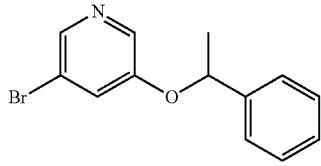 [SMILES: CC(Oc1cncc(Br)c1)c1ccccc1]

Potassium carbonate (1.59 g, 11.5 mmol) was added to a stirred solution of 5-bromopyridin-3-ol (1.0 g, 5.75 mmol) in DMF (10 mL). The reaction mixture was stirred at 60° C. for 30 minutes, then (1-bromoethyl)benzyl bromide (1.12 g, 824 µl, 6.05 mmol) was added. The reaction mixture was stirred at 60° C. for 2 hours. The reaction mixture was cooled to room temperature and partitioned between ethyl acetate (50 mL) and water (25 mL). The organic phase was separated, washed with water and brine, dried and evaporated. The residue was purified by chromatography on silica gel eluting with DCM to give 3-bromo-5-(1-phenylethoxy) pyridine (890 mg, 3.20 mmol, 55.7% yield) as a yellow oil. LCMS (2 min, Formic): Rt=1.18 min, MH+ 278/280

Intermediate 28

3-(1-phenylethoxy)-5-(4,4,5,5-tetramethyl-1,3,2-dioxaborolan-2-yl)pyridine

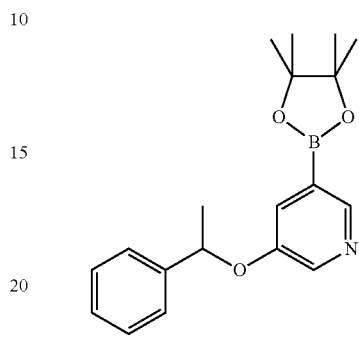

A solution of 3-bromo-5-(1-phenylethoxy)pyridine (for a preparation see Intermediate 27, 278 mg, 1.0 mmol) in 1,4-dioxane (8 mL) was added to a mixture of bis(pinacolato)diboron (1.27 g, 5.0 mmol), potassium acetate (392 mg, 4.0 mmol) and [1,1'-bis(diphenylphosphino)ferrocene]dichloropalladium(II), (PdCl$_2$(dppf)) (37 mg, 5 mol %). The reaction mixture was heated in a microwave at 110° C. for 30 minutes. The cooled reaction mixture was diluted with ethyl acetate (20 mL) and filtered through Celite. The filtrate was dried and evaporated to give 3-(1-phenylethoxy)-5-(4,4,5,5-tetramethyl-1,3,2-dioxaborolan-2-yl)pyridine (325 mg, 0.999 mmol, 100% yield). Quantitative yield assumed. The material was used crude in the next step without further purification.

LCMS (2 min, Formic): Rt=0.62 min, MH+ 244 (observed mass ion corresponds to the boronic acid)

Intermediate 29

3-bromo-N-(1-phenylethyl)aniline

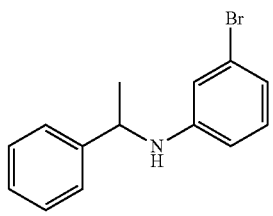 [SMILES: CC(Nc1cccc(Br)c1)c1ccccc1]

3-Bromoaniline (3.10 g, 18.0 mmol) was added to a stirred solution of acetophenone (1.80 g, 15.0 mmol) in MeOH (18 mL) and glacial acetic acid (2 mL). The mixture was stirred at room temperature for 15 minutes then 2-picoline borane complex (1.765 g, 16.5 mmol) was added portionwise over 5 minutes. The reaction mixture was stirred at room temperature over the weekend. The solvent was evaporated. Saturated sodium bicarbonate solution (30 mL) was added. The mixture was extracted with DCM (3×50 mL). The combined extracts were dried and evaporated. The residue was purified by chromatography on silica gel eluting with 10-30% ethyl acetate/hexane to give 3-bromo-N-(1- phenylethyl)aniline (2.93 g, 10.61 mmol, 70.7% yield, ~30% impurity present by NMR) as a pale yellow oil.

$^{1}$H NMR (400 MHz, CDCl$_{3}$) δ-ppm 7.34-7.28 (m, 4H), 7.22 (m, 1H), 6.9 (t, 1H), 6.73 (m, 1H), 6.66 (t, 1H), 6.38 (m, 1H), 4.44 (q, 1H), 1.49 (d, 3H)

Intermediate 30

N-(1-phenylethyl)-3-(4,4,5,5-tetramethyl-1,3,2-dioxaborolan-2-yl)aniline

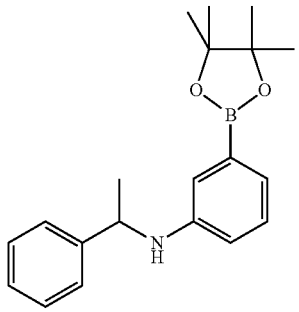 [SMILES: CC(Nc1cccc(B2OC(C)(C)C(C)(C)O2)c1)c1ccccc1]

A solution of 3-bromo-N-(1-phenylethyl)aniline (for a preparation see Intermediate 29, 276 mg, 1.0 mmol) in 1,4-dioxane (8 mL) was added to a mixture of bis(pinacolato)diboron (1.27 g, 5.0 mmol), potassium acetate (392 mg, 4.0 mmol) and [1,1'-bis(diphenylphosphino)ferrocene]dichloropalladium(II), (PdCl$_{2}$(dppf)) (37 mg, 5 mol %). The reaction mixture was heated in a microwave at 110° C. for 30 minutes. The cooled reaction mixture was diluted with ethyl acetate (20 mL) and filtered through Celite. The filtrate was dried and evaporated to give N-(1-phenylethyl)-3-(4,4,5,5-tetramethyl-1,3,2-dioxaborolan-2-yl)aniline (323 mg, 0.999 mmol, 100% yield). Quantitative yield assumed. The material was used crude in the next step without further purification.

LCMS (2 min, Formic): Rt=1.34 min, MH$^{+}$ 324 and Rt=0.76 min, MH$^{+}$ 242 (additional mass ion corresponds to the boronic acid)

Intermediate 31

4-bromo-2-(cyclopropylmethoxy)pyridine

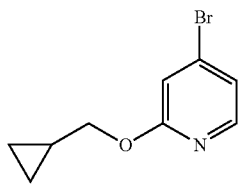 [SMILES: Brc1ccnc(OCC2CC2)c1]

To a stirred suspension of cyclopropylmethanol (0.493 mL, 6.24 mmol) in THF (10 mL) under nitrogen, was added sodium hydride (249 mg, 6.24 mmol) portion wise. After ~30 min, 4-bromo-2-chloropyridine (0.346 mL, 3.12 mmol) was added. The reaction was stirred for 3 days. The mixture was diluted with diethyl ether (30 mL) and water (30 mL). The aqueous phase was re-extracted with diethyl ether (2×30 mL). The combined organic layers were washed with brine (30 mL) and concentrated in vacuo to give a yellow oil (685 mg, 96%, ~59% purity by LCMS). The material was used crude in the next step without further purification.

LCMS (2 min, Formic): Rt=1.21 min, MH$^{+}$ 228/230

Intermediate 32

2-(cyclopropylmethoxy)-4-(4,4,5,5-tetramethyl-1,3,2-dioxaborolan-2-yl)pyridine

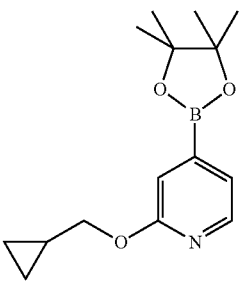 [SMILES: CC1(C)OB(c2ccnc(OCC3CC3)c2)OC1(C)C]

To a stirred suspension of 4-bromo-2-(cyclopropylmethoxy)pyridine (for a preparation see Intermediate 31, 679 mg, 2.98 mmol) in 1,4-dioxane (8 mL), was added 4,4,4',4',5,5,5',5'-octamethyl-2,2'-bi(1,3,2-dioxaborolane) (1512 mg, 5.95 mmol), potassium acetate (876 mg, 8.93 mmol) and PdCl$_{2}$(dppf) (218 mg, 0.298 mmol). This was sealed in a microwave vial and heated to 100° C. in a microwave for 60 minutes. The mixture was dissolved in ethyl acetate and eluted through a Celite cartridge with ethyl acetate. The solvent was evaporated under reduced pressure to give 2-(cyclopropylmethoxy)-4-(4,4,5,5-tetramethyl-1,3,2-dioxaborolan-2-yl)pyridine (2.18 g, 333%) as brown gum. The product was taken through the next synthetic step as crude material: 100% conversion assumed therefore maximum purity of crude material is 30%

LCMS (2 min, Formic): Rt=0.61 min, MH$^{+}$ 194 (observed mass ion corresponds to the boronic acid)

Intermediate 33

N-(4-bromopyridin-2-yl)cyclopropanecarboxamide

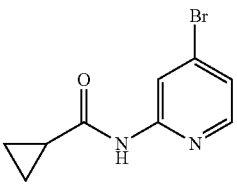 [SMILES: O=C(Nc1cc(Br)ccn1)C1CC1]

Pyridine (0.467 mL, 5.78 mmol) was added to a solution of 4-bromopyridin-2-amine (500 mg, 2.89 mmol) in DCM (10 mL) and stirred at rt for 20 min. Cyclopropanecarbonyl chloride (0.302 mL, 3.32 mmol) was added and the solution was stirred for 4 hours. Further portions of cyclopropanecarbonyl chloride (0.302 mL, 3.32 mmol) and pyridine (0.234 mL, 2.89 mmol) were added and the reaction was left to stir for 5 hours. Water was added and the product was extracted with DCM. The organic layer was washed with brine, filtered through a hydrophobic frit and concentrated in vacuo. The residue was dissolved in MeOH and passed through an aminopropyl column (10 g), eluting with MeOH.

The solvent was evaporated to give N-(4-bromopyridin-2-yl)cyclopropanecarboxamide (610 mg, 2.53 mmol, 88% yield) as a white solid. LCMS (2 min, Formic): Rt=0.84 min, MH+ 241/243

Intermediate 34

N-(4-(4,4,5,5-tetramethyl-1,3,2-dioxaborolan-2-yl)pyridin-2-yl)cyclopropanecarboxamide

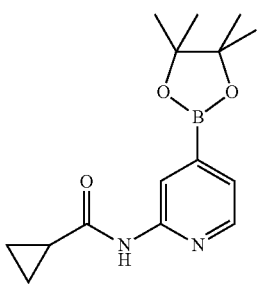 [SMILES: CC1(C)OB(c2ccnc(NC(=O)C3CC3)c2)OC1(C)C]

A mixture of N-(4-bromopyridin-2-yl)cycopropanecarboxamide (for a preparation see Intermediate 33, 504 mg, 2.091 mmol), bis(pinacolato)diboron (1062 mg, 4.18 mmol), PdCl$_2$(dppf) (153 mg, 0.209 mmol) and potassium acetate (616 mg, 6.27 mmol) in 1,4-dioxane (5 mL) was heated in a microwave at 100° C. for 30 min. The reaction was diluted with ethyl acetate and filtered through a Celite column. The filtrate was evaporated to give N-(4-(4,4,5,5-tetramethyl-1,3,2-dioxaborolan-2-yl)pyridin-2-yl)cyclopropanecarboxamide as a brown residue. The yield was assumed to be 100% (602 mg, 2.089 mmol). The material was used crude in the next reaction without further purification. LCMS (2 min, Formic): Rt=0.37 min, MH+ 207 (observed mass ion is consistent with hydrolysis to boronic acid under LCMS conditions).

Intermediate 35

N-(4-bromopyridin-2-yl)propionamide

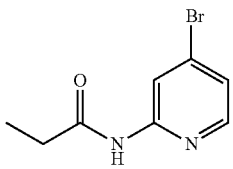

Pyridine (0.374 mL, 4.62 mmol) was added to a solution of 4-bromopyridin-2-amine (400 mg, 2.312 mmol) in DCM (10 mL) and stirred at rt for 20 min. Propionyl chloride (0.232 mL, 2.66 mmol) was added and the solution was stirred at rt overnight. Water was added and the product was extracted with DCM. The organic layer was washed with brine, dried through a hydrophobic frit, and concentrated in vacuo. The residue was dissolved in MeOH and passed through an aminopropyl column (10 g), eluting with MeOH. The solvent was evaporated to give N-(4-bromopyridin-2-yl)propionamide (464 mg, 2.026 mmol, 88% yield) as a white solid.

LCMS (2 min, High pH): Rt=0.84 min, MH+ 229/231

Intermediate 36

N-(4-(4,4,5,5-tetramethyl-1,3,2-dioxaborolan-2-yl)pyridin-2-yl)propionamide

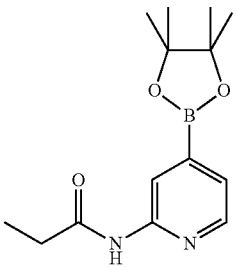 [SMILES: CCC(=O)Nc1cc(B2OC(C)(C)C(C)(C)O2)ccn1]

A mixture of N-(4-bromopyridin-2-yl)propionamide (for a preparation see Intermediate 35, 200 mg, 0.873 mmol), bis(pinacolato)diboron (665 mg, 2.62 mmol), PdCl$_2$(dppf) (63.9 mg, 0.087 mmol) and potassium acetate (257 mg, 2.62 mmol) in 1,4-dioxane (5 mL) was heated in a microwave at 100° C. for 30 min. The reaction was diluted with ethyl acetate and filtered through a Celite column. The filtrate was evaporated to give N-(4-(4,4,5,5-tetramethyl-1,3,2-dioxaborolan-2-yl)pyridin-2-yl)propionamide as a brown residue. The yield was assumed to be 100% (241 mg, 0.873 mmol). The material was used crude in the next stage without further purification.

LCMS (2 min, Formic): Rt=0.34 min, MH+ 195 (observed mass ion is consistent with hydrolysis to boronic acid under LCMS conditions).

Intermediate 37

4-bromo-2-(2-methoxyethoxy)pyridine

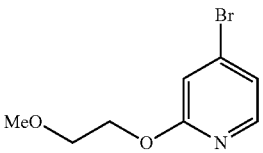 [SMILES: COCCOc1cc(Br)ccn1]

2-Methoxyethanol (0.820 mL, 10.39 mmol) was dissolved in THF (30 mL) and sodium hydride (60% w/w) (0.416 g, 10.39 mmol) was added under nitrogen and left to stir at rt for 15 min. 4-bromo-2-chloropyridine (0.577 mL, 5.20 mmol) was added and the reaction was left stirring at rt overnight. Further 2-methoxyethanol (0.410 mL, 5.19 mmol) was dissolved in 1,2-DME (10 mL) and sodium hydride (60% w/w) (0.208 mg, 5.19 mmol) was added. After 15 min at rt under nitrogen, this was added to the reaction mixture and left stirring at rt for 3 days. Water was added (40 mL) and the organic product was extracted with ethyl acetate. The organic layer was washed with brine, dried through a hydrophobic frit and concentrated in vacuo. The residue was purified by chromatography on silica gel eluting with 0-20% ethyl acetate in cyclohexane. Fractions containing product were concentrated in vacuo to give 4-bromo-2-

(2-methoxyethoxy)pyridine (314 mg, 1.353 mmol, 26.0% yield) as a colourless liquid. LCMS (2 min, Formic): Rt=0.93 min, MH+ 232/234

Intermediate 38

2-(2-methoxyethoxy)-4-(4,4,5,5-tetramethyl-1,3,2-dioxaborolan-2-yl)pyridine

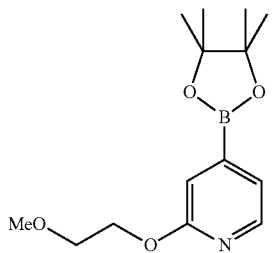 [SMILES: COCCOc1cc(B2OC(C)(C)C(C)(C)O2)ccn1]

A mixture of 4-bromo-2-(2-methoxyethoxy)pyridine (for a preparation see Intermediate 37, 306 mg, 1.319 mmol), bis(pinacolato)diboron (1004 mg, 3.96 mmol), PdCl₂(dppf) (96 mg, 0.132 mmol) and potassium acetate (388 mg, 3.96 mmol) in 1,4-dioxane (10 mL) was heated in a microwave at 100° C. for 30 min. The reaction was diluted with ethyl acetate and filtered through a Celite column. The filtrate was evaporated to give 2-(2-methoxyethoxy)-4-(4,4,5,5-tetramethyl-1,3,2-dioxaborolan-2-yl)pyridine as a brown residue. The yield was assumed to be 100% (368 mg, 1.319 mmol). The material was used crude in the next stage without further purification.

LCMS (2 min, Formic): Rt=0.44 min, MH+ 198 (observed mass ion is consistent with hydrolysis to boronic acid under LCMS conditions).

Intermediate 39

4-bromo-2-(2-(pyrrolidin-1-yl)ethoxy)pyridine

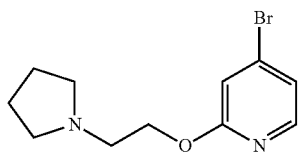 [SMILES: Brc1ccnc(OCCN2CCCC2)c1]

2-(Pyrrolidin-1-yl)ethanol (1.240 mL, 10.39 mmol) was dissolved in THF (30 mL) and sodium hydride (60% w/w) (0.416 g, 10.39 mmol) was added portion-wise under nitrogen. This was left to stir for 15 minutes at rt before 4-bromo-2-chloropyridine (0.577 mL, 5.20 mmol) was added. The reaction was stirred at rt for 3 days. Water was added (40 mL) and the organic product was extracted with ethyl acetate. The organic layer was washed with brine, dried through a hydrophobic frit and concentrated in vacuo. The residue was purified by chromatography on silica gel eluting with 0-5% MeOH/NH₃ in DCM. Fractions containing product were combined and concentrated in vacuo to give 4-bromo-2-(2-(pyrrolidin-1-yl)ethoxy)pyridine (314 mg, 22%). LCMS (2 min, Formic): Rt=0.54 min, MH+ 271/273

Intermediate 40

2-(2-(pyrrolidin-1-yl)ethoxy)-4-(4,4,5,5-tetramethyl-1,3,2-dioxaborolan-2-yl)pyridine

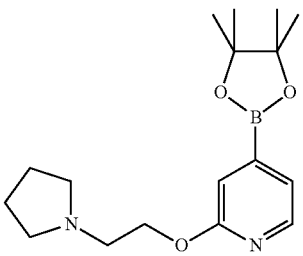 [SMILES: CC1(C)OB(c2ccnc(OCCN3CCCC3)c2)OC1(C)C]

A mixture of 4-bromo-2-(2-(pyrrolidin-1-yl)ethoxy)pyridine (for a preparation see Intermediate 39, 400 mg, 1.475 mmol), bis(pinacolato)diboron (1124 mg, 4.43 mmol), PdCl₂(dppf) (108 mg, 0.148 mmol) and potassium acetate (434 mg, 4.43 mmol) in 1,4-dioxane (10 mL) was heated in a microwave at 100° C. for 30 min. The reaction was diluted with ethyl acetate and filtered through a Celite column. The filtrate was evaporated to give 2-(2-(pyrrolidin-1-yl)ethoxy)-4-(4,4,5,5-tetramethyl-1,3,2-dioxaborolan-2-yl) pyridine as a brown residue. The yield was assumed to be 100% 469 mg, 1.474 mmol). The material was used crude in the next stage without further purification.

LCMS (2 min, Formic): Rt=0.33 min, MH+ 237 (observed mass ion is consistent with hydrolysis to boronic acid under LCMS conditions).

Intermediate 41

7-bromo-2-((1,1-dioxidothiomorpholino)methyl)-5-methylfuro[3,2-c]pyridin-4(5H)-one

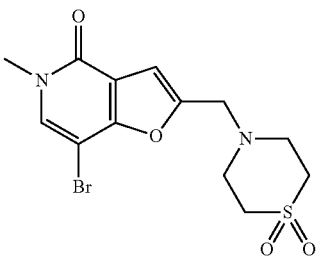 [SMILES: Cn1cc(Br)c2oc(CN3CCS(=O)(=O)CC3)cc2c1=O]

To a mixture of 7-bromo-5-methyl-4-oxo-4,5-dihydrofuro[3,2-c]pyridine-2-carbaldehyde (for a preparation see Intermediate 2, 200 mg, 0.781 mmol) and thiomorpholine 1,1-dioxide (317 mg, 2.343 mmol) in MeOH (10 mL) was added sodium cyanoborohydride (196 mg, 3.12 mmol). The reaction was stirred at 20° C. overnight. The mixture was extracted with DCM and washed with brine. The organic layer was evaporated in vacuo. The crude product was purified by chromatography on silica gel eluting with DCM/MeOH. Appropriate fractions were combined and evaporated to give 7-bromo-2-((1,1-dioxidothiomorpholino)methyl)-5-methylfuro[3,2-c]pyridin-4(5H)-one (215 mg, 0.516 mmol, 66.0% yield) as a white solid. LCMS: MH+ 375

Intermediate 42

7-chloro-2-(4-(methylsulfonyl)piperazine-1-carbonyl)furo[2,3-d]pyridazin-4(5H)-one

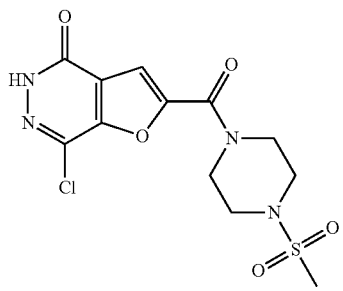 [SMILES: CS(=O)(=O)N1CCN(C(=O)c2cc3c(=O)[nH]nc(Cl)c3o2)CC1]

To triethylamine (0.908 mL, 6.52 mmol) in NMP (2 mL) was added 7-chloro-4-oxo-4,5-dihydrofuro[2,3-d]pyridazine-2-carboxylic acid (Peakdale) (250 mg, 1.165 mmol), 1-(methylsulfonyl)piperazine (265 mg, 1.614 mmol), 1H-benzo[d][1,2,3]triazol-1-ol hydrate (215 mg, 1.404 mmol) and 2-(3H-[1,2,3]triazolo[4,5-b]pyridin-3-yl)-1,1,3,3-tetramethylisouronium hexafluorophosphate(V) (134 mg, 0.352 mmol). The reaction was stirred at room temperature under nitrogen overnight. The reaction mixture was purified by MDAP. Appropriate fractions were combined and the solvent removed to give 7-chloro-2-(4-(methylsulfonyl)piperazine-1-carbonyl)furo[2,3-d]pyridazin-4(5H)-one (208 mg, 42%) as a white solid.

LCMS (2 min, Formic): Rt=0.59 min, MH+ 361

Intermediate 43

7-chloro-5-methyl-2-(4-(methylsulfonyl)piperazine-1-carbonyl)furo[2,3-d]pyridazin-4(5H)-one

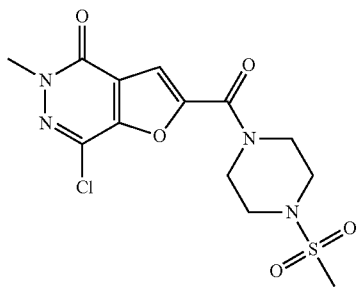 [SMILES: Cn1nc(Cl)c2oc(C(=O)N3CCN(S(C)(=O)=O)CC3)cc2c1=O]

To 7-chloro-2-(4-(methylsulfonyl)piperazine-1-carbonyl)furo[2,3-d]pyridazin-4(5H)-one (for a preparation see Intermediate 42, 100 mg, 0.277 mmol) in DMF (3 mL) was added sodium hydride (11.09 mg, 0.277 mmol) and methyl iodide (11 µL, 0.176 mmol). The mixture was stirred overnight under nitrogen at room temperature. Additional sodium hydride (11.09 mg, 0.277 mmol) and methyl iodide (11 µL, 0.176 mmol) were added and the reaction was stirred for 4 hours at room temperature under nitrogen. Water was added and the solvent removed. The residue was dissolved in DCM/water and partitioned (×2). The combined organic layers were washed with water, the solvent removed and dried under high vacuum overnight to give 7-chloro-5-methyl-2-(4-(methylsulfonyl)piperazine-1-carbonyl)furo[2,3-d]pyridazin-4(5H)-one (106 mg, 95%) as a yellow solid.

LCMS (2 min, Formic): Rt=0.7 min, MH+ 375

Intermediate 44

5-methyl-2-(4-(methylsulfonyl)piperazine-1-carbonyl)-7-(2-((tetrahydro-2H-pyran-4-yl)methoxy)pyridin-4-yl)furo[2,3-d]pyridazin-4(5H)-one

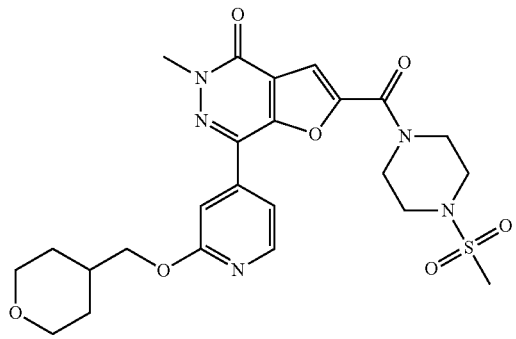 [SMILES: Cn1nc(-c2ccnc(OCC3CCOCC3)c2)c2oc(C(=O)N3CCN(S(C)(=O)=O)CC3)cc2c1=O]

To 7-chloro-5-methyl-2-(4-(methylsulfonyl)piperazine-1-carbonyl)furo[2,3-d]pyridazin-4(5H)-one (for a preparation see Intermediate 43, 106 mg, 0.283 mmol) in 1,4-dioxane (6 mL) and water (3 mL) was added sodium carbonate (120 mg, 1.131 mmol), tetrakis(triphenylphosphine)palladium(0) (32.7 mg, 0.028 mmol) and 2-((tetrahydro-2H-pyran-4-yl)methoxy)-4-(4,4,5,5-tetramethyl-1,3,2-dioxaborolan-2-yl)pyridine (108 mg, 0.339 mmol). The mixture was refluxed at 110° C. under nitrogen for 2 hours. After cooling, the solvent was removed and the residue was purified by MDAP. Appropriate fractions were combined and the solvent was removed. The residue was dried under high vacuum for 3 hours and triturated with MeOH-d4 to give 5-methyl-2-(4-(methylsulfonyl)piperazine-1-carbonyl)-7-(2-((tetrahydro-2H-pyran-4-yl)methoxy)pyridin-4-yl)furo[2,3-d]pyridazin-4(5H)-one (50 mg, 30%) as a white solid.

LCMS (2 min, Formic): Rt=0.87 min, MH+ 532

Intermediate 45

N-(4-bromopyridin-2-yl)acetamide

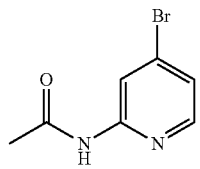

Pyridine (0.374 mL, 4.62 mmol) was added to a solution of 4-bromopyridin-2-amine (Princeton BioMolecular Research) (400 mg, 2.312 mmol) in DCM (10 mL) and stirred at rt for 20 min. Acetyl chloride (0.190 mL, 2.66 mmol) was added and the solution was stirred at rt overnight. Water was added and the product was extracted with DCM. The organic layer was washed with brine, filtered through a hydrophobic frit, and concentrated in vacuo. The residue was dissolved in MeOH and passed through a 10 g aminopropyl column, eluting with MeOH. The solvent was evaporated give the title compound as a white solid (404 mg, 1.879 mmol, 81% yield).

LCMS (2 min, High pH): Rt=0.65 min, MH$^+$ 215/217

Intermediate 46

N-(4-bromopyridin-2-yl)-N-methylacetamide

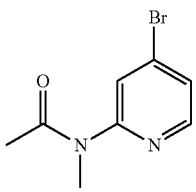

N-(4-Bromopyridin-2-yl)acetamide (for a preparation see Intermediate 45, 406 mg, 1.888 mmol) was dissolved in DMF and cooled to 0° C. Sodium hydride (60% w/w) (91 mg, 2.266 mmol) was added and the mixture was stirred for 15 minutes. Iodomethane (142 µl, 2.266 mmol) was added at rt and the reaction was stirred for 2 h. Water was added and the product was extracted with diethyl ether (×4). The combined organics were evaporated to leave a residue which was purified by silica gel column chromatography (50-100% EtOAc/cyclohexane). Fractions containing product were combined and concentrated in vacuo to give the title compound as a colourless oil (252 mg, 1.100 mmol, 58.3% yield). LCMS (2 min, High pH): Rt=0.69 min, MH$^+$ 229/231

Intermediate 47

N-methyl-N-(4-(4,4,5,5-tetramethyl-1,3,2-dioxaborolan-2-yl)pyridin-2-yl)acetamide

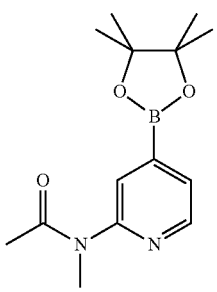 [SMILES: CC(=O)N(C)c1cc(B2OC(C)(C)C(C)(C)O2)ccn1]

A mixture of N-(4-bromopyridin-2-yl)-N-methylacetamide (for a preparation see Intermediate 46, 248 mg, 1.083 mmol), bis(pinacolato)diboron (779 mg, 3.07 mmol), PdCl$_2$(dppf) (79 mg, 0.108 mmol) and potassium acetate (319 mg, 3.25 mmol) in 1,4-dioxane (5 mL) was heated in a microwave at 100° C. for 30 min. The reaction was diluted with ethyl acetate and filtered through a Celite column. The filtrate was evaporated to give N-methyl-N-(4-(4,4,5,5-tetramethyl-1,3,2-dioxaborolan-2-yl)pyridin-2-yl)acetamide as a brown residue. Conversion was assumed to be 100% (299 mg, 1.083 mmol, 100% yield). The material was used crude in the next reaction without further purification.

LCMS (2 min, Formic): Rt=0.37 min, MH$^+$=195 (observed mass ion is consistent with hydrolysis to boronic acid under LCMS conditions).

Intermediate 48

4-bromo-3-(cyclopropylmethoxy)pyridine

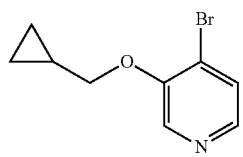 [SMILES: Brc1ccncc1OCC1CC1]

Sodium hydride (60% w/w) (110 mg, 2.76 mmol) was added to 4-bromopyridin-3-ol (400 mg, 2.299 mmol) in DMF (15 mL) at 0° C. and left stirring for 30 minutes. (Bromomethyl)cyclopropane (0.268 mL, 2.76 mmol) was added and the reaction was warmed to rt and stirred overnight. Water was added (40 mL) and the organic product was extracted with EtOAc and washed with brine, dried through a hydrophobic frit and concentrated in vacuo. The residue was purified by silica gel column chromatography [0-5% MeOH/NH$_3$ in DCM] and fractions containing product were combined and concentrated in vacuo to give 4-bromo-3-(cyclopropylmethoxy)pyridine (234 mg, 1.026 mmol, 44.6% yield) as a brown oil. LCMS (2 min, Formic): Rt=0.87 min, MH$^+$=228/230.

Intermediate 49

3-(cyclopropylmethoxy)-4-(4,4,5,5-tetramethyl-1,3,2-dioxaborolan-2-yl)pyridine

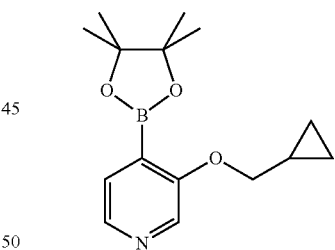

A mixture of 4-bromo-3-(cyclopropylmethoxy)pyridine (for a preparation see Intermediate 48, 228 mg, 1.000 mmol), bis(pinacolato)diboron (508 mg, 1.999 mmol), PdCl$_2$(dppf) (73.1 mg, 0.100 mmol) and potassium acetate (294 mg, 3.00 mmol) in 1,4-dioxane (5 mL) was heated in a microwave at 100° C. for 30 min. The reaction was diluted with ethyl acetate and filtered through a Celite column. The filtrate was evaporated to give 3-(cyclopropylmethoxy)-4-(4,4,5,5-tetramethyl-1,3,2-dioxaborolan-2-yl)pyridine as a brown residue. Conversion was assumed to be 100% (275 mg, 0.999 mmol, 100% yield). The material was used crude in the next reaction without further purification.

LCMS (2 min, Formic): Rt=0.35 min, MH$^+$ 194 (observed mass ion is consistent with hydrolysis to boronic acid under LCMS conditions).

Intermediate 50

7-(3,4-dimethoxyphenyl)-4-oxo-4,5-dihydrofuro[2,3-d]pyridazine-2-carboxylic acid

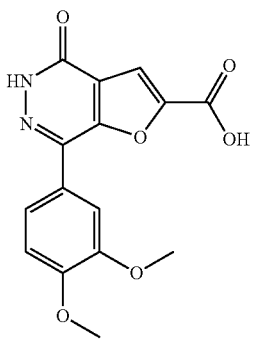 [SMILES: COc1ccc(-c2n[nH]c(=O)c3cc(C(=O)O)oc23)cc1OC]

To 7-chloro-4-oxo-4,5-dihydrofuro[2,3-d]pyridazine-2-carboxylic acid (Peakdale) (220 mg, 1.025 mmol) and (3,4-dimethoxyphenyl)boronic acid (187 mg, 1.025 mmol) in 1,4-dioxane (3 mL) and water (1.5 mL) was added sodium carbonate (435 mg, 4.10 mmol) and tetrakis(triphenylphosphine)palladium(0) (110 mg, 0.095 mmol). The reaction was heated in the microwave at 80° C. for 2 hours and at 100° C. for a further 2 hours. The solvent was removed and the residue was suspended in DMSO, filtered and purified by MDAP. Appropriate fractions were combined and the solvent removed to give 7-(3,4-dimethoxyphenyl)-4-oxo-4,5-dihydrofuro[2,3-d]pyridazine-2-carboxylic acid (25 mg, 7%) as a yellow solid.

LCMS (2 min, Formic): Rt=0.57 min, MH$^+$ 317

The filter cake was washed with DCM and subsequently washed with 1M HCl and dried under suction filtration to give 7-(3,4-dimethoxyphenyl)-4-oxo-4,5-dihydrofuro[2,3-d]pyridazine-2-carboxylic acid (79 mg, 24%) as a yellow solid.

LCMS (2 min, Formic): Rt=0.57 min, MH$^+$ 317

Intermediate 51

7-(3,4-dimethoxyphenyl)-2-(4-(methylsulfonyl)piperazine-1-carbonyl)furo[2,3-d]pyridazin-4(5H)-one

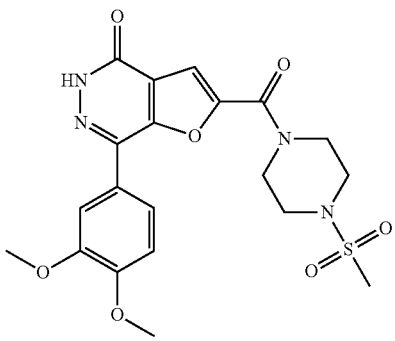 [SMILES: COc1ccc(-c2n[nH]c(=O)c3cc(C(=O)N4CCN(S(C)(=O)=O)CC4)oc23)cc1OC]

To 7-(3,4-dimethoxyphenyl)-4-oxo-4,5-dihydrofuro[2,3-d]pyridazine-2-carboxylic acid (for a preparation see Intermediate 50, 25 mg, 0.079 mmol) in NMP (2 mL) was added 1H-benzo[d][1,2,3]triazol-1-ol hydrate (24.21 mg, 0.158 mmol), 2-(3H-[1,2,3]triazolo[4,5-b]pyridin-3-yl)-1,1,3,3-tetramethylisouronium hexafluorophosphate(V) (60.1 mg, 0.158 mmol) and triethylamine (0.033 mL, 0.237 mmol), followed by 1-(methylsulfonyl)piperazine (19.47 mg, 0.119 mmol). The mixture was stirred overnight under nitrogen at room temperature. The reaction mixture was purified by MDAP. Appropriate fractions were combined and the solvent removed to give 7-(3,4-dimethoxyphenyl)-2-(4-(methylsulfonyl)piperazine-1-carbonyl)furo[2,3-d]pyridazin-4(5H)-one (45 mg, >100%) as an off white solid. LCMS (2 min, Formic): Rt=0.7 min, MH$^+$ 463

Intermediate 52

7-(3,4-dimethoxyphenyl)-5-methyl-2-(4-(methylsulfonyl)piperazine-1-carbonyl)furo[2,3-d]pyridazin-4(5H)-one

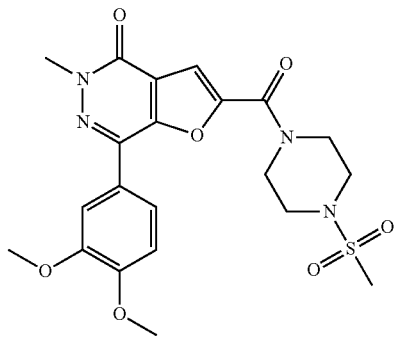 [SMILES: COc1ccc(-c2nn(C)c(=O)c3cc(C(=O)N4CCN(S(C)(=O)=O)CC4)oc23)cc1OC]

To 7-(3,4-dimethoxyphenyl)-2-(4-(methylsulfonyl)piperazine-1-carbonyl)furo[2,3-d]pyridazin-4(5H)-one (for a preparation see Intermediate 51, 0.062 mL, 0.097 mmol) in DMF (3 mL) was added sodium hydride (60% dispersion in mineral oil) (7.78 mg, 0.195 mmol) and methyl iodide (0.030 mL, 0.487 mmol). The mixture was stirred overnight under nitrogen at room temperature. Water was added and the solvent removed. The residue was dissolved in DCM/water and partitioned (×2). The combined organic layers were washed with water and the solvent removed to give a yellow solid. This was purified by MDAP. Appropriate fractions were combined, evaporated and dried under high vacuum for 3 hours to give 7-(3,4-dimethoxyphenyl)-5-methyl-2-(4-(methylsulfonyl)piperazine-1-carbonyl)furo[2,3-d]pyridazin-4(5H)-one (18 mg, 39%).

LCMS (2 min, Formic): Rt=0.8 min, MH⁺ 477

Intermediate 53 tert-butyl 4-((7-bromo-5-methyl-4-oxo-4,5-dihydrofuro[3,2-c]pyridin-2-yl)methyl)-1,4-diazepane-1-carboxylate

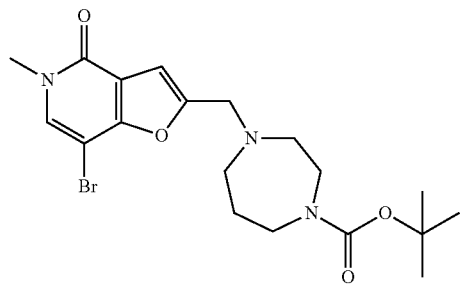 [SMILES: Cn1cc(Br)c2oc(CN3CCCN(C(=O)OC(C)(C)C)CC3)cc2c1=O]

7-Bromo-5-methyl-4-oxo-4,5-dihydrofuro[3,2-c]pyridine-2-carbaldehyde (for a preparation see Intermediate 2, 500 mg, 1.953 mmol), tert-butyl 1,4-diazepane-1-carboxylate (782 mg, 3.91 mmol) and AcOH (0.011 mL, 0.195 mmol) in MeOH (30 mL) was stirred at 25° C. for 3 hrs. Sodium cyanoborohydride (245 mg, 3.91 mmol) was added and the reaction was stirred overnight. Water (60 mL) was added and the mixture was extracted with DCM (2×100 mL). The organic phase was washed with brine (100 mL) and concentrated in vacuo and purified by chromatography on silica gel (DCM:MeOH=8:1) to obtain tert-butyl 4-((7-bromo-5-methyl-4-oxo-4,5-dihydrofuro[3,2-c]pyridin-2-yl)methyl)-1,4-diazepane-1-carboxylate (500 mg, 1.136 mmol, 58.2% yield) as a yellow oil.

LCMS: MH⁺ 440/442

Intermediate 54

4-bromo-N-(pyridin-2-ylmethyl)pyridin-2-amine

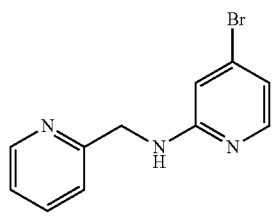 [SMILES: Brc1ccnc(NCc2ccccn2)c1]

To a solution of 4-bromo-2-fluoropyridine (3.58 g, 20.34 mmol) in NMP (17 mL) was added pyridin-2-ylmethanamine (2 g, 18.49 mmol). The reaction mixture was stirred at 100° C. for 1 h then cooled to rt and partitioned between DCM (100 mL) and water (100 mL). The organic phase was washed with saturated brine (50 mL), dried over sodium sulphate and concentrated in vacuo to give the title compound (6 g, 3.25 mmol, 17.56% yield) as a yellow oil (containing NMP) that was used without further purification on the next step. LCMS: MH⁺ 264.

Intermediate 55

N-(Pyridin-2-ylmethyl)-4-(4,4,5,5-tetramethyl-1,3,2-dioxaborolan-2-yl)pyridin-2-amine

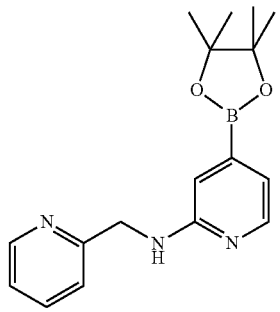 [SMILES: CC1(C)OB(c2ccnc(NCc3ccccn3)c2)OC1(C)C]

To a suspension of crude 4-bromo-N-(pyridin-2-ylmethyl)pyridin-2-amine (for a preparation see Intermediate 54, 5.8 g, 3.07 mmol), 4,4',4',5,5,5',5'-octamethyl-2,2'-bi(1,3,2-dioxaborolane) (3.90 g, 15.37 mmol) and potassium acetate (0.905 g, 9.22 mmol) in 1,4-dioxane (30 mL) stirred under nitrogen at rt, was added 1,1'-bis(diphenylphosphino)ferrocene-palladium(II) dichloride-DCM complex (0.251 g, 0.307 mmol). The reaction mixture was stirred at 100° C. for 2 h. The reaction mixture was cooled to rt and filtered. The filtrate was concentrated and the residue was purified by combi-flash chromatography on silica gel (40 g) eluting with EtOAc/petroleum (0-100% over 40 min, 100% over 40 min) to give a crude product as a brown solid. The solid was further purified by re-crystallization with ether/hexane (1:30, 1 mL/30 mL) to give the title compound (700 mg, 2.249 mmol, 73.2% yield) as a brown solid.

LCMS: M/Z 230 indicates hydrolysis of boronate ester under LCMS conditions.

¹H NMR (400 MHz, CDCl₃) δ-ppm 8.56 (1H, d), 8.14 (1H, d), 7.61 (1H, t), 7.31 (1H, d), 7.17 (1H, t), 6.89 (2H, m), 6.67 (1H, br.s), 4.69 (2H, d), 1.31 (12H, s).

Intermediate 56 tert-butyl 4-((5-methyl-4-oxo-7-(2-((pyridin-2-ylmethyl)amino)pyridin-4-yl)-4,5-dihydrofuro[3,2-c]pyridin-2-yl)methyl)-1,4-diazepane-1-carboxylate

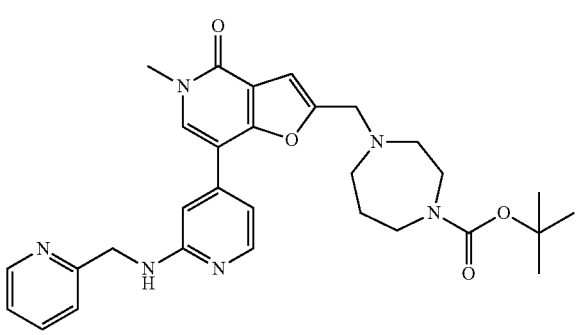 [SMILES: Cn1cc(-c2ccnc(NCc3ccccn3)c2)c2oc(CN3CCCN(C(=O)OC(C)(C)C)CC3)cc2c1=O]

To a solution of tert-butyl 4-((7-bromo-5-methyl-4-oxo-4,5-dihydrofuro[3,2-c]pyridin-2-yl)methyl)-1,4-diazepane-1-carboxylate (for a preparation see Intermediate 53, 400 mg, 0.908 mmol) in 1,4-dioxane (24 mL) was added N-(pyridin-2-ylmethyl)-4-(4,4,5,5-tetramethyl-1,3,2-dioxaborolan-2-yl)pyridin-2-amine (for a preparation see Intermediate 55, 424 mg, 1.363 mmol) and Pd(Ph$_3$P)$_4$ (52.5 mg, 0.045 mmol). The reaction was evacuated and purged with nitrogen, followed by addition of Cs$_2$CO$_3$ (592 mg, 1.817 mmol) and water (6 mL). The mixture was heated to 100° C. overnight. The reaction mixture was cooled to rt. The organic layer was removed and the aqueous layer was extracted with EtOAc (3×60 mL). The combined organic extracts were washed with brine (100 mL) and concentrated in vacuo. The crude product was purified by chromatography on silica gel (DCM:MeOH=8:1) to give tert-butyl 4-((5-methyl-4-oxo-7-(2-((pyridin-2-ylmethyl)amino)pyridin-4-yl)-4,5-dihydrofuro[3,2-c]pyridin-2-yl)methyl)-1,4-diazepane-1-carboxylate (220 mg, 0.404 mmol, 44.5% yield) as an brown oil. LCMS: MH$^+$ 545

Intermediate 57

1-(2-((4-bromopyridin-2-yl)oxy)ethyl)pyrrolidin-2-one

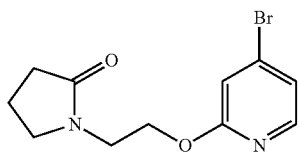 [SMILES: O=C1CCCN1CCOc1cc(Br)ccn1]

A stirred suspension of 1-(2-hydroxyethyl)pyrrolidin-2-one (0.324 mL, 2.87 mmol), triphenylphosphine (904 mg, 3.45 mmol) and 4-bromopyridin-2-ol (500 mg, 2.87 mmol) in THF (10 mL) was flushed with nitrogen and cooled in an ice bath for 15 min before the addition of DIAD (0.670 mL, 3.45 mmol) portion-wise. The mixture was left to stir for 1 h. The mixture was diluted with EtOAc (20 mL) and water (20 mL). Two layers separated and the aqueous layer was further extracted with EtOAc (2×20 mL). The organic extracts were evaporated to dryness and the remaining yellow solid was dissolved in DCM and purified by chromatography on silica gel (100 g) eluting with a gradient of 5% MeOH in EtOAc. Appropriate fractions were combined and reduced in vacuo to give 1-(2-((4-bromopyridin-2-yl)oxy)ethyl)pyrrolidin-2-one as a clear oil (490 mg, 59.8%).
LCMS (2 min, Formic): Rt=0.82 min, MH$^+$ 285/287

Intermediate 58

1-(2-((4-(4,4,5,5-Tetramethyl-1,3,2-dioxaborolan-2-yl)pyridin-2-yl)oxy)ethyl)pyrrolidin-2-one

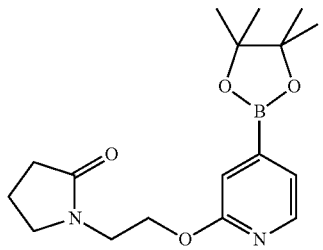 [SMILES: CC1(C)OB(c2ccnc(OCCN3CCCC3=O)c2)OC1(C)C]

To a stirred suspension of 1-(2-((4-bromopyridin-2-yl)oxy)ethyl)pyrrolidin-2-one (for a preparation see Intermediate 57, 490 mg, 1.718 mmol), 4,4,4',4',5,5,5',5'-octamethyl-2,2'-bi(1,3,2-dioxaborolane) (873 mg, 3.44 mmol) and potassium acetate (506 mg, 5.16 mmol) was added PdCl$_2$(dppf) (126 mg, 0.172 mmol). The mixture was placed in a microwave vial and heated in a microwave at 100° for 1 h. The mixture was diluted in ethyl acetate and filtered through a Celite cartridge (10 g). The solvent was evaporated to give a brown oil (1.35 g, 4.06 mmol, 236%). This crude material was used in the next step without further purification: 100% conversion assumed therefore maximum purity of crude material is 42%.
LCMS (2 min, Formic): Rt=0.46 min, MH$^+$=251 consistent with hydrolysis to boronic acid under LCMS conditions
$^1$H NMR (400 MHz, CDCl$_3$) δ-ppm 8.15 (1H, d), 7.19 (1H, d), 7.12 (1H, s), 4.42 (2H, t), 3.67 (2H, t), 3.53 (2H, t), 2.38 (2H, t), 2.00 (2H, m), 1.34 (12H, s).

Intermediate 59

N-(5-iodo-4-methoxy-1-methyl-6-oxo-1,6-dihydro-[3,4'-bipyridin]-2'-yl)acetamide

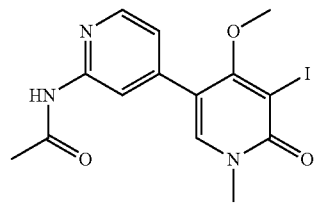 [SMILES: COc1c(-c2ccnc(NC(C)=O)c2)cn(C)c(=O)c1I]

A solution of TPPTS (0.022 g, 0.039 mmol), 3,5-diiodo-4-methoxy-1-methylpyridin-2(1H)-one (for a preparation see Intermediate 18, 0.2 g, 0.512 mmol), N-(4-(4,4,5,5-tetramethyl-1,3,2-dioxaborolan-2-yl)pyridin-2-yl)acetamide (Milestone Pharma Tech) (0.174 g, 0.665 mmol), and diacetoxypalladium (6.89 mg, 0.031 mmol) in acetonitrile (2 mL) and water (0.667 mL) was treated with DIPEA (0.116 mL, 0.665 mmol). The reaction mixture was heated at 60° C. under nitrogen for 16 h.

The mixture was concentrated under reduced pressure, suspended in DCM (insoluble) and purified by chromatography on silica gel (100 g) eluting with a 0 to 20% 2N ammonia in MeOH/DCM gradient. Fractions containing product were combined and concentrated under reduced pressure to give material of <70% purity. The crude material was dissolved in MeOH and loaded onto a MeOH-preconditioned SCX column (10 g) which was eluted with MeOH followed by 2N ammonia in MeOH. UV active material eluted in the first fraction of the ammonia wash, this was concentrated under reduced pressure to give N-(5-iodo-4-methoxy-1-methyl-6-oxo-1,6-dihydro-[3,4'-bipyridin]-2'-yl)acetamide (80 mg, 39%) as a clear, colourless gum.

LCMS (2 min, High pH): Rt=0.67 min, MH+ 400

Intermediate 60

N-(5-bromopyridin-3-yl)acetamide

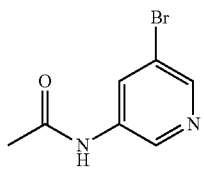

To a stirred suspension of 5-bromopyridin-3-amine (500 mg, 2.89 mmol) in DCM (10 mL), was added pyridine (0.467 mL, 5.78 mmol). The mixture was stirred for 20 min and acetyl chloride (0.236 mL, 3.32 mmol) was added. The mixture was stirred for 3 h.

The mixture was diluted with water (20 mL) and DCM (20 mL). The layers were separated and the aqueous layer was re-extracted with DCM (3×20 mL). The combined organics were washed with brine (20 mL), dried using a hydrophobic frit and concentrated in vacuo to give N-(5-bromopyridin-3-yl)acetamide as an orange solid (563 mg, 91%).

LCMS (2 min, Formic): Rt=0.59 min, MH+ 215/217

Intermediate 61

N-(5-(4,4,5,5-tetramethyl-1,3,2-dioxaborolan-2-yl)pyridin-3-yl)acetamide

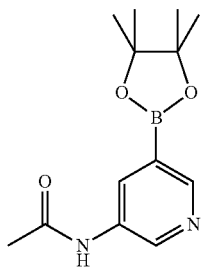 [SMILES: CC(=O)Nc1cncc(B2OC(C)(C)C(C)(C)O2)c1]

To a suspension of N-(5-bromopyridin-3-yl)acetamide (for a preparation see Intermediate 60, 563 mg, 2.62 mmol), 4,4,4',4',5,5,5',5'-octamethyl-2,2'-bi(1,3,2-dioxaborolane) (1330 mg, 5.24 mmol) and potassium acetate (771 mg, 7.85 mmol) in 1,4-dioxane (8 mL) in a microwave vial, was added PdCl$_2$(dppf) (192 mg, 0.262 mmol). The vial was sealed and the mixture was heated in a microwave at 100° C. for 1 h. The mixture was dissolved in ethyl acetate and filtered through a Celite cartridge (10 g). The solvent was evaporated under reduced pressure to give N-(5-(4,4,5,5-tetramethyl-1,3,2-dioxaborolan-2-yl)pyridin-3-yl)acetamide as a brown oil (1.77 g, 258%). This crude material was used in the next step without further purification: 100% conversion assumed therefore maximum purity of crude material is 39%. LCMS (2 min, High pH): Rt=0.47 min, MH+ 263

Intermediate 62 tert-butyl (4-(5-methyl-2-((4-(methylsulfonyl)piperazin-1-yl)methyl)-4-oxo-4,5-dihydrofuro[3,2-c]pyridin-7-yl)pyridin-3-yl)carbamate

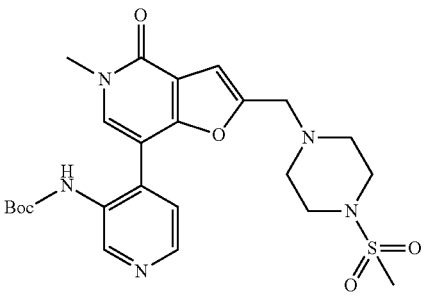 [SMILES: Cn1cc(-c2ccncc2NC(=O)OC(C)(C)C)c2oc(CN3CCN(S(C)(=O)=O)CC3)cc2c1=O]

(3-((tert-Butoxycarbonyl)amino)pyridin-4-yl)boronic acid (Peptech) (100 mg, 0.420 mmol), 7-bromo-5-methyl-2-((4-(methylsulfonyl)piperazin-1-yl)methyl)furo[3,2-c]pyridin-4(5H)-one (for a preparation see Intermediate 3, 170 mg, 0.420 mmol), tetrakis(triphenylphosphine)palladium(0) (24.27 mg, 0.021 mmol) and aqueous sodium carbonate (1.680 mL, 3.36 mmol) were mixed in 1,2-DME (3 mL) and heated in the microwave for 2 hours at 120° C. The reaction was diluted with ethyl acetate and water and filtered. The organic layer was separated and concentrated in vacuo. The resulting residue was purified by chromatography on silica gel (25 g) eluting with 0-5% MeOH in DCM. Appropriate fractions were combined and concentrated in vacuo to give tert-butyl (4-(5-methyl-2-((4-(methylsulfonyl)piperazin-1-yl)methyl)-4-oxo-4,5-dihydrofuro[3,2-c]pyridin-7-yl)pyridin-3-yl)carbamate (8 mg, 0.015 mmol, 3.68% yield) as a white solid.

LCMS (2 min, Formic): Rt=0.55 min, MH+ 518

Further fractions containing product were combined and concentrated in vacuo to give tert-butyl (4-(5-methyl-2-((4-(methylsulfonyl)piperazin-1-yl)methyl)-4-oxo-4,5-dihydrofuro[3,2-c]pyridin-7-yl)pyridin-3-yl)carbamate (74 mg, 0.143 mmol, 34.0% yield) as a white solid.

LCMS (2 min, Formic): Rt=0.55 min, MH+ 518

Intermediate 63

7-(3-aminopyridin-4-yl)-5-methyl-2-((4-(methylsulfonyl)piperazin-1-yl)methyl)furo[3,2-c]pyridin-4(5H)-one

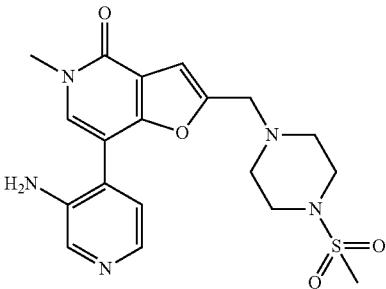 [SMILES: Cn1cc(-c2ccncc2N)c2oc(CN3CCN(S(C)(=O)=O)CC3)cc2c1=O]

tert-Butyl (4-(5-methyl-2-((4-(methylsulfonyl)piperazin-1-yl)methyl)-4-oxo-4,5-dihydrofuro[3,2-c]pyridin-7-yl)pyridin-3-yl)carbamate (for a preparation see Intermediate 62, 74 mg, 0.143 mmol) was suspended in DCM (2 mL) and TFA (2 mL, 26.0 mmol) was added. The resulting solution was stirred at rt for 30 min. The solvent was evaporated and the resulting yellow solid was dissolved in MeOH and eluted through an aminopropyl cartridge (50 g) with MeOH. The fractions were concentrated in vacuo to give 7-(3-aminopyridin-4-yl)-5-methyl-2-((4-(methylsulfonyl)piperazin-1-yl)methyl)furo[3,2-c]pyridin-4(5H)-one (72 mg, 0.138 mmol, 97% yield) as a yellow solid.

LCMS (2 min, Formic): Rt=0.33 min, MH+ 418

Intermediate 64

(R)-tert-butyl (4-(5-methyl-2-((2-methyl-4-(methylsulfonyl)piperazin-1-yl)methyl)-4-oxo-4,5-dihydrofuro[3,2-c]pyridin-7-yl)pyridin-3-yl)carbamate

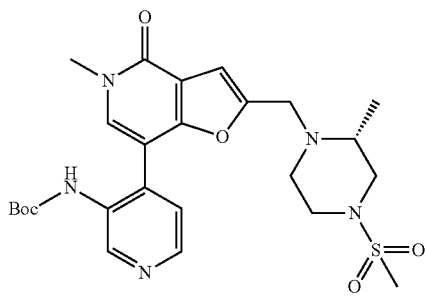 [SMILES: C[C@@H]1CN(S(C)(=O)=O)CCN1Cc1cc2c(=O)n(C)cc(-c3ccncc3NC(=O)OC(C)(C)C)c2o1]

(3-((tert-Butoxycarbonyl)amino)pyridin-4-yl)boronic acid (Peptech) (100 mg, 0.420 mmol), (R)-7-bromo-5-methyl-2-((2-methyl-4-(methylsulfonyl)piperazin-1-yl)methyl)furo[3,2-c]pyridin-4(5H)-one (for a preparation see Intermediate 5, 176 mg, 0.420 mmol), tetrakis(triphenylphosphine)palladium(0) (24.27 mg, 0.021 mmol) and aqueous sodium carbonate (1.680 mL, 3.36 mmol) were mixed in 1,2-DME (3 mL) and heated in the microwave for 2 hours at 120° C. The reaction was diluted with ethyl acetate and water. The organic layer was separated and concentrated in vacuo. The residue was purified by column chromatography on silica gel (25 g) eluting with 0-5% MeOH in DCM. Fractions containing product were combined and concentrated in vacuo to give (R)-tert-butyl (4-(5-methyl-2-((2-methyl-4-(methylsulfonyl)piperazin-1-yl)methyl)-4-oxo-4,5-dihydrofuro[3,2-c]pyridin-7-yl)pyridin-3-yl)carbamate (87 mg, 0.164 mmol, 39.0% yield) as a white solid. LCMS (2 min, Formic): Rt=0.56 min, MH+ 532

Intermediate 65

(R)-7-(3-aminopyridin-4-yl)-5-methyl-2-((2-methyl-4-(methylsulfonyl)piperazin-1-yl)methyl)furo[3,2-c]pyridin-4(5H)-one

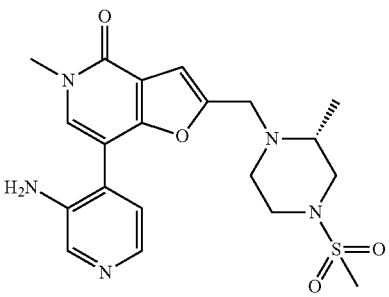

(R)-tert-butyl (4-(5-methyl-2-((2-methyl-4-(methylsulfonyl)piperazin-1-yl)methyl)-4-oxo-4,5-dihydrofuro[3,2-c]pyridin-7-yl)pyridin-3-yl)carbamate (for a preparation see Intermediate 64, 87 mg, 0.164 mmol) was suspended in DCM (2 mL) and TFA (2 mL, 26.0 mmol) was added. The resulting solution was stirred at rt for 30 min. The solvent was evaporated and the resulting yellow solid was dissolved in MeOH and eluted through an aminopropyl cartridge (50 g) with MeOH. The solvent was concentrated in vacuo to give (R)-7-(3-aminopyridin-4-yl)-5-methyl-2-((2-methyl-4-(methylsulfonyl)piperazin-1-yl)methyl)furo[3,2-c]pyridin-4(5H)-one (81 mg, 0.160 mmol, 97% yield) as a yellow solid. LCMS (2 min, Formic): Rt=0.34 min, MH+ 432.

Intermediate 66

Oxetan-2-ylmethyl methanesulfonate

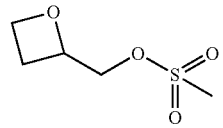

To a solution of oxetan-2-ylmethanol (0.370 mL, 4.54 mmol, ex.TCI) in DCM (15 mL) at 0° C., was added triethylamine (1.898 mL, 13.62 mmol) and methanesulfonyl chloride (0.387 mL, 4.99 mmol). The mixture was stirred at 0° C. for 1 h. The mixture was diluted with water (20 mL) and partitioned with DCM (20 mL). The aqueous phase was re-extracted with DCM (3×20 mL). The organic phase was dried using a hydrophobic frit and concentrated in vacuo to give a yellow oil (572 mg, 76%) which was used crude in the next step.

Intermediate 67

4-Bromo-3-(oxetan-2-ylmethoxy)pyridine

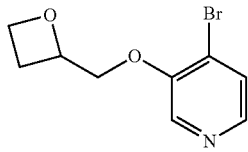 [SMILES: Brc1ccncc1OCC1CCO1]

To a stirred suspension of 4-bromopyridin-3-ol (300 mg, 1.724 mmol) in DMF (11 mL) was added sodium hydride (83 mg, 60% w/w, 2.069 mmol). This was cooled to 0° C. and left to stir for 30 min after which crude oxetan-2-ylmethyl methanesulfonate (for a preparation see Intermediate 66, 344 mg, 2.069 mmol) was added and the mixture was again left to stir for 4 h. All starting material remained so additional sodium hydride (60%) (83 mg, 2.069 mmol) was added and the mixture was cooled to 0° C. for 30 min before the addition of further crude oxetan-2-ylmethyl methanesulfonate (228 mg). The reaction was left to stir over night, then heated to 60° C. and stirred overnight. The mixture was diluted with EtOAc (20 mL) and partitioned with water (20 mL). Two layers separated and the aqueous phase was re-extracted with EtOAc (3×20 mL). The organic phase was dried using a hydrophobic frit and concentrated in vacuo to give a yellow liquid. This was diluted with 10% LiCl solution and partitioned with EtOAc (20 mL). Two layers separated and the aqueous phase was re-extracted with EtOAc (3×20 mL). The organic phase was dried using a hydrophobic frit and concentrated in vacuo to give 4-bromo-3-(oxetan-2-ylmethoxy)pyridine as a yellow oil (708 mg, 168%). LCMS (2 min, Formic): Rt=0.60 min, MH$^+$ 244/246. Purity estimated at 59.5% and material was used crude in the next step.

Intermediate 68

(R)-4-bromo-3-(oxiran-2-ylmethoxy)pyridine

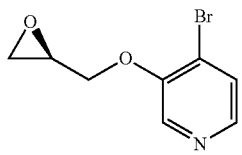 [SMILES: Brc1ccncc1OC[C@H]1CO1]

4-Bromopyridin-3-ol (36.9 g, 212 mmol) was taken up in DMF (667 mL) under nitrogen. Cesium carbonate (189 g, 579 mmol) was added in one portion and the mixture stirred for 10 min. (R)-oxiran-2-ylmethyl 3-nitrobenzenesulfonate (50 g, 193 mmol) was added over ~10 min and the reaction left to stir at room temperature overnight. The reaction was cooled in an ice-bath and water (1000 mL) was added slowly (exothermic). The solution was extracted with EtOAc (2×500 mL). The aqueous layer was diluted with brine (1000 mL) and then re-extracted with EtOAc (2×1000 mL). The combined organics were washed with water (2×2000 mL) and 5% LiCl (2000 mL) and then dried with Na$_2$SO$_4$, filtered and concentrated in vacuo to give (R)-4-bromo-3-(oxiran-2-ylmethoxy)pyridine (39.4 g) as an orange oil. $^1$H NMR (400 MHz, CDCl$_3$) δ-ppm 8.27 (1H, s), 8.10 (1H, d), 7.52 (1H, d), 4.44 (1H, dd) 4.15 (1H, dd), 3.43 (1H, m), 2.95 (1H, m), 2.87 (1H, dd). LCMS (2 min, Formic): Rt=0.60 min, MH$^+$ 230/232. The oil was taken up immediately into tBuOH (100 mL) for use in the next reaction.

Intermediate 69

(R)-4-Bromo-3-(oxetan-2-ylmethoxy)pyridine

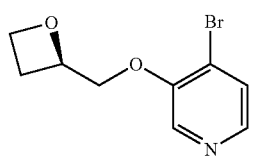 [SMILES: Brc1ccncc1OC[C@H]1CCO1]

Potassium tert-butoxide (26.2 g, 234 mmol) was taken up in tBuOH (450 mL) under nitrogen. Trimethylsulfoxonium iodide (34.3 g, 156 mmol) was added in one portion and the reaction mixture heated to 80° C. for 10 min then cooled to room temperature. (R)-4-bromo-3-(oxiran-2-ylmethoxy)pyridine (for a preparation see intermediate 68, 39.4 g, 171 mmol) was added as a solution in tBuOH (100 mL) and the mixture stirred at 60° C. for 4 h. Initially, a white suspension formed which went orange after addition of the oxirane. After 6 h the reaction was left to cool and stand at room temperature overnight. The reaction was concentrated to ~⅓ volume and partitioned between water (500 mL) and EtOAc (500 mL). The aqueous was re-extracted with EtOAc (3×500 mL). The combined organics were washed with water (1000 mL) and brine (1000 mL) and then dried with MgSO4, filtered and concentrated in vacuo to give (R)-4-bromo-3-(oxetan-2-ylmethoxy)pyridine (18.8 g) as an orange oil. $^1$H NMR (400 MHz, CDCl$_3$) δ-ppm 8.30 (1H, s), 8.09 (1H, d), 7.52 (1H, d), 5.17 (1H, m), 4.74 (2H, m) 4.34 (1H, dd), 4.25 (1H, dd), 2.85 (2H, m). LCMS (2 min, Formic): Rt=0.62 min, MH$^+$ 244/246.

Intermediate 70

4-bromo-3-(oxetan-3-ylmethoxy)pyridine

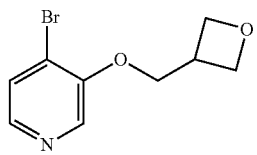 [SMILES: Brc1ccncc1OCC1COC1]

The title compound was prepared from 4-bromo-3-pyridinol and 3-(bromomethyl)oxetane in a manner similar to that described for Intermediate 48.

LCMS (2 min, Formic): Rt=0.57 min, MH$^+$=244/246.

Intermediate 71

3-(oxetan-3-ylmethoxy)-4-(4,4,5,5-tetramethyl-1,3,2-dioxaborolan-2-yl)pyridine

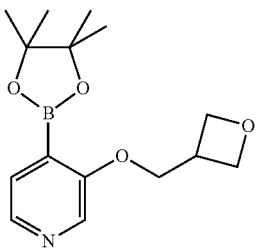 [SMILES: CC1(C)OB(c2ccncc2OCC2COC2)OC1(C)C]

To a suspension of 4-bromo-3-(oxetan-3-ylmethoxy)pyridine (for a preparation see Intermediate 70, 300 mg, 1.229 mmol), 4,4,4',4',5,5,5',5'-octamethyl-2,2'-bi(1,3,2-dioxaborolane) (624 mg, 2.458 mmol), potassium acetate (362 mg) in 1,4-dioxane (10 mL) in a microwave vial, was added PdCl$_2$(dppf) (90 mg). The vial was sealed and the mixture was heated in a Biotage initiator microwave at 100° C. for 1 h with normal absorption. Additional 4,4,4',4',5,5,5',5'-octamethyl-2,2'-bi(1,3,2-dioxaborolane) (624 mg), potassium acetate (362 mg) and PdCl$_2$(dppf) (90 mg) were added and the reaction was heated in the microwave for a further 1 h. The mixture was diluted with ethyl acetate and filtered through a celite cartridge (5 g). The solvent was reduced in vacuo to give a brown oil (1.72 g, 481%). This crude material was used in the next step without further purification: 100% conversion assumed therefore maximum purity of crude material was 21%.

Intermediate 72

4-bromo-3-((2,2-difluorocyclopropyl)methoxy)pyridine

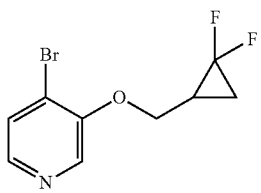 [SMILES: FC1(F)CC1COc1cnccc1Br]

The title compound was prepared from 4-bromo-3-pyridinol and 2-(bromomethyl)-1,1-difluorocyclopropane in a manner similar to that described for Intermediate 48.

LCMS (2 min, Formic): Rt=0.87 min, MH$^+$=264/266.

Intermediate 73

4-bromo-3-(2-methoxyethoxy)pyridine

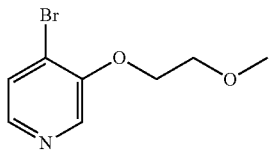

The title compound was prepared from 4-bromo-3-pyridinol and 1-bromo-2-methoxyethane in a manner similar to that described for Intermediate 48.

LCMS (2 min, Formic): Rt=0.61 min, MH$^+$=232/234.

Intermediate 74

3-(2-methoxyethoxy)-4-(4,4,5,5-tetramethyl-1,3,2-dioxaborolan-2-yl)pyridine

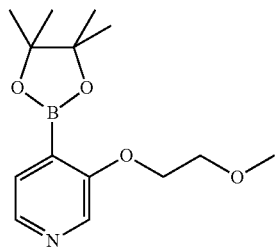

The title compound was prepared from Intermediate 73 in a manner similar to that described for Intermediate 71 and used crude in the next step.

Intermediate 75

4-bromo-3-((tetrahydrofuran-3-yl)methoxy)pyridine

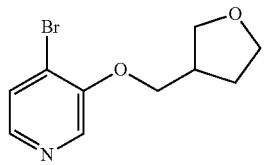 [SMILES: Brc1ccncc1OCC1CCOC1]

The title compound was prepared from 4-bromo-3-pyridinol and 3-(bromomethyl)tetrahydrofuran in a manner similar to that described for Intermediate 48.

LCMS (2 min, Formic): Rt=0.69 min, MH$^+$=258/260.

Intermediate 76

4-bromo-2-((tetrahydrofuran-3-yl)methoxy)pyridine

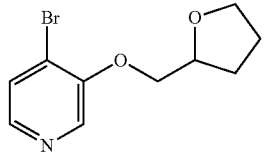 [SMILES: Brc1ccncc1OCC1CCCO1]

The title compound was prepared from 4-bromo-3-pyridinol and 2-(bromomethyl)tetrahydrofuran in a manner similar to that described for Intermediate 48.

LCMS (2 min, Formic): Rt=0.71 min, MH$^+$=258/260.

Intermediate 77

1-(2-methylbut-3-yn-2-yl)-4-(methylsulfonyl)piperazine

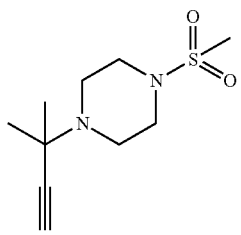

A mixture of 3-chloro-3-methylbut-1-yne (1 g, 9.75 mmol), copper (12 mg, 0.195 mmol) and copper (I) chloride (19 mg, 0.195 mmol) and 1-(methylsulfonyl)piperazine (4.32 g, 26.3 mmol) in diethyl ether (15 mL) and water (5 mL) was stirred at room temperature under nitrogen for 16 h. Water (150 mL) and diethyl ether (150 mL) were added and the organic layer was isolated. The aqueous layer was re-extracted with diethyl ether (2×150 mL). The combined organic layers were passed through a hydrophobic frit then concentrated under reduced pressure. The crude material was purified by silica gel column chromatography eluting with 80 to 100% EtOAc/cHex. Appropriate fractions were combined then concentrated under reduced pressure to give 1-(2-methylbut-3-yn-2-yl)-4-(methylsulfonyl)piperazine as a white solid (1.76 g, 78%). $^1$H NMR (400 MHz, DMSO-d$_6$) δ-ppm 3.22 (1H, s), 3.11 (4H, m), 2.86 (3H, s), 2.61 (4H, m), 1.31 (6H, s).

Intermediate 78

7-bromo-2-(hydroxymethyl)-5-methylfuro[3,2-c]pyridin-4(5H)-one

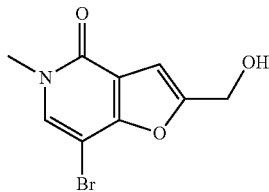

Sodium borohydride (2.216 g, 58.6 mmol) was added to a suspension of 7-bromo-5-methyl-4-oxo-4,5-dihydrofuro[3,2-c]pyridine-2-carbaldehyde (for a preparation see Intermediate 2, 5 g, 19.53 mmol) in ethanol (100 mL) at 0° C. The mixture was stirred for 2 h, then quenched by cautious dropwise addition of saturated ammonium chloride solution (100 mL). The resulting solid was collected by filtration and washed with water (2×30 mL) to give 7-bromo-2-(hydroxymethyl)-5-methylfuro[3,2-c]pyridin-4(5H)-one (3.3 g, 12.79 mmol, 65.5% yield) as a beige powder. $^1$H NMR (400 MHz, DMSO-d$_6$) δ-ppm 8.00 (1H, s), 6.86 (1H, s), 5.51 (1H, s), 4.53 (2H, s), 3.50 (3H, s). LCMS (2 min, Formic): Rt=0.58 min, MH$^+$ 258/260.

Intermediate 79

N-(4-bromopyridin-2-yl)acetamide

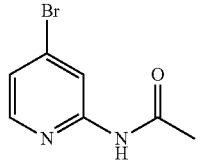

4-Bromopyridin-2-amine (10 g, 57.8 mmol) was taken up in DCM (75 mL) and pyridine (75 mL) under nitrogen. Acetic anhydride (8.18 mL, 87 mmol) was added and the reaction stirred at room temperature. The reaction was left to stand overnight and then concentrated in vacuo. The residue was dried in the vac oven to give N-(4-bromopyridin-2-yl)acetamide (12.4 g, 54.8 mmol, 95% yield) as a cream solid. $^1$H NMR (400 MHz, CDCl$_3$) δ-ppm 8.48 (1H, s), 8.14 (1H, br. s), 8.09 (1H, d), 7.23 (1H, dd), 2.23 (3H, s). LCMS (2 min, Formic): Rt=0.65 min, MH$^+$ 215/217.

Intermediate 80

N-(4-(2-(Hydroxymethyl)-5-methyl-4-oxo-4,5-dihydrofuro[3,2-c]pyridin-7-yl)pyridin-2-yl)acetamide

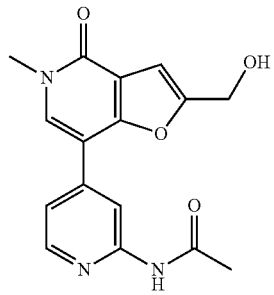 [SMILES: CC(=O)Nc1cc(-c2cn(C)c(=O)c3cc(CO)oc23)ccn1]

4,4,5,5-Tetramethyl-1,3,2-dioxaborolane (11.13 mL, 77 mmol) was added to a mixture of 7-bromo-2-(hydroxymethyl)-5-methylfuro[3,2-c]pyridin-4(5H)-one (for a preparation see Intermediate 78, 3.3 g, 12.79 mmol) and triethylamine (10.71 mL, 77 mmol) in 1,4-dioxane (20 mL) and the mixture was stirred for 5 min under nitrogen. Pd(PPh$_3$)$_4$ (1.478 g, 1.279 mmol) was added and the mixture heated to 100° C. for 18 h. The mixture was cooled in an ice bath, then isopropanol (20.00 mL) was added, initially very cautiously, followed by water (10 mL), potassium carbonate (5.30 g, 38.4 mmol), PEPPSI-SIPr (0.871 g, 1.279 mmol) and N-(4-bromopyridin-2-yl)acetamide (for a preparation see Intermediate 79, 3.02 g, 14.07 mmol). The mixture was heated to 80° C. for 2 h under nitrogen, then allowed to stand over the weekend. The mixture was diluted with ether (100 mL) and stirred for 10 min, then filtered and the solid was washed with water (50 mL) and dried under vacuum for 10 min to give the crude product. The resulting solid was heated in methanol (50 mL) to reflux, then cooled in an ice bath and the solid product collected by filtration to give N-(4-(2-(hydroxymethyl)-5-methyl-4-oxo-4,5-dihydrofuro[3,2-c]pyridin-7-yl)pyridin-2-yl)acetamide (2.76 g, 8.81 mmol, 68.9% yield) as a colourless solid. $^1$H NMR (400 MHz, DMSO-d$_6$) δ-ppm 10.53 (1H, s), 8.50 (1H, s), 8.38 (1H, d), 8.13 (1H, s), 7.48 (1H, m), 6.85 (1H, s), 5.46 (1H, m), 4.55 (2H, d), 3.61 (3H, s), 2.13 (3H, s). LCMS (2 min, Formic): Rt=0.55 min, MH$^+$ 314.

Intermediate 81

N-(4-(2-(Bromomethyl)-5-methyl-4-oxo-4,5-dihydrofuro[3,2-c]pyridin-7-yl)pyridin-2-yl)acetamide

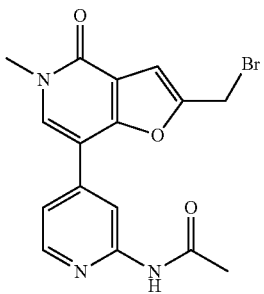 [SMILES: CC(=O)Nc1cc(-c2cn(C)c(=O)c3cc(CBr)oc23)ccn1]

N-(4-(2-(Hydroxymethyl)-5-methyl-4-oxo-4,5-dihydrofuro[3,2-c]pyridin-7-yl)pyridin-2-yl)acetamide (for a preparation see Intermediate 80, 1.4 g, 4.47 mmol) was suspended in 1,4-dioxane (50 mL) and heated to 60° C., then PBr$_3$ (2.107 mL, 22.34 mmol) was added in small portions and the suspension heated overnight at 60° C. The suspension was diluted with DCM (100 mL) and filtered, and the yellow solid washed with DCM and dried in the vacuum oven to give N-(4-(2-(bromomethyl)-5-methyl-4-oxo-4,5-dihydrofuro[3,2-c]pyridin-7-yl)pyridin-2-yl)acetamide (1.9 g, 5.05 mmol, 113% yield) that was used crude in the next step without further purification. $^1$H NMR (400 MHz, DMSO-d$_6$) δ-ppm 11.48 (1H, s), 8.48 (1H, s), 8.41 (1H, d), 8.31 (1H, s), 7.72 (1H, m), 7.17 (1H, s), 4.94 (2H, s), 3.64 (3H, s), 2.24 (3H, s).

Intermediate 82

N-(4-(2-(Chloromethyl)-5-methyl-4-oxo-4,5-dihydrofuro[3,2-c]pyridin-7-yl)pyridin-2-yl)acetamide

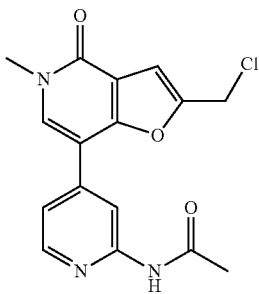 [SMILES: CC(=O)Nc1cc(-c2cn(C)c(=O)c3cc(CCl)oc23)ccn1]

Methanesulfonyl chloride (2.75 mL, 35.2 mmol) was added to a suspension of N-(4-(2-(hydroxymethyl)-5-methyl-4-oxo-4,5-dihydrofuro[3,2-c]pyridin-7-yl)pyridin-2-yl)acetamide (for a preparation see Intermediate 80, 2.76 g, 8.81 mmol) in DCM (20 mL) and Et$_3$N (5.53 mL, 39.6 mmol), and the mixture was stirred at room temperature overnight. The reaction mixture was filtered and the solid was washed with DCM (20 mL) the dried to give N-(4-(2-(hydroxymethyl)-5-methyl-4-oxo-4,5-dihydrofuro[3,2-c]pyridin-7-yl)pyridin-2-yl)acetamide (1.4 g, 4.47 mmol, 50.7% yield) recovered starting material. The filtrate was evaporated in vacuo and the residue was re-dissolved in a mixture of DCM (200 mL) and methanol (30 mL), washed with water (2×100 mL) and brine (100 mL), dried and evaporated to give a brown gum. This was purified by silica gel column chromatography eluting with 0-10% MeOH/DCM and product containing fractions were evaporated in vacuo to give N-(4-(2-(chloromethyl)-5-methyl-4-oxo-4,5-dihydrofuro[3,2-c]pyridin-7-yl)pyridin-2-yl)acetamide (0.20 g, 0.603 mmol, 6.84% yield) as a brown solid. $^1$H NMR (400 MHz, DMSO-d$_6$) δ-ppm 10.54 (1H, s), 8.54 (1H, s), 8.39 (1H, d), 8.21 (1H, s), 7.46 (1H, dd), 7.13 (1H, s), 4.97 (2H, s), 3.62 (3H, s), 2.13, (3H, s). The material was used in the next step without further purification.

Example 1

7-[3,4-bis(methyloxy)phenyl]-5-methyl-2-{[4-(methylsulfonyl)-1-piperazinyl]methyl}furo[3,2-c]pyridin-4(5H)-one

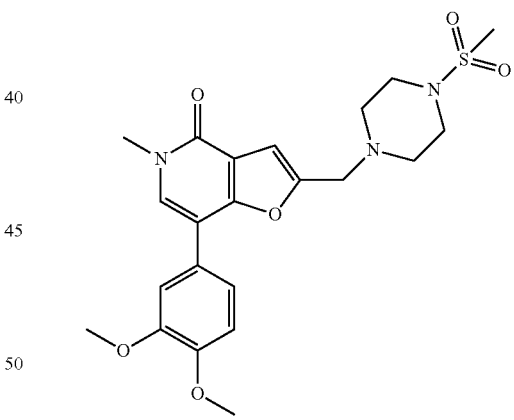

A mixture of 7-bromo-5-methyl-2-((4-(methylsulfonyl)piperazin-1-yl)methyl)furo[3,2-c]pyridin-4(5H)-one (for a preparation see Intermediate 3, 52 mg, 0.129 mmol), (3,4-dimethoxyphenyl)boronic acid (46.8 mg, 0.257 mmol), potassium carbonate (53.3 mg, 0.386 mmol) and bis(triphenylphosphine)palladium(II) chloride (9.03 mg, 0.013 mmol) in water (0.5 mL) and 1,2-DME (1.5 mL) was heated in a microwave at 120° C. for 20 minutes. The cooled reaction mixture was diluted with ethyl acetate and the solution dried over MgSO$_4$ and evaporated. The residue was purified via MDAP to give 7-[3,4-bis(methyloxy)phenyl]-5-methyl-2-{[4-(methylsulfonyl)-1-piperazinyl]methyl}furo[3,2-c]pyridin-4(5H)-one (31 mg, 52%) as a white solid.

LCMS (2 min, Formic): Rt=0.59 min, MH+ 462

Example 2

(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide

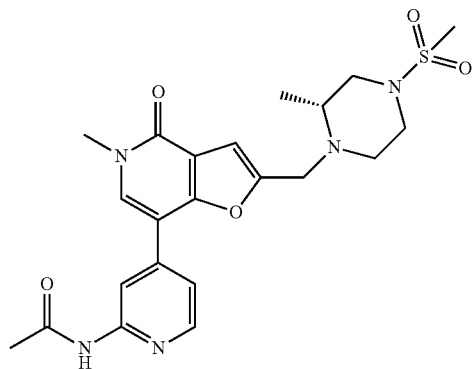 [SMILES: CC(=O)Nc1cc(-c2cn(C)c(=O)c3cc(CN4CCN(S(C)(=O)=O)C[C@H]4C)oc23)ccn1]

A mixture of (R)-7-bromo-5-methyl-2-((2-methyl-4-(methylsulfonyl)piperazin-1-yl)methyl)furo[3,2-c]pyridin-4(5H)-one (for a preparation see Intermediate 5, 345 mg, 0.825 mmol), N-(4-(4,4,5,5-tetramethyl-1,3,2-dioxaborolan-2-yl)pyridin-2-yl)acetamide (Milestone Pharma tech USA) (432 mg, 1.650 mmol), potassium carbonate (456 mg, 3.30 mmol) and bis(triphenylphosphine)palladium(II) chloride (57.9 mg, 0.082 mmol) in water (1.5 mL) and 1,2-DME (4.5 mL) was heated in a microwave at 120° C. for 20 minutes. The cooled reaction mixture was diluted with ethyl acetate and the solution dried over MgSO4 and evaporated. The residue was purified via MDAP to give (R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide (96 mg, 25%) as a viscous light yellow oil.

LCMS (2 min, Formic): Rt=0.46 min, MH+ 474

Example 3

7-(3-(benzyloxy)phenyl)-5-methyl-2-((4-(methylsulfonyl)piperazin-1-yl)methyl)furo[3,2-c]pyridin-4(5H)-one

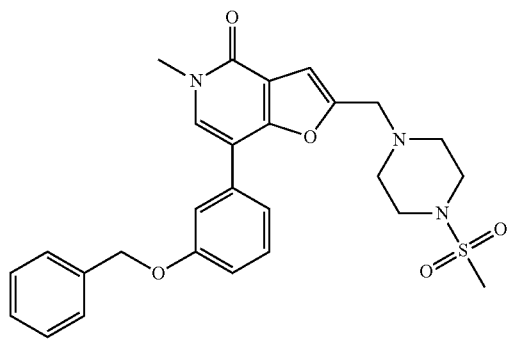 [SMILES: Cn1cc(-c2cccc(OCc3ccccc3)c2)c2oc(CN3CCN(S(C)(=O)=O)CC3)cc2c1=O]

A mixture of potassium carbonate (273 mg, 1.979 mmol), bis(triphenylphosphine)palladium(II) chloride (13.33 mg, 0.019 mmol), 7-bromo-5-methyl-2-((4-(methylsulfonyl)piperazin-1-yl)methyl)furo[3,2-c]pyridin-4(5H)-one (for a preparation see Intermediate 3, 160 mg, 0.396 mmol), 2-(3-(benzyloxy)phenyl)-4,4,5,5-tetramethyl-1,3,2-dioxaborolane (for a preparation see Intermediate 22, 310 mg, 0.999 mmol) in EtOH (2 mL) and toluene (2 mL) was heated in the microwave at 80° C. for 20 min. The cooled reaction mixture was diluted in 10 mL of ethyl acetate and evaporated. The residue was diluted with ethyl acetate (20 mL) and was washed with water (20 mL). The aqueous layer was extracted with ethyl acetate (2×20 mL). The combined organic layers were washed with brine (2×20 mL), dried and concentrated in vacuo. The residue was dissolved in MeOH, loaded onto a 20 g SCX column and eluted with MeOH followed by 2M methanolic ammonia. The basic fractions were concentrated in vacuo to give 7-(3-(benzyloxy)phenyl)-5-methyl-2-((4-(methylsulfonyl)piperazin-1-yl)methyl)furo[3,2-c]pyridin-4(5H)-one (15 mg, 7%) as a black gum.

LCMS (2 min, High pH): Rt=1.10 min, MH+ 508,

Example 4

7-(3-(benzylamino)phenyl)-5-methyl-2-((4-(methylsulfonyl)piperazin-1-yl)methyl)furo[3,2-c]pyridin-4(5H)-one

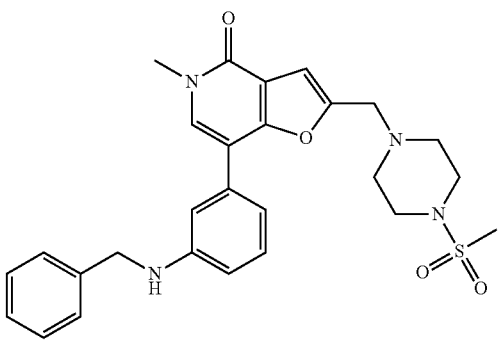 [SMILES: Cn1cc(-c2cccc(NCc3ccccc3)c2)c2oc(CN3CCN(S(C)(=O)=O)CC3)cc2c1=O]

A mixture of 7-bromo-5-methyl-2-((4-(methylsulfonyl)piperazin-1-yl)methyl)furo[3,2-c]pyridin-4(5H)-one (for a preparation see Intermediate 3, 85.2 mg, 0.211 mmol), N-benzyl-3-(4,4,5,5-tetramethyl-1,3,2-dioxaborolan-2-yl)aniline (for a preparation see Intermediate 24, 102.1 mg, 0.330 mmol), potassium carbonate (146.7 mg, 1.061 mmol), trans-dichloro(triphenylphosphine)palladium(II) (7.7 mg, 10.97 μmol) in EtOH (2 mL) and toluene (2 mL) was heated with stirring in a sealed vial in a microwave reactor for 20 min at 80° C., and then at 100° C. for a further 20 min. The solvents were evaporated under a stream of nitrogen. The solid was washed with sodium bicarbonate solution (5 mL) and extracted with DCM (4×5 mL). The DCM was evaporated. The brown solid residue was purified by MDAP. The appropriate fractions were collected and evaporated under a stream of nitrogen to give 7-(3-(benzylamino)phenyl)-5-methyl-2-((4-(methylsulfonyl)piperazin-1-yl)methyl)furo[3,2-c]pyridin-4(5H)-one (18.3 mg, 17%) as a pale brown gum.

LCMS (2 min, High pH): Rt=1.04 min, MH$^+$=507

Example 5

2-(((2-aminoethyl)amino)methyl)-7-(3,4-dimethoxyphenyl)-5-methylfuro[3,2-c]pyridin-4(5H)-one dihydrochloride

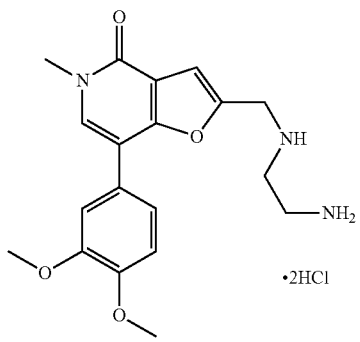 [SMILES: COc1ccc(-c2cn(C)c(=O)c3cc(CNCCN)oc23)cc1OC]

•2HCl tert-Butyl(2-(((7-(3,4-dimethoxyphenyl)-5-methyl-4-oxo-4,5-dihydrofuro[3,2-c]pyridin-2-yl)methyl)amino)ethyl)carbamate (for a preparation see Intermediate 7, 25 mg, 0.055 mmol) was dissolved in EtOH (2 mL) and HCl (4M in 1,4-dioxane) (2 mL, 8.00 mmol) was added. The reaction was left stirring at room temperature for 1 hour yielding a white precipitate. The product was concentrated in vacuo to give 2-(((2-aminoethyl)amino)methyl)-7-(3,4-dimethoxyphenyl)-5-methylfuro[3,2-c]pyridin-4(5H)-one dihydrochloride (19 mg, 81%) as a white solid.

LCMS (2 min, Formic): Rt=0.48 min, MH$^+$=358

Example 6

7-(4-(aminomethyl)phenyl)-5-methyl-2-((4-(methylsulfonyl)piperazin-1-yl)methyl)furo[3,2-c]pyridin-4(5H)-one hydrochloride

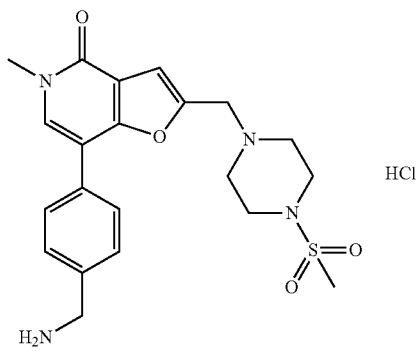 [SMILES: Cn1cc(-c2ccc(CN)cc2)c2oc(CN3CCN(S(C)(=O)=O)CC3)cc2c1=O ; Cl]

HCl 1,4-Dioxane (1 mL) and HCl (4M in 1,4-dioxane) (1.435 mL, 5.74 mmol) were added to tert-butyl 4-(5-methyl-2-((4-(methylsulfonyl)piperazin-1-yl)methyl)-4-oxo-4,5-dihydrofuro[3,2-c]pyridin-7-yl)benzylcarbamate (for a preparation see Intermediate 8, 152.31 mg, 0.287 mmol) and the reaction was stirred overnight. The volatiles were removed under reduced pressure. Trituration with diethyl ether was performed to give a white/yellow powder. This was dried further in the oven at 40° C. for 1 h to give 7-(4-(aminomethyl)phenyl)-5-methyl-2-((4-(methylsulfonyl)piperazin-1-yl)methyl)furo[3,2-c]pyridin-4(5H)-one hydrochloride (89 mg, 66.4%) as a white/yellow powder.

LCMS (2 min, High pH): Rt=0.65 min, MH$^+$=431

Example 7

5-methyl-2-((4-(methylsulfonyl)piperazin-1-yl)methyl)-7-(2-((tetrahydro-2H-pyran-4-yl)methoxy)pyridin-4-yl)furo[3,2-c]pyridin-4(5H)-one

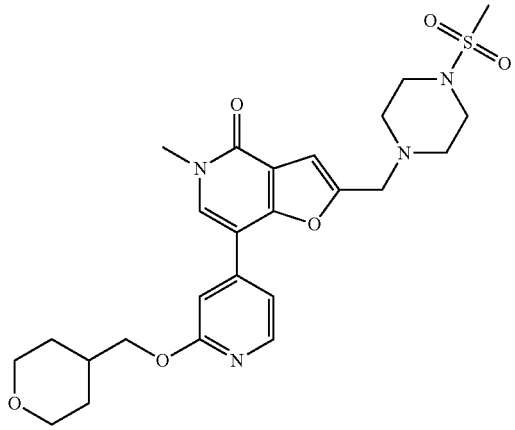 [SMILES: Cn1cc(-c2ccnc(OCC3CCOCC3)c2)c2oc(CN3CCN(S(C)(=O)=O)CC3)cc2c1=O]

A mixture of 7-bromo-5-methyl-2-((4-(methylsulfonyl)piperazin-1-yl)methyl)furo[3,2-c]pyridin-4(5H)-one (for a preparation see Intermediate 3, 165 mg, 0.408 mmol), 2-((tetrahydro-2H-pyran-4-yl)methoxy)-4-(4,4,5,5-tetramethyl-1,3,2-dioxaborolan-2-yl)pyridine (BoroPharm Inc) (261 mg, 0.816 mmol), potassium carbonate (169 mg, 1.224 mmol) and bis(triphenylphosphine)palladium(II) chloride (28.6 mg, 0.041 mmol) in water (1.5 mL) and 1,2-DME (4.5 mL) was heated in a microwave at 120° C. for 20 minutes. The cooled reaction mixture was diluted with ethyl acetate and the solution dried over MgSO$_4$ and evaporated. The residue was purified via MDAP to give 5-methyl-2-((4-(methylsulfonyl)piperazin-1-yl)methyl)-7-(2-((tetrahydro- 2H-pyran-4-yl)methoxy)pyridin-4-yl)furo[3,2-c]pyridin-4 (5H)-one (59 mg, 28%) as a white solid.

LCMS (2 min, Formic): Rt=0.64 min, MH+ 517

Example 8

7-(3,4-dimethoxyphenyl)-5-methyl-2-(piperidin-1-ylmethyl)furo[3,2-c]pyridin-4(5H)-one

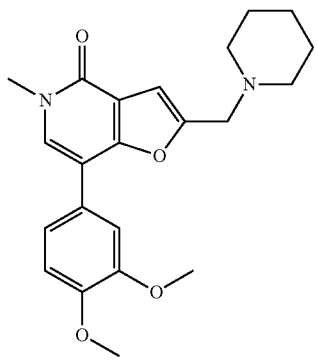 [SMILES: COc1ccc(-c2cn(C)c(=O)c3cc(CN4CCCCC4)oc23)cc1OC]

A mixture of 7-bromo-5-methyl-2-(piperidin-1-ylmethyl)furo[3,2-c]pyridin-4(5H)-one (for a preparation see Intermediate 9, 35 mg, 0.108 mmol), (3,4-dimethoxyphenyl) boronic acid (29 mg, 0.159 mmol), potassium carbonate (75 mg, 0.543 mmol) and bis(triphenylphosphine)palladium(II) chloride (8 mg, 0.011 mmol) in EtOH (2 mL) and toluene (2 mL) were heated in a microwave at 100° C. for 1 hour. The mixture was dried using a hydrophobic frit and evaporated under reduced pressure to give a yellow oil. The residue was purified by MDAP. Appropriate fractions were combined and concentrated in vacuo to give an off white gum (40.5 mg). This was dissolved in MeOH and loaded onto an amino propyl cartridge (10 g). Product was eluted with MeOH and concentrated in vacuo to give 7-(3,4-dimethoxyphenyl)-5-methyl-2-(piperidin-1-ylmethyl)furo[3,2-c]pyridin-4(5H)-one (24.2 mg, 58%) as a white gum. LCMS (2 min, Formic): Rt=0.6 min, MH+=383

Example 9

7-(3,4-dimethoxyphenyl)-5-methyl-2-(morpholinomethyl)furo[3,2-c]pyridin-4(5H)-one

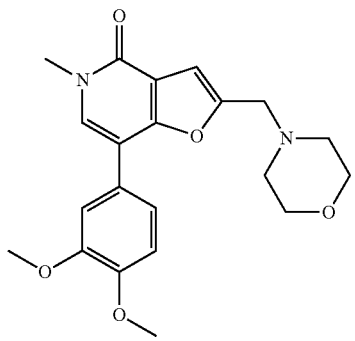 [SMILES: COc1ccc(-c2cn(C)c(=O)c3cc(CN4CCOCC4)oc23)cc1OC]

A mixture of 7-bromo-5-methyl-2-(morpholinomethyl) furo[3,2-c]pyridin-4(5H)-one (for a preparation see Intermediate 10, 54 mg, 0.165 mmol), potassium carbonate (113 mg, 0.818 mmol), bis(triphenylphosphine)palladium(II) chloride (6 mg, 8.55 µmol) and (3,4-dimethoxyphenyl) boronic acid (46 mg, 0.253 mmol) in toluene (2 mL) and EtOH (2 mL) was heated in a microwave at 80° C. for 20 minutes. LCMS (2 min, Formic): indicated that the product had been formed but a large quantity of starting material remained.

Bis(triphenylphosphine)palladium(II) chloride (8 mg, 0.011 mmol) was added to the mixture and the reaction was heated in a microwave at 80° C. for 20 minutes. LCMS (2 min, Formic): indicated there was still un-reacted starting material.

Further portions of (3,4-dimethoxyphenyl)boronic acid (46 mg, 0.253 mmol) and bis(triphenylphosphine)palladium (II) chloride (8 mg, 0.011 mmol) were added and the mixture was heated in the microwave at 80° C. for 20 minutes. LCMS (2 min, Formic): indicated that there was un-reacted starting material remaining.

A further portion of bis(triphenylphosphine)palladium(II) chloride (8 mg, 0.011 mmol) was added to the mixture and it was heated in a microwave at 80° C. for 40 minutes. LCMS (2 min, Formic): indicated that there was un-reacted starting material remaining.

A further portion of bis(triphenylphosphine)palladium(II) chloride (8 mg, 0.011 mmol) was added to the mixture and it was heated in a microwave at 80° C. for 30 minutes. LCMS (2 min, Formic): indicated that the final product had formed and less starting material remained. The reaction mixture was diluted with ethyl acetate (10 mL), dried ($Na_2SO_4$), filtered and evaporated to give a yellow solid (123 mg). The crude yellow solid was purified by chromatography on silica gel eluting with a 0-10% MeOH/DCM gradient. Appropriate fractions were combined and evaporated to give 7-(3,4-dimethoxyphenyl)-5-methyl-2-(morpholinomethyl)furo[3,2-c]pyridin-4(5H)-one (8 mg, 11% yield) as a orange oil.

LCMS (2 min, Formic): Rt=0.55 min, MH+ 385

Example 10

(R)-7-(3,4-dimethoxyphenyl)-5-methyl-2-((2-methyl-4-(methylsulfonyl)piperazin-1-yl)methyl) furo[3,2-c]pyridin-4(5H)-one

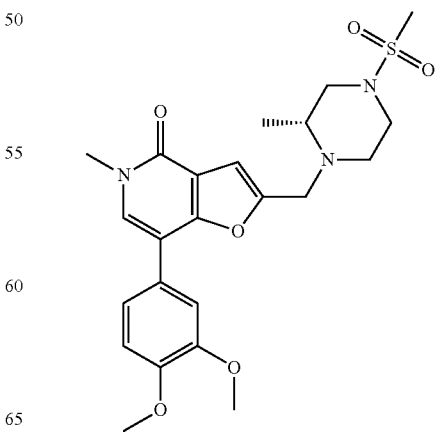

A mixture of (R)-7-bromo-5-methyl-2-((2-methyl-4-(methylsulfonyl)piperazin-1-yl)methyl)furo[3,2-c]pyridin-4(5H)-one (for a preparation see Intermediate 5, 64 mg, 0.153 mmol), (3,4-dimethoxyphenyl)boronic acid (57.6 mg, 0.317 mmol), bis(triphenylphosphine)palladium(II) chloride (5.15 mg, 7.34 µmol) and potassium carbonate (106 mg, 0.765 mmol) in toluene (2 mL) and EtOH (2 mL) was heated in a microwave at 80° C. for 20 min. The mixture was diluted with ethyl acetate (10 mL), filtered and evaporated in vacuo. The resulting residue was purified by chromatography on silica gel using a gradient of 2-4% DCM-MeOH. The appropriate fractions were combined and blown down under a stream of nitrogen to give (R)-7-(3,4-dimethoxyphenyl)-5-methyl-2-((2-methyl-4-(methylsulfonyl)piperazin-1-yl)methyl)furo[3,2-c]pyridin-4(5H)-one (51 mg, 70%) as an off-white solid. LCMS (2 min, Formic): Rt=0.63 min, $MH^+$=476

Example 11

2-((1,4-diazepan-1-yl)methyl)-7-(3,4-dimethoxyphenyl)-5-methylfuro[3,2-c]pyridin-4(5H)-one

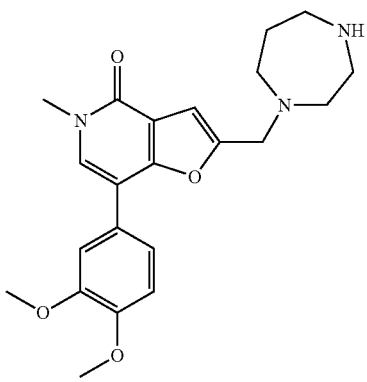 [SMILES: COc1ccc(-c2cn(C)c(=O)c3cc(CN4CCCNCC4)oc23)cc1OC]

tert-Butyl 4-((7-(3,4-dimethoxyphenyl)-5-methyl-4-oxo-4,5-dihydrofuro[3,2-c]pyridin-2-yl)methyl)-1,4-diazepane-1-carboxylate (for a preparation see Intermediate 12, 50 mg, 0.100 mmol) was dissolved in 1,4-dioxane (1 mL) and 4M HCl in 1,4-dioxane (0.5 mL) was added. The reaction mixture was stirred for 2 h. Diethyl ether (10 mL) was added to precipitate the product. The supernatent was removed. The residue was triturated further with diethyl ether (10 mL) and dried under vacuum to give 2-((1,4-diazepan-1-yl)methyl)-7-(3,4-dimethoxyphenyl)-5-methylfuro[3,2-c]pyridin-4(5H)-one (30 mg, 75%) as a white powder. LCMS (2 min, High pH): Rt=0.72 min, $MH^+$ 398

Example 12

5-methyl-2-((4-(methylsulfonyl)piperazin-1-yl)methyl)-7-(5-(1-phenylethoxy)pyridin-3-yl)furo[3,2-c]pyridin-4(5H)-one

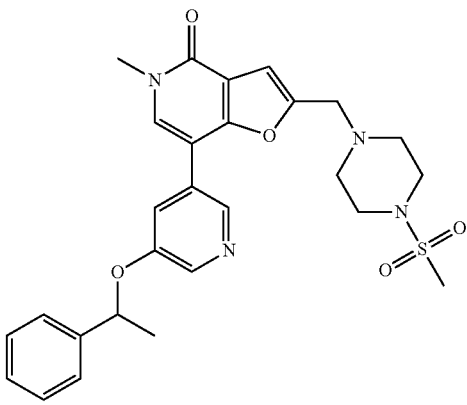 [SMILES: CC(Oc1cncc(-c2cn(C)c(=O)c3cc(CN4CCN(S(C)(=O)=O)CC4)oc23)c1)c1ccccc1]

7-Bromo-5-methyl-2-((4-(methylsulfonyl)piperazin-1-yl)methyl)furo[3,2-c]pyridin-4(5H)-one (for a preparation see Intermediate 3, 100 mg, 0.247 mmol), 3-(1-phenylethoxy)-5-(4,4,5,5-tetramethyl-1,3,2-dioxaborolan-2-yl)pyridine (for a preparation see Intermediate 28, 80 mg, 0.247 mmol), potassium carbonate (171 mg, 1.237 mmol) and bis(triphenylphosphine)palladium(II) chloride (8.68 mg, 0.012 mmol) were dissolved in EtOH (2 mL) and toluene (2 mL) and heated in a microwave for 20 min at 120° C. Ethyl acetate (20 mL) was added. The mixture was dried over $MgSO_4$, filtered and the solvent removed in vacuo. The product was purified by chromatography on silica gel using a 0-5% MeOH/DCM gradient. The appropriate fractions were combined and evaporated in vacuo to give 5-methyl-2-((4-(methylsulfonyl)piperazin-1-yl)methyl)-7-(5-(1-phenylethoxy)pyridin-3-yl)furo[3,2-c]pyridin-4(5H)-one (36 mg, 28%) as a yellow oil. LCMS (2 min, High pH): Rt=0.97 min, $MH^+$ 523

Example 13

2-((3,3-difluoropiperidin-1-yl)methyl)-5-methyl-7-(2-((tetrahydro-2H-pyran-4-yl)methoxy)pyridin-4-yl)furo[3,2-c]pyridin-4(5H)-one

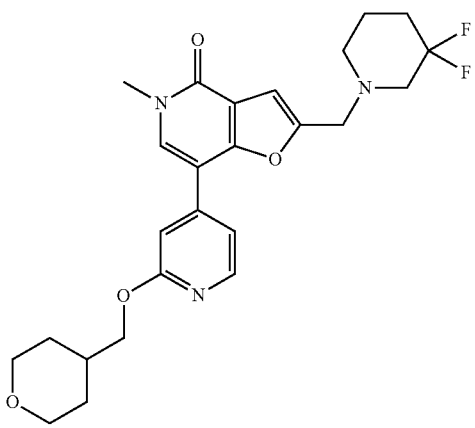 [SMILES: Cn1cc(-c2ccnc(OCC3CCOCC3)c2)c2oc(CN3CCCC(F)(F)C3)cc2c1=O]

7-Bromo-2-((3,3-difluoropiperidin-1-yl)methyl)-5-methylfuro[3,2-c]pyridin-4(5H)-one (for a preparation see Intermediate 13, 75 mg, 0.208 mmol), 2-((tetrahydro-2H-pyran-4-yl)methoxy)-4-(4,4,5,5-tetramethyl-1,3,2-dioxaborolan-2-yl)pyridine (BoroPharm Inc) (99 mg, 0.311 mmol), potassium carbonate (143 mg, 1.038 mmol) and bis(triphenylphosphine)palladium(II) chloride (7.29 mg, 10.38 µmol) were dissolved in EtOH (2 mL) and toluene (2 mL) and heated in a microwave for 20 min at 120° C. Ethyl acetate (15 mL) was added. The mixture was dried over MgSO$_4$, filtered and the solvent evaporated in vacuo. The residue was purified by chromatography on silica gel using a 0-5% MeOH/DCM gradient. Appropriate fractions were combined and evaporated in vacuo to give 2-((3,3-difluoropiperidin-1-yl)methyl)-5-methyl-7-(2-((tetrahydro-2H-pyran-4-yl)methoxy)pyridin-4-yl)furo[3,2-c]pyridin-4(5H)-one (62 mg, 59%) as an orange oil.

LCMS (2 min, High pH): Rt=1.02 min, MH$^+$ 474

Example 14

5-methyl-2-((4-(methylsulfonyl)piperazin-1-yl)methyl)-7-(2-((1-phenylethyl)amino)pyridin-4-yl)furo[3,2-c]pyridin-4(5H)-one

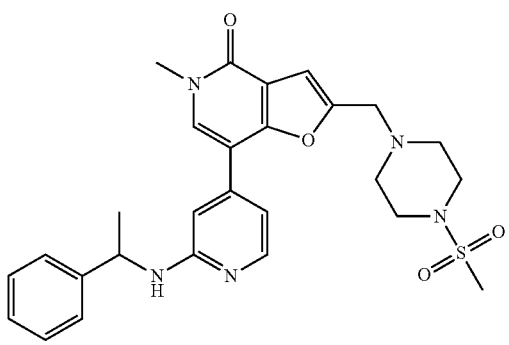 [SMILES: CC(Nc1cc(-c2cn(C)c(=O)c3cc(CN4CCN(S(C)(=O)=O)CC4)oc23)ccn1)c1ccccc1]

7-Bromo-5-methyl-2-((4-(methylsulfonyl)piperazin-1-yl)methyl)furo[3,2-c]pyridin-4(5H)-one (for a preparation see Intermediate 3, 100 mg, 0.247 mmol), N-(1-phenylethyl)-4-(4,4,5,5-tetramethyl-1,3,2-dioxaborolan-2-yl)pyridin-2-amine (for a preparation see Intermediate 26, 292 mg, 0.901 mmol), potassium carbonate (171 mg, 1.237 mmol) and bis(triphenylphosphine)palladium(II) chloride (8.68 mg, 0.012 mmol) were dissolved in EtOH (5 mL) and toluene (5 mL) and heated in the microwave for 20 min at 120° C. A further portion of bis(triphenylphosphine)palladium(II) chloride (16 mg, 0.024 mmol) was added to the reaction mixture and heated in the microwave for 20 min at 120° C. Ethyl acetate (20 mL) was added and the mixture was dried over MgSO$_4$, filtered and the solvent evaporated in vacuo. The residue was purified by chromatography on silica gel using a 0-10% MeOH/DCM gradient. Appropriate fractions were combined and evaporated in vacuo to give a brown oil. The impure oil was purified further by MDAP. Appropriate fractions were combined and evaporated to give 5-methyl-2-((4-(methylsulfonyl)piperazin-1-yl)methyl)-7-(2-((1-phenylethyl)amino)pyridin-4-yl)furo[3,2-c]pyridin-4(5H)-one (16 mg, 12%) as a bright orange powder. LCMS (2 min, High pH): Rt=0.94 min, MH$^+$ 521

Example 15

5-methyl-2-((4-(methylsulfonyl)piperazin-1-yl)methyl)-7-(3-((1-phenylethyl)amino)phenyl)furo[3,2-c]pyridin-4(5H)-one

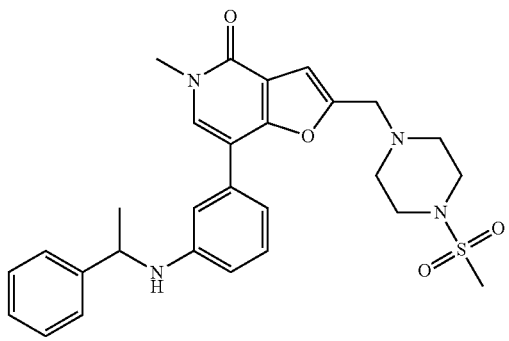 [SMILES: CC(Nc1cccc(-c2cn(C)c(=O)c3cc(CN4CCN(S(C)(=O)=O)CC4)oc23)c1)c1ccccc1]

7-Bromo-5-methyl-2-((4-(methylsulfonyl)piperazin-1-yl)methyl)furo[3,2-c]pyridin-4(5H)-one (for a preparation see Intermediate 3, 101 mg, 0.250 mmol), bis(triphenylphosphine)palladium(II) chloride (8.42 mg, 0.012 mmol) and potassium carbonate (173 mg, 1.249 mmol) were placed in a microwave vial. To this was added N-(1-phenylethyl)-3-(4,4,5,5-tetramethyl-1,3,2-dioxaborolan-2-yl)aniline (for a preparation see Intermediate 30, 323 mg, 1 mmol) in EtOH (5 mL) and toluene (5 mL). The reaction vessel was sealed and heated in the microwave at 80° C. for 20 minutes. LCMS (2 min, Formic): showed no reaction. A further portion of bis(triphenylphosphine)palladium(II) chloride (8.42 mg, 0.012 mmol) was added, and the reaction was heated in a microwave at 80° C. for 20 minutes. LCMS (2 min, Formic): showed no reaction. Nitrogen gas was bubbled through the reaction mixture and a further portion of bis(triphenylphosphine)palladium(II) chloride (19 mg) was added. The reaction mixture was heated in the microwave at 90° C. for 20 minutes. LCMS (2 min, Formic): showed no reaction. The reaction mixture was heated further in the microwave at 120° C. for 20 minutes. LCMS (2 min, Formic): showed no reaction had taken place.

The reaction mixture was filtered through a Celite cartridge and evaporated in vacuo. The residue was dissolved in toluene (2 mL) and EtOH (2 mL) and potassium carbonate (186 mg) and bis(triphenylphosphine)palladium(II) chloride (8.7 mg) were added. The reaction vessel was sealed and heated in the microwave at 80° C. for 20 minutes. The mixture was diluted with ethyl acetate (10 mL), dried with sodium sulphate, filtered and evaporated in vacuo.

The residue was purified by chromatography on silica gel (25 g) eluting with a 0%-10% MeOH/DCM gradient. Appropriate fractions were combined and evaporated. The resulting impure residue was re-purified by MDAP to give 5-methyl-2-((4-(methylsulfonyl)piperazin-1-yl)methyl)-7-(3-(((1-phenylethyl)amino)phenyl)furo[3,2-c]pyridin-4(5H)-one (11.4 mg, 9%).
LCMS (2 min, Formic): Rt=0.89 min, MH+ 522

Example 16

7-(3,4-dimethoxyphenyl)-5-methyl-2-((3-methylmorpholino)methyl)furo[3,2-c]pyridin-4(5H)-one

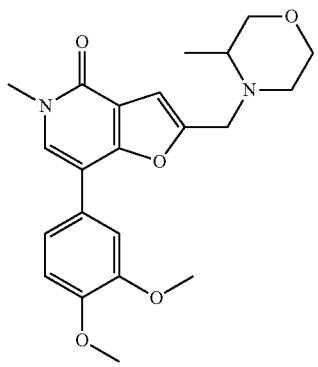 [SMILES: COc1ccc(-c2cn(C)c(=O)c3cc(CN4CCOCC4C)oc23)cc1OC]

A mixture of 7-bromo-5-methyl-2-((3-methylmorpholino)methyl)furo[3,2-c]pyridin-4(5H)-one (for a preparation see Intermediate 14, 22 mg, 0.064 mmol), (3,4-dimethoxyphenyl)boronic acid (17.60 mg, 0.097 mmol), potassium carbonate (44.6 mg, 0.322 mmol) and bis(triphenylphosphine)palladium(II) chloride (4 mg, 5.70 μmol) in toluene (1 mL) and EtOH (1 mL) was heated in a microwave at 80° C. for 20 minutes. The cooled reaction mixture was diluted with ethyl acetate (10 mL), dried and evaporated. The residue was purified by MDAP. The appropriate fractions were combined and evaporated. The residue was loaded onto a 5 g SCX column and eluted with MeOH (10 mL) followed by 2M MeOH/NH3 (10 mL). The basic fraction was evaporated to give 7-(3,4-dimethoxyphenyl)-5-methyl-2-((3-methylmorpholino)methyl)furo[3,2-c]pyridin-4(5H)-one (8 mg, 26%) as a cream solid. LCMS (2 min, High pH): Rt=0.82 min, MH+ 399

Example 17

N-(4-(2-((3-fluoropiperidin-1-yl)methyl)-5-methyl-4-oxo-4,5-dihydrofuro[3,2-c]pyridin-7-yl)pyridin-2-yl)acetamide

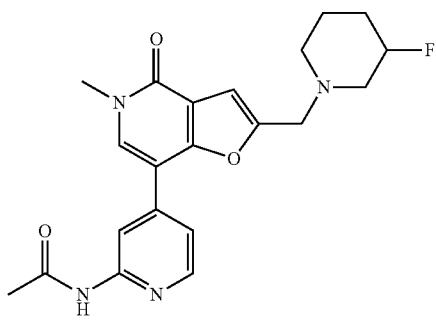 [SMILES: CC(=O)Nc1cc(-c2cn(C)c(=O)c3cc(CN4CCCC(F)C4)oc23)ccn1]

7-Bromo-2-((3-fluoropiperidin-1-yl)methyl)-5-methylfuro[3,2-c]pyridin-4(5H)-one (for a preparation see Intermediate 15, 82.5 mg, 0.240 mmol), N-(4-(4,4,5,5-tetramethyl-1,3,2-dioxaborolan-2-yl)pyridin-2-yl)acetamide (Milestone Pharm tech USA) (95 mg, 0.361 mmol), potassium carbonate (166 mg, 1.202 mmol) and bis(triphenylphosphine)palladium(II) chloride (8.44 mg, 0.012 mmol) were dissolved in EtOH (2 mL) and toluene (2 mL) and heated in a microwave for 20 min at 120° C. Ethyl acetate (15 mL) was added and the mixture was dried over MgSO4, filtered and evaporated. The residue was purified by chromatography on silica gel using a 0-10% MeOH/DCM gradient. The appropriate fractions were combined and evaporated in vacuo to give N-(4-(2-((3,3-difluoropiperidin-1-yl)methyl)-5-methyl-4-oxo-4,5-dihydrofuro[3,2-c]pyridin-7-yl)pyridin-2-yl)acetamide (55 mg, 64%) as a bright yellow solid LCMS (2 min, High pH): Rt=0.73 min, MH+ 399

Example 18

N-(4-(2-((3,3-difluoropiperidin-1-yl)methyl)-5-methyl-4-oxo-4,5-dihydrofuro[3,2-c]pyridin-7-yl)pyridin-2-yl)acetamide

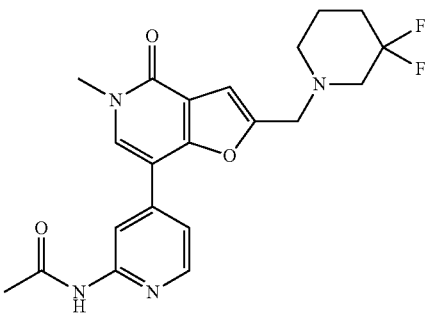 [SMILES: CC(=O)Nc1cc(-c2cn(C)c(=O)c3cc(CN4CCCC(F)(F)C4)oc23)ccn1]

7-Bromo-2-((3,3-difluoropiperidin-1-yl)methyl)-5-methylfuro[3,2-c]pyridin-4(5H)-one (for a preparation see Intermediate 13, 75 mg, 0.208 mmol), N-(4-(4,4,5,5-tetramethyl-1,3,2-dioxaborolan-2-yl)pyridin-2-yl)acetamide (Milestone Pharm tech USA) (82 mg, 0.311 mmol), potassium carbonate (143 mg, 1.038 mmol) and bis(triphenylphosphine)palladium(II) chloride (7.29 mg, 10.38 μmol) were dissolved in EtOH (2 mL) and toluene (2 mL) and heated in a microwave for 20 min at 120° C. Ethyl acetate (15 mL) was added and the mixture was dried over MgSO4, filtered and evaporated. The residue was purified by chromatography on silica gel using a 0-5% MeOH/DCM gradient. The appropriate fractions were combined and evaporated in vacuo to give N-(4-(2-((3,3-difluoropiperidin-1-yl)methyl)-5-methyl-4-oxo-4,5-dihydrofuro[3,2-c]pyridin-7-yl)pyridin-2-yl)acetamide (55 mg, 64%) as a translucent oil. LCMS (2 min, High pH): Rt=0.78 min, MH+ 417

Example 19

2-((3-fluoropiperidin-1-yl)methyl)-7-(4-methoxyphenyl)-5-methylfuro[3,2-c]pyridin-4(5H)-one hydrochloride

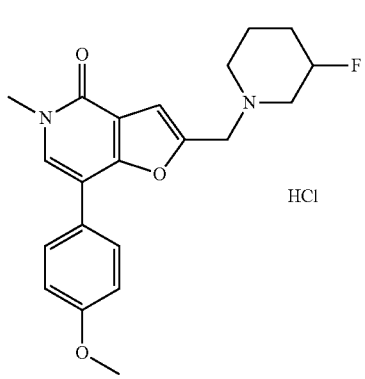 [SMILES: COc1ccc(-c2cn(C)c(=O)c3cc(CN4CCCC(F)C4)oc23)cc1 ; Cl]

7-Bromo-2-((3-fluoropiperidin-1-yl)methyl)-5-methyl-furo[3,2-c]pyridin-4(5H)-one (for a preparation see Intermediate 15, 82.5 mg, 0.240 mmol), (4-methoxyphenyl) boronic acid (54.8 mg, 0.361 mmol), potassium carbonate (166 mg, 1.202 mmol) and bis(triphenylphosphine)palladium(II) chloride (8.44 mg, 0.012 mmol) were dissolved in EtOH (2 mL) and toluene (2 mL) and heated in a microwave for 20 min at 120° C. Further portions of (4-methoxyphenyl) boronic acid (36.5 mg) and bis(triphenylphosphine)palladium(II) chloride (8.44 mg, 0.012 mmol) were added and the reaction was heated in a microwave for 20 min at 120° C. Ethyl acetate (15 mL) was added and the mixture was dried over MgSO$_4$, filtered and evaporated. The residue was purified by chromatography on silica gel using a 0-5% MeOH/DCM gradient. The appropriate fractions were combined and evaporated and purified further via MDAP. The appropriate fractions were combined and evaporated to give a brown gum. This gum was triturated with diethyl ether (10 mL) and HCl in ether (0.5 mL) was added to precipitate the product. The supernatant was removed. The residue was triturated with diethyl ether and dried to give 2-((3-fluoropiperidin-1-yl)methyl)-7-(4-methoxyphenyl)-5-methylfuro[3,2-c]pyridin-4(5H)-one hydrochloride (54 mg, 0.133 mmol, 55.2% yield) as a white solid.

LCMS (2 min, High pH): Rt=1.0 min, MH$^+$ 371

Example 20

5-methyl-2-(morpholinomethyl)-7-(2-((tetrahydro-2H-pyran-4-yl)methoxy)pyridin-4-yl)furo[3,2-c]pyridin-4(5H)-one

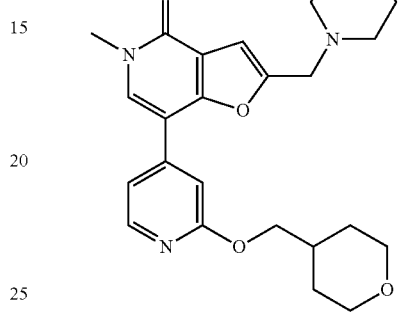

A mixture of 7-bromo-5-methyl-2-(morpholinomethyl)furo[3,2-c]pyridin-4(5H)-one (for a preparation see Intermediate 10, 80 mg, 0.24 mmol), 2-((tetrahydro-2H-pyran-4-yl)methoxy)-4-(4,4,5,5-tetramethyl-1,3,2-dioxaborolan-2-yl)pyridine (BoroPharm Inc) (156 mg, 0.49 mmol), potassium carbonate (169 mg, 1.22 mmol) and bis(triphenylphosphine)palladium(II) chloride (17 mg, 10 mol %) in toluene (2 mL) and EtOH (2 mL) was heated in a microwave at 130° C. for 45 minutes. The cooled reaction mixture was diluted with ethyl acetate (25 mL), dried over sodium sulfate and filtered. The solvent was evaporated from the filtrate and the residue was purified by chromatography on silica gel eluting with 2% MeOH/DCM. Appropriate fractions were combined and evaporated. The residue was triturated with diethyl ether to give 5-methyl-2-(morpholinomethyl)-7-(2-((tetrahydro-2H-pyran-4-yl)methoxy)pyridin-4-yl)furo[3,2-c]pyridin-4(5H)-one (71 mg, 66%) as a brown solid.

LCMS (2 min, Formic): Rt=0.6 min, MH$^+$ 440

Example 21

5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one formate

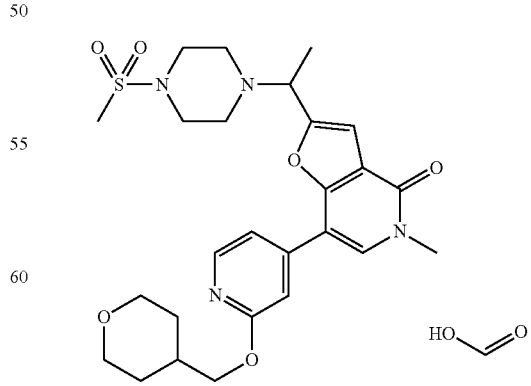

A solution of 5-iodo-4-methoxy-1-methyl-2'-((tetrahydro-2H-pyran-4-yl)methoxy)-[3,4'-bipyridin]-6(1H)-one (for a preparation see Intermediate 19, 90 mg, 0.197 mmol) in acetonitrile (4 mL) was treated with 1-(but-3-yn-2-yl)-4-(methylsulfonyl)piperazine (for a preparation see Intermediate 20, 68 mg, 0.236 mmol), copper(I) iodide (4 mg, 0.021 mmol), bis(triphenylphosphine)palladium(II) dichloride (7 mg, 9.97 μmol) and triethylamine (4 mL, 28.7 mmol). The reaction mixture was heated at 80° C. under nitrogen for 4 days, by which time the mixture had gone to dryness to form a brown gum that hardened on cooling to room temperature.

The reaction mixture was partitioned between EtOAc (30 mL) and water (30 mL). The aqueous layer was re-extracted with EtOAc (30 mL×2). The combined organic layers were passed through a hydrophobic frit and concentrated under reduced pressure. The residue was purified by MDAP. The fraction containing product was concentrated under reduced pressure to give 5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one formate (6 mg, 6%) as a clear, yellow gum.

LCMS (2 min, Formic): Rt=0.67 min, MH+ 531

Examples 21a and Example 21b (S)-5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one and (R)-5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one A mixture of 5-iodo-4-methoxy-1-methyl-2'-((tetrahydro-2H-pyran-4-yl)methoxy)-[3,4'-bipyridin]-6(1H)-one (for a preparation see Intermediate 19, 250 mg, 0.548 mmol), 1-(but-3-yn-2-yl)-4-(methylsulfonyl)piperazine (for a preparation see Intermediate 20, 356 mg, 1.644 mmol), copper(I) 10 iodide (25.04 mg, 0.131 mmol), and bis(triphenylphosphine)palladium(II) dichloride (15.00 mg, 0.021 mmol) in DMF (0.5 mL) was heated at 120° C. for 6 h using a microwave.

The reaction was repeated as above with a second batch of reagents. The two reaction mixtures were combined and concentrated under reduced pressure and purified by column chromatography on silica gel (100 g) eluting with 0 to 1% 2M ammonia in MeOH/EtOAc followed by 0 to 10% 2M ammonia in MeOH/EtOAc. Desired product was found to elute in the last few fractions of the second elution gradient. Appropriate fractions were combined and concentrated under reduced pressure to give crude product (~260 mg). This was purified by MDAP to give 5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one (60 mg, 10%) as a pale yellow gum.

LCMS (2 min, Formic): Rt=0.67 min, MH+ 531

This material was separated into its two component enantiomers by preparative chiral HPLC.

Approx 60 mg of racemate was dissolved in 1 mL EtOH and 2 mL of heptane. 1 mL portions of the solution were injected onto a 30 mm×25 cm Chiralpak AD-H column. The column was eluted with 50% EtOH/Heptane, flow rate=30 mL/min, wavelength, 215 nm. Appropriate fractions were combined and evaporated to give the two enantiomers:

Example 21a: 20 mg, white solid. LCMS (2 min, Formic): Rt=0.67 min, MH+ 531. Enantiomeric purity by chiral HPLC=>99% e.e Example 21b: 19 mg, white solid. LCMS (2 min, Formic): Rt=0.67 min, MH+ 531. Enantiomeric purity by chiral HPLC=98% e.e Absolute stereochemistry was not assigned.

Example 22

2-((1,4-oxazepan-4-yl)methyl)-5-methyl-7-(2-((tetrahydro-2H-pyran-4-yl)methoxy)pyridin-4-yl)furo[3,2-c]pyridin-4(5H)-one

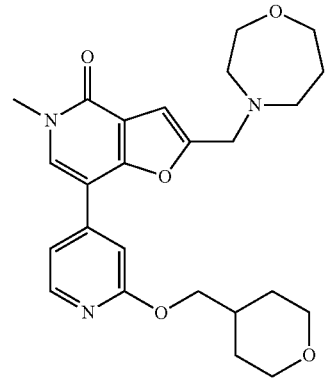 [SMILES: Cn1cc(-c2ccnc(OCC3CCOCC3)c2)c2oc(CN3CCCOCC3)cc2c1=O]

A mixture of 2-((1,4-oxazepan-4-yl)methyl)-7-bromo-5-methylfuro[3,2-c]pyridin-4(5H)-one (for a preparation see Intermediate 16, 40 mg, 0.12 mmol), 2-((tetrahydro-2H-pyran-4-yl)methoxy)-4-(4,4,5,5-tetramethyl-1,3,2-dioxaborolan-2-yl)pyridine (BoroPharm Inc) (75 mg, 0.24 mmol), potassium carbonate (81 mg, 0.57 mmol) and bis(triphenylphosphine)palladium(II) chloride (8 mg, 10 mol %) in toluene (2 mL) and EtOH (2 mL) was heated in a microwave at 130° C. for 45 minutes. The cooled reaction mixture was diluted with ethyl acetate (25 mL). The mixture was dried over sodium sulfate and filtered. The solvent was evaporated from the filtrate and the residue was purified by chromatography on silica gel eluting with 2% MeOH/DCM to give crude product. This was re-purified by MDAP to give 2-((1,4-oxazepan-4-yl)methyl)-5-methyl-7-(2-((tetrahydro-2H-pyran-4-yl)methoxy)pyridin-4-yl)furo[3,2-c]pyridin-4(5H)-one (28 mg, 53%) as a colourless glass.

LCMS (2 min, Formic): Rt=0.6 min, MH+ 454

Example 23

(R)-7-(2-(cyclopropylmethoxy)pyridin-4-yl)-5-methyl-2-((2-methyl-4-(methylsulfonyl)piperazin-1-yl)methyl)furo[3,2-c]pyridin-4(5H)-one

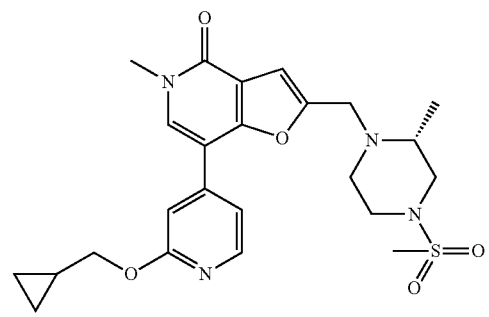 [SMILES: C[C@@H]1CN(S(C)(=O)=O)CCN1Cc1cc2c(=O)n(C)cc(-c3ccnc(OCC4CC4)c3)c2o1]

To a stirred suspension of 2-(cyclopropylmethoxy)-4-(4,4,5,5-tetramethyl-1,3,2-dioxaborolan-2-yl)pyridine (for a preparation see Intermediate 32, 438 mg, 0.478 mmol) in 1,2-DME (4 mL), was added potassium carbonate (99 mg, 0.717 mmol), (R)-7-bromo-5-methyl-2-((2-methyl-4-(methylsulfonyl)piperazin-1-yl)methyl)furo[3,2-c]pyridin-4(5H)-one (for a preparation see Intermediate 5, 100 mg, 0.239 mmol) and tetrakis(triphenylphosphine)palladium(0) (11 mg, 9.52 μmol). The contents were sealed in a microwave vial and heated at 120° C. for 2 h. The mixture was dissolved in ethyl acetate (20 mL) and water (20 mL) and the layers separated. The aqueous layer was further extracted with ethyl acetate (3×20 mL). The solvent was concentrated in vacuo to give a brown oil. This was purified by MDAP. The appropriate fractions were combined and concentrated in vacuo to give (R)-7-(2-(cyclopropylmethoxy)pyridin-4-yl)-5-methyl-2-((2-methyl-4-(methylsulfonyl)piperazin-1-yl)methyl)furo[3,2-c]pyridin-4(5H)-one (17 mg, 15%) as a brown oil LCMS (2 min, Formic): Rt=0.74 min, MH+ 487

Example 24

(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)cyclopropanecarboxamide

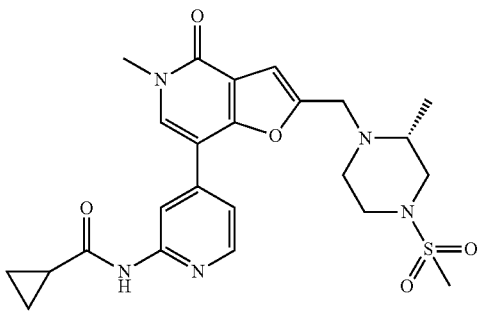 [SMILES: C[C@@H]1CN(S(C)(=O)=O)CCN1Cc1cc2c(=O)n(C)cc(-c3ccnc(NC(=O)C4CC4)c3)c2o1]

N-(4-(4,4,5,5-Tetramethyl-1,3,2-dioxaborolan-2-yl)pyridin-2-yl)cyclopropanecarboxamide (for a preparation see Intermediate 34, 85 mg, 0.294 mmol), (R)-7-bromo-5-methyl-2-((2-methyl-4-(methylsulfonyl)piperazin-1-yl)methyl)furo[3,2-c]pyridin-4(5H)-one (for a preparation see Intermediate 5, 100 mg, 0.239 mmol), tetrakis(triphenylphosphine)palladium(0) (13.81 mg, 0.012 mmol) and aqueous sodium carbonate (0.956 mL, 1.912 mmol) were mixed in 1,2-DME (3 mL), and heated in the microwave for 2 hours at 120° C. The reaction was diluted with ethyl acetate and water and filtered through cotton wool. The organic layer was separated and concentrated in vacuo. The crude material was purified by MDAP to give (R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)cyclopropanecarboxamide (80 mg, 67%) as a brown solid.
LCMS (2 min, Formic): Rt=0.56 min, MH+=500

Example 25

(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)propionamide

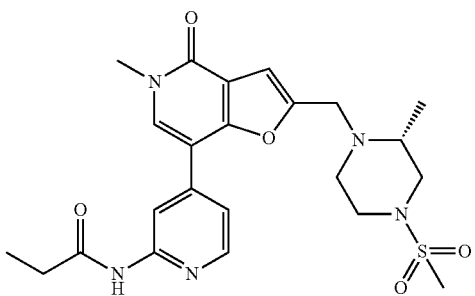 [SMILES: CCC(=O)Nc1cc(-c2cn(C)c(=O)c3cc(CN4CCN(S(C)(=O)=O)C[C@H]4C)oc23)ccn1]

N-(4-(4,4,5,5-tetramethyl-1,3,2-dioxaborolan-2-yl)pyridin-2-yl)propionamide (for a preparation see Intermediate 36, 80 mg, 0.291 mmol), (R)-7-bromo-5-methyl-2-((2-methyl-4-(methylsulfonyl)piperazin-1-yl)methyl)furo[3,2-c]pyridin-4(5H)-one (for a preparation see Intermediate 5, 100 mg, 0.239 mmol), tetrakis(triphenylphosphine)palladium(0) (13.81 mg, 0.012 mmol) and aqueous sodium carbonate (0.956 mL, 1.912 mmol) were mixed in 1,2-DME (2 mL), and heated in the microwave for 2 hours at 120° C. The reaction was diluted with ethyl acetate and water and filtered. The organic layer was separated and concentrated in vacuo. The crude product was purified by MDAP to give (R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)propionamide (28 mg, 24%) as a brown solid.
LCMS (2 min, Formic): Rt=0.53 min, MH+=488

Example 26

(R)-7-(2-(2-methoxyethoxy)pyridin-4-yl)-5-methyl-2-((2-methyl-4-(methylsulfonyl)piperazin-1-yl)methyl)furo[3,2-c]pyridin-4(5H)-one

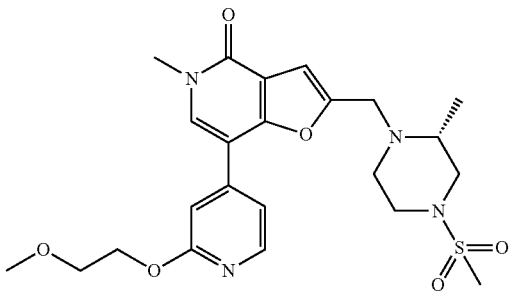 [SMILES: COCCOc1cc(-c2cn(C)c(=O)c3cc(CN4CCN(S(C)(=O)=O)C[C@H]4C)oc23)ccn1]

2-(2-Methoxyethoxy)-4-(4,4,5,5-tetramethyl-1,3,2-dioxaborolan-2-yl)pyridine (for a preparation see Intermediate 38, 81 mg, 0.289 mmol), (R)-7-bromo-5-methyl-2-((2-methyl-4-(methylsulfonyl)piperazin-1-yl)methyl)furo[3,2-c]pyridin-4(5H)-one (for a preparation see Intermediate 5, 100 mg, 0.239 mmol), tetrakis(triphenylphosphine)palladium(0) (13.81 mg, 0.012 mmol) and sodium carbonate (2M) (0.956 mL, 1.912 mmol) were mixed in 1,2-DME (3 mL), and heated in the microwave for 2 hours at 120° C. The reaction was diluted with ethyl acetate and water and filtered through cotton wool. The organic layer was separated and concentrated in vacuo. The crude product was purified by MDAP to give (R)-7-(2-(2-methoxyethoxy)pyridin-4-yl)-5-methyl-2-((2-methyl-4-(methylsulfonyl)piperazin-1-yl)methyl)furo[3,2-c]pyridin-4(5H)-one (36 mg, 31%) as a brown solid. LCMS (2 min, Formic): Rt=0.61 min, MH⁺=491

Example 27

(R)-5-methyl-2-((2-methyl-4-(methylsulfonyl)piperazin-1-yl)methyl)-7-(2-(2-(pyrrolidin-1-yl)ethoxy)pyridin-4-yl)furo[3,2-c]pyridin-4(5H)-one

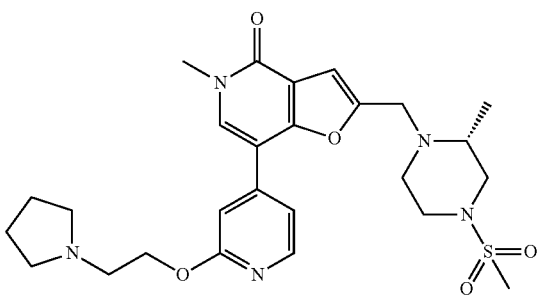 [SMILES: C[C@@H]1CN(S(C)(=O)=O)CCN1Cc1cc2c(=O)n(C)cc(-c3ccnc(OCCN4CCCC4)c3)c2o1]

2-(2-(Pyrrolidin-1-yl)ethoxy)-4-(4,4,5,5-tetramethyl-1,3,2-dioxaborolan-2-yl)pyridine (for a preparation see Intermediate 40, 70.3 mg, 0.221 mmol), (R)-7-bromo-5-methyl-2-((2-methyl-4-(methylsulfonyl)piperazin-1-yl)methyl)furo[3,2-c]pyridin-4(5H)-one (for a preparation see Intermediate 5, 80 mg, 0.191 mmol), tetrakis(triphenylphosphine)palladium(0) (11.05 mg, 9.56 µmol) and sodium carbonate (2M) (0.765 mL, 1.530 mmol) were mixed in 1,2-DME (2 mL), and heated in the microwave for 2 hours at 120° C. The reaction was diluted with ethyl acetate and water and filtered through cotton wool. The organic layer was separated and concentrated in vacuo. The crude product was purified by MDAP to give (R)-5-methyl-2-((2-methyl-4-(methylsulfonyl)piperazin-1-yl)methyl)-7-(2-(2-(pyrrolidin-1-yl)ethoxy)pyridin-4-yl)furo[3,2-c]pyridin-4(5H)-one (36 mg, 36%) as a brown solid. LCMS (2 min, Formic): Rt=0.47 min, MH⁺=530

Example 28

2-((1,1-dioxidothiomorpholino)methyl)-5-methyl-7-(2-((tetrahydro-2H-pyran-4-yl)methoxy)pyridin-4-yl)furo[3,2-c]pyridin-4(5H)-one

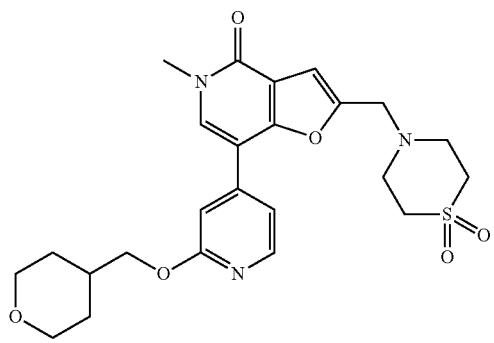 [SMILES: Cn1cc(-c2ccnc(OCC3CCOCC3)c2)c2oc(CN3CCS(=O)(=O)CC3)cc2c1=O]

A mixture of 7-bromo-2-((1,1-dioxidothiomorpholino)methyl)-5-methylfuro[3,2-c]pyridine-4(5H)-one (for a preparation see Intermediate 41, 200 mg, 0.533 mmol), 2-((tetrahydro-2H-pyran-4-yl)methoxy)-4-(4,4,5,5-tetramethyl-1,3,2-dioxaborolan-2-yl)pyridine (BoroPharm Inc) (204 mg, 0.640 mmol) and K₂CO₃ (147 mg, 1.066 mmol) in 1,4-dioxane (100 mL) was degassed with N₂, and then tetrakis(triphenylphosphine)palladium(0) (61.6 mg, 0.053 mmol) was added. The resulting reaction was heated to 100° C. for 2 h. The residues were partitioned between EtOAc (100 mL) and water (100 mL). The aqueous was re-extracted with EtOAc (100 mL). The combined organics were washed with brine (200 mL), dried with Na₂SO₄, filtered and concentrated to yield a crude solid. The crude product was purified by column chromatography on silica gel eluting with DCM/MeOH to give the desired product 2-((1,1-dioxidothiomorpholino)methyl)-5-methyl-7-(2-((tetrahydro-2H-pyran-4-yl)methoxy)pyridin-4-yl)furo[3,2-c]pyridin-4(5H)-one (125 mg, 0.256 mmol, 48.1% yield). LCMS: MH⁺ 488

Example 29

5-methyl-2-((4-(methylsulfonyl)piperazin-1-yl)methyl)-7-(2-((tetrahydro-2H-pyran-4-yl)methoxy)pyridin-4-yl)furo[2,3-d]pyridazin-4(5H)-one

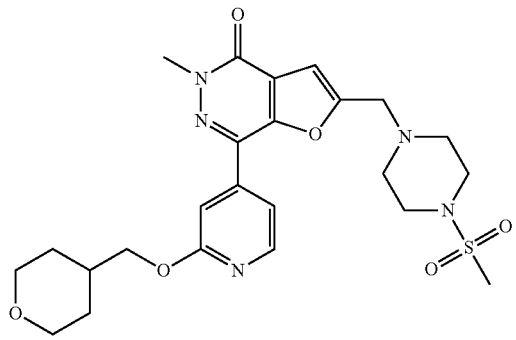 [SMILES: Cn1nc(-c2ccnc(OCC3CCOCC3)c2)c2oc(CN3CCN(S(C)(=O)=O)CC3)cc2c1=O]

To 5-methyl-2-(4-(methylsulfonyl)piperazine-1-carbonyl)-7-(2-((tetrahydro-2H-pyran-4-yl)methoxy)pyridin-4- yl)furo[2,3-d]pyridazin-4(5H)-one (for a preparation see Intermediate 44, 45 mg, 0.085 mmol) was added borane-THF complex (5 mL, 5.00 mmol, 1M solution in THF) and the mixture was stirred overnight under nitrogen at room temperature. Methanol was added and the solvent removed. The residue was purified by MDAP. Appropriate fractions were combined and the solvent removed to give 5-methyl-2-((4-(methylsulfonyl)piperazin-1-yl)methyl)-7-(2-((tetrahydro-2H-pyran-4-yl)methoxy)pyridin-4-yl)furo[2,3-d]pyridazin-4(5H)-one (2.0 mg, 5%) as a white solid LCMS (2 min, Formic): Rt=0.78 min, MH+ 518

Example 30

(R)—N-methyl-N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide

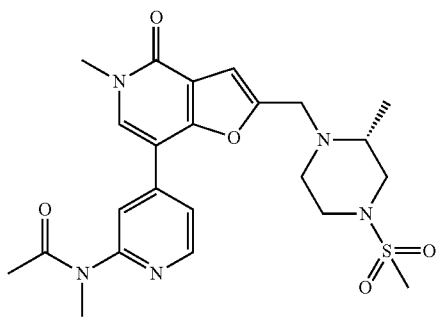 [SMILES: CC(=O)N(C)c1cc(-c2cn(C)c(=O)c3cc(CN4CCN(S(C)(=O)=O)C[C@H]4C)oc23)ccn1]

(R)-7-Bromo-5-methyl-2-((2-methyl-4-(methylsulfonyl)piperazin-1-yl)methyl)furo[3,2-c]pyridin-4(5H)-one (for a preparation see Intermediate 5, 95 mg, 0.227 mmol), N-methyl-N-(4-(4,4,5,5-tetramethyl-1,3,2-dioxaborolan-2-yl)pyridin-2-yl)acetamide (for a preparation see Intermediate 47, 71.2 mg, 0.258 mmol), tetrakis(triphenylphosphine)palladium(0) (13.12 mg, 0.011 mmol) and aqueous sodium carbonate (2M) (0.908 mL, 1.817 mmol) in 1,2-DME (3 mL) was heated for 2 hours at 120° C. in the microwave. The reaction was diluted with ethyl acetate and water and filtered through cotton wool. The organic layer was separated and concentrated in vacuo. The crude material was purified by MDAP and fractions containing product were concentrated in vacuo. The impure product was purified further by MDAP and concentrated in vacuo. The resulting product was dissolved in MeOH and eluted through an aminopropyl cartridge (1 g). The solvent was evaporated to give (R)—N-methyl-N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide (34 mg, 0.070 mmol, 30.7% yield) as a white solid. LCMS (2 min, Formic): Rt=0.51 min, MH+ 488

Example 31

7-(3-(cyclopropylmethoxy)pyridin-4-yl)-5-methyl-2-((4-(methylsulfonyl)piperazin-1-yl)methyl)furo[3,2-c]pyridin-4(5H)-one

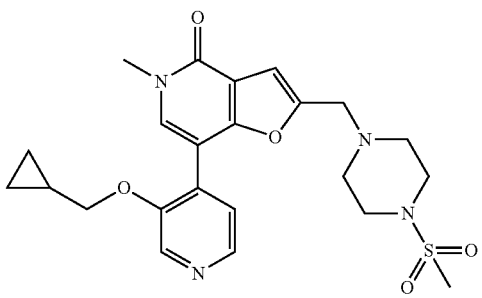 [SMILES: Cn1cc(-c2ccncc2OCC2CC2)c2oc(CN3CCN(S(C)(=O)=O)CC3)cc2c1=O]

7-Bromo-5-methyl-2-((4-(methylsulfonyl)piperazin-1-yl)methyl)furo[3,2-c]pyridin-4(5H)-one (for a preparation see Intermediate 3, 90 mg, 0.223 mmol), 3-(cyclopropylmethoxy)-4-(4,4,5,5-tetramethyl-1,3,2-dioxaborolan-2-yl)pyridine (for a preparation see Intermediate 49, 73.2 mg, 0.266 mmol), tetrakis(triphenylphosphine)palladium(0) (12.86 mg, 0.011 mmol) and aqueous sodium carbonate (2M) (0.890 mL, 1.781 mmol) in 1,2-DME (3 mL) was heated for 2 hours at 120° C. in the microwave. The reaction was diluted with ethyl acetate and water and filtered through cotton wool. The organic layer was separated and concentrated in vacuo. The crude material was purified by MDAP and fractions containing product were combined and concentrated in vacuo. The impure product was further purified by MDAP and fractions containing product were combined and concentrated in vacuo. The resulting product was dissolved in MeOH and eluted through an aminopropyl cartridge (1 g) with MeOH. The solvent was evaporated to give 7-(3-(cyclopropylmethoxy)pyridin-4-yl)-5-methyl-2-((4-(methylsulfonyl)piperazin-1-yl)methyl)furo[3,2-c]pyridin-4(5H)-one (49 mg, 0.104 mmol, 46.6% yield) as a white solid. LCMS (2 min, Formic): Rt=0.53 min, MH+ 473

Example 32

(R)-7-(3-(cyclopropylmethoxy)pyridin-4-yl)-5-methyl-2-((2-methyl-4-(methylsulfonyl)piperazin-1-yl)methyl)furo[3,2-c]pyridin-4(5H)-one

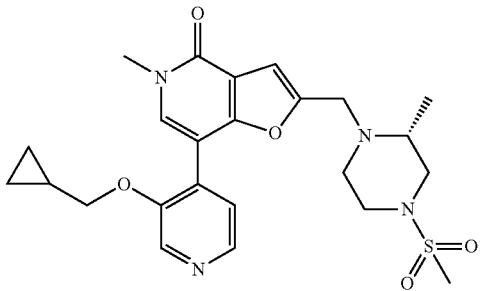 [SMILES: C[C@@H]1CN(S(C)(=O)=O)CCN1Cc1cc2c(=O)n(C)cc(-c3ccncc3OCC3CC3)c2o1]

(R)-7-bromo-5-methyl-2-((2-methyl-4-(methylsulfonyl)piperazin-1-yl)methyl)furo[3,2-c]pyridin-4(5H)-one (for a preparation see Intermediate 5, 95 mg, 0.227 mmol), 3-(cyclopropylmethoxy)-4-(4,4,5,5-tetramethyl-1,3,2-dioxaborolan-2-yl)pyridine (for a preparation see Intermediate 49, 73.2 mg, 0.266 mmol), tetrakis(triphenylphosphine)palladium(0) (13.12 mg, 0.011 mmol) and aqueous sodium carbonate (2M) (0.908 mL, 1.817 mmol) in 1,2-DME (3 mL) was heated for 2 hours at 120° C. in the microwave. The reaction was diluted with ethyl acetate and water and filtered through cotton wool. The organic layer was separated and concentrated in vacuo. The crude material was purified by MDAP and fractions containing product were concentrated in vacuo. The resulting product was dissolved in MeOH and eluted through an aminopropyl cartridge (5 g) with MeOH. The solvent was evaporated to give (R)-7-(3-(cyclopropylmethoxy)pyridin-4-yl)-5-methyl-2-((2-methyl-4-(methylsulfonyl)piperazin-1-yl)methyl)furo[3,2-c]pyridin-4(5H)-one (54 mg, 0.111 mmol, 48.9% yield) as a white solid. LCMS (2 min, Formic): Rt=0.55 min, MH+ 487

Example 33

7-(3,4-dimethoxyphenyl)-5-methyl-2-((4-(methylsulfonyl)piperazin-1-yl)methyl)furo[2,3-d]pyridazin-4(5H)-one

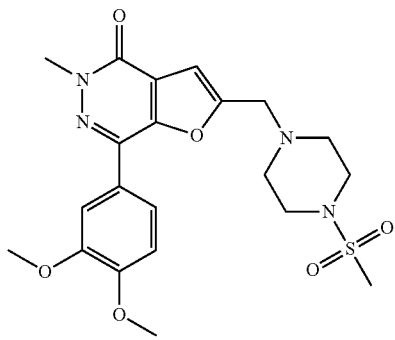 [SMILES: COc1ccc(-c2nn(C)c(=O)c3cc(CN4CCN(S(C)(=O)=O)CC4)oc23)cc1OC]

To 7-(3,4-dimethoxyphenyl)-5-methyl-2-(4-(methylsulfonyl)piperazine-1-carbonyl)furo[2,3-d]pyridazin-4(5H)-one (for a preparation see Intermediate 52, 0.025 mL, 0.038 mmol) was added borane-THF complex (4 mL, 4.00 mmol, 1M solution in THF) and the mixture was stirred overnight under nitrogen at room temperature. Methanol was added and the solvent removed. The residue was purified by MDAP. Appropriate fractions were combined and the solvent removed. The residue was dried under high vacuum for 2 hours to give 7-(3,4-dimethoxyphenyl)-5-methyl-2-((4-(methylsulfonyl)piperazin-1-yl)methyl)furo[2,3-d]pyridazin-4(5H)-one (10 mg, 57%) as a fine white solid. LCMS (2 min, Formic): Rt=0.7 min, MH+ 463

Example 34

2-((1,4-diazepan-1-yl)methyl)-5-methyl-7-(2-((pyridin-2-ylmethyl)amino)pyridine-4-yl)furo[3,2-c]pyridin-4(5H)-one hydrochloride

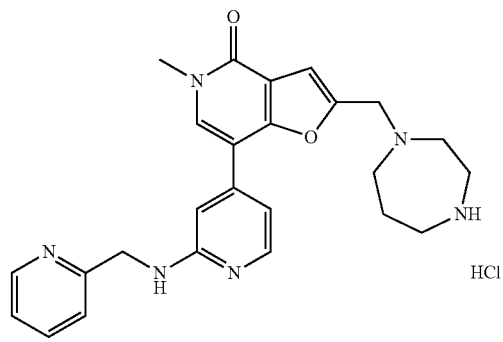 [SMILES: Cn1cc(-c2ccnc(NCc3ccccn3)c2)c2oc(CN3CCCNCC3)cc2c1=O ; Cl]

To a solution of tert-butyl 4-((5-methyl-4-oxo-7-(2-((pyridin-2-ylmethyl)amino)pyridin-4-yl)-4,5-dihydrofuro[3,2-c]pyridin-2-yl)methyl)-1,4-diazepane-1-carboxylate (for a preparation see Intermediate 56, 130 mg, 0.239 mmol) in DCM (5 mL) was added TFA (0.919 mL, 11.93 mmol). The mixture was stirred at 25° C. for 2 h. The mixture was concentrated in vacuo. The residue was combined with another batch of crude product (120 mg) which was prepared using the same conditions. The crude material was concentrated in vacuo and purified by MDAP, 1M HCl (0.5 mL) was added to the fraction containing product. The appropriate fractions were combined and evaporated to give 2-((1,4-diazepan-1-yl)methyl)-5-methyl-7-(2-((pyridin-2-ylmethyl)amino)pyridin-4-yl)furo[3,2-c]pyridin-4(5H)-one hydrochloride (100 mg, 0.225 mmol, 39% yield from combined reactions) as a white solid. LCMS: MH+ 445

Example 35

(R)-5-methyl-2-((2-methyl-4-(methylsulfonyl)piperazin-1-yl)methyl)-7-(2-(2-(2-oxopyrrolidin-1-yl)ethoxy)pyridin-4-yl)furo[3,2-c]pyridin-4(5H)-one

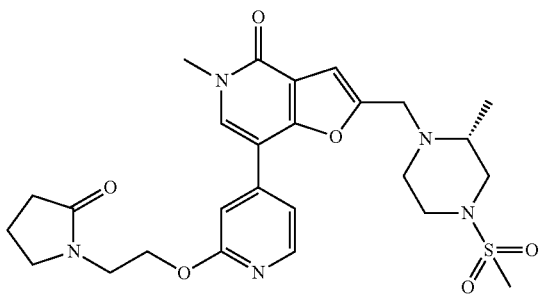 [SMILES: C[C@@H]1CN(S(C)(=O)=O)CCN1Cc1cc2c(=O)n(C)cc(-c3ccnc(OCCN4CCCC4=O)c3)c2o1]

1-(2-((4-(4,4,5,5-Tetramethyl-1,3,2-dioxaborolan-2-yl)pyridin-2-yl)oxy)ethyl)pyrrolidin-2-one (for a preparation see Intermediate 58, 376 mg, 42% w/w, 0.475 mmol), (R)-7-bromo-5-methyl-2-((2-methyl-4-(methylsulfonyl)piperazin-1-yl)methyl)furo[3,2-c]pyridin-4(5H)-one (for a preparation see Intermediate 5, 100 mg, 0.239 mmol), tetrakis(triphenylphosphine)palladium(0) (13.81 mg, 0.012 mmol) and potassium carbonate (99 mg, 0.717 mmol) were dissolved in 1,2-DME (3 mL) in a microwave vial. The mixture was heated to 120° C. for 2 h in a microwave reactor. The mixture was diluted with ethyl acetate (20 mL) and water (20 mL). The layers were separated and the aqueous phase was extracted with ethyl acetate (3×20 mL). The combined organics were dried using a hydrophobic frit and concentrated in vacuo. The residue was purified by MDAP. Appropriate fractions were combined and reduced in vacuo. The residue was dissolved in methanol and loaded onto a pre-conditioned (with methanol) aminopropyl cartridge (1 g) and eluted with methanol. Appropriate fractions were combined and reduced in vacuo to give (R)-5-methyl-2-((2-methyl-4-(methylsulfonyl)piperazin-1-yl)methyl)-7-(2-(2-(2-oxopyrrolidin-1-yl)ethoxy)pyridin-4-yl)furo[3,2-c]pyridin-4(5H)-one (11 mg, 8.46%) as a yellow oil. LCMS (2 min, High pH): Rt=0.73 min, MH$^+$ 544

Example 36

N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide, formic acid salt

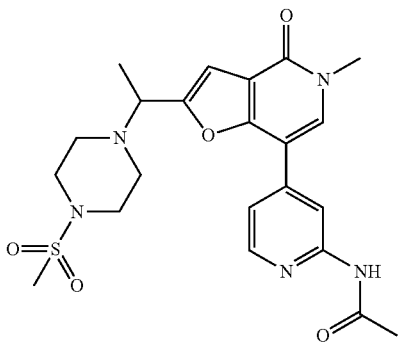 [SMILES: CC(=O)Nc1cc(-c2cn(C)c(=O)c3cc(C(C)N4CCN(S(C)(=O)=O)CC4)oc23)ccn1]

A mixture of 1-(but-3-yn-2-yl)-4-(methylsulfonyl)piperazine (for a preparation see Intermediate 20, 130 mg, 0.601 mmol), N-(5-iodo-4-methoxy-1-methyl-6-oxo-1,6-dihydro-[3,4'-bipyridin]-2'-yl)acetamide (for a preparation see Intermediate 59, 80 mg, 0.200 mmol), copper(I) iodide (8 mg, 0.042 mmol), triethylamine (0.999 mL, 7.17 mmol) and bis(triphenylphosphine)palladium(II) dichloride (14.07 mg, 0.020 mmol) in DMF (0.333 mL) was heated at 120° C. for 6 h using a microwave. The reaction mixture was concentrated under reduced pressure and purified by MDAP. The fraction containing desired product was concentrated under reduced pressure to give a yellow gum. The impure material was re-purified by MDAP. The fraction containing desired product was concentrated under reduced pressure to give N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide, formic acid salt (3 mg, 2.9%) as a yellow gum. LCMS (2 min, Formic): Rt=0.48 min, MH$^+$ 474

Example 36a and 36b (R)—N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide and (S)—N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide

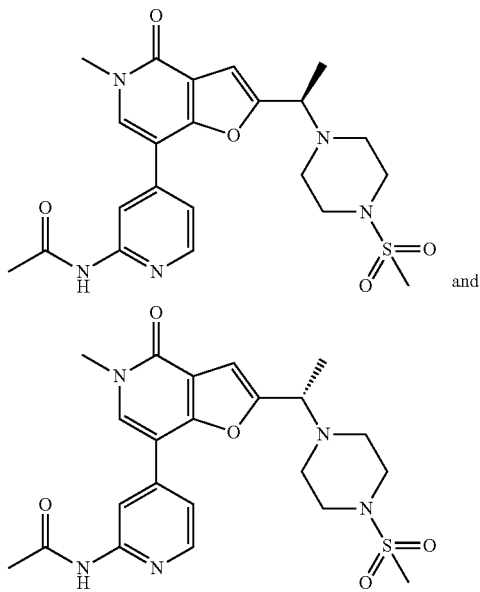

A sample of N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide (Example 36) was purified by chiral column chromatography using a Chiralpak ID 250 mm×30 mm, 5 micron column. The sample (39 mg) was dissolved in 3/7 ethanol/methanol (10 mL) and 2-2.5 mL batches were injected onto the column. The sample was eluted using 0.2% v/v isopropylamine in methanol at f=55 mL/min with UV DAD detection (280 nm, bandwidth 140 nm, reference 400 nm (bandwidth 20 nm)). Appropriate fractions were pooled and concentrated to give the two enantiomers:

(R)—N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide and (S)—N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide. Absolute stereochemistry not assigned for each sample.

First eluting isomer (18 mg), 99.8% single enantiomer by chiral analytical HPLC. LCMS (2 min, Formic): Rt=0.49 min, MH$^+$ 474.

Second eluting isomer (19 mg), 99.6% single enantiomer by chiral analytical HPLC. LCMS (2 min, Formic): Rt=0.48 min, MH$^+$ 474.

Analytical method: Chiralpak ID3 50 mm×4.6 mm, 3 micron column. Mobile phase: 0.2% v/v isopropylamine in methanol at f=1 mL/min with UV DAD detection (280 nm, bandwidth 140 nm, reference 400 nm (bandwidth 20 nm)).

Example 37

N-(4-(5-methyl-2-((4-(methylsulfonyl)piperazin-1-yl)methyl)-4-oxo-4,5-dihydrofuro[3,2-c]pyridin-7-yl)pyridin-2-yl)acetamide

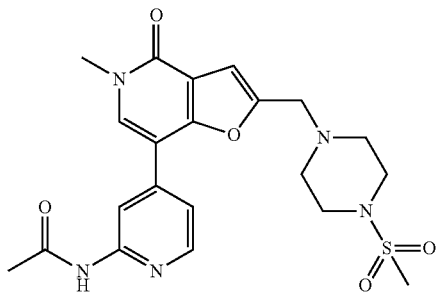 [SMILES: CC(=O)Nc1cc(-c2cn(C)c(=O)c3cc(CN4CCN(S(C)(=O)=O)CC4)oc23)ccn1]

To a stirred suspension of 7-bromo-5-methyl-2-((4-(methylsulfonyl)piperazin-1-yl)methyl)furo[3,2-c]pyridin-4(5H)-one (for a preparation see Intermediate 3, 100 mg, 0.247 mmol), N-(4-(4,4,5,5-tetramethyl-1,3,2-dioxaborolan-2-yl)pyridin-2-yl)acetamide (Milestone Pharma Tech) (104 mg, 0.396 mmol), potassium carbonate (103 mg, 0.742 mmol) in 1,2-DME (3 mL) in a microwave vial, was added tetrakis(triphenylphosphine)palladium(0) (14.29 mg, 0.012 mmol). The microwave vial was sealed and heated in a microwave at 120° C. for 2 h. The mixture was dissolved in methanol and concentrated in vacuo. The residue was re-dissolved in methanol and loaded onto an SCX cartridge (1 g) and eluted with 2M ammonia in methanol. Appropriate fractions were combined and concentrated in vacuo. The residue was purified by MDAP. Appropriate fractions were combined and concentrated in vacuo to give N-(4-(5-methyl-2-((4-(methylsulfonyl)piperazin-1-yl)methyl)-4-oxo-4,5-dihydrofuro[3,2-c]pyridin-7-yl)pyridin-2-yl)acetamide (45 mg, 39.6%) as a white solid.

LCMS (2 min, High pH): Rt=0.64 min, MH$^+$ 460

Example 38

(R)—N-(5-(5-methyl-2-((2-methyl-4-(methylsulfonyl)piperazin-1-yl)methyl)-4-oxo-4,5-dihydrofuro[3,2-c]pyridin-7-yl)pyridin-3-yl)acetamide

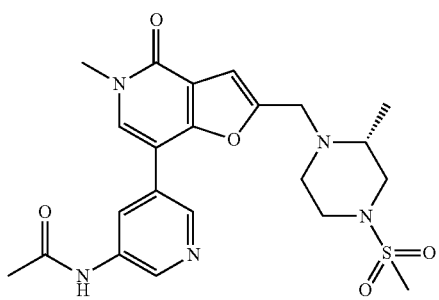 [SMILES: CC(=O)Nc1cncc(-c2cn(C)c(=O)c3cc(CN4CCN(S(C)(=O)=O)C[C@H]4C)oc23)c1]

To a stirred suspension of (R)-7-bromo-5-methyl-2-((2-methyl-4-(methylsulfonyl)piperazin-1-yl)methyl)furo[3,2-c]pyridin-4(5H)-one (for a preparation see Intermediate 5, 100 mg, 0.239 mmol), N-(5-(4,4,5,5-tetramethyl-1,3,2-dioxaborolan-2-yl)pyridin-3-yl)acetamide (for a preparation see Intermediate 61, 258 mg, 39% w/w, 0.382 mmol), potassium carbonate (99 mg, 0.717 mmol) in 1,2-DME (3 mL) in a microwave vial, was added tetrakis(triphenylphosphine)palladium(0) (13.81 mg, 0.012 mmol). The microwave vial was sealed and heated in a microwave at 120° C. for 2 h. The mixture was dissolved in ethyl acetate and filtered through a Celite cartridge. The solvent was evaporated under reduced pressure and the residue was purified by MDAP. Appropriate fractions were combined and concentrated in vacuo. The residue was dissolved in methanol and eluted through an amino propyl cartridge (500 mg). Appropriate fractions were reduced in vacuo. The residue was combined with another batch of crude product which was prepared using the same conditions. The crude material was purified by MDAP. Appropriate fractions were combined and concentrated in vacuo to give (R)—N-(5-(5-methyl-2-((2-methyl-4-(methylsulfonyl)piperazin-1-yl)methyl)-4-oxo-4,5-dihydrofuro[3,2-c]pyridin-7-yl)pyridin-3-yl)acetamide (5.9 mg, 2.6% yield from combined reactions) as a white gum. LCMS (2 min, High pH): Rt=0.62 min, MH$^+$ 474

Example 39

7-(3-((cyclopropylmethyl)amino)pyridin-4-yl)-5-methyl-2-((4-(methylsulfonyl)piperazin-1-yl)methyl)furo[3,2-c]pyridin-4(5H)-one

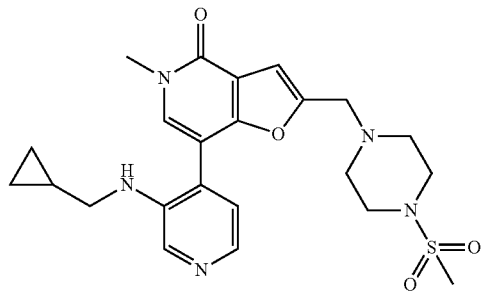

7-(3-Aminopyridin-4-yl)-5-methyl-2-((4-(methylsulfonyl)piperazin-1-yl)methyl)furo[3,2-c]pyridin-4(5H)-one (for a preparation see Intermediate 63, 72 mg, 0.138 mmol) was added to a suspension of cyclopropanecarbaldehyde (10.31 μL, 0.138 mmol) in methanol (9 mL) and acetic acid (1 mL) and stirred for 30 min at rt. 2-Picoline borane complex (22.14 mg, 0.207 mmol) was added and the mixture was left stirring at room temperature overnight. The solvent was evaporated and saturated aqueous sodium bicarbonate (10 mL) was added. The product was extracted with DCM (2×10 mL), filtered through a hydrophobic frit and concentrated in vacuo. The residue was purified by MDAP to give a brown solid. This was re-purified by MDAP to give 7-(3-((cyclopropylmethyl)amino)pyridin-4-yl)-5-methyl-2-((4-(methylsulfonyl)piperazin-1-yl)methyl)furo[3,2-c]pyridin-4(5H)-one (21 mg, 0.045 mmol, 32.3% yield) as a white solid. LCMS (2 min, High pH): Rt=0.76 min, MH$^+$ 472

Example 40

(R)-7-(3-((cyclopropylmethyl)amino)pyridin-4-yl)-5-methyl-2-((2-methyl-4-(methylsulfonyl)piperazin-1-yl)methyl)furo[3,2-c]pyridin-4(5H)-one

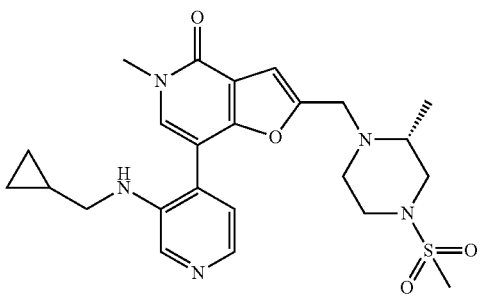

(R)-7-(3-Aminopyridin-4-yl)-5-methyl-2-((2-methyl-4-(methylsulfonyl)piperazin-1-yl)methyl)furo[3,2-c]pyridin-4(5H)-one (for a preparation see Intermediate 65, 81 mg, 0.160 mmol) was added to a suspension of cyclopropanecarbaldehyde (0.012 mL, 0.160 mmol) in methanol (9 mL) and acetic acid (1 mL) and stirred for 30 min at rt. 2-Picoline borane complex (25.6 mg, 0.239 mmol) was added and the mixture was left stirring at room temperature overnight. The solvent was evaporated and saturated aqueous sodium bicarbonate (20 mL) was added. The product was extracted with DCM (2×10 mL), filtered through a hydrophobic frit and concentrated in vacuo. The residue was purified by MDAP. The resulting impure product was further purified by MDAP. Fractions containing product were concentrated in vacuo to give a yellow oil. This was dissolved in MeOH and eluted through an aminopropyl cartridge (1 g) with MeOH. The solvent was concentrated in vacuo to give (R)-7-(3-((cyclopropylmethyl)amino)pyridin-4-yl)-5-methyl-2-((2-methyl-4-(methylsulfonyl)piperazin-1-yl)methyl)furo[3,2-c]pyridin-4(5H)-one (22 mg, 0.045 mmol, 28.4% yield) as a white solid.

LCMS (2 min, Formic): Rt=0.48 min, MH+ 486.

Example 41

5-methyl-2-(((R)-2-methyl-4-(methylsulfonyl)piperazin-1-yl)methyl)-7-(3-(oxetan-2-ylmethoxy)pyridin-4-yl)furo[3,2-c]pyridin-4(5H)-one

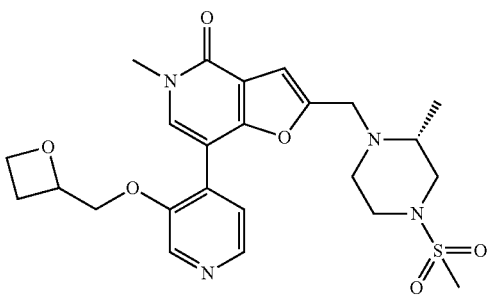 [SMILES: C[C@@H]1CN(S(C)(=O)=O)CCN1Cc1cc2c(=O)n(C)cc(-c3ccncc3OCC3CCO3)c2o1]

Step 1

To a suspension of (R)-7-bromo-5-methyl-2-((2-methyl-4-(methylsulfonyl)piperazin-1-yl)methyl)furo[3,2-c]pyridin-4(5H)-one (for a preparation see Intermediate 5, 120 mg, 0.287 mmol), 4,4,5,5-tetramethyl-1,3,2-dioxaborolane (0.250 mL, 1.721 mmol), and triethylamine (0.160 mL, 1.147 mmol) in 1,4-dioxane (5 mL), was added PEPPSI-SIPr (17 mg, 0.025 mmol). The mixture was refluxed at 100° C. for 3 h. The reaction mixture was diluted with EtOAc and filtered through Celite then concentrated in vacuo to give crude (R)-5-methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one as a yellow oil (391 mg). Purity estimated at 22.3% and used directly in Step 2 without further purification.

Step 2

To a stirred suspension of crude (R)-5-methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one from Step 1 (391 mg, 22.3% w/w, 0.187 mmol), crude 4-bromo-3-(oxetan-2-ylmethoxy)pyridine (for a preparation see Intermediate 67, 80 mg, 59.5% w/w, 0.195 mmol) and 2M sodium carbonate in water (0.749 mL, 1.499 mmol) in 1,2-DME (3 mL) in a microwave vial, was added tetrakis(triphenylphosphine)palladium(0) (12 mg, 10.38 µmol). The microwave vial was sealed and placed in a Biotage initiator microwave and heated at 120° C. for 30 min. The mixture was diluted with EtOAc (25 mL) and water (25 mL). Two layers were separated and the aqueous phase was re-extracted with EtOAc (5×25 mL). The organic phase was dried using a hydrophobic frit and concentrated in vacuo. The residue was dissolved in DMSO (4 mL) and purified by MDAP. Appropriate fractions were combined and concentrated in vacuo to give a yellow oil. The residue was dissolved in MeOH and loaded onto an amino-propyl cartridge (2 g) that had been pre-conditioned with MeOH. The cartridge was eluted with MeOH and appropriate fractions were combined and concentrated in vacuo to give 5-methyl-2-(((R)-2-methyl-4-(methylsulfonyl)piperazin-1-yl)methyl)-7-(3-(oxetan-2-ylmethoxy)pyridin-4-yl)furo[3,2-c]pyridin-4(5H)-one as a yellow oil (32.2 mg, 34.2%).

LCMS (2 min, Formic): Rt=0.44 min, MH+ 503.

Example 42

5-methyl-2-(((R)-2-methyl-4-(methylsulfonyl)piperazin-1-yl)methyl)-7-(3-((R)-oxetan-2-ylmethoxy)pyridin-4-yl)furo[3,2-c]pyridin-4(5H)-one

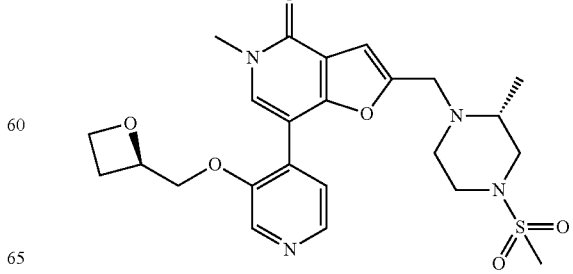

Example 43

5-methyl-2-(((R)-2-methyl-4-(methylsulfonyl)piperazin-1-yl)methyl)-7-(3-((S)-oxetan-2-ylmethoxy)pyridin-4-yl)furo[3,2-c]pyridin-4(5H)-one

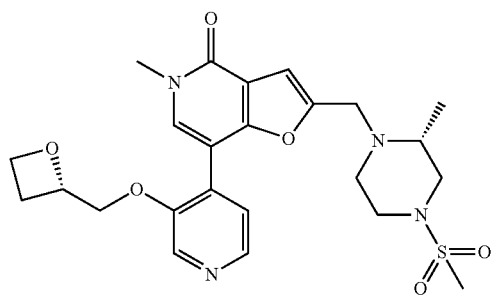 [SMILES: C[C@@H]1CN(S(C)(=O)=O)CCN1Cc1cc2c(=O)n(C)cc(-c3ccncc3OC[C@@H]3CCO3)c2o1]

5-Methyl-2-(((R)-2-methyl-4-(methylsulfonyl)piperazin-1-yl)methyl)-7-(3-(oxetan-2-ylmethoxy)pyridin-4-yl)furo[3,2-c]pyridin-4(5H)-one (Example 41) was purified by chiral HPLC using a Chiralpak IA 30 mm×25 cm column. The sample (120 mg) was dissolved at 20 mg/mL and 2 mL batches were injected onto the column. The sample was eluted using 40% EtOH/hexane at f=30 mL/min with detection at 215 nm. Appropriate fractions were pooled and concentrated to give:

5-methyl-2-(((R)-2-methyl-4-(methylsulfonyl)piperazin-1-yl)methyl)-7-(3-((R)-oxetan-2-ylmethoxy)pyridin-4-yl)furo[3,2-c]pyridin-4(5H)-one (Example 42) (32 mg). Chiral HPLC—98.8% pure (4.6 mm×25 cm Chiralpak IA column, 40% EtOH/Heptane, f=1.0 mL/min, wavelength 215 nm). LCMS (2 min, Formic): Rt=0.42 min, MH+ 503.

Also obtained was:

5-methyl-2-(((R)-2-methyl-4-(methylsulfonyl)piperazin-1-yl)methyl)-7-(3-((S)-oxetan-2-ylmethoxy)pyridin-4-yl)furo[3,2-c]pyridin-4(5H)-one (Example 43) (36 mg). Chiral HPLC 98.4% pure (4.6 mm×25 cm Chiralpak IA column, 40% EtOH/Heptane, f=1.0 mL/min, wavelength 215 nm). LCMS (2 min, Formic): Rt=0.42 min, MH+ 503.

Example 42

5-methyl-2-(((R)-2-methyl-4-(methylsulfonyl)piperazin-1-yl)methyl)-7-(3-((R)-oxetan-2-ylmethoxy)pyridin-4-yl)furo[3,2-c]pyridin-4(5H)-one

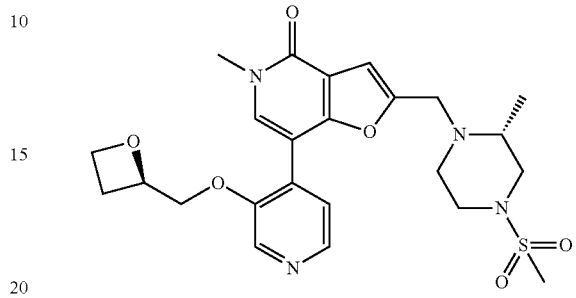

Alternative Preparation (R)-4-bromo-3-(oxetan-2-ylmethoxy)pyridine (for a preparation see Intermediate 69, 19.83 g, 81 mmol) was mixed with cesium carbonate (37.8 g, 116 mmol), toluene (200 mL) and methanol (60 mL), and degassed by bubbling nitrogen through the reaction mixture for 20 min. Pd(PPh$_3$)$_4$ (6.70 g, 5.80 mmol) and (R)-5-methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one (for a preparation see Intermediate 5a, 30 g, 58.0 mmol) were added and heating continued for 18 h. The mixture was cooled and evaporated in vacuo and the residue partitioned between DCM (300 mL) and water (500 mL). The aqueous layer was extracted with DCM (300 mL) and the combined organics were dried and evaporated in vacuo to give a pale yellow foam. The impure product was loaded onto a 750 g silica column and eluted with 10 volumes of acetone, then with 30% methanol/acetone. Appropriate fractions were evaporated in vacuo to give a pale yellow foam, which was dissolved in DCM (300 mL) and treated with thioureidopropyl silica (Aldrich, 30 g). The mixture was stirred for 30 min then filtered. The silica was washed with DCM (200 mL) and the filtrate evaporated in vacuo the title compound (11.1 g, 22.09 mmol, 38.1% yield) as a beige foam. This was combined with further batches for a final purification by chiral HPLC using a ChiralPak 1A 20 um 5×20 cm column. The mobile phase was methanol with a flow rate of 118 mL/min and detection at 230 nm. Appropriate fractions were combined and the methanol was evaporated. The residue was re-evaporated from DCM and EtOAc to give a pale yellow foam which was dried in a vacuum oven to give the title compound. $^1$H NMR (400 MHz, CDCl$_3$) δ-ppm 8.46 (1H, s), 8.38 (1H, d), 7.88 (1H, s), 7.59 (1H, d), 6.88 (1H, s), 5.13 (1H, m), 4.68 (1H, m), 4.43 (1H, m), 4.30 (2H, d), 3.90 (2H, s), 3.68 (3H, s), 3.50 (2H, m), 2.93 (2H, m), 2.73 (3H, s), 2.74 (1H, m), 2.60 (4H, m), 1.22 (3H, d). LCMS (2 min, Formic): Rt=0.44 min, MH+ 503. Chiral HPLC purity >99%.

Further compounds of formula (I) that have been prepared include:

| Example No. | Structure | Name | LCMS method | Rt min | MH+ |
|---|---|---|---|---|---|
| 44 | 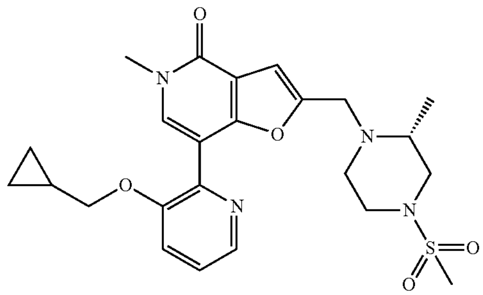 [SMILES: C[C@@H]1CN(S(C)(=O)=O)CCN1Cc1cc2c(=O)n(C)cc(-c3ncccc3OCC3CC3)c2o1] | (R)-7-(3-(cyclopropylmethoxy)pyridin-2-yl)-5-methyl-2-((2-methyl-4-(methylsulfonyl)piperazin-1-yl)methyl)furo[3,2-c]pyridin-4(5H)-one | Formic | 0.67 | 487 |
| 45 | 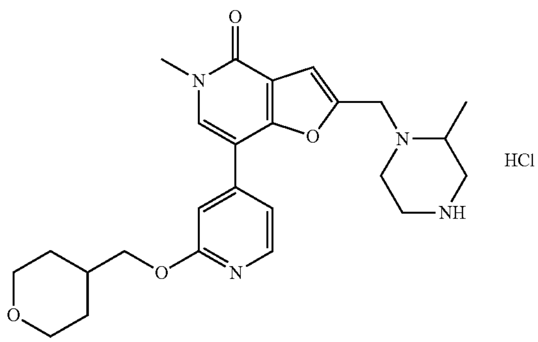 [SMILES: CC1CNCCN1Cc1cc2c(=O)n(C)cc(-c3ccnc(OCC4CCOCC4)c3)c2o1 ; Cl] | 5-methyl-2-((2-methylpiperazin-1-yl)methyl)-7-(2-((tetrahydro-2H-pyran-4-yl)methoxy)pyridin-4-yl)furo[3,2-c]pyridin-4(5H)-one hydrochloride | Formic 2.5 min run | 1.21 | 453 |
| 46 | 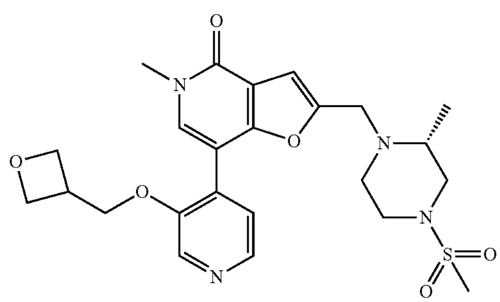 [SMILES: C[C@@H]1CN(S(C)(=O)=O)CCN1Cc1cc2c(=O)n(C)cc(-c3ccncc3OCC3COC3)c2o1] | (R)-5-methyl-2-((2-methyl-4-(methylsulfonyl)piperazin-1-yl)methyl)-7-(3-(oxetan-3-ylmethoxy)pyridin-4-yl)furo[3,2-c]pyridin-4(5H)-one | Formic | 0.44 | 503 |
| 47 | 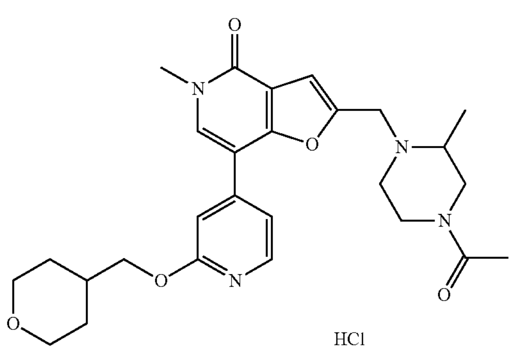 [SMILES: CC(=O)N1CCN(Cc2cc3c(=O)n(C)cc(-c4ccnc(OCC5CCOCC5)c4)c3o2)C(C)C1 ; Cl] | 2-((4-acetyl-2-methylpiperazin-1-yl)methyl)-5-methyl-7-(2-((tetrahydro-2H-pyran-4-yl)methoxy)pyridin-4-yl)furo[3,2-c]pyridin-4(5H)-one hydrochloride | Formic | 1.20 | 495 |

-continued

| Example No. | Structure | Name | LCMS method | Rt min | MH+ |
|---|---|---|---|---|---|
| 48 | 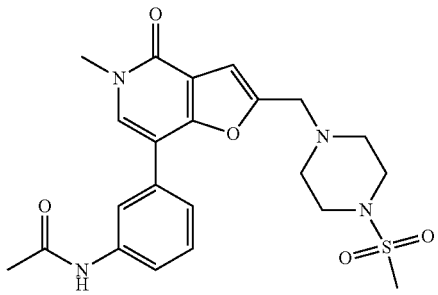 [SMILES: CC(=O)Nc1cccc(-c2cn(C)c(=O)c3cc(CN4CCN(S(C)(=O)=O)CC4)oc23)c1] | N-(3-(5-methyl-2-((4-(methylsulfonyl)piperazin-1-yl)methyl)-4-oxo-4,5-dihydrofuro[3,2-c]pyridin-7-yl)phenyl)acetamide | Formic | 0.54 | 459 |
| 49 | 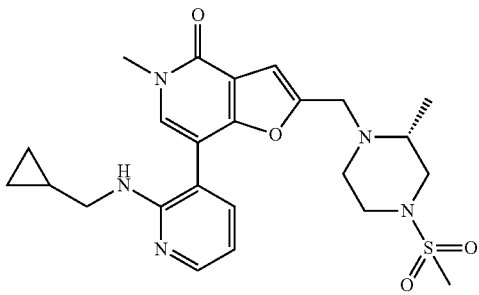 [SMILES: C[C@@H]1CN(S(C)(=O)=O)CCN1Cc1cc2c(=O)n(C)cc(-c3cccnc3NCC3CC3)c2o1] | (R)-7-(2-((cyclopropylmethyl)amino)pyridin-3-yl)-5-methyl-2-((2-methyl-4-(methylsulfonyl)piperazin-1-yl)methyl)furo[3,2-c]pyridin-4(5H)-one | Formic | 0.46 | 486 |
| 50 | 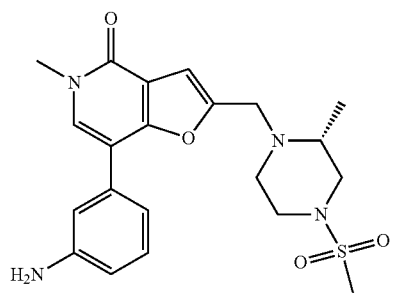 [SMILES: C[C@@H]1CN(S(C)(=O)=O)CCN1Cc1cc2c(=O)n(C)cc(-c3cccc(N)c3)c2o1] | (R)-7-(3-aminophenyl)-5-methyl-2-((2-methyl-4-(methylsulfonyl)piperazin-1-yl)methyl)furo[3,2-c]pyridin-4(5H)-one | Formic | 0.47 | 431 |
| 51 | 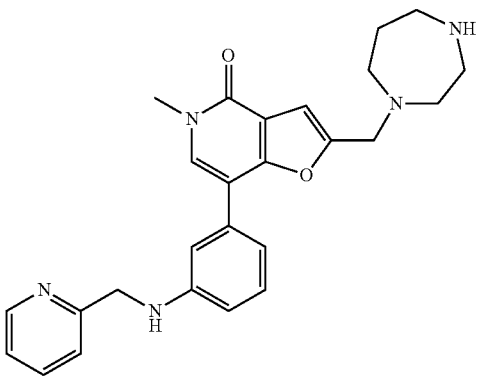 [SMILES: Cn1cc(-c2cccc(NCc3ccccn3)c2)c2oc(CN3CCCNCC3)cc2c1=O] | 2-((1,4-diazepan-1-yl)methyl)-5-methyl-7-(3-((pyridin-2-ylmethyl)amino)phenyl)furo[3,2-c]pyridin-4(5H)-one hydrochloride | Formic 2.5 min run | 1.14 | 444 |

| Example No. | Structure | Name | LCMS method | Rt min | MH+ |
|---|---|---|---|---|---|
| 52 | 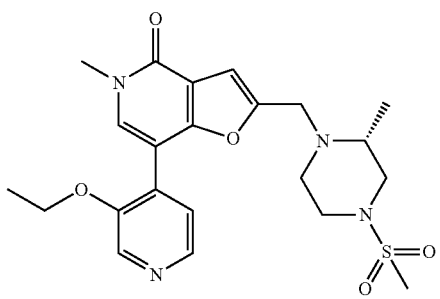 [SMILES: CCOc1cnccc1-c1cn(C)c(=O)c2cc(CN3CCN(S(C)(=O)=O)C[C@H]3C)oc12] | (R)-7-(3-ethoxypyridin-4-yl)-5-methyl-2-((2-methyl-4-(methylsulfonyl)piperazin-1-yl)methyl)furo[3,2-c]pyridin-4(5H)-one | Formic | 0.47 | 461 |
| 53 | 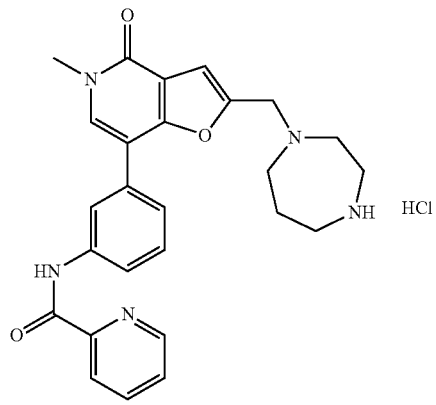 [SMILES: Cn1cc(-c2cccc(NC(=O)c3ccccn3)c2)c2oc(CN3CCCNCC3)cc2c1=O ; Cl] | N-(3-(2-((1,4-diazepan-1-yl)methyl)-5-methyl-4-oxo-4,5-dihydrofuro[3,2-c]pyridin-7-yl)phenyl)picolinamide hydrochloride | Formic 2.5 min run | 1.16 | 458 |
| 54 | 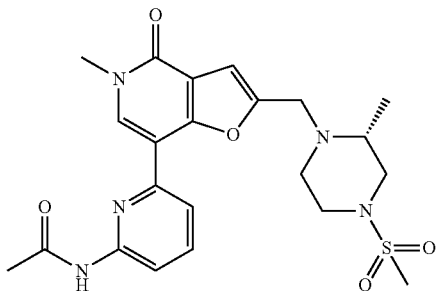 [SMILES: CC(=O)Nc1cccc(-c2cn(C)c(=O)c3cc(CN4CCN(S(C)(=O)=O)C[C@H]4C)oc23)n1] | (R)-N-(6-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide | Formic | 0.55 | 474 |
| 55 | 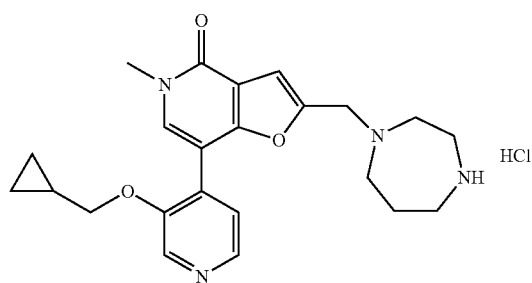 [SMILES: Cn1cc(-c2ccncc2OCC2CC2)c2oc(CN3CCCNCC3)cc2c1=O ; Cl] | 2-((1,4-diazepan-1-yl)methyl)-7-(3-(cyclopropylmethoxy)pyridin-4-yl)-5-methylfuro[3,2-c]pyridin-4(5H)-one hydrochloride | Formic 2.5 min run | 1.09 | 409 |

| Example No. | Structure | Name | LCMS method | Rt min | MH+ |
|---|---|---|---|---|---|
| 56 | 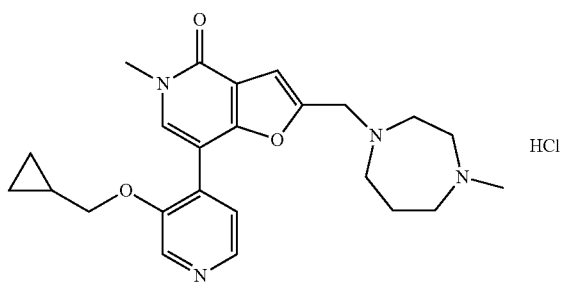 [SMILES: CN1CCCN(Cc2cc3c(=O)n(C)cc(-c4ccncc4OCC4CC4)c3o2)CC1 ; Cl] | 7-(3-(cyclopropylmethoxy)pyridin-4-yl)-5-methyl-2-((4-methyl-1,4-diazepan-1-yl)methyl)furo[3,2-c]pyridin-4(5H)-one hydrochloride | Formic 2.5 min run | 1.12 | 423 |
| 57 | 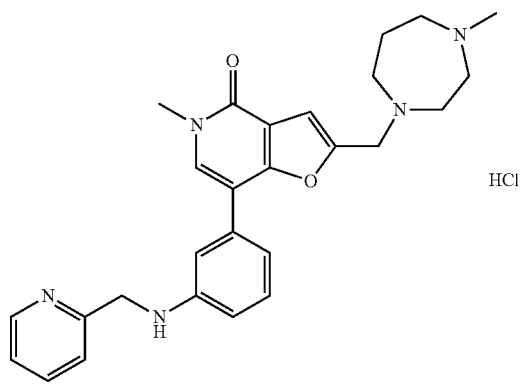 [SMILES: CN1CCCN(Cc2cc3c(=O)n(C)cc(-c4cccc(NCc5ccccn5)c4)c3o2)CC1 ; Cl] | 5-methyl-2-((4-methyl-1,4-diazepan-1-yl)methyl)-7-(3-((pyridin-2-ylmethyl)amino)phenyl)furo[3,2-c]pyridin-4(5H)-one hydrochloride | Formic 2.5 min run | 1.20 | 458 |
| 58 | 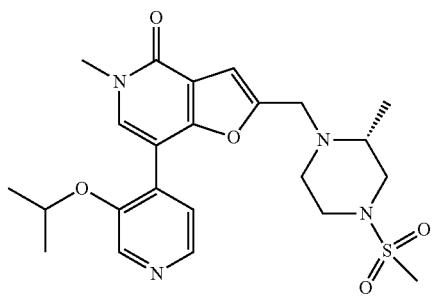 [SMILES: CC(C)Oc1cnccc1-c1cn(C)c(=O)c2cc(CN3CCN(S(C)(=O)=O)C[C@H]3C)oc12] | (R)-7-(3-isopropoxypyridin-4-yl)-5-methyl-2-((2-methyl-4-(methylsulfonyl)piperazin-1-yl)methyl)furo[3,2-c]pyridin-4(5H)-one | Formic | 0.49 | 475 |
| 59 | 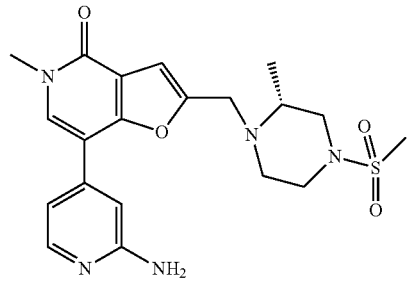 | (R)-7-(2-aminopyridin-4-yl)-5-methyl-2-((2-methyl-4-(methylsulfonyl)piperazin-1-yl)methyl)furo[3,2-c]pyridin-4(5H)-one | Formic | 0.38 | 432 |

| Example No. | Structure | Name | LCMS method | Rt min | MH+ |
|---|---|---|---|---|---|
| 60 | 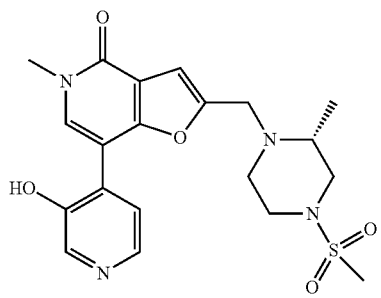 [SMILES: C[C@@H]1CN(S(C)(=O)=O)CCN1Cc1cc2c(=O)n(C)cc(-c3ccncc3O)c2o1] | (R)-7-(3-hydroxypyridin-4-yl)-5-methyl-2-((2-methyl-4-(methylsulfonyl)piperazin-1-yl)methyl)furo[3,2-c]pyridin-4(5H)-one | High pH | 0.55 | 433 |
| 61 | 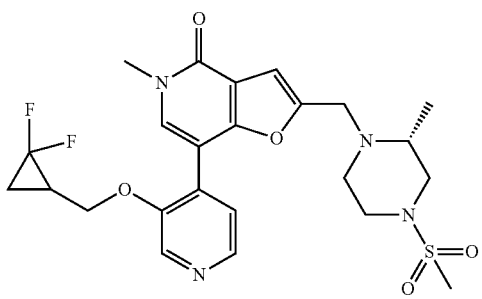 [SMILES: C[C@@H]1CN(S(C)(=O)=O)CCN1Cc1cc2c(=O)n(C)cc(-c3ccncc3OCC3CC3(F)F)c2o1] | 7-(3-((2,2-difluorocyclopropyl)methoxy)pyridin-4-yl)-5-methyl-2-(((R)-2-methyl-4-(methylsulfonyl)piperazin-1-yl)methyl)furo[3,2-c]pyridin-4(5H)-one | Formic | 0.57 | 523 |
| 62 | 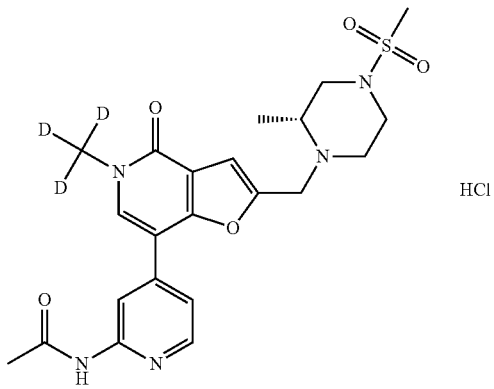 [SMILES: [2H]C([2H])([2H])n1cc(-c2ccnc(NC(C)=O)c2)c2oc(CN3CCN(S(C)(=O)=O)C[C@H]3C)cc2c1=O ; Cl] | (R)-N-(4-(5-($^2$H$_3$)methyl-2-((2-methyl-4-(methylsulfonyl)piperazin-1-yl)methyl)-4-oxo-4,5-dihydrofuro[3,2-c]pyridin-7-yl)pyridin-2-yl)acetamide | Formic 2.5 min run | 1.12 | 477 |
| 63 | 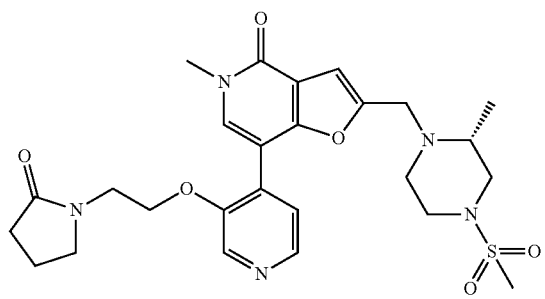 [SMILES: C[C@@H]1CN(S(C)(=O)=O)CCN1Cc1cc2c(=O)n(C)cc(-c3ccncc3OCCN3CCCC3=O)c2o1] | (R)-5-methyl-2-((2-methyl-4-(methylsulfonyl)piperazin-1-yl)methyl)-7-(3-(2-(2-oxopyrrolidin-1-yl)ethoxy)pyridin-4-yl)furo[3,2-c]pyridin-4(5H)-one | High pH | 0.64 | 544 |

| Example No. | Structure | Name | LCMS method | Rt min | MH+ |
|---|---|---|---|---|---|
| 64 | 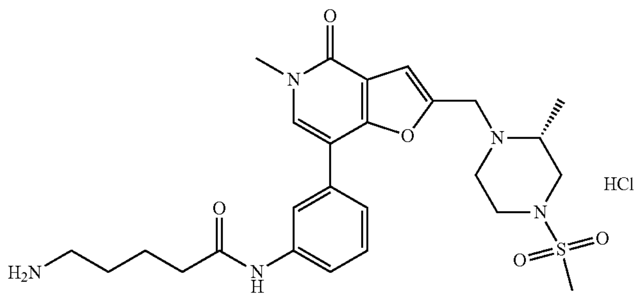 [SMILES: C[C@@H]1CN(S(C)(=O)=O)CCN1Cc1cc2c(=O)n(C)cc(-c3cccc(NC(=O)CCCCN)c3)c2o1 ; Cl] | (R)-5-amino-N-(3-(5-methyl-2-((2-methyl-4-(methylsulfonyl)piperazin-1-yl)methyl)-4-oxo-4,5-dihydrofuro[3,2-c]pyridin-7-yl)phenyl)pentanamide hydrochloride | Formic | 0.48 | 530 |
| 65 | 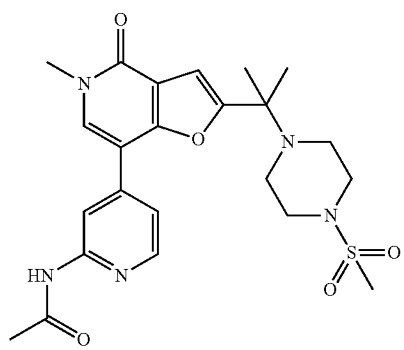 [SMILES: CC(=O)Nc1cc(-c2cn(C)c(=O)c3cc(C(C)(C)N4CCN(S(C)(=O)=O)CC4)oc23)ccn1] | N-(4-(5-methyl-2-(2-(4-(methylsulfonyl)piperazin-1-yl)propan-2-yl)-4-oxo-4,5-dihydrofuro[3,2-c]pyridin-7-yl)pyridin-2-yl)acetamide | Formic | 0.50 | 488 |
| 66 | 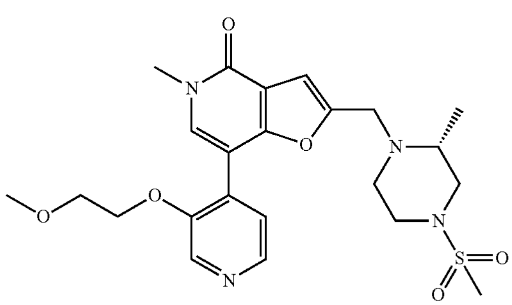 | (R)-7-(3-(2-methoxyethoxy)pyridin-4-yl)-5-methyl-2-((2-methyl-4-(methylsulfonyl)piperazin-1-yl)methyl)furo[3,2-c]pyridin-4(5H)-one | Formic | 0.45 | 491 |
| 67 | 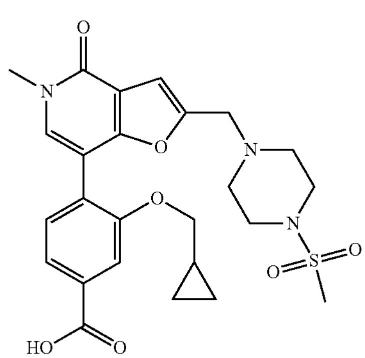 [SMILES: Cn1cc(-c2ccc(C(=O)O)cc2OCC2CC2)c2oc(CN3CCN(S(C)(=O)=O)CC3)cc2c1=O] | 3-(cyclopropylmethoxy)-4-(5-methyl-2-((4-(methylsulfonyl)piperazin-1-yl)methyl)-4-oxo-4,5-dihydrofuro[3,2-c]pyridin-7-yl)benzoic acid | Formic | 0.65 | 516 |

| Example No. | Structure | Name | LCMS method | Rt min | MH+ |
|---|---|---|---|---|---|
| 68 | 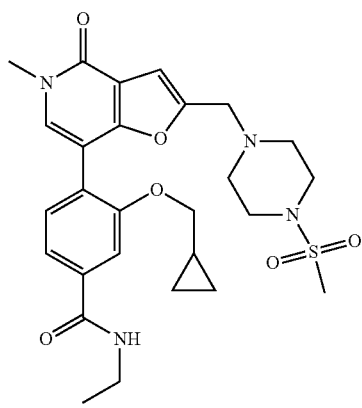 [SMILES: CCNC(=O)c1ccc(-c2cn(C)c(=O)c3cc(CN4CCN(S(C)(=O)=O)CC4)oc23)c(OCC2CC2)c1] | 3-(cyclopropylmethoxy)-N-ethyl-4-(5-methyl-2-((4-(methylsulfonyl)piperazin-1-yl)methyl)-4-oxo-4,5-dihydrofuro[3,2-c]pyridin-7-yl)benzamide | Formic | 0.69 | 543 |
| 69 | 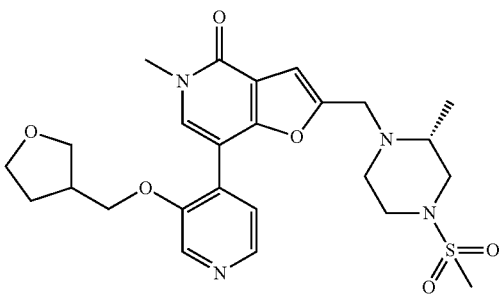 [SMILES: C[C@@H]1CN(S(C)(=O)=O)CCN1Cc1cc2c(=O)n(C)cc(-c3ccncc3OCC3CCOC3)c2o1] | 5-methyl-2-(((R)-2-methyl-4-(methylsulfonyl)piperazin-1-yl)methyl)-7-(3-((tetrahydrofuran-3-yl)methoxy)pyridin-4-yl)furo[3,2-c]pyridin-4(5H)-one | Formic | 0.48 | 517 |
| 70 | 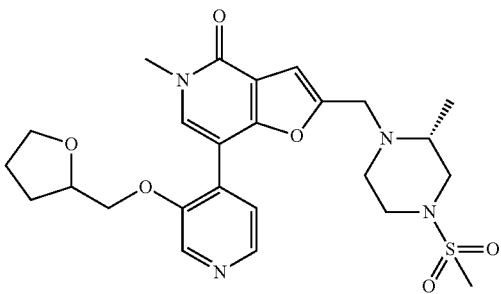 [SMILES: C[C@@H]1CN(S(C)(=O)=O)CCN1Cc1cc2c(=O)n(C)cc(-c3ccncc3OCC3CCCO3)c2o1] | 5-methyl-2-(((R)-2-methyl-4-(methylsulfonyl)piperazin-1-yl)methyl)-7-(3-((tetrahydrofuran-2-yl)methoxy)pyridin-4-yl)furo[3,2-c]pyridin-4(5H)-one | Formic | 0.50 | 517 |
| 71 | 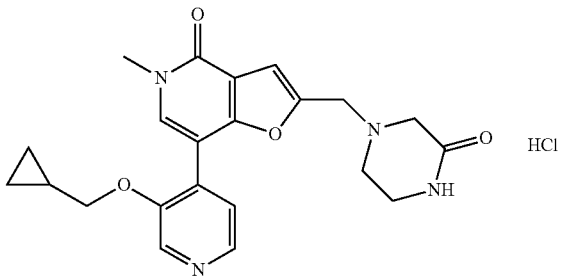 [SMILES: Cn1cc(-c2ccncc2OCC2CC2)c2oc(CN3CCNC(=O)C3)cc2c1=O ; Cl] | 7-(3-(cyclopropylmethoxy)pyridin-4-yl)-5-methyl-2-((3-oxopiperazin-1-yl)methyl)furo[3,2-c]pyridin-4(5H)-one hydrochloride | Formic 2.5 min run | 1.12 | 409 |

| Example No. | Structure | Name | LCMS method | Rt min | MH+ |
|---|---|---|---|---|---|
| 72 | 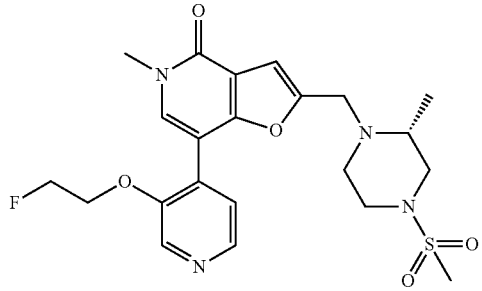 [SMILES: C[C@@H]1CN(S(C)(=O)=O)CCN1Cc1cc2c(=O)n(C)cc(-c3ccncc3OCCF)c2o1] | (R)-7-(3-(2-fluoroethoxy)pyridin-4-yl)-5-methyl-2-((2-methyl-4-(methylsulfonyl)piperazin-1-yl)methyl)furo[3,2-c]pyridin-4(5H)-one | High pH | 0.70 | 479 |
| 73 | 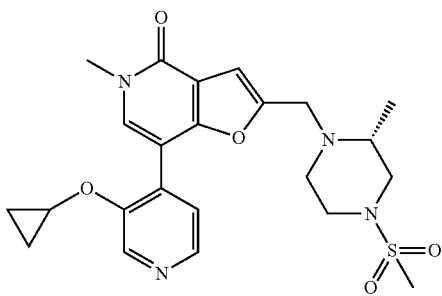 [SMILES: C[C@@H]1CN(S(C)(=O)=O)CCN1Cc1cc2c(=O)n(C)cc(-c3ccncc3OC3CC3)c2o1] | (R)-7-(3-cyclopropoxypyridin-4-yl)-5-methyl-2-((2-methyl-4-(methylsulfonyl)piperazin-1-yl)methyl)furo[3,2-c]pyridin-4(5H)-one | Formic | 0.49 | 473 |
| 74 | 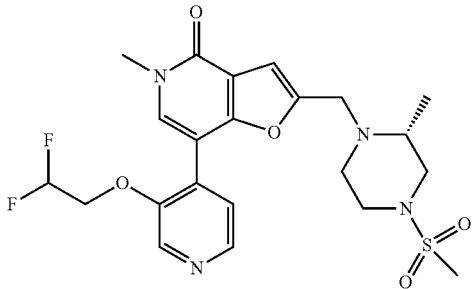 [SMILES: C[C@@H]1CN(S(C)(=O)=O)CCN1Cc1cc2c(=O)n(C)cc(-c3ccncc3OCC(F)F)c2o1] | (R)-7-(3-(2,2-difluoroethoxy)pyridin-4-yl)-5-methyl-2-((2-methyl-4-(methylsulfonyl)piperazin-1-yl)methyl)furo[3,2-c]pyridin-4(5H)-one | Formic | 0.49 | 497 |
| 75 | 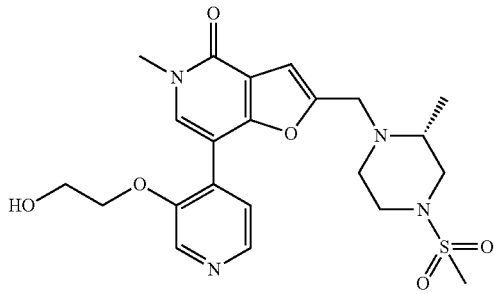 [SMILES: C[C@@H]1CN(S(C)(=O)=O)CCN1Cc1cc2c(=O)n(C)cc(-c3ccncc3OCCO)c2o1] | (R)-7-(3-(2-hydroxyethoxy)pyridin-4-yl)-5-methyl-2-((2-methyl-4-(methylsulfonyl)piperazin-1-yl)methyl)furo[3,2-c]pyridin-4(5H)-one | Formic | 0.38 | 477 |
| 76 | 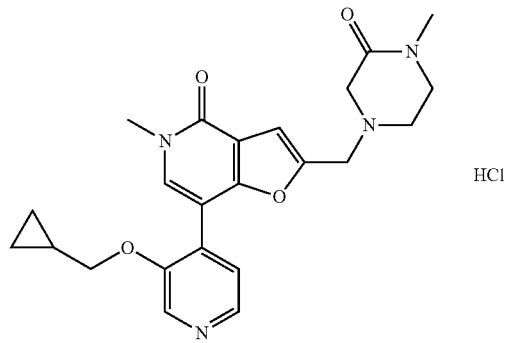 [SMILES: CN1CCN(Cc2cc3c(=O)n(C)cc(-c4ccncc4OCC4CC4)c3o2)CC1=O ; Cl] | 7-(3-(cyclopropylmethoxy)pyridin-4-yl)-5-methyl-2-((4-methyl-3-oxopiperazin-1-yl)methyl)furo[3,2-c]pyridin-4(5H)-one hydrochloride | Formic 2.5 min run | 1.16 | 423 |

| Example No. | Structure | Name | LCMS method | Rt min | MH+ |
|---|---|---|---|---|---|
| 77 | 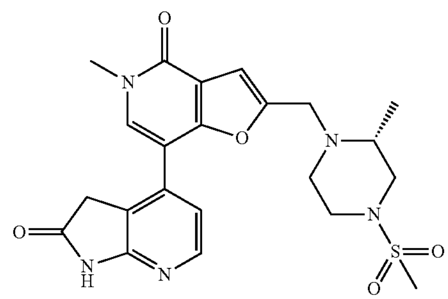 [SMILES: C[C@@H]1CN(S(C)(=O)=O)CCN1Cc1cc2c(=O)n(C)cc(-c3ccnc4c3CC(=O)N4)c2o1] | (R)-5-methyl-2-((2-methyl-4-(methylsulfonyl)piperazin-1-yl)methyl)-7-(2-oxo-2,3-dihydro-1H-pyrrolo[2,3-b]pyridin-4-yl)furo[3,2-c]pyridin-4(5H)-one | Formic | 0.46 | 472 |
| 78 | 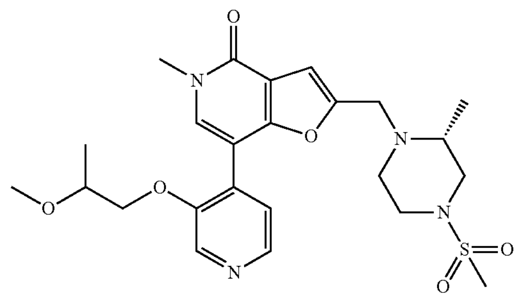 [SMILES: COC(C)COc1cnccc1-c1cn(C)c(=O)c2cc(CN3CCN(S(C)(=O)=O)C[C@H]3C)oc12] | 7-(3-(2-methoxypropoxy)pyridin-4-yl)-5-methyl-2-(((R)-2-methyl-4-(methylsulfonyl)piperazin-1-yl)methyl)furo[3,2-c]pyridin-4(5H)-one | Formic | 0.50 | 505 |
| 79 | 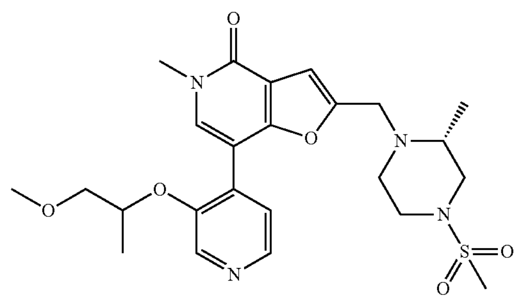 [SMILES: COCC(C)Oc1cnccc1-c1cn(C)c(=O)c2cc(CN3CCN(S(C)(=O)=O)C[C@H]3C)oc12] | 7-(3-((1-methoxypropan-2-yl)oxy)pyridin-4-yl)-5-methyl-2-(((R)-2-methyl-4-(methylsulfonyl)piperazin-1-yl)methyl)furo[3,2-c]pyridin-4(5H)-one | Formic | 0.50 | 505 |
| 80 | 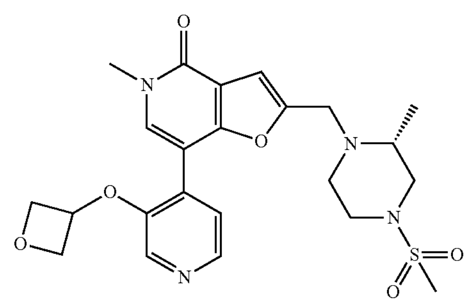 [SMILES: C[C@@H]1CN(S(C)(=O)=O)CCN1Cc1cc2c(=O)n(C)cc(-c3ccncc3OC3COC3)c2o1] | (R)-5-methyl-2-((2-methyl-4-(methylsulfonyl)piperazin-1-yl)methyl)-7-(3-(oxetan-3-yloxy)pyridin-4-yl)furo[3,2-c]pyridin-4(5H)-one | Formic | 0.44 | 489 |
| 81 | 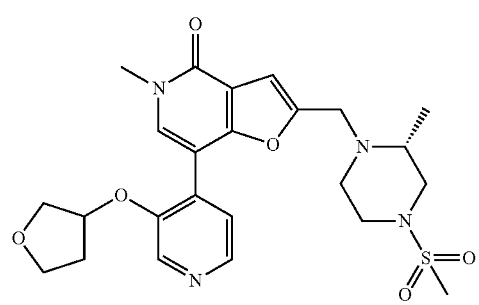 [SMILES: C[C@@H]1CN(S(C)(=O)=O)CCN1Cc1cc2c(=O)n(C)cc(-c3ccncc3OC3CCOC3)c2o1] | 5-methyl-2-(((R)-2-methyl-4-(methylsulfonyl)piperazin-1-yl)methyl)-7-(3-((tetrahydrofuran-3-yl)oxy)pyridin-4-yl)furo[3,2-c]pyridin-4(5H)-one | Formic | 0.42 | 503 |

| Example No. | Structure | Name | LCMS method | Rt min | MH+ |
|---|---|---|---|---|---|
| 81a & 81b | 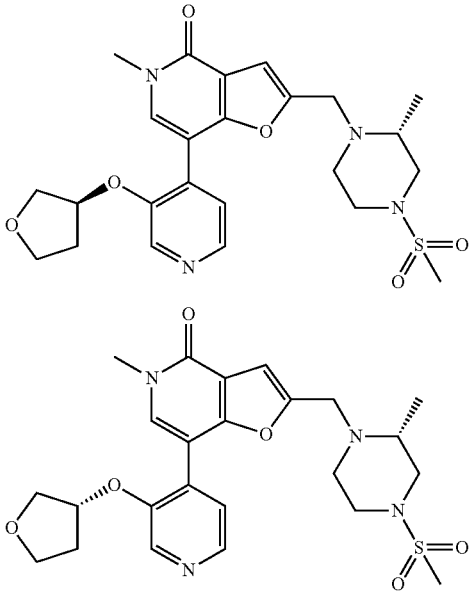 Separated diastereoisomers | 5-methyl-2-(((R)-2-methyl-4-(methylsulfonyl)piperazin-1-yl)methyl)-7-(3-(((S)-tetrahydrofuran-3-yl)oxy)pyridin-4-yl)furo[3,2-c]pyridin-4(5H)-one and 5-methyl-2-(yR)-2-methyl-4-(methylsulfonyl)piperazin-1-yl)methyl)-7-(3-(((R)-tetrahydrofuran-3-yl)oxy)pyridin-4-yl)furo[3,2-c]pyridin-4(5H)-one | Formic | 0.45 | 503 |

Example 46

(R)-5-methyl-2-((2-methyl-4-(methylsulfonyl)piperazin-1-yl)methyl)-7-(3-(oxetan-3-ylmethoxy)pyridin-4-yl)furo[3,2-c]pyridin-4(5H)-one

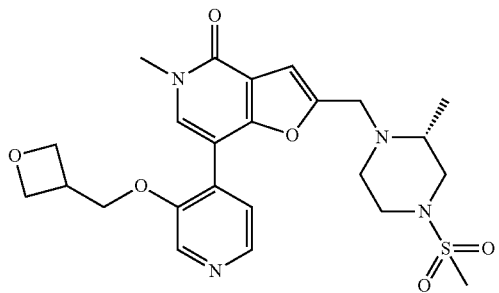 [SMILES: C[C@@H]1CN(S(C)(=O)=O)CCN1Cc1cc2c(=O)n(C)cc(-c3ccncc3OCC3COC3)c2o1]

To a stirred suspension of (R)-7-bromo-5-methyl-2-((2-methyl-4-(methylsulfonyl)piperazin-1-yl)methyl)furo[3,2-c]pyridin-4(5H)-one (for a preparation see Intermediate 5, 110 mg, 0.263 mmol), 3-(oxetan-3-ylmethoxy)-4-(4,4,5,5-tetramethyl-1,3,2-dioxaborolan-2-yl)pyridine (for a preparation see Intermediate 71, 589 mg, 0.421 mmol), potassium carbonate (109 mg, 0.789 mmol) in 1,2-DME (3 mL) in a microwave vial, was added Pd(PPh$_3$)$_4$(15.19 mg, 0.013 mmol). The microwave vial was sealed and placed in a Biotage initiator microwave to 120° C. for 2 h at normal absorption. The mixture was diluted with ethyl acetate (25 mL) and water (25 mL). Two layers were separated and the aqueous layer was re-extracted with ethyl acetate (4×25 mL). The organic phase was concentrated in vacuo. The residue was dissolved in 3 mL of DMSO and purified by MDAP. Appropriate fractions were combined and concentrated in vacuo. The resulting yellow oil was dissolved in methanol and loaded on to a pre-conditioned (with methanol) amino propyl cartridge (1 g) and the product was eluted with methanol. Appropriate fractions were combined and concentrated in vacuo to give (R)-5-methyl-2-((2-methyl-4-(methylsulfonyl)piperazin-1-yl)methyl)-7-(3-(oxetan-3-ylmethoxy)pyridin-4-yl)furo[3,2-c]pyridin-4(5H)-one as a yellow oil (18 mg, 13.6%). $^1$H NMR (600 MHz, MeOH-d$_4$) δ-ppm 8.47 (1H, s), 8.30 (1H, d), 7.97 (1H, s), 7.65 (1H, d), 6.91 (1H, s), 4.76 (2H, ddd), 4.48 (2H, td), 4.36 (2H, d), 3.93-3.99 (1H, m), 3.88-3.93 (1H, m), 3.68 (3H, s), 3.48 (1H, m), 3.40-3.44 (1H, m), 3.35-3.40 (1H, m), 2.90-2.97 (1H, m), 2.89-2.96 (1H, m), 2.79 (3H, s), 2.61-2.67 (1H, m), 2.52-2.59 (1H, m), 2.48-2.54 (1H, m), 1.20 (3H, d). LCMS (2 min, Formic): Rt=0.44 min, MH+ 503.

Example 61

7-(3-((2,2-difluorocyclopropyl)methoxy)pyridin-4-yl)-5-methyl-2-(((R)-2-methyl-4-(methylsulfonyl)piperazin-1-yl)methyl)furo[3,2-c]pyridin-4(5H)-one

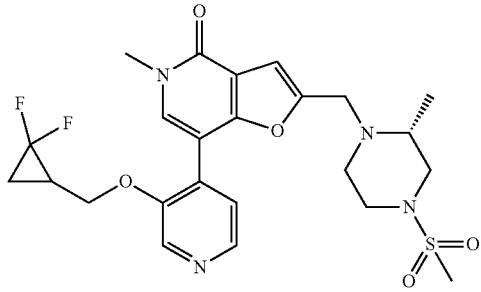 [SMILES: C[C@@H]1CN(S(C)(=O)=O)CCN1Cc1cc2c(=O)n(C)cc(-c3ccncc3OCC3CC3(F)F)c2o1]

(R)-5-Methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one (from Intermediate 5a alternative preparation, 522 mg, 17% w/w, 0.191 mmol), 4-bromo-3-((2,2-difluorocyclopropyl)methoxy)pyridine (for a preparation see Intermediate 72, 179 mg, 0.407 mmol), Tetrakis(triphenylphosphine)palladium (0) (22.03 mg, 0.019 mmol) and aqueous sodium carbonate (0.763 mL, 1.525 mmol) were mixed in 1,2-DME (3 mL) and heated in the microwave to 120° C. for 30 min. The solution was diluted with water and ethyl acetate. The organic product was extracted with ethyl acetate (3×20 mL) and the organic layers were combined, filtered through a hydrophobic frit and concentrated in vacuo to give the crude product that was purified by formic MDAP. Fractions containing product were combined and concentrated in vacuo then dissolved in MeOH and eluted with MeOH through an aminopropyl cartridge (2 g). The solvent was evaporated in vacuo to leave a brown solid. This was re-purified by high pH MDAP and fractions containing compound were combined and concentrated in vacuo to give 7-(3-((2,2-difluorocyclopropyl)methoxy)pyridin-4-yl)-5-methyl-2-(((R)-2-methyl-4-(methylsulfonyl)piperazin-1-yl)methyl)furo[3,2-c]pyridin-4(5H)-one as a white solid (20 mg, 0.038 mmol, 20.07% yield). LCMS (2 min, Formic): Rt=0.55 min, MH+ 523.

Example 65

N-(4-(5-methyl-2-(2-(4-(methylsulfonyl)piperazin-1-yl)propan-2-yl)-4-oxo-4,5-dihydrofuro[3,2-c]pyridin-7-yl)pyridin-2-yl)acetamide

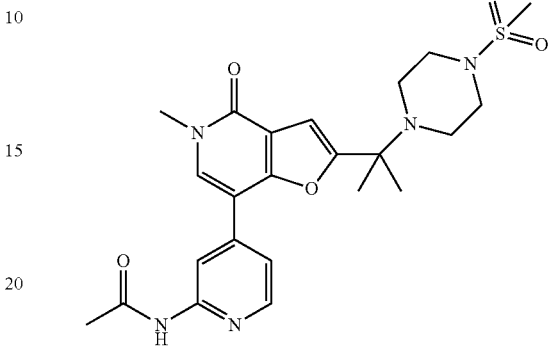

A mixture of N-(5-iodo-4-methoxy-1-methyl-6-oxo-1,6-dihydro-[3,4'-bipyridin]-2'-yl)acetamide (for a preparation see Intermediate 59, 263 mg, 0.659 mmol), 1-(2-methylbut-3-yn-2-yl)-4-(methylsulfonyl)piperazine (for a preparation see Intermediate 77, 455 mg, 1.977 mmol), copper(I) iodide (30.1 mg, 0.158 mmol), and PdCl$_2$(PPh$_3$)$_2$(26 mg, 0.037 mmol) in DMF (1 mL) was heated at 120° C. for 6 h using a microwave. The reaction mixture was concentrated under reduced pressure then the crude material was purified by silica gel column chromatography eluting with 0 to 10% 2M ammonia in MeOH/EtOAc. Appropriate fractions were combined then concentrated under reduced pressure to give crude product (~140 mg). The crude product was purified by MDAP to give N-(4-(5-methyl-2-(2-(4-(methylsulfonyl)piperazin-1-yl)propan-2-yl)-4-oxo-4,5-dihydrofuro[3,2-c]pyridin-7-yl)pyridin-2-yl)acetamide (25 mg, 8%). $^1$H NMR (400 MHz, MeOH-d$_4$) δ-ppm 8.70 (1H, s), 8.36 (1H, d), 8.08 (1H, s), 7.49 (1H, dd), 6.88 (1H, s), 3.75 (3H, s), 3.22 (4H, m), 2.82 (3H, s), 2.71 (4H, m), 2.22 (3H, s), 1.61 (6H, s). LCMS (2 min, Formic): Rt=0.50 min, MH+ 488.

Example 66

(R)-7-(3-(2-methoxyethoxy)pyridin-4-yl)-5-methyl-2-((2-methyl-4-(methylsulfonyl)piperazin-1-yl)methyl)furo[3,2-c]pyridin-4(5H)-one

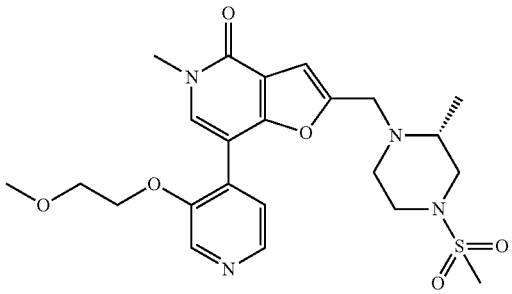 [SMILES: COCCOc1cnccc1-c1cn(C)c(=O)c2cc(CN3CCN(S(C)(=O)=O)C[C@H]3C)oc12]

The title compound was prepared from (R)-7-bromo-5-methyl-2-((2-methyl-4-(methylsulfonyl)piperazin-1-yl)

methyl)furo[3,2-c]pyridin-4(5H)-one (Intermediate 5) and 3-(2-methoxyethoxy)-4-(4,4,5,5-tetramethyl-1,3,2-dioxaborolan-2-yl)pyridine (Intermediate 74) using a method similar to that described for Example 46. LCMS (2 min, Formic): Rt=0.45 min, MH⁺ 491.

Example 69

5-methyl-2-(((R)-2-methyl-4-(methylsulfonyl)piperazin-1-yl)methyl)-7-(3-((tetrahydrofuran-3-yl)methoxy)pyridin-4-yl)furo[3,2-c]pyridin-4(5H)-one

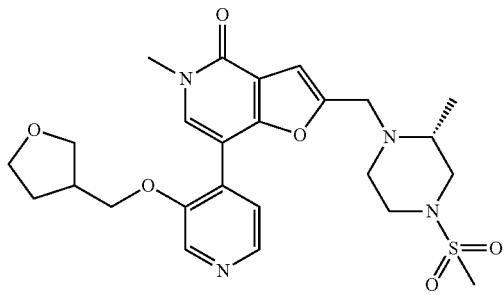 [SMILES: C[C@@H]1CN(S(C)(=O)=O)CCN1Cc1cc2c(=O)n(C)cc(-c3ccncc3OCC3CCOC3)c2o1]

The title compound was prepared from (R)-5-methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one (for a preparation see Intermediate 5a alternative preparation) and 4-bromo-3-((tetrahydrofuran-3-yl)methoxy)pyridine (Intermediate 75) using a method similar to that described for Example 61.

LCMS (2 min, Formic): Rt=0.48 min, MH⁺ 517.

Example 70

5-methyl-2-(((R)-2-methyl-4-(methylsulfonyl)piperazin-1-yl)methyl)-7-(3-((tetrahydrofuran-2-yl)methoxy)pyridin-4-yl)furo[3,2-c]pyridin-4(5H)-one

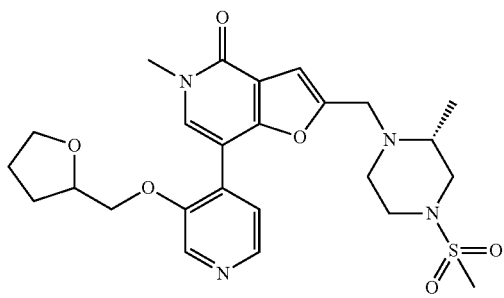 [SMILES: C[C@@H]1CN(S(C)(=O)=O)CCN1Cc1cc2c(=O)n(C)cc(-c3ccncc3OCC3CCCO3)c2o1]

The title compound was prepared from (R)-5-methyl-2-((2-methyl-4-(methylsulfonyl)piperazin-1-yl)methyl)-7-(4,4,5,5-tetramethyl-1,3,2-dioxaborolan-2-yl)furo[3,2-c]pyridin-4(5H)-one (for a preparation see Intermediate 5a alternative preparation) and 4-bromo-2-((tetrahydrofuran-3-yl)methoxy)pyridine (Intermediate 76) using a method similar to that described for Example 61.

LCMS (2 min, Formic): Rt=0.50 min, MH⁺ 517.

Example 82

N-(4-(5-methyl-4-oxo-2-((5-oxo-1,4-diazepan-1-yl)methyl)-4,5-dihydrofuro[3,2-c]pyridin-7-yl)pyridin-2-yl)acetamide

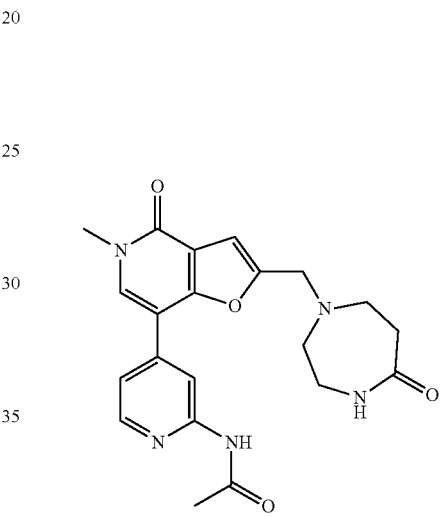

A stock solution of N-(4-(2-(bromomethyl)-5-methyl-4-oxo-4,5-dihydrofuro[3,2-c]pyridin-7-yl)pyridin-2-yl)acetamide (for a preparation see Intermediate 81) was prepared (300 mg dissolved/suspended in DMF (3 mL)). An aliquot (0.5 mL) was dispensed to a microwave vial containing 1,4-diazepan-5-one (18 mg, 0.159 mmol). DIPEA (51.5 mg, 0.399 mmol) was then added and the reaction vessel was sealed and heated in an Anton Parr microwave at 600 W to 110° C. for 30 min. On cooling, DMF (0.5 mL) was added and the reaction mixture was purified by MDAP to give N-(4-(5-methyl-4-oxo-2-((5-oxo-1,4-diazepan-1-yl)methyl)-4,5-dihydrofuro[3,2-c]pyridin-7-yl)pyridin-2-yl)acetamide (13.9 mg, 23% yield). LCMS (2 min, Formic): Rt=0.39 min, MH⁺ 410.

The examples in the following table, Examples 83-106 were prepared in manner similar to that described for Example 82.

| Example No. | Structure | Name | LCMS method | Rt min | MH+ |
|---|---|---|---|---|---|
| 83 | 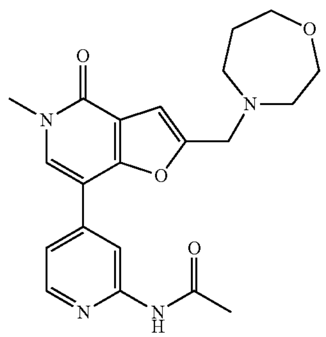 [SMILES: CC(=O)Nc1cc(-c2cn(C)c(=O)c3cc(CN4CCCOCC4)oc23)ccn1] | N-(4-(2-((1,4-oxazepan-4-yl)methyl)-5-methyl-4-oxo-4,5-dihydrofuro[3,2-c]pyridin-7-yl)pyridin-2-yl)acetamide | Formic | 0.42 | 397 |
| 84 | 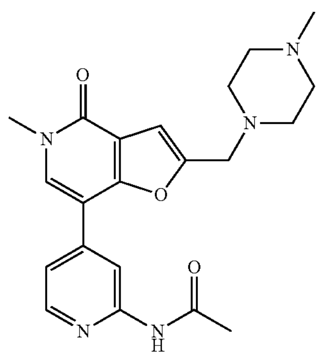 | N-(4-(5-methyl-2-((4-methylpiperazin-1-yl)methyl)-4-oxo-4,5-dihydrofuro[3,2-c]pyridin-7-yl)pyridin-2-yl)acetamide | Formic | 0.42 | 396 |
| 85 | 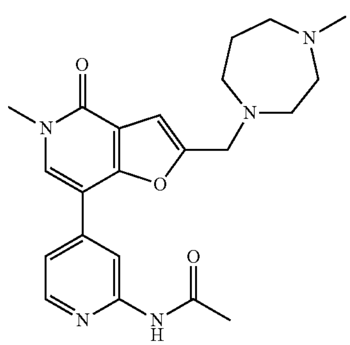 | N-(4-(5-methyl-2-((4-methyl-1,4-diazepan-1-yl)methyl)-4-oxo-4,5-dihydrofuro[3,2-c]pyridin-7-yl)pyridin-2-yl)acetamide | Formic | 0.40 | 410 |
| 86 | 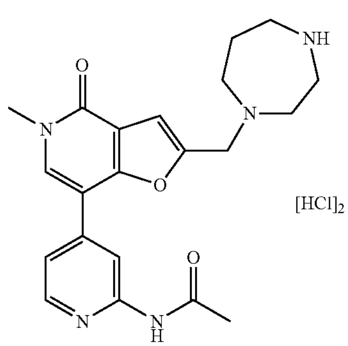 | N-(4-(2-((1,4-diazepan-1-yl)methyl)-5-methyl-4-oxo-4,5-dihydrofuro[3,2-c]pyridin-7-yl)pyridin-2-yl)acetamide dihydrochloride | Formic | 0.37 | 396 |

| Example No. | Structure | Name | LCMS method | Rt min | MH+ |
|---|---|---|---|---|---|
| 87 | 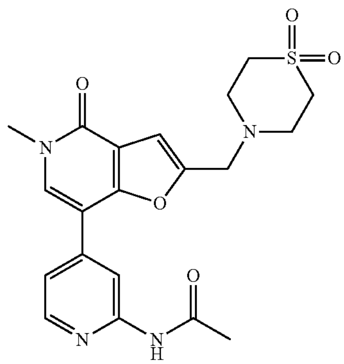 [SMILES: CC(=O)Nc1cc(-c2cn(C)c(=O)c3cc(CN4CCS(=O)(=O)CC4)oc23)ccn1] | N-(4-(2-((1,1-dioxidothiomorpholino)methyl)-5-methyl-4-oxo-4,5-dihydrofuro[3,2-c]pyridin-7-yl)pyridin-2-yl)acetamide | Formic | 0.50 | 431 |
| 88 | 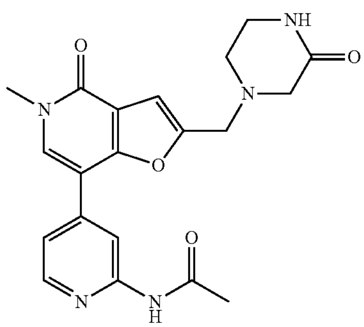 [SMILES: CC(=O)Nc1cc(-c2cn(C)c(=O)c3cc(CN4CCNC(=O)C4)oc23)ccn1] | N-(4-(5-methyl-4-oxo-2-((3-oxopiperazin-1-yl)methyl)-4,5-dihydrofuro[3,2-c]pyridin-7-yl)pyridin-2-yl)acetamide | Formic | 0.43 | 396 |
| 89 | 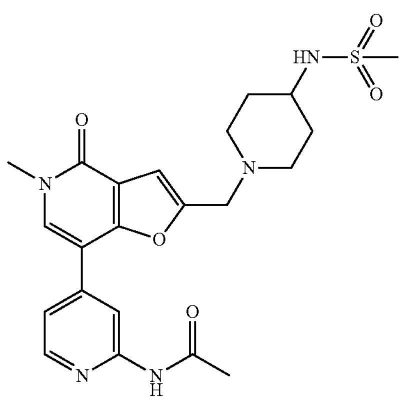 | N-(4-(5-methyl-2-((4-(methylsulfonamido)piperidin-1-yl)methyl)-4-oxo-4,5-dihydrofuro[3,2-c]pyridin-7-yl)pyridin-2-yl)acetamide | Formic | 0.42 | 474 |
| 90 | 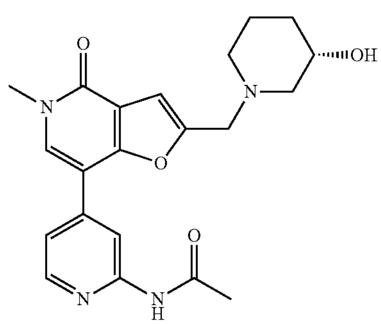 [SMILES: CC(=O)Nc1cc(-c2cn(C)c(=O)c3cc(CN4CCC[C@H](O)C4)oc23)ccn1] | (S)-N-(4-(2-((3-hydroxypiperidin-1-yl)methyl)-5-methyl-4-oxo-4,5-dihydrofuro[3,2-c]pyridin-7-yl)pyridin-2-yl)acetamide | Formic | 0.41 | 397 |

-continued

| Example No. | Structure | Name | LCMS method | Rt min | MH+ |
|---|---|---|---|---|---|
| 91 | 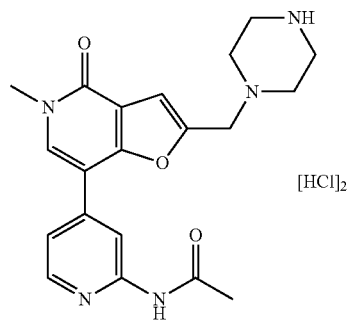 [HCl]₂ | N-(4-(5-methyl-4-oxo-2-(piperazin-1-ylmethyl)-4,5-dihydrofuro[3,2-c]pyridin-7-yl)pyridin-2-yl)acetamide dihydrochloride | Formic | 0.41 | 382 |
| 92 | 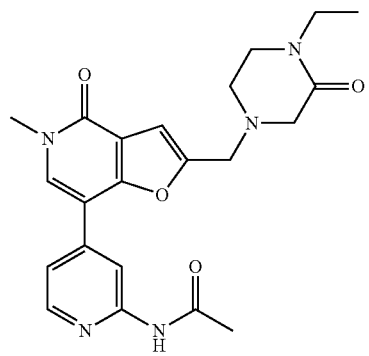 [SMILES: CCN1CCN(Cc2cc3c(=O)n(C)cc(-c4ccnc(NC(C)=O)c4)c3o2)CC1=O] | N-(4-(2-((4-ethyl-3-oxopiperazin-1-yl)methyl)-5-methyl-4-oxo-4,5-dihydrofuro[3,2-c]pyridin-7-yl)pyridin-2-yl)acetamide | Formic | 0.49 | 424 |
| 93 | 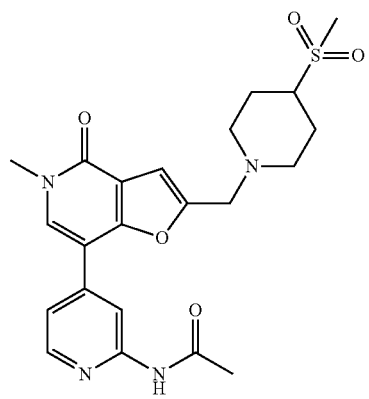 [SMILES: CC(=O)Nc1cc(-c2cn(C)c(=O)c3cc(CN4CCC(S(C)(=O)=O)CC4)oc23)ccn1] | N-(4-(5-methyl-2-((4-(methylsulfonyl)piperidin-1-yl)methyl)-4-oxo-4,5-dihydrofuro[3,2-c]pyridin-7-yl)pyridin-2-yl)acetamide | Formic | 0.41 | 459 |
| 94 | 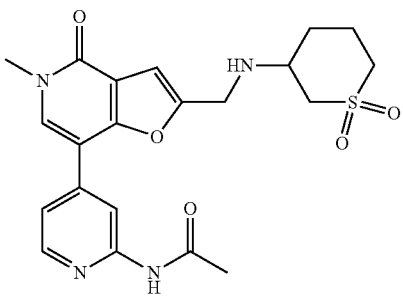 [SMILES: CC(=O)Nc1cc(-c2cn(C)c(=O)c3cc(CNC4CCCS(=O)(=O)C4)oc23)ccn1] | N-(4-(2-(((1,1-dioxidotetrahydro-2H-thiopyran-3-yl)amino)methyl)-5-methyl-4-oxo-4,5-dihydrofuro[3,2-c]pyridin-7-yl)pyridin-2-yl)acetamide | Formic | 0.42 | 445 |

| Example No. | Structure | Name | LCMS method | Rt min | MH+ |
|---|---|---|---|---|---|
| 95 | 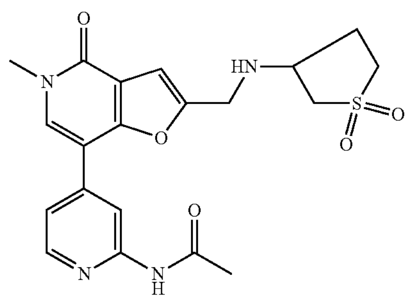 [SMILES: CC(=O)Nc1cc(-c2cn(C)c(=O)c3cc(CNC4CCS(=O)(=O)C4)oc23)ccn1] | N-(4-(2-(((1,1-dioxidotetrahydrothiophen-3-yl)amino)methyl)-5-methyl-4-oxo-4,5-dihydrofuro[3,2-c]pyridin-7-yl)pyridin-2-yl)acetamide | Formic | 0.42 | 431 |
| 96 | 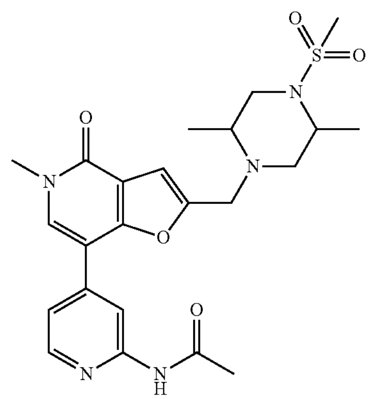 | N-(4-(2-((2,5-dimethyl-4-(methylsulfonyl)piperazin-1-yl)methyl)-5-methyl-4-oxo-4,5-dihydrofuro[3,2-c]pyridin-7-yl)pyridin-2-yl)acetamide | Formic | 0.49 | 488 |
| 97 | 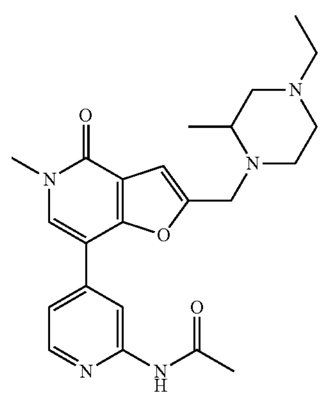 [SMILES: CCN1CCN(Cc2cc3c(=O)n(C)cc(-c4ccnc(NC(C)=O)c4)c3o2)C(C)C1] | N-(4-(2-((4-ethyl-2-methylpiperazin-1-yl)methyl)-5-methyl-4-oxo-4,5-dihydrofuro[3,2-c]pyridin-7-yl)pyridin-2-yl)acetamide | Formic | 0.46 | 424 |
| 98 | 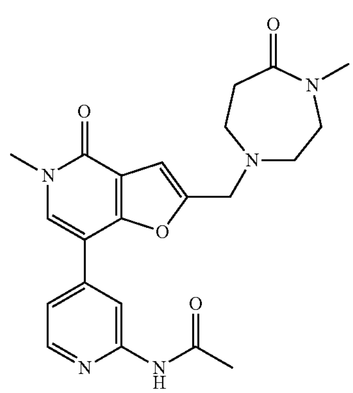 | N-(4-(5-methyl-2-((4-methyl-5-oxo-1,4-diazepan-1-yl)methyl)-4-oxo-4,5-dihydrofuro[3,2-c]pyridin-7-yl)pyridin-2-yl)acetamide | Formic | 0.41 | 424 |

| Example No. | Structure | Name | LCMS method | Rt min | MH+ |
|---|---|---|---|---|---|
| 99 | 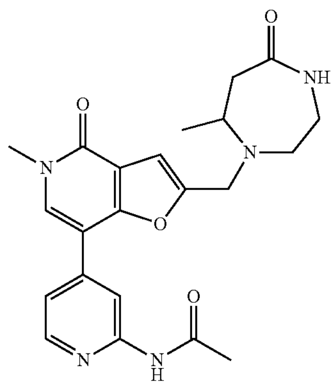 [SMILES: CC(=O)Nc1cc(-c2cn(C)c(=O)c3cc(CN4CCNC(=O)CC4C)oc23)ccn1] | N-(4-(5-methyl-2-((7-methyl-5-oxo-1,4-diazepan-1-yl)methyl)-4-oxo-4,5-dihydrofuro[3,2-c]pyridin-7-yl)pyridin-2-yl)acetamide | Formic | 0.41 | 424 |
| 100 | 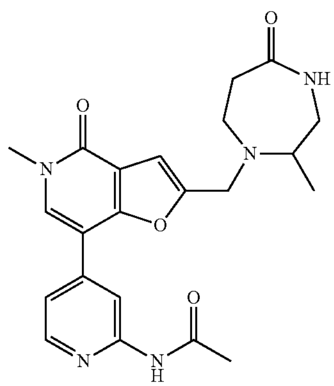 [SMILES: CC(=O)Nc1cc(-c2cn(C)c(=O)c3cc(CN4CCC(=O)NCC4C)oc23)ccn1] | N-(4-(5-methyl-2-((2-methyl-5-oxo-1,4-diazepan-1-yl)methyl)-4-oxo-4,5-dihydrofuro[3,2-c]pyridin-7-yl)pyridin-2-yl)acetamide | Formic | 0.42 | 424 |
| 101 | 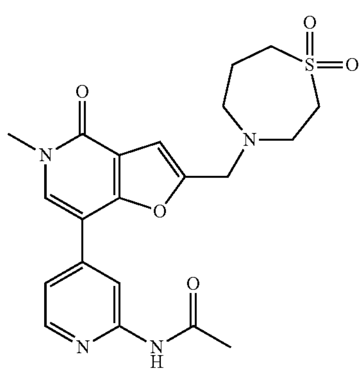 [SMILES: CC(=O)Nc1cc(-c2cn(C)c(=O)c3cc(CN4CCCS(=O)(=O)CC4)oc23)ccn1] | N-(4-(2-((1,1-dioxido-1,4-thiazepan-4-yl)methyl)-5-methyl-4-oxo-4,5-dihydrofuro[3,2-c]pyridin-7-yl)pyridin-2-yl)acetamide | Formic | 0.48 | 445 |
| 102 | 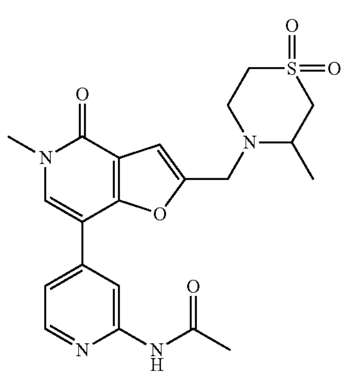 [SMILES: CC(=O)Nc1cc(-c2cn(C)c(=O)c3cc(CN4CCS(=O)(=O)CC4C)oc23)ccn1] | N-(4-(5-methyl-2-((3-methyl-1,1-dioxidothiomorpholino)methyl)-4-oxo-4,5-dihydrofuro[3,2-c]pyridin-7-yl)pyridin-2-yl)acetamide | Formic | 0.55 | 445 |

| Example No. | Structure | Name | LCMS method | Rt min | MH+ |
|---|---|---|---|---|---|
| 103 | 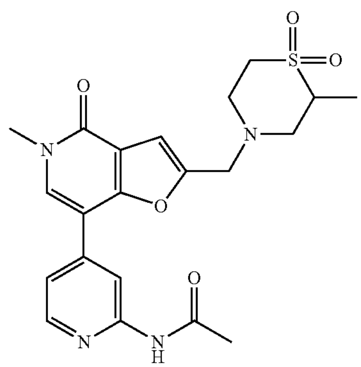 | N-(4-(5-methyl-2-((2-methyl-1,1-dioxidothiomorpholino)methyl)-4-oxo-4,5-dihydrofuro[3,2-c]pyridin-7-yl)pyridin-2-yl)acetamide | Formic | 0.56 | 445 |
| 104 | 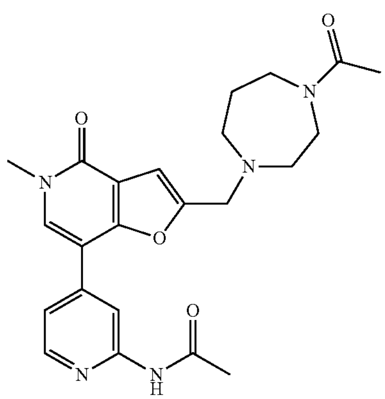 [SMILES: CC(=O)Nc1cc(-c2cn(C)c(=O)c3cc(CN4CCCN(C(C)=O)CC4)oc23)ccn1] | N-(4-(2-((4-acetyl-1,4-diazepan-1-yl)methyl)-5-methyl-4-oxo-4,5-dihydrofuro[3,2-c]pyridin-7-yl)pyridin-2-yl)acetamide | High pH | 0.61 | 438 |
| 105 | 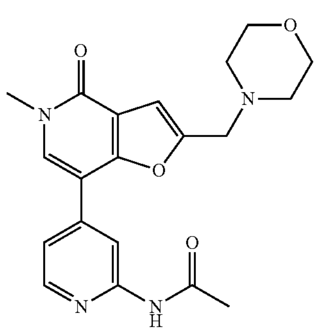 [SMILES: CC(=O)Nc1cc(-c2cn(C)c(=O)c3cc(CN4CCOCC4)oc23)ccn1] | N-(4-(5-methyl-2-(morpholinomethyl)-4-oxo-4,5-dihydrofuro[3,2-c]pyridin-7-yl)pyridin-2-yl)acetamide | Formic | 0.41 | 383 |
| 106 | 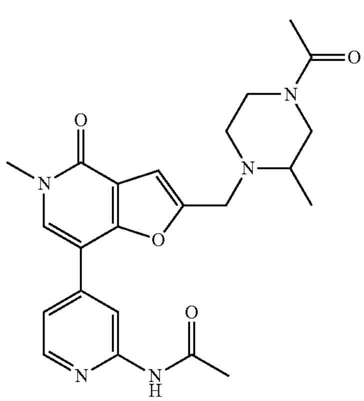 [SMILES: CC(=O)Nc1cc(-c2cn(C)c(=O)c3cc(CN4CCN(C(C)=O)CC4C)oc23)ccn1] | N-(4-(2-((4-acetyl-2-methylpiperazin-1-yl)methyl)-5-methyl-4-oxo-4,5-dihydrofuro[3,2-c]pyridin-7-yl)pyridin-2-yl)acetamide | High pH | 0.61 | 438 |

Example 107

N-(4-(5-methyl-2-((4-methyl-3-oxopiperazin-1-yl)methyl)-4-oxo-4,5-dihydrofuro[3,2-c]pyridin-7-yl)pyridin-2-yl)acetamide

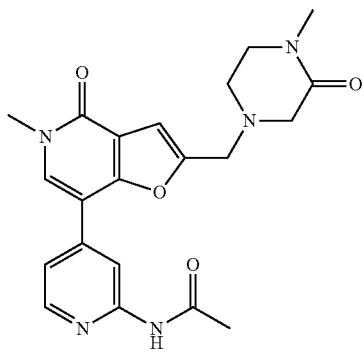 [SMILES: CC(=O)Nc1cc(-c2cn(C)c(=O)c3cc(CN4CCN(C)C(=O)C4)oc23)ccn1]

N-(4-(2-(Chloromethyl)-5-methyl-4-oxo-4,5-dihydrofuro[3,2-c]pyridin-7-yl)pyridin-2-yl)acetamide (for a preparation see Intermediate 82, 50 mg, 0.151 mmol) was dissolved in DMF (5 mL), potassium carbonate (62.5 mg, 0.452 mmol) was added, followed by 1-methylpiperazin-2-one (17.20 mg, 0.151 mmol). The mixture was stirred for 3 h at room temperature. The mixture was diluted with water (10 mL) and extracted with a mixture of methanol (3 mL) and DCM (15 mL), the organic layer was dried and evaporated in vacuo and the residue purified by MDAP to give N-(4-(5-methyl-2-((4-methyl-3-oxopiperazin-1-yl)methyl)-4-oxo-4,5-dihydrofuro[3,2-c]pyridin-7-yl)pyridin-2-yl)acetamide (25 mg, 0.061 mmol, 40.5% yield). LCMS (2 min, High pH): Rt=0.58 min, MH+ 410.

Example 108

(S)—N-(4-(5-methyl-2-((3-methyl-4-(methylsulfonyl)piperazin-1-yl)methyl)-4-oxo-4,5-dihydrofuro[3,2-c]pyridin-7-yl)pyridin-2-yl)acetamide

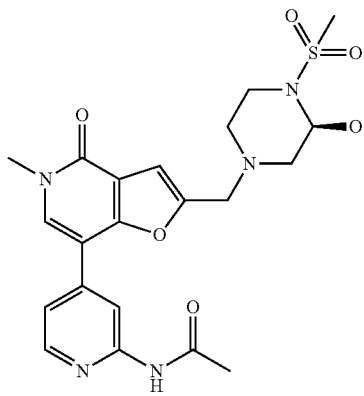 [SMILES: CC(=O)Nc1cc(-c2cn(C)c(=O)c3cc(CN4CCN(S(C)(=O)=O)[C@@H](O)C4)oc23)ccn1]

The title compound was prepared from N-(4-(2-(Chloromethyl)-5-methyl-4-oxo-4,5-dihydrofuro[3,2-c]pyridin-7-yl)pyridin-2-yl)acetamide (for a preparation see Intermediate 82) and (S)-2-methyl-1-(methylsulfonyl)piperazine in a manner similar to that described for Example 107. LCMS (2 min, High pH): Rt=0.68 min, MH+ 474.

Example 109

N-(4-(5-methyl-2-((4-(methylsulfonyl)-2-oxopiperazin-1-yl)methyl)-4-oxo-4,5-dihydrofuro[3,2-c]pyridin-7-yl)pyridin-2-yl)acetamide

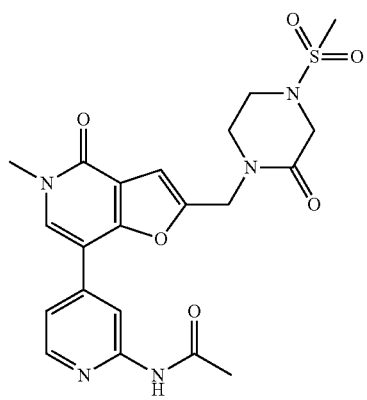 [SMILES: CC(=O)Nc1cc(-c2cn(C)c(=O)c3cc(CN4CCN(S(C)(=O)=O)CC4=O)oc23)ccn1]

4-(Methylsulfonyl)piperazin-2-one (193 mg, 1.085 mmol) was dissolved in DMF (3 mL), NaH (43.4 mg, 60% w/w, 1.085 mmol) was added and the mixture was stirred for 10 min, then added to a solution of N-(4-(2-(chloromethyl)-5-methyl-4-oxo-4,5-dihydrofuro[3,2-c]pyridin-7-yl)pyridin-2-yl)acetamide (for a preparation see Intermediate 82, 180 mg, 0.543 mmol) in DMF (3 mL) at room temperature. The mixture was stirred for 1 h, then quenched by addition of acetic acid (2 drops) and evaporated in vacuo. The crude product was purified by MDAP to give the title compound, N-(4-(5-methyl-2-((4-(methylsulfonyl)-2-oxopiperazin-1-yl)methyl)-4-oxo-4,5-dihydrofuro[3,2-c]pyridin-7-yl)pyridin-2-yl)acetamide (15 mg, 0.032 mmol, 5.84% yield). $^1$H NMR (400 MHz, DMSO-$d_6$) δ-ppm 10.56 (1H, s), 8.56 (1H, s), 8.37 (1H, d), 8.20 (1H, s), 7.45 (1H, dd), 6.94 (1H, s), 4.72 (2H, s), 3.88 (2H, s), 3.61 (3H, s), 3.57 (2H, m), 3.48 (2H, m), 2.99 (3H, s), 2.13 (3H, s). LCMS (2 min, High pH): Rt=0.60 min, MH+ 474.

Also obtained was by-product, N-(4-(2,5-dimethyl-3-(4-(methylsulfonyl)-2-oxopiperazin-1-yl)-4-oxo-4,5-dihydrofuro[3,2-c]pyridin-7-yl)pyridin-2-yl)acetamide (18 mg, 7% yield). $^1$H NMR (400 MHz, DMSO-d$_6$) δ-ppm 10.55 (1H, s), 8.58 (1H, s), 8.38 (1H, d), 8.17 (1H, s), 7.46 (1H, dd), 4.02 (3H, m), 3.61 (3H, m), 3.59 (3H, s), 3.10 (3H, s), 2.30 (3H, s), 2.13 (3H, s). LCMS (2 min, High pH): Rt=0.65 min, MH$^+$ 474.

The following compounds of Formula (I) were also prepared:

| Example No. | Structure | Name |
|---|---|---|
| 110 | 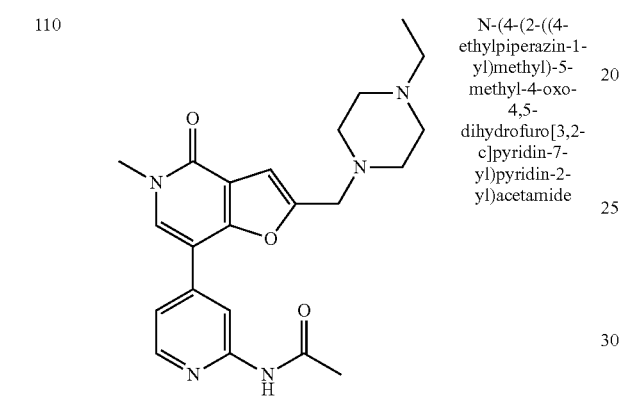 | N-(4-(2-((4-ethylpiperazin-1-yl)methyl)-5-methyl-4-oxo-4,5-dihydrofuro[3,2-c]pyridin-7-yl)pyridin-2-yl)acetamide |
| 111 | 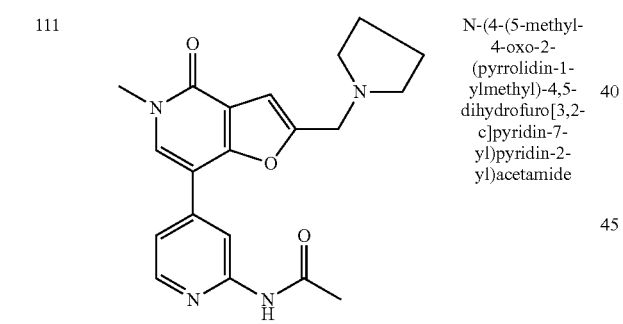 | N-(4-(5-methyl-4-oxo-2-(pyrrolidin-1-ylmethyl)-4,5-dihydrofuro[3,2-c]pyridin-7-yl)pyridin-2-yl)acetamide |
| 112 | 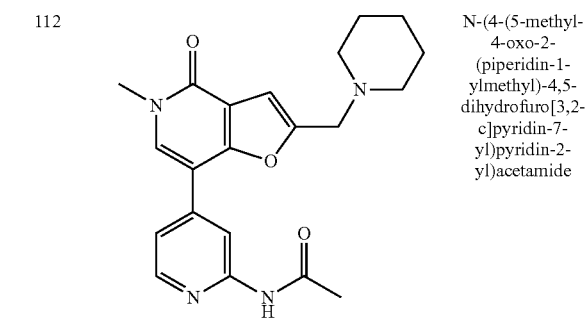 | N-(4-(5-methyl-4-oxo-2-(piperidin-1-ylmethyl)-4,5-dihydrofuro[3,2-c]pyridin-7-yl)pyridin-2-yl)acetamide |
| 113 | | N-(4-(5-methyl-4-oxo-2-((3-oxo-1,4-diazepan-1-yl)methyl)-4,5-dihydrofuro[3,2-c]pyridin-7-yl)pyridin-2-yl)acetamide |
| 114 | | (R)-N-(4-(5-methyl-2-((2-methyl-3-oxopiperazin-1-yl)methyl)-4-oxo-4,5-dihydrofuro[3,2-c]pyridin-7-yl)pyridin-2-yl)acetamide |

Biological Test Methods

The compounds of formula (I) may be tested in one or more of the following assays:

Time Resolved Fluorescence Resonance Energy Transfer (TR-FRET) Assay

Binding was assessed using a time resolved fluorescent resonance energy transfer binding assay. This utilises a 6 His purification tag at the N-terminal of the proteins as an epitope for an anti-6 His antibody labeled with Europium chelate (PerkinElmer AD0111) allowing binding of the Europium to the proteins which acts as the donor fluorophore. A small molecule, high affinity binder of the bromodomains BRD2, BRD3, BRD4 and BRDT has been labeled with Alexa Fluor647 (Reference Compound X) and this acts as the acceptor in the FRET pair.

Reference Compound X 4-((Z)-3-(6-((5-(2-((4S)-6-(4-chlorophenyl)-8-methoxy-1-methyl-4H-benzo[f][1,2,4]triazolo[4,3-a][1,4]diazepin-4-yl)acetamido)pentyl)amino)-6-oxohexyl)-2-((2E,4E)-5-(3,3-dimethyl-5-sulfo-1-(4-sulfobutyl)-3H-indol-1-ium-2-yl)penta-2,4-dien-1-ylidene)-3-methyl-5-sulfoindolin-1-yl)butane-1-sulphonate)

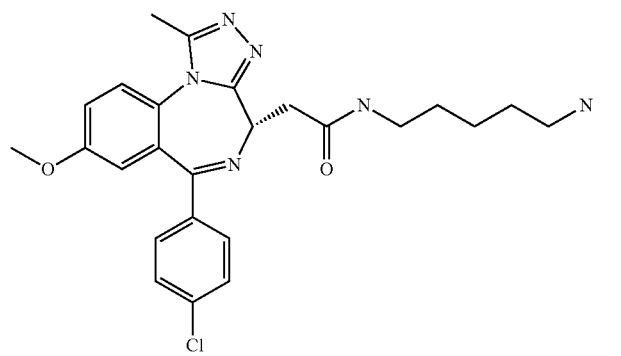

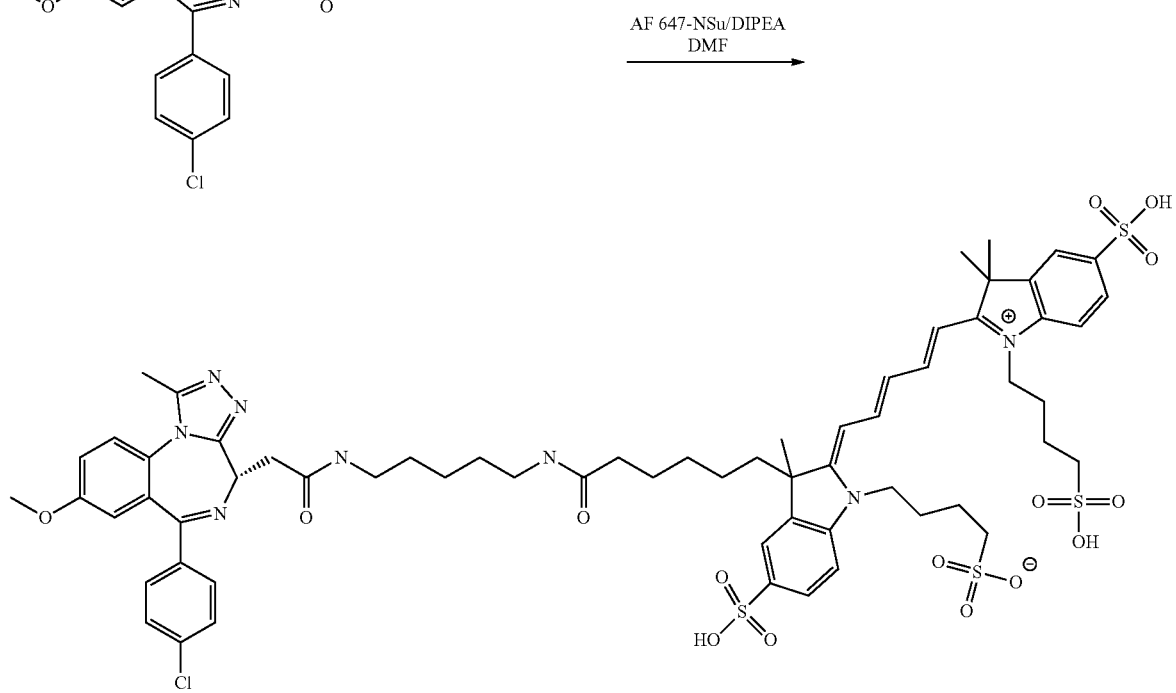

To a solution of N-(5-aminopentyl)-2-((4S)-6-(4-chlorophenyl)-8-methoxy-1-methyl-4H-benzo[f][1,2,4]triazolo[4,3-a][1,4]diazepin-4-yl)acetamide (for a preparation see Reference Compound J, WO2011/054848A1, 1.7 mg, 3.53 µmol) in DMF (40 µl) was added a solution of AlexaFluor647-ONSu (2.16 mg, 1.966 µmol) also in DMF (100 µl). The mixture was basified with DIPEA (1 µl, 5.73 µmol) and agitated overnight on a vortex mixer.

The reaction mixture was evaporated to dryness. The solid was dissolved in acetonitrile/water/acetic acid (5/4/1, <1 mL) filtered and was applied to a Phenomenex Jupiter C18 preparative column and eluted with the following gradient (A=0.1% trifluoroacetic acid in water, B=0.1% TFA/90% acetonitrile/10% water): Flow rate=10 mL/min., AU=20/10 (214 nm):

5-35%, t=0 min: B=5%; t=10 min: B=5%; t=100 min: B=35%; t=115 min: B=100% (Sep. grad: 0.33%/min)

The major component was eluted over the range 26-28% B but appeared to be composed of two peaks. The middle fraction (F1.26) which should contain "both" components was analysed by analytical HPLC (Spherisorb ODS2, 1 to 35% over 60 min): single component eluting at 28% B.

Fractions F1.25/26&27 were combined and evaporated to dryness. Transferred with DMF, evaporated to dryness, triturated with dry ether and the blue solid dried overnight at <0.2 mbar: 1.54 mg.

Analytical HPLC (Sphersisorb ODS2, 1 to 35% B over 60 min): MSM10520-1: [M$^+$H]$^+$ (obs): 661.8/– corresponding with M-29. This equates to [(M+2H)/2]$^+$ for a calculated mass of 1320.984 which is M-29. This is a standard occurrence with the Alexa Fluor 647 dye and represents a theoretical loss of two methylene groups under the conditions of the mass spectrometer.

Assay Principle: In the absence of a competing compound, excitation of the Europium causes the donor to emit at λ618 nm which excites the Alexa labelled bromodomain binding compound leading to an increased energy transfer that is measurable at λ647 nM. In the presence of a sufficient concentration of a compound that can bind these proteins, the interaction is disrupted leading to a quantifiable drop in fluorescent resonance energy transfer.

The binding of the compounds of formula (I) to Bromodomains BRD2, BRD3, BRD4 and BRDT was assessed using mutated proteins to detect differential binding to either Binding Domain 1 (BD1) or Binding Domain 2 (BD2) on the bromodomain. These single residue mutations in the acetyl lysine binding pocket greatly lower the affinity of the fluoroligand (Reference Compound X) for the mutated domain (>1000 fold selective for the non-mutated domain). Therefore in the final assay conditions, binding of the fluoroligand to the mutated domain cannot be detected and subsequently the assay is suitable to determine the binding of compounds to the single non-mutated bromodomain.

Protein production: Recombinant Human Bromodomains [(BRD2 (1-473) (Y113A) and (Y386A), BRD3 (1-435) (Y73A) and (Y348A) BRD4 (1-477) (Y97A) and (Y390A) and BRDT (1-397) (Y66A) and (Y309A)] were expressed in E. coli cells (in pET15b vector for BRD2/3/4 and in pET28a vector for BRDT) with a 6-His tag at the N-terminal. The His-tagged Bromodomain pellet was resuspended in 50 mM HEPES (pH7.5), 300 mM NaCl, 10 mM imidazole & 1 µl/mL protease inhibitor cocktail and extracted from the E. coli cells using sonication and purified using a nickel sepharose high performance column, the proteins were washed and then eluted with a linear gradient of 0-500 mM imidazole with buffer 50 mM HEPES (pH7.5), 150 mM NaCl, 500 mM imidazole, over 20 column volumes. Final purification was completed by Superdex 200 prep grade size exclusion column. Purified protein was stored at −80° C. in 20 mM HEPES pH 7.5 and 100 mM NaCl. Protein identity was confirmed by peptide mass fingerprinting and predicted molecular weight confirmed by mass spectrometry.

Protocol for Bromodomain BRD2, 3, 4 and T, BD1$^+$BD2 mutant assays: All assay components were dissolved in buffer composition of 50 mM HEPES pH7.4, 50 mM NaCl, 5% Glycerol, 1 mM DTT and 1 mM CHAPS. The final concentration of bromodomain proteins were 10 nM and the Alexa Fluor647 ligand was at Kd. These components were premixed and 5 µl of this reaction mixture was added to all wells containing 50 nl of various concentrations of test compound or DMSO vehicle (0.5% DMSO final) in Greiner 384 well black low volume microtitre plates and incubated in dark for 30 minutes at room temperature. 5 µl of detection mixture containing 1.5 nM final concentration anti-6His Europium chelate was added to all wells and a further dark incubation of at least 30 minutes was performed. Plates were then read on the Envision platereader, ($\lambda$ex=317 nm, donor $\lambda$em=615 nm; acceptor $\lambda$em=665 nm; Dichroic LANCE dual). Time resolved fluorescent intensity measurements were made at both emission wavelengths and the ratio of acceptor/donor was calculated and used for data analysis. All data was normalized to the mean of 16 high (inhibitor control—Example 11 of WO 2011/054846A1) and 16 low (DMSO) control wells on each plate. A four parameter curve fit of the following form was then applied:

$$y=a^+((b-a)/(1^+(10\hat{} x/10\hat{} c)\hat{} d)$$

Where 'a' is the minimum, 'b' is the Hill slope, 'c' is the pIC50 and 'd' is the maximum.

Examples 1-81b were each tested in at least one of the BRD2, BRD3, BRD4 or BRDT, BD1 or BD2 assays described above and were found to have a pIC$_{50}$≥5.0 in at least one assay.

Examples 1-7, 9-15, 20-81b, 82, 83, 85-89, 94-96, 98, 100-104, 106, 108 and 109 were found to have a pIC$_{50}$≥6.0 in the BRD4 BD1 assay.

Examples 1-4, 7, 10, 12, 14, 15, 21, 21a, 21b and 23-27, 30-32 and 34-44, 46-50, 52, 54-62, 64-74, 76, 78, 80-81b, 82, 87, 96, 100, 102 and 108 were found to have a pIC$_{50}$≥7.0 in the BRD4 BD1 assay.

Examples 32, 35, 61 and 67 were found to have a pIC$_5$≥8.0 in the BRD4 BD1 assay.

Calculation of selectivity for BRD4 BD1 over BRD4 BD2

Selectivity for BRD4 BD1 over BRD4 BD2 was calculated as follows:

Selectivity=BRD4 BD1 pIC$_{50}$−BRD4 BD2 pIC$_{50}$ pIC$_{50}$ values are expressed as log$_{10}$ units.

Examples 1-7, 9-16, 20-81b and 82-109 were found to have selectivity for BRD4 BD1 over BRD4 BD2 of ≥1 log unit in the TR-FRET assays described above, hence are at least 10 fold selective for BRD4 BD1 over BRD4 BD2.

Examples 1-4, 7, 10, 12, 14, 15, 21, 21a, 21b, 23-28, 30-32, 34-44, 46, 48-52, 54, 56-67, 69, 70, 72-75, 77, 78, 80-81b, 82, 87, 96, 98, 100-103 and 108 were found to have selectivity for BRD4 BD1 over BRD4 BD2 of >2 log unit in the TR-FRET assays described above, hence are at least 100 fold selective for BRD4 BD1 over BRD4 BD2.

What is claimed is:

1. A compound of formula (I):

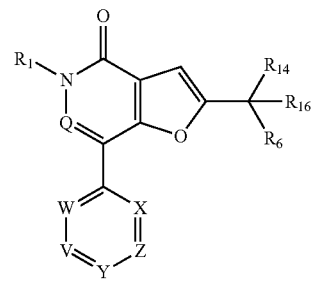

(I)

wherein:

V is N or C—R$_2$

W is N or C—R$_8$;

X is N, CH or C(CH$_3$);

Y is N or C—R$_5$;

Z is N or C—R$_{15}$;

Q is N or CH;

R$_1$ is C$_{1-4}$ alkyl or deuterated C$_{1-4}$ alkyl;

R$_2$, when present, is H, OH, C$_{1-4}$alkyl, halo, —CF$_3$, —NH$_2$, —OC$_{1-4}$alkyl, —NHC(O)H, —NHC(O)C$_{1-4}$ alkyl, —N(CH$_3$)C(O)C$_{1-4}$alkyl, —NHC(O)NH$_2$, —NHC(O)C$_{1-4}$alkyleneNH$_2$, —N(CH$_3$)C(O)NH$_2$, —N(CH$_3$)C(O)C$_{1-4}$alkyleneNH$_2$, —NHC$_{2-4}$alkyleneOCH$_3$, —N(CH$_3$)C$_{2-4}$alkyleneOCH$_3$, —OC$_{2-4}$alkyleneOCH$_3$, —OC$_{2-4}$alkyleneOH or R$_2$ is a group selected from -G-CH$_2$CH(R$_3$)(R$_4$), -G-CH(R$_3$)(R$_4$) and -G-R$_3$ in which G is NH, N(CH$_3$), O, C(O)NH or NHC(O);

R$_3$ is phenyl, pyridinyl, C$_{3-7}$cycloalkyl or a heterocycle optionally substituted by =O; and R$_4$ is H or C$_{1-4}$ alkyl;

R$_5$, when present, is H, C$_{1-4}$alkyl, halo, —CF$_3$, CN, OH, —OC$_{1-4}$ alkyl, —CH$_2$NH$_2$, —OCF$_3$, —SO$_2$CH$_3$, —C(O)NHC$_{1-4}$alkyl or —CO$_2$H;

R$_6$ is —NR$_{11}$R$_{12}$ or a group

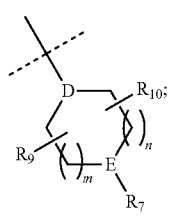

D is CH or N;

E is N, O, CH or SO$_2$;

R$_7$, when present, is H, OH, C$_{1-4}$alkyl, —NH$_2$, —SO$_2$C$_{1-4}$alkyl, —SO$_2$phenyl, —SO$_2$benzyl, —SO$_2$N(CH$_3$)$_2$, —NHSO$_2$CH$_3$, —C(O)C$_{1-4}$alkyl, —C(O)phenyl;

R$_8$, when present, is H, C$_{1-4}$alkyl, halo, —CF$_3$, CN, OH, —OC$_{1-4}$alkyl, —OC$_{2-4}$alkyleneOC$_{1-4}$alkyl, —OCF$_3$, —OC$_{1-4}$alkyleneF, —OC$_{1-4}$alkyleneCHF$_2$, —OC$_{2-4}$alkyleneOH, —Ophenyl, —OC$_{1-4}$alkylenephenyl, —NHC$_{3-7}$cycloalkyl, —NHC$_{1-4}$alkyleneC$_{3-7}$cycloalkyl, —OC$_{3-7}$cycloalkyl, —OC$_{1-4}$alkyleneC$_{3-7}$cycloalkyl, —NHC$_{4-6}$heterocycle-NHC$_{1-4}$alkyleneC$_{4-6}$heterocycle, —OC$_{4-6}$heterocycle or —OC$_{1-4}$alkyleneC$_{4-6}$heterocycle wherein the C$_{3-7}$cycloalkyl or the C$_{4-6}$heterocycle are each optionally substituted by one or two substituents independently selected from halo, OH, oxo, C$_{1-4}$alkyl and —NH$_2$; or R$_8$ and R$_2$ together with the carbon atoms to which they are attached, form 2,3-dihydro-1H-pyrrolo[2,3-b]pyridine optionally substituted by oxo;

R$_9$ is H, C$_{1-4}$alkyl, —C(O)NH$_2$, —CO$_2$CH$_3$, —CF$_3$, halo, OH, —OC$_{1-4}$alkyl, —CH$_2$OH, —C(O)NHCH$_3$, —C(O)NH(CH$_3$)$_2$, —CH$_2$OC$_{1-4}$alkyl or —CH$_2$OCH$_2$C$_{3-7}$cycloalkyl;

R$_{10}$ is H, C$_{1-4}$alkyl, —C(O)NH$_2$, —CO$_2$CH$_3$, —CF$_3$, halo, OH, —OC$_{1-4}$alkyl or oxo;

R$_{11}$ is H, C$_{1-4}$alkyl or SO$_2$CH$_3$;

R$_{12}$ is H, C$_{1-4}$alkyl, C$_{2-4}$alkyleneNHR$_{13}$, SO$_2$CH$_3$, a heterocycle or a heterocycle comprising SO$_2$;

R$_{13}$ is H or SO$_2$CH$_3$;

R$_{14}$ is H or C$_{1-4}$alkyl;

R$_{15}$ is H, C$_{1-4}$alkyl or NHC(O)C$_{1-4}$alkyl;

R$_{16}$ is H or C$_{1-4}$alkyl: and n and m are each an integer independently selected from 0, 1 and 2; subject to proviso that no more than 2 of V, W, X, Y and Z are N; or a salt thereof.

2. A compound or a salt thereof according to claim 1 wherein V is C—R$_2$ and W is C—R$_8$.

3. A compound or a salt thereof according to claim 1 wherein R$_8$ is H, OH, —OCH$_2$CH$_3$, —OCH(CH$_3$)$_2$, —OCH$_2$CH$_2$OCH$_3$, —OCH$_2$CH(CH$_3$)OCH$_3$, —OCH(CH$_3$)CH$_2$OCH$_3$, —OCH$_2$CH$_2$F, —OCH$_2$CHF$_2$, —OCH$_2$CH$_2$OH, —NHCH$_2$cyclopropyl, —Ocyclopropyl, —OCH$_2$cyclopropyl, —Otetrahydrofuranyl, —Ooxetanyl, —OCH$_2$tetrahydrofuranyl, —OCH$_2$oxetanyl or —OCH$_2$CH$_2$pyrrolidinyl, wherein the C$_{3-7}$cycloalkyl or the C$_{4-6}$heterocycle are each optionally substituted by one or two substituents independently selected from fluoro and oxo.

4. A compound or a salt thereof according to claim 1 wherein X is CH; Y is N; Z is CH; and Q is CH.

5. A compound or a salt thereof according to claim 1 wherein R$_1$ is methyl.

6. A compound or a salt thereof according to claim 1 wherein R$_2$ is H, —OC$_{1-4}$alkyl, —NHC(O)C$_{1-4}$alkyl or —N(CH$_3$)C(O)C$_{1-4}$alkyl.

7. A compound or a salt thereof according to claim 1 wherein R$_6$ is a group

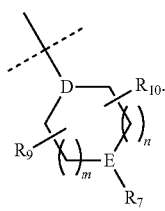

8. A compound or a salt thereof according to claim 1 wherein D is N and E is N, O or CH.

9. A compound or a salt thereof according to claim 1 wherein R$_7$ is —SO$_2$CH$_3$.

10. A compound selected from:

7-[3,4-bis(methyloxy)phenyl]-5-methyl-2-{[4-(methylsulfonyl)-1-piperazinyl]methyl}furo[3,2-c]pyridin-4(5H)-one;

(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide;

7-(3-(benzyloxy)phenyl)-5-methyl-2-((4-(methylsulfonyl)piperazin-1-yl)methyl)furo[3,2-c]pyridin-4(5H)-one;

7-(3-(benzylamino)phenyl)-5-methyl-2-((4-(methylsulfonyl)piperazin-1-yl)methyl)furo[3,2-c]pyridin-4(5H)-one;

2-(((2-aminoethyl)amino)methyl)-7-(3,4-dimethoxyphenyl)-5-methylfuro[3,2-c]pyridin-4(5H)-one;

7-(4-(aminomethyl)phenyl)-5-methyl-2-((4-(methylsulfonyl)piperazin-1-yl)methyl)furo[3,2-c]pyridin-4(5H)-one;

5-methyl-2-((4-(methylsulfonyl)piperazin-1-yl)methyl)-7-(2-((tetrahydro-2H-pyran-4-yl)methoxy)pyridin-4-yl)furo[3,2-c]pyridin-4(5H)-one;

7-(3,4-dimethoxyphenyl)-5-methyl-2-(piperidin-1-ylmethyl)furo[3,2-c]pyridin-4(5H)-one;

7-(3,4-dimethoxyphenyl)-5-methyl-2-(morpholinomethyl)furo[3,2-c]pyridin-4(5H)-one;

(R)-7-(3,4-dimethoxyphenyl)-5-methyl-2-((2-methyl-4-(methylsulfonyl)piperazin-1-yl)methyl)furo[3,2-c]pyridin-4(5H)-one;

2-((1,4-diazepan-1-yl)methyl)-7-(3,4-dimethoxyphenyl)-5-methylfuro[3,2-c]pyridin-4(5H)-one;

5-methyl-2-((4-(methylsulfonyl)piperazin-1-yl)methyl)-7-(5-(1-phenylethoxy)pyridin-3-yl)furo[3,2-c]pyridin-4(5H)-one;

2-((3,3-difluoropiperidin-1-yl)methyl)-5-methyl-7-(2-((tetrahydro-2H-pyran-4-yl)methoxy)pyridin-4-yl)furo[3,2-c]pyridin-4(5H)-one;

5-methyl-2-((4-(methylsulfonyl)piperazin-1-yl)methyl)-7-(2-((1-phenylethyl)amino)pyridin-4-yl)furo[3,2-c]pyridin-4(5H)-one;

5-methyl-2-((4-(methylsulfonyl)piperazin-1-yl)methyl)-7-(3-((1-phenylethyl)amino)phenyl)furo[3,2-c]pyridin-4(5H)-one;

7-(3,4-dimethoxyphenyl)-5-methyl-2-((3-methylmorpholino)methyl)furo[3,2-c]pyridin-4(5H)-one;

N-(4-(2-((3-fluoropiperidin-1-yl)methyl)-5-methyl-4-oxo-4,5-dihydrofuro[3,2-c]pyridin-7-yl)pyridin-2-yl)acetamide;

N-(4-(2-((3,3-difluoropiperidin-1-yl)methyl)-5-methyl-4-oxo-4,5-dihydrofuro[3,2-c]pyridin-7-yl)pyridin-2-yl)acetamide;

2-((3-fluoropiperidin-1-yl)methyl)-7-(4-methoxyphenyl)-5-methylfuro[3,2-c]pyridin-4(5H)-one;

5-methyl-2-(morpholinomethyl)-7-(2-((tetrahydro-2H-pyran-4-yl)methoxy)pyridin-4-yl)furo[3,2-c]pyridin-4(5H)-one;

5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one;

(S)-5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one;

(R)-5-methyl-2-(1-(4-(methylsulfonyl)piperazin-1-yl)ethyl)-7-(2-((tetrahydro-2H-pyran-4-yl)methoxy)pyridin-4-yl)furo[3,2-c]pyridin-4(5H)-one;
2-((1,4-oxazepan-4-yl)methyl)-5-methyl-7-(2-((tetrahydro-2H-pyran-4-yl)methoxy)pyridin-4-yl)furo[3,2-c]pyridin-4(5H)-one;
(R)-7-(2-(cyclopropylmethoxy)pyridin-4-yl)-5-methyl-2-((2-methyl-4-(methylsulfonyl)piperazin-1-yl)methyl)furo[3,2-c]pyridin-4(5H)-one;
(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)cyclopropanecarboxamide;
(R)—N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)propionamide;
(R)-7-(2-(2-methoxyethoxy)pyridin-4-yl)-5-methyl-2-((2-methyl-4-(methylsulfonyl)piperazin-1-yl)methyl)furo[3,2-c]pyridin-4(5H)-one;
(R)-5-methyl-2-((2-methyl-4-(methylsulfonyl)piperazin-1-yl)methyl)-7-(2-(2-(pyrrolidin-1-yl)ethoxy)pyridin-4-yl)furo[3,2-c]pyridin-4(5H)-one;
2-((1,1-dioxidothiomorpholino)methyl)-5-methyl-7-(2-((tetrahydro-2H-pyran-4-yl)methoxy)pyridin-4-yl)furo[3,2-c]pyridin-4(5H)-one;
5-methyl-2-((4-(methylsulfonyl)piperazin-1-yl)methyl)-7-(2-((tetrahydro-2H-pyran-4-yl)methoxy)pyridin-4-yl)furo[2,3-d]pyridazin-4(5H)-one;
(R)—N-methyl-N-(4-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide;
7-(3-(cyclopropylmethoxy)pyridin-4-yl)-5-methyl-2-((4-(methylsulfonyl)piperazin-1-yl)methyl)furo[3,2-c]pyridin-4(5H)-one;
(R)-7-(3-(cyclopropylmethoxy)pyridin-4-yl)-5-methyl-2-((2-methyl-4-(methylsulfonyl)piperazin-1-yl)methyl)furo[3,2-c]pyridin-4(5H)-one;
7-(3,4-dimethoxyphenyl)-5-methyl-2-((4-(methylsulfonyl)piperazin-1-yl)methyl)furo[2,3-d]pyridazin-4(5H)-one;
2-((1,4-diazepan-1-yl)methyl)-5-methyl-7-(2-((pyridin-2-ylmethyl)amino)pyridine-4-yl)furo[3,2-c]pyridin-4(5H)-one;
(R)-5-methyl-2-((2-methyl-4-(methylsulfonyl)piperazin-1-yl)methyl)-7-(2-(2-(2-oxopyrrolidin-1-yl)ethoxy)pyridin-4-yl)furo[3,2-c]pyridin-4(5H)-one;
N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide;
(R)—N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide;
(S)—N-(4-(5-methyl-2-(1-(4-(methylsulfonyl)piperazin-1-yl)ethyl)-4-oxo-4,5-dihydrofuro[3,2-c]pyridin-7-yl)pyridin-2-yl)acetamide;
N-(4-(5-methyl-2-((4-(methylsulfonyl)piperazin-1-yl)methyl)-4-oxo-4,5-dihydrofuro[3,2-c]pyridin-7-yl)pyridin-2-yl)acetamide;
(R)—N-(5-(5-methyl-2-((2-methyl-4-(methylsulfonyl)piperazin-1-yl)methyl)-4-oxo-4,5-dihydrofuro[3,2-c]pyridin-7-yl)pyridin-3-yl)acetamide;
7-(3-((cyclopropylmethyl)amino)pyridin-4-yl)-5-methyl-2-((4-(methylsulfonyl)piperazin-1-yl)methyl)furo[3,2-c]pyridin-4(5H)-one;
(R)-7-(3-((cyclopropylmethyl)amino)pyridin-4-yl)-5-methyl-2-((2-methyl-4-(methylsulfonyl)piperazin-1-yl)methyl)furo[3,2-c]pyridin-4(5H)-one;
5-methyl-2-(((R)-2-methyl-4-(methylsulfonyl)piperazin-1-yl)methyl)-7-(3-(oxetan-2-ylmethoxy)pyridin-4-yl)furo[3,2-c]pyridin-4(5H)-one;
5-methyl-2-(((R)-2-methyl-4-(methylsulfonyl)piperazin-1-yl)methyl)-7-(3-((R)-oxetan-2-ylmethoxy)pyridin-4-yl)furo[3,2-c]pyridin-4(5H)-one;
5-methyl-2-(((R)-2-methyl-4-(methylsulfonyl)piperazin-1-yl)methyl)-7-(3-((S)-oxetan-2-ylmethoxy)pyridin-4-yl)furo[3,2-c]pyridin-4(5H)-one;
(R)-7-(3-(cyclopropylmethoxy)pyridin-2-yl)-5-methyl-2-((2-methyl-4-(methylsulfonyl)piperazin-1-yl)methyl)furo[3,2-c]pyridin-4(5H)-one;
5-methyl-2-((2-methylpiperazin-1-yl)methyl)-7-(2-((tetrahydro-2H-pyran-4-yl)methoxy)pyridin-4-yl)furo[3,2-c]pyridin-4(5H)-one hydrochloride;
(R)-5-methyl-2-((2-methyl-4-(methylsulfonyl)piperazin-1-yl)methyl)-7-(3-(oxetan-3-ylmethoxy)pyridin-4-yl)furo[3,2-c]pyridin-4(5H)-one;
2-((4-acetyl-2-methylpiperazin-1-yl)methyl)-5-methyl-7-(2-((tetrahydro-2H-pyran-4-yl)methoxy)pyridin-4-yl)furo[3,2-c]pyridin-4(5H)-one hydrochloride;
N-(3-(5-methyl-2-((4-(methylsulfonyl)piperazin-1-yl)methyl)-4-oxo-4,5-dihydrofuro[3,2-c]pyridin-7-yl)phenyl)acetamide;
(R)-7-(2-((cyclopropylmethyl)amino)pyridin-3-yl)-5-methyl-2-((2-methyl-4-(methylsulfonyl)piperazin-1-yl)methyl)furo[3,2-c]pyridin-4(5H)-one;
(R)-7-(3-aminophenyl)-5-methyl-2-((2-methyl-4-(methylsulfonyl)piperazin-1-yl)methyl)furo[3,2-c]pyridin-4(5H)-one;
2-((1,4-diazepan-1-yl)methyl)-5-methyl-7-(3-((pyridin-2-ylmethyl)amino)phenyl)furo[3,2-c]pyridin-4(5H)-one;
(R)-7-(3-ethoxypyridin-4-yl)-5-methyl-2-((2-methyl-4-(methylsulfonyl)piperazin-1-yl)methyl)furo[3,2-c]pyridin-4(5H)-one;
N-(3-(2-((1,4-diazepan-1-yl)methyl)-5-methyl-4-oxo-4,5-dihydrofuro[3,2-c]pyridin-7-yl)phenyl)picolinamide;
(R)—N-(6-(5-methyl-2-((2-methyl-4-(methylsulfonyl)piperazin-1-yl)methyl)-4-oxo-4,5-dihydrofuro[3,2-c]pyridin-7-yl)pyridin-2-yl)acetamide;
2-((1,4-diazepan-1-yl)methyl)-7-(3-(cyclopropylmethoxy)pyridin-4-yl)-5-methylfuro[3,2-c]pyridin-4(5H)-one;
7-(3-(cyclopropylmethoxy)pyridin-4-yl)-5-methyl-2-((4-methyl-1,4-diazepan-1-yl)methyl)furo[3,2-c]pyridin-4(5H)-one;
5-methyl-2-((4-methyl-1,4-diazepan-1-yl)methyl)-7-(3-((pyridin-2-ylmethyl)amino)phenyl)furo[3,2-c]pyridin-4(5H)-one hydrochloride;
(R)-7-(3-isopropoxypyridin-4-yl)-5-methyl-2-((2-methyl-4-(methylsulfonyl)piperazin-1-yl)methyl)furo[3,2-c]pyridin-4(5H)-one;
(R)-7-(2-aminopyridin-4-yl)-5-methyl-2-((2-methyl-4-(methylsulfonyl)piperazin-1-yl)methyl)furo[3,2-c]pyridin-4(5H)-one;
(R)-7-(3-hydroxypyridin-4-yl)-5-methyl-2-((2-methyl-4-(methylsulfonyl)piperazin-1-yl)methyl)furo[3,2-c]pyridin-4(5H)-one;
7-(3-((2,2-difluorocyclopropyl)methoxy)pyridin-4-yl)-5-methyl-2-(((R)-2-methyl-4-(methylsulfonyl)piperazin-1-yl)methyl)furo[3,2-c]pyridin-4(5H)-one;
(R)—N-(4-(5-($^2H_3$)methyl-2-((2-methyl-4-(methylsulfonyl)piperazin-1-yl)methyl)-4-oxo-4,5-dihydrofuro[3,2-c]pyridin-7-yl)pyridin-2-yl)acetamide;

(R)-5-methyl-2-((2-methyl-4-(methylsulfonyl)piperazin-1-yl)methyl)-7-(3-(2-(2-oxopyrrolidin-1-yl)ethoxy)pyridin-4-yl)furo[3,2-c]pyridin-4(5H)-one;

(R)-5-amino-N-(3-(5-methyl-2-((2-methyl-4-(methylsulfonyl)piperazin-1-yl)methyl)-4-oxo-4,5-dihydrofuro[3,2-c]pyridin-7-yl)phenyl)pentanamide;

N-(4-(5-methyl-2-(2-(4-(methylsulfonyl)piperazin-1-yl)propan-2-yl)-4-oxo-4,5-dihydrofuro[3,2-c]pyridin-7-yl)pyridin-2-yl)acetamide;

(R)-7-(3-(2-methoxyethoxy)pyridin-4-yl)-5-methyl-2-((2-methyl-4-(methylsulfonyl)piperazin-1-yl)methyl)furo[3,2-c]pyridin-4(5H)-one;

3-(cyclopropylmethoxy)-4-(5-methyl-2-((4-(methylsulfonyl)piperazin-1-yl)methyl)-4-oxo-4,5-dihydrofuro[3,2-c]pyridin-7-yl)benzoic acid;

3-(cyclopropylmethoxy)-N-ethyl-4-(5-methyl-2-((4-(methylsulfonyl)piperazin-1-yl)methyl)-4-oxo-4,5-dihydrofuro[3,2-c]pyridin-7-yl)benzamide;

5-methyl-2-(((R)-2-methyl-4-(methylsulfonyl)piperazin-1-yl)methyl)-7-(3-((tetrahydrofuran-3-yl)methoxy)pyridin-4-yl)furo[3,2-c]pyridin-4(5H)-one;

5-methyl-2-(((R)-2-methyl-4-(methylsulfonyl)piperazin-1-yl)methyl)-7-(3-((tetrahydrofuran-2-yl)methoxy)pyridin-4-yl)furo[3,2-c]pyridin-4(5H)-one;

7-(3-(cyclopropylmethoxy)pyridin-4-yl)-5-methyl-2-((3-oxopiperazin-1-yl)methyl)furo[3,2-c]pyridin-4(5H)-one;

(R)-7-(3-(2-fluoroethoxy)pyridin-4-yl)-5-methyl-2-((2-methyl-4-(methylsulfonyl)piperazin-1-yl)methyl)furo[3,2-c]pyridin-4(5H)-one;

(R)-7-(3-cyclopropoxypyridin-4-yl)-5-methyl-2-((2-methyl-4-(methylsulfonyl)piperazin-1-yl)methyl)furo[3,2-c]pyridin-4(5H)-one;

(R)-7-(3-(2,2-difluoroethoxy)pyridin-4-yl)-5-methyl-2-((2-methyl-4-(methylsulfonyl)piperazin-1-yl)methyl)furo[3,2-c]pyridin-4(5H)-one;

(R)-7-(3-(2-hydroxyethoxy)pyridin-4-yl)-5-methyl-2-((2-methyl-4-(methylsulfonyl)piperazin-1-yl)methyl)furo[3,2-c]pyridin-4(5H)-one;

7-(3-(cyclopropylmethoxy)pyridin-4-yl)-5-methyl-2-((4-methyl-3-oxopiperazin-1-yl)methyl)furo[3,2-c]pyridin-4(5H)-one;

(R)-5-methyl-2-((2-methyl-4-(methylsulfonyl)piperazin-1-yl)methyl)-7-(2-oxo-2,3-dihydro-1H-pyrrolo[2,3-b]pyridin-4-yl)furo[3,2-c]pyridin-4(5H)-one;

7-(3-(2-methoxypropoxy)pyridin-4-yl)-5-methyl-2-(((R)-2-methyl-4-(methylsulfonyl)piperazin-1-yl)methyl)furo[3,2-c]pyridin-4(5H)-one;

7-(3-((1-methoxypropan-2-yl)oxy)pyridin-4-yl)-5-methyl-2-(((R)-2-methyl-4-(methylsulfonyl)piperazin-1-yl)methyl)furo[3,2-c]pyridin-4(5H)-one;

(R)-5-methyl-2-((2-methyl-4-(methylsulfonyl)piperazin-1-yl)methyl)-7-(3-(oxetan-3-yloxy)pyridin-4-yl)furo[3,2-c]pyridin-4(5H)-one;

5-methyl-2-(((R)-2-methyl-4-(methylsulfonyl)piperazin-1-yl)methyl)-7-(3-((tetrahydrofuran-3-yl)oxy)pyridin-4-yl)furo[3,2-c]pyridin-4(5H)-one;

5-methyl-2-(((R)-2-methyl-4-(methylsulfonyl)piperazin-1-yl)methyl)-7-(3-(((S)-tetrahydrofuran-3-yl)oxy)pyridin-4-yl)furo[3,2-c]pyridin-4(5H)-one; and 5-methyl-2-(((R)-2-methyl-4-(methylsulfonyl)piperazin-1-yl)methyl)-7-(3-(((R)-tetrahydrofuran-3-yl)oxy)pyridin-4-yl)furo[3,2-c]pyridin-4(5H)-one;

N-(4-(5-methyl-4-oxo-2-((5-oxo-1,4-diazepan-1-yl)methyl)-4,5-dihydrofuro[3,2-c]pyridin-7-yl)pyridin-2-yl)acetamide;

N-(4-(2-((1,4-oxazepan-4-yl)methyl)-5-methyl-4-oxo-4,5-dihydrofuro[3,2-c]pyridin-7-yl)pyridin-2-yl)acetamide;

N-(4-(5-methyl-2-((4-methylpiperazin-1-yl)methyl)-4-oxo-4,5-dihydrofuro[3,2-c]pyridin-7-yl)pyridin-2-yl)acetamide;

N-(4-(5-methyl-2-((4-methyl-1,4-diazepan-1-yl)methyl)-4-oxo-4,5-dihydrofuro[3,2-c]pyridin-7-yl)pyridin-2-yl)acetamide;

N-(4-(2-((1,4-diazepan-1-yl)methyl)-5-methyl-4-oxo-4,5-dihydrofuro[3,2-c]pyridin-7-yl)pyridin-2-yl)acetamide;

N-(4-(2-((1,1-dioxidothiomorpholino)methyl)-5-methyl-4-oxo-4,5-dihydrofuro[3,2-c]pyridin-7-yl)pyridin-2-yl)acetamide;

N-(4-(5-methyl-4-oxo-2-((3-oxopiperazin-1-yl)methyl)-4,5-dihydrofuro[3,2-c]pyridin-7-yl)pyridin-2-yl)acetamide;

N-(4-(5-methyl-2-((4-(methylsulfonamido)piperidin-1-yl)methyl)-4-oxo-4,5-dihydrofuro[3,2-c]pyridin-7-yl)pyridin-2-yl)acetamide;

(S)—N-(4-(2-((3-hydroxypiperidin-1-yl)methyl)-5-methyl-4-oxo-4,5-dihydrofuro[3,2-c]pyridin-7-yl)pyridin-2-yl)acetamide;

N-(4-(5-methyl-4-oxo-2-(piperazin-1-ylmethyl)-4,5-dihydrofuro[3,2-c]pyridin-7-yl)pyridin-2-yl)acetamide;

N-(4-(2-((4-ethyl-3-oxopiperazin-1-yl)methyl)-5-methyl-4-oxo-4,5-dihydrofuro[3,2-c]pyridin-7-yl)pyridin-2-yl)acetamide;

N-(4-(5-methyl-2-((4-(methylsulfonyl)piperidin-1-yl)methyl)-4-oxo-4,5-dihydrofuro[3,2-c]pyridin-7-yl)pyridin-2-yl)acetamide;

N-(4-(2-(((1,1-dioxidotetrahydro-2H-thiopyran-3-yl)amino)methyl)-5-methyl-4-oxo-4,5-dihydrofuro[3,2-c]pyridin-7-yl)pyridin-2-yl)acetamide;

N-(4-(2-(((1,1-dioxidotetrahydrothiophen-3-yl)amino)methyl)-5-methyl-4-oxo-4,5-dihydrofuro[3,2-c]pyridin-7-yl)pyridin-2-yl)acetamide;

N-(4-(2-((2,5-dimethyl-4-(methylsulfonyl)piperazin-1-yl)methyl)-5-methyl-4-oxo-4,5-dihydrofuro[3,2-c]pyridin-7-yl)pyridin-2-yl)acetamide;

N-(4-(2-((4-ethyl-2-methylpiperazin-1-yl)methyl)-5-methyl-4-oxo-4,5-dihydrofuro[3,2-c]pyridin-7-yl)pyridin-2-yl)acetamide;

N-(4-(5-methyl-2-((4-methyl-5-oxo-1,4-diazepan-1-yl)methyl)-4-oxo-4,5-dihydrofuro[3,2-c]pyridin-7-yl)pyridin-2-yl)acetamide;

N-(4-(5-methyl-2-((7-methyl-5-oxo-1,4-diazepan-1-yl)methyl)-4-oxo-4,5-dihydrofuro[3,2-c]pyridin-7-yl)pyridin-2-yl)acetamide;

N-(4-(5-methyl-2-((2-methyl-5-oxo-1,4-diazepan-1-yl)methyl)-4-oxo-4,5-dihydrofuro[3,2-c]pyridin-7-yl)pyridin-2-yl)acetamide;

N-(4-(2-((1,1-dioxido-1,4-thiazepan-4-yl)methyl)-5-methyl-4-oxo-4,5-dihydrofuro[3,2-c]pyridin-7-yl)pyridin-2-yl)acetamide;

N-(4-(5-methyl-2-((3-methyl-1,1-dioxidothiomorpholino)methyl)-4-oxo-4,5-dihydrofuro[3,2-c]pyridin-7-yl)pyridin-2-yl)acetamide;

N-(4-(5-methyl-2-((2-methyl-1,1-dioxidothiomorpholino)methyl)-4-oxo-4,5-dihydrofuro[3,2-c]pyridin-7-yl)pyridin-2-yl)acetamide;

N-(4-(2-((4-acetyl-1,4-diazepan-1-yl)methyl)-5-methyl-4-oxo-4,5-dihydrofuro[3,2-c]pyridin-7-yl)pyridin-2-yl)acetamide;

N-(4-(5-methyl-2-(morpholinomethyl)-4-oxo-4,5-dihydrofuro[3,2-c]pyridin-7-yl)pyridin-2-yl)acetamide;

N-(4-(2-((4-acetyl-2-methylpiperazin-1-yl)methyl)-5-methyl-4-oxo-4,5-dihydrofuro[3,2-c]pyridin-7-yl)pyridin-2-yl)acetamide;

N-(4-(5-methyl-2-((4-methyl-3-oxopiperazin-1-yl)methyl)-4-oxo-4,5-dihydrofuro[3,2-c]pyridin-7-yl)pyridin-2-yl)acetamide;

(S)—N-(4-(5-methyl-2-((3-methyl-4-(methylsulfonyl)piperazin-1-yl)methyl)-4-oxo-4,5-dihydrofuro[3,2-c]pyridin-7-yl)pyridin-2-yl)acetamide;

N-(4-(5-methyl-2-((4-(methylsulfonyl)-2-oxopiperazin-1-yl)methyl)-4-oxo-4,5-dihydrofuro[3,2-c]pyridin-7-yl)pyridin-2-yl)acetamide;

N-(4-(2-((4-ethylpiperazin-1-yl)methyl)-5-methyl-4-oxo-4,5-dihydrofuro[3,2-c]pyridin-7-yl)pyridin-2-yl)acetamide;

N-(4-(5-methyl-4-oxo-2-(pyrrolidin-1-ylmethyl)-4,5-dihydrofuro[3,2-c]pyridin-7-yl)pyridin-2-yl)acetamide N-(4-(5-methyl-4-oxo-2-(piperidin-1-ylmethyl)-4,5-dihydrofuro[3,2-c]pyridin-7-yl)pyridin-2-yl)acetamide;

N-(4-(5-methyl-4-oxo-2-((3-oxo-1,4-diazepan-1-yl)methyl)-4,5-dihydrofuro[3,2-c]pyridin-7-yl)pyridin-2-yl)acetamide;

(R)—N-(4-(5-methyl-2-((2-methyl-3-oxopiperazin-1-yl)methyl)-4-oxo-4,5-dihydrofuro[3,2-c]pyridin-7-yl)pyridin-2-yl)acetamide;

or a salt thereof.

11. A compound which is 5-methyl-2-(((R)-2-methyl-4-(methylsulfonyl)piperazin-1-yl)methyl)-7-(3-((R)-oxetan-2-ylmethoxy)pyridin-4-yl)furo[3,2-c]pyridin-4(5H)-one or a salt thereof.

12. A compound according to claim 1, or a pharmaceutically acceptable salt thereof.

13. A pharmaceutical composition which comprises a compound of formula (I) or a pharmaceutically acceptable salt thereof as defined in claim 12 and one or more pharmaceutically acceptable carriers, diluents or excipients.

* * * * *